(12) United States Patent
McFarland et al.

(10) Patent No.: US 11,891,630 B2
(45) Date of Patent: Feb. 6, 2024

(54) BACTERIOPHAGE ENGINEERING VIA SEMI-SYNTHESIS

(71) Applicant: The Charles Stark Draper Laboratory, Inc., Cambridge, MA (US)

(72) Inventors: Kirsty A. McFarland, Boston, MA (US); Miles T. Rogers, Boston, MA (US); Connor McBrine, Somerville, MA (US); Jason W. Holder, Swampscott, MA (US)

(73) Assignee: The Charles Stark Draper Laboratory, Inc.

( * ) Notice: Subject to any disclaimer, the term of this patent is extended or adjusted under 35 U.S.C. 154(b) by 1427 days.

(21) Appl. No.: 16/057,416

(22) Filed: Aug. 7, 2018

(65) Prior Publication Data

US 2019/0048325 A1 Feb. 14, 2019

Related U.S. Application Data

(60) Provisional application No. 62/542,609, filed on Aug. 8, 2017.

(51) Int. Cl.
*C12N 7/02* (2006.01)
*C12N 15/66* (2006.01)
*C12N 15/10* (2006.01)
*C12N 15/63* (2006.01)

(52) U.S. Cl.
CPC ............ *C12N 7/02* (2013.01); *C12N 7/025* (2013.01); *C12N 15/1031* (2013.01); *C12N 15/63* (2013.01); *C12N 15/66* (2013.01); *C12N 2795/00041* (2013.01); *C12N 2800/202* (2013.01)

(58) Field of Classification Search
None
See application file for complete search history.

(56) References Cited

U.S. PATENT DOCUMENTS

2005/0273869 A1 12/2005 Court et al.
2008/0194000 A1* 8/2008 Pasternack ............... C12N 7/00
435/235.1

FOREIGN PATENT DOCUMENTS

EP          3 064 599 A1   9/2016
WO   WO-2016/100389 A1   6/2016

OTHER PUBLICATIONS

Thomason et al., Modifying bacteriophage lambda with recombineering, Methods Mol Biol, 2009, pp. 239-251.*
Smith et al., Generating a synthetic genome by whole genome assembly: X174 bacteriophage from synthetic oligonucleotides, PNAS, 2003, vol. 100, No. 26, pp. 15440-15445.*
GenBank Accession EU734173, Klebsiella phage K11, complete genome, 2008.*
Daniel G Gibson et al., "Enzymatic assembly of DNA molecules up to several hundred kilobases" Nature Methods, vol. 6, No. 5, Apr. 12, 2009 (Apr. 12, 2009). pp. 343-345, XP055224105, New York.
Diana P. Pires et al: "Summary", Microbiology and molecular biology reviews, vol. 80, No. 3, Jun. 1, 2016 (Jun. 1, 2016), pp. 523-543, XP055385259.
E. Magda Barbu et al: "Phage Therapy in the Era of Synthetic Biology", Cold spring harbor perspectives in biology, vol. 8, No. 10, Aug. 1, 2016 (Aug. 1, 2016), p. a023879, XP055526638.
International Search Report and Written Opinion for International Appl. No. PCT/US2018/045597, dated Feb. 15, 2019.
Robert J Citorik et al: "Bacteriophage-based synthetic biology for the study of infectious diseases", Current Opinion in Microbiology, vol. 19, Jun. 1, 2014 (Jun. 1, 2014), pp. 59-69, XP055256177, GB.
Samuel Kilcher et al: "Cross-genus rebooting of custom-made, synthetic bacteriophage genomes in L-form bacteria", Proceedings of the national sciences of the United States of America, vol. 115 , No. 3 , Jan. 3, 2018 (Jan. 3, 2018), pp. 567-572, XP055526643.

* cited by examiner

*Primary Examiner* — Benjamin P Blumel
(74) *Attorney, Agent, or Firm* — Foley & Lardner LLP

(57) ABSTRACT

The present disclosure provides methods of generating recombinant bacteriophage genomes via semi-synthesis. Specifically, the present technology provides methods of integrating a heterologous nucleic acid sequence into a bacteriophage genome, and isolating recombinant bacteriophages that express the heterologous nucleic acid sequence.

8 Claims, 37 Drawing Sheets
Specification includes a Sequence Listing.

>DLPKPN1_nanoluciferase_K11 (SEQ ID NO: 1)

TCTCACAGTTTACACTTTTGGTTATCCCCCCGGTACCCTCCAGTTCACCCAAAGTAACCTAGGGTACCCCTCTTTACC
TTTGGTTTAACCTTGGGTGGTACCTTGGGAATCCCTTAGGTGATACCATATGTTGGGGTAATGGTGACCTGAGGAC
ACTATATGTTGATGTCTCTGTGTCCCTATCTGTTGGTACTCATTAAGTCACACCTCAAGTCGCCACCTGAGGTTAGA
CCAGAGGTAACCACCTGAGGTTATACCTGAGACCATATACCTAAGGTGAGCTGACTGCTCACGAGGTTCACCGTTT
GACTAACGTTTAGCAGTGACTGTTAGTAGGTCACATTAAGAGAGTCGGTGCTATTAGTAATAGCGGTAAGTATCTC
GTTTAGCAGTCCCTGAGACACTGAGAGCGGGACAAGAGGGTATCGGTGAGTCATCACTATAAGGGCTATTGGTG
GTCAGTGTCAACACCATAATCAATTAGGACACACTATAGGGAGACACTTAAAGTATTACTATGAGACCATCACCAT
AAAGATCACTATCACTATAGGTCTAACTAAAAGTTTAACTTTAAGTGTTGACATTCAGATTCCTTTATGAGACATTA
GCAACCGTTGAGAGACACAACGTCACCAACGACCAGACAATACCACGAGTTATCTGGTTAGACTGAGGGTCTCAA
GTAGTCATCAACCGGACATACGAAAGTGGTTGACTCAACGATGAACAAGTAGTAAGATGTACCACAGATTCACGA
AGCACCGCTCTTTAACAATATGGATTAGTCGCTGATATGTACACCATGACATTAGTGTTTAACTAGTGGTTACATTC
AGGTCTCTGGCAAGGTACGTCCTGTCACCCTGAGAGTAGCCACGATGATAACCACTAACATCGAGGATACACAGC
ATGGAAATCGTAATGCAGGCACTGAACCACGGGGTCATTATGACGACAGCACGGGACTACACCGGGGCCACCAA
ATACATGGTGCAATACGGCTTACAGTTCACGGTGTTTGACTCGTTCCGTGAGGCACTGCAAGATTACACAGATTTG
CGTCACCCATTTCGCAAGAGTGTGGGGACTAGCGGTTAACGACAGGTCATCCAAGCGGTGGCCTGAAAGATAACC
ACTAACTGAAGGATATACACGATGATTTTCACTAAAGAGCCAGCAAATAAAGCCTTCGTATTCGTAACCGCTTACC
GTGGCTATGAGTCGCTCGAAGTTAACGAGAAGGTCCTCAAGGGTCTCATCCGCACCATTAAGACCTATCCGGGTG
CTTACGGTAACATCCGCGATGAGAATGTTGTGGGATGCTTCAAAGAGGCTGGCATGGAGTACGCAACGGAAGAG
CGCACGCTCAAGGTTGAATGCACCGTTAAACAAGCGGCTGAACTGGCGTGGCTGGCATGTAAGACCTACCATCAA
GACGCTGTACTAGTGGTTAACTCACAGACCCACACAGCCTCCTTATGGTCTATTGAGAACGTAGGGGAGTATCCTC
AGGTATACCCACGCTTGAAAGAGGTGTCTTTAGGTGGTACGCTGCAACAAGTTGATGCACCTAAGGGTGAATGCT
ATTCAGTCATCGACGGGCAATACTGGGAGGTGGCGTGATGGTTGACTATGGTCTCACACAAGAACACTTGAAGTT
ATACCGCACGGCCATGGCATATGGTGCATCGTTCGGTTACTGTATGGCCCAACTGGCCCAGACCTACCGCACACGC
AAGGTGATGTATGGTAACCCTGTTCGTAATTAGTGTGTACGCCCTGATTGTCCTGTACTTTGTGCGGGACTTTCGCA
AGGGCCTCAAGGTGCACAAAGCATCATTCAGTTACATGAAGTGGGGCGTGTTACCTCGCTTTACTGTACGGCTACC
TAATGGCCGCTTTAAGGCTAACAAGGTAGGTATTTTCTATATCGCAACCCATTAACACATCGCACATAAGGAAACA
ACCAAATGAACTACACCGACATGCAAGAGCGCTTAGACGTCGTCCGTAACCTGCCAATCTGTGAACTCGACAAGC
GCCAGCCGCTGCTGGTAGCACTCATGGCGGACATTGTGAACGCTGAGACGTCCGATGGTGACGATACGGATAGC
GGTTGGGGTCTGGAACGTCAGGACTACTGGCAAACCCTGAAGATTAAGGCCAAAGATGCTGGGTTTAACCTGCTG
GGCAACGGTCACTTCAGCGCAGCGTTTAAGCACGAGCTGCTACCGGGTAGGGCCATTAAGGTTGGCTTTAAGAAA
GAGGACTCAGGGGCCGCATACGTGGCTTTCTGCCGGATGCACCAAGGACGGGTAGGGATACCTAACGTCTATCAC
GTAGCGCGTCACGCTGGGTGCTACACGGTGGTACTTGATGAGCTGGAACCGTGCCAGCGCAGTGGGAACGATGA
GCACGAGCACTACGCAGACCTAGCGTATTACTTTGTCGAAGGTGAATCGGACCCAGCGGACTACTCGGAGGGCGA
CCAGCCGTTTATTGAGACGTGCCAAATGATTCGCAAGTTCTTCTACGGGATTGCGTCCTTTGATATGCACAGCGGT
AACATCATGTTCACCAAGGACGGCAAGCCAGTGATTACCGACCCGGTGTCATTCTCAGCGGACCGGGACCGGGAG
CCTTTCTCACTGGAACCTGAGGACCTGCTCGCAGAGATTGAGCAGATAGCGCACGACAAGATGATCGAACGCTGT
AAGCGCAACAAGGCTAAGCGTGACCCGAACGGAGAGCTGCGCATCGCACGCCGTAAGGCCAATAAGGAACGTCG
AGCACGCCGTAAGGCACACGCTCGGTGGCGTAAGGAGCGCGAGCGTATTAACGCTGATGCCTTAAAGTTTGACCT
TGCTAAAATCGAGGAGCGGGTACTAGCGTGGCAAATGGGACCAGGCCTGGCGATACAAATGGGCAAGCCGTTAC

Figure 13(b)

```
CACTCGACAACTACCTTCAGGGTAGACTTATGGGTTAACGAGGTGTATCTTAGGTGTCTCCGAACGGTGAGGCACC
CATAGATAAACTTTATCCACAAAGAGGCACACAATGAACGCATTAAACATTGCACGTAATGACTTCTCCGAGATTG
AACTTGCTGCTATTCCGTACAACATCCTCAGCGAGCACTACGGGGACAAGCTGGCACGTGAGCAGTTAGCACTGG
AGCATGAAGCGTACGAGCTTGGCGAACAACGTTTCCTGAAGATGTTAGAACGTCAGGTGAAAGCTGGTGAGTTCG
CTGACAACGCGGCCGCTAAGCCGCTGGTCTTAACGTTGCACCCACAGCTGACCAAGCGCATTGACGACTGGAAGG
AGGAGCAAGCAAACGCTCGCGGTAAGAAGCCTCGCGCATACTACCCGATTAAGCACGGCGTCGCCTCAAAGTTAG
CTGTTAGCATGGGCGCTGAGGTGCTAAAAGAGAAGCGCGGAGTGTCCAGTGAGGCAATCGCACTGCTGACCATT
AAGGTCGTCTTGGGGACGCTCACAGACGCCTCAAAGGCCACAATCCAGCAGGTATCCTCTCAGTTAGGCAAGGCT
CTTGAGGATGAGGCCCGCTTCGGTCGTATCCGTGAGCAGGAAGCCGCATACTTCAAGAAGAACGTAGCGGACCA
GCTGGACAAGCGAGTAGGCCACGTGTACAAGAAGGCTTTCATGCAGGTAGTCGAGGCCGATATGATATCCAAAG
GGATGCTGGGCGGCGACAACTGGGCGAGCTGGAAAACTGACGAGCAGATGCACGTAGGGACCAAGCTGCTGGA
GCTACTCATTGAGGGAACTGGTCTGGTGGAAATGACCAAGAACAAGATGGCCGATGGCTCCGATGATGTAACCA
GTATGCAGATGGTCCAGCTGGCTCCGGCCTTTGTGGAACTCCTGAGCAAACGGGCAGGCGCACTCGCGGGTATCA
GCCCGATGCACCAGCCGTGCGTAGTCCCTCCGAAACCTTGGGTGGAGACCGTAGGCGGTGGCTACTGGTCAGTCG
GTCGCCGTCCGCTGGCACTGGTGCGTACCCACTCCAAGAAGGCGCTGCGCCGCTACGCTGACGTGCACATGCCAG
AGGTATACAAGGCGGTAAACCTCGCGCAAAACACGCCGTGGAAGGTGAACAAGAAGGTGCTGGCGGTAGTCAAC
GAGATTGTCAACTGGAAGCACTGCCCGGTAGGTGACGTCCCAGCGATTGAACGCGAAGAGTTACCGCCGCGCCC
GGACGATATTGACACCAACGAGGTGGCACGTAAGGCATGGCGCAAGGAGGCCGCAGCGGTCTACCGTAAGGACA
AGGCCCGCCAGTCTCGCCGTTTGTCGATGGAGTTCATGGTCGCACAGGCTAACAAGTTCGCTAACCACAAGGCCAT
TTGGTTCCCGTACAACATGGACTGGCGCGGGCGTGTGTACGCTGTGAGCATGTTCAACCCACAGGGTAACGATAT
GACCAAGGGGATGCTGACGCTGGCCAAGGGTAAGCCAATTGGTCTCGACGGGTTCTACTGGCTGAAGATTCACG
GCGCAAACTGTGCAGGTGTCGACAAGGTTCCCTTCCCTGAGCGCATCAAGTTCATCGAAGAGAACGAGGGCAACA
TTCTGGCGAGCGCAGCGGACCCGCTGAATAACACTTGGTGGACCCAGCAAGATTCGCCGTTCTGTTTCTTAGCGTT
CTGCTTCGAGTACGCAGGTGTTAAGCATCACGGCCTGAATTACAACTGCTCGCTGCCGCTGGCGTTCGATGGGTCC
TGCTCTGGGATTCAGCACTTCAGCGCGATGCTCCGAGATTCCATCGGTGGTCGTGCGGTTAACCTGCTGCCTTCTG
ATACCGTGCAGGATATCTACAAGATTGTGGCCGACAAGGTGAACGAAGTGCTCCACCAGCACGCCGTCAACGGGT
CTCAGACCGTGGTCGAGCAGATTGCTGACAAAGAGACTGGCGAGTTTCACGAGAAGGTGACTCTGGGCGAGTCC
GTACTGGCTGCGCAGTGGTTGCAATATGGTGTGACCCGCAAGGTGACTAAGCGTTCGGTCATGACGCTGGCATAC
GGTTCCAAAGAGTTTGGCTTCCGCCAGCAGGTTCTTGAGGACACCATTCAGCCTGCTATTGACAACGGCGAGGGC
CTGATGTTTACGCACCCTAACCAAGCAGCTGGCTACATGGCTAAGCTGATTTGGGACGCTGTGACCGTGACCGTAG
TGGCCGCTGTCGAGGCAATGAACTGGCTGAAGTCTGCCGCTAAGCTGCTGGCTGCTGAAGTCAAGGACAAGAAG
ACCAAAGAGGTGCTGCGTAAGCGCTGCGCAATCCACTGGGTAACACCCGATGGCTTCCCGGTGTGGCAGGAGTAC
CGCAAGCAGAACCAAGCGCGCCTGAAGCTGGTCTTCCTCGGGCAGGCCAACGTCAAGATGACGTATAACACTGGG
AAGGACTCCGAGATTGATGCCCACAAGCAGGAATCCGGCATCGCTCCTAACTTTGTTCACTCACAGGATGGCAGTC
ACCTGCGCATGACTGTAGTACACGCCAACGAGGTCTACGGGATTGACTCCTTCGCACTCATTCACGACTCCTTTGG
GACCATTCCGGCTGACGCTGGGAATCTCTTTAAGGCAGTCCGCGAGACGATGGTCAAGACCTACGAGGACAACGA
TGTAATTGCAGACTTCTACGACCAGTTTGCCGACCAGCTGCACGAGTCTCAACTGGACAAGATGCCTGCGGTTCCG
GCCAAAGGTGACCTGAATCTGCGCGATATCTTGGAGTCTGACTTCGCGTTTGCGTAAGGTCTCAGGCAATTAGGG
CACACTATAGGGAACCTTCGAATGACCGAGGGTTCCATTACTTAAAGTCTTAACTTAAAGAATACTTAAAGAGGCA
CGCTATGACTTACTCAATCGTTGTAACCATCTTGTTAATCATCACCCTTACGCTCCTCATTAACACCATACGCAATTC
ACTACGCAGCGAGGAGCGGCTGGGGCGCAAGGTCCAAGAGGCCAACTCCGCGTTTAGCAGTGAGTCCTGCAAGG
TCCTGCGTCTGGCAGACAGGGCTGACTCGCTCAGTAGACAGGTTCGTTACTTAGAGGGTGAGCTTGAGAGCGAGA
AACAGAAGGTGCGCGATGTGAACGAACTTCGAGAGCACCAGCGGGAACGCATGAAGTTTCTTCGTAAGTCCCTGA
```

Figure 13(c)

```
AGGAAGCACAAGACGAGCTGATGATGGTCTCCGACCTGATTCACGTTAAGTTCACCGCAGTGTTGCCAGACGGTA
CCCACTCTAAGACGATCTTTAAGTTAGGACTCGGGCCGTGTGGTCTGCACGTTAAGTCCCTGCGCTGGACCGAGCT
GGACGACCGCTATCTGATAGACCAGCTGTGCACCAACGGTGAGCGCAAGCAGTTCGTCTACTACAAGAGCGAAGT
AGTAGGGCGCATCGAGTTCCGCCACGGTAAGCTGTAATTAGGACCCACTATCAGGAACATACTCAAGGTCATCATT
CGGTGGCCTTCATGAATGTCCCTTACTATCACAATCAGGAGCAACACCATGTATCAGAACACAATCAATTTCGAGC
GCAACCGTGAACGTCAGCAGACTGAGGGTTATATCCCTAAGGGCCGCAAGCTGAACAAGACGAAGCGCGGCGGT
GGCGTGAAGGGTTCCTTCCGTAACGCTAAGGGTGACAGCGTTGTTAACCAAGAGAAATACTTCGTAGGAGCGTAA
CAAATGGCTACGGAAAAAGATGGCTCTTCGATGGAAGCACCTCACAATGGTCTCGTTTAGGAGCAGCGGAGCGT
AGACTACTAGATACGACAGGCCTGCACGTGGTCATGCTTGACGACCCATTCACTAACACCGTGCTGTTCAACGTAT
TCGAGCCACGCGGGTCACTTCTAATAAGTAAGCGGTTCAGCCACTGGTCGATTGACTCAGCGTCAGACTGGCTGG
CAAAACTCACCGCAGACTACTCGAGCTGGAAGTAATTAGGACACACTATAGGCAGACTCAAGGTCATCGGATTCC
GGCGGCCTTTATGATTGCTTATTGCACACTAAATGAACACTACACTTCGGAGACATCATCATGATGAACATTAAGA
CTAATCCATTTAAGGCCGTATCGTTCGTTCGCTCTGCTATCGAGAAGGCGCTGGAGACTTCCGGTTACCTCATCGCA
GACACTAAGCATGATGGTGTACGCGGGAACATTTGCGTAGACAACACGGCTAACTCATCGTGGCTCAGCCGGGTC
TCCAAGACCATTCCGGCCCTTGAGCACCTCAACGGTTTCGACCAGCGCTGGCAGAAGTTACTGAAAGATGACCGCT
GGATTTTCCCGGATGGCTTCATGCTTGATGGTGAACTCATGGTCAAAGGCGTGGACTTCAACACCGGGTCTGGCCT
GCTGCGCACCAAGTGGCTCAAAGAGACCAACTGGATGTACTCCAGCAAGGATGGAGTGGTGAAGGGCAAGAAG
GAACCTTTCGAGCTGGATACCAAGCAACTAAAAGTTGTCCTCTATGATATCATTCCGCTTGACATTATCGAGTCCGG
TGATGACTACAACGTGATGACCCTCCTCCGCCTTGAGCATGTCAAGGTAGCCTTACCAGTCCTGCAAGACCACTTCC
CTGAAGTCGAGTGGTGCCTCTCGGAGTCCCATGAAGTTTACGACATGGACGAACTCGAAGCGCTGTACCGACAGA
AACGTGAAGAAGGTCACGAAGGTCTGGTGGTCAAGGACCCTCAGGGCATCTACAAGCGTGGTAAGAAGTCCGGC
TGGTGGAAGATGAAGCCAGAGAATGAAGCTGACGGTGTAGTTGTGGGACTCAACTGGGGAACTCCCGGTCTTGC
CAACGAGGGCAAGGTGATTGGCTTCGAGGTCCTCCTTGAGTCTGGTCGCGTGGTATCCGCCAACAACATCTCTCAG
GCACTTATGGAGGAGTTCACAGCCAAAGTTAAGGCCCACACCATGTGCGCCAATGGTTGCCGGATGTCTAAGGAT
GTCGGTATGGATAATCACTCCTGCGCTGGCAAGTGTGCTTACGACCAACACCCGTCGAATAACCCTTATGAGGGCT
GGGCGTGCCAAATCAAGTACATGGAGGAAACTCCAGACGGCTCCCTGCGTCACCCGACCGTTCGACAAATGGCGT
GGCACTGAGGCTGACCCGACCATCAAGATGTAATTAGGACCCACTATAGGAGACACCAAATGTCTATCAACCTGAT
TCTAATCATCGTGCTCATCCTCGCGGCTATCGTGTGGTCAATGAATGACGAGCCACCTAAAGGAGCATAAACCATG
CGCTTACACTTCAATAAATCCAACGGTATCTTCTCGGTTCGCCGGGAGGACCGCAGCACTGTAGCGGCCACCGAGC
GCCACGGTAAGATTCCACGTATCGGCGACACCTTCGAGCTGGCACCTAGCGTTCACATCTTGGTTACTCGCGGTCT
CTACGAATTGGCTCAGACCAAGAGCCGTCCTTTCGTACCCGTTGTGGTAACCAAGTGGCCACGCCTTCGTCTGTTCT
GGGAGCGCATCAAGGAGGTGGTCAATGACTGAACGTGAAATTCAAGTTGTGGACCTTCTGGTTGGGCAAAACACT
GACCGCCCAGACTCCACAACGTGCGCTGATGGCGTCATATGCTACAAGGTATCGTGTAGCGAGTGTCCGCTAAAC
GTCAAAGGTACGACCATTGGGGAGGTCCGTACAATGAAGGACAGCAAAGGCTCCGCCCACTTCCGGAGTGCAA
GATATGGAACGGCGCTGGTCAGTGTACCTGCGAGCCGACCCGAGACGACGGTGTTAAGCAGCCGAGCCACTACC
AGCTGTTCGACGGTGTCGAGGCCATCGAGGTGATTGCTCGCAGCATGACCCAAGAGATGTTTAAGGGGTACTGCC
TCGGGAACATCCTCAAGTACCGCCTTCGGGCCGGGAAGAAGTCCGAGCTGGCTACCTTAGAGAAAGACATGGCG
AAGGCCGCTTTCTATCTGGAGCTGTACACCAAGCACAAGGGTCTGTGTTATGACGCCAAGTGAGTGGGCAAGAAA
GATGTACGAGAAGACGCTCGACCCTGCGTACATCACCCTGTATAACATGTGGAAGGAGCGAGAAGATGCAAAAG
TTCGTCGTAACGGTCGAGACAGCTAACGCATCGTACGAACTCCCGGTACACGCTGGGTCTCTTGATGAGGCCCTCG
AAGTTGCCGAGGCGGAGTACGAAGAGTTAGGCCAAGTGACTCGGGTACGCCCGGATAGTCATTAGGACACACTA
TAGGGACACAGGTTGTCCCTCTTTCTGTTATAAACCAAAGGAGATTCACCATGGCATTCGCTAAGAAGAAATTTA
CACCACCAAGATTGGTACCTGTGAGCCGTACGCTTACTTCAACAAGCCGGACTATGGCGGTGAGGGTTTTGAGAA
```

Figure 13(d)

```
CCCACGTGGTACCTACAAAGGTTACGTAACGTTCAAGAACGAAGACTGTCAGGAGCTGGTAGACCTCATCGTTAA
GACCCATGAGGAAAACTACGCCGCTCGTCTGGAAGCGCACGAAGCGAACCCGCCTAAGGTTCAGAAGGGTAAGA
AACCTCTGAAGCCGTATGAAGGCGACATGCCGTTCTTCGATAACGGTGACGGCACCACCACGTTCAACTTCAAGTG
CTACGGTTCGTACGAGGACAAGAAGACTGGCGAGACCAAGAAGATTGTTCTGGGCGTAGTAGACGCGAAGGGCA
AGCGCATTCAGGACGTTCCGATTATCGGTGGCGGCTCCAAAGTGAAGATTCGCTTCTCGCTGGTACCGTACGGCTG
GTCTGCGGTAGCTGGCGCTTCCGTTAAGTTGCAGCTGGAAGGCGTGATGCTGGTCGAACTGGCTACCTTTGGTGG
TGGCGAAGACGACTGGGCTGACGAAGCCGTAGAAGGCGGTTACGAAGCGGACGAATCTCGCAGCCGTAAACCTC
AGGAAGACCCGGAAGACTGGTCTGGTGAGGAAGCTGACGAGGGCGAAGCCGAAGAAGACGATGACTTCTAATG
GCGGGCTATGGGGCCAAAGGGATTCGGAAGGTGGGTGCCTTCCGGTCTGGCCTTGAGGACAAGGTGTCCAAGCA
GTTAGAAGCAAAGGGCGTCACGTTCGATTACGAATTGTGGCGCATCCCTTACGTTATTCCTGCGAGTGACCACCTT
TACACTCCAGACTTCTTGTTACCCAACGGTATCTTCGTGGAGACTAAGGGTCTCTGGGAAGCCGAGGACCGCAAG
AAGCACCTACTGATTCGTGAGCAGCACCCGGAGTTAGACATCCGGTTAGTGTTCTCTTCGAGTCGCACTAAGATTT
ACAAAGGGTCACCAACCAGTTACGCTGAGTGGTGTGAGAAGCATAACATCTTGTTTGCCGACAAACTGATTCCCGT
AGACTGGCTGAAGGAGCCGAAGCGTGATGTACCGTTCGGCAAGTTCAAGCAGAAGAAAGGAGCAAAGTAAGTAT
GGCCAAGGTTCAATTCACTAAGCGACAGGAGACCTCTCAGATTTTCGTTCACTGTTCCGCCACCAAGGCAAACATG
GACGTAGGCGTCCGTGAGATTCGCCAGTGGCACAAAGAGCAGGGCTGGCTGGATGTAGGGTATCACTTCATCATC
CGTCGTGACGGTACCGTTGAGGCGGGCCGCGACCAAGACGCTGTGGGTTCACACGTCAAGGGATACAACTCGAC
CTCTGTCGGTGTGTGTCTGGTAGGTGGTATCGACGCCAAGGGTAACCCCGAGGCAAACTTCACGCCTCAGCAGAT
GAGCGCACTGAATGGGTTGCTGCACGAGCTGAGGGGGACCTACCCCAAGGCTGTCATTATGGCGCACCACGATGT
AGCGCCGAAGGCTTGTCCTAGCTTCGACCTGCAACGTTGGGTAAAGACTGGCGAGCTGGTCACTTCTGACCGTGG
GTAAACATTAGGGCACACTACAGGGAGACAATTACGTTTCCCTGTTGTCACACATTCTGTACAAATTATGGTCAGG
CTAAGGTGCACTTGGCGTAGCGCTGCGTTTCATTCGGGTTCGATTCCCGGACTGACCACACCAACGGAGATTACTT
TATGAACAAGTTCAAAGAACACTTTGCTGACTCATGGCCACTGTATGTGTACGCATCGGCATTCATCATTGGCGCA
CTGCGAGTGTTGCTCCCATGAGTTACGGGACAGTCGAGAAGACGGTCAGGAAAGTATCTTCCTGTTCCACGCTC
CGTGCGAAAACTGTGGTTCTTCTGATGGTAACTCAGTGTACTCTGACGGGCATGAGTATTGCTTCGTGTGTCAACA
CCGGGTTCCCGGCTCAGAGGAACGTACCGAAAAGTTATCATCGAGAAGACCCAAAGGAGGGAATTACGGGATGA
ATACACAAGGCTCAGGACTACTGGTATTCGGCGAGAGTGACGGTCGGTACACTGACCTGACTGCTCGTGGTATCT
CAAAGGCGACATGCCAGAAGGCTGGCTATTGGGTCGCCAAGGTCAGAGGAACCGCCTATCAGGTGGCCGACTAT
CGTGACCAGAATGGCTCCATCGTCTCCCAGAAGCTGAGGGACAAGGAGAAGAACTTCTCTACCCGAGGGTCCCAC
AAAGGGGATGCACTGTTTGGTAAGCACCTATGGAATGGTGGTAAGAAGATTGTCATCACCGAGGGTGAAATCGA
CATGCTAACCGTGATGCAACTACAGGACTGTAAGTGGCCTGTGGTTTCTCTCGGTCACGGTGCGTCAGCCGCTAAG
AAAACTTGTAGTGCAAACTACGAGTATTTTGATAGCTTCGACCAGATTATCCTGATGTTCGACATGGATGACCCCG
GTCGGGCAGCTGTAGAGGAAGCCGCTCAGGTTCTCCCTCCCGGTAAGGTGCACGTAGCTGTGCTGACCGAGAAG
GATGCCAACGAGTGTTTACTCAAAGGTAAGGGAAGGAGGTTCTCGACCAGATATGGAACGCGGCACCTTGGGT
ACCTGATGGTGTCATCGGTGCGATGTCCATGAAGGACCGAGTGCGTGAGGCCATGACCAGCGAACAAAGCGTAG
GATACCTTTTCTCGGGATGCCCGGGACTGAATGACCGAACCTTGGGTGCACGTGGTGGCGAAGTCATCATGGTCA
CTTCTGGGTCAGGAATGGGTAAGTCTACGTTCGTTCGTCAGCAGGCTCTAGGGTTCGCCAGAGGGCAAGGACTGA
GGGTAGGCATGGCGATGCTTGAGGAGTCCGTAGAGGAGACCATGGAGGATGTCCTAGGGATTGCTAACGGAATC
CGCTTACGGCAGCAGCCTCGGGAGTTCAAGCAGAAACTCATTGAGGATGGTACGTACGATGAGTGGTTCGATGA
GCTGTATGGCTCCGACCAGTTCCATCTCTACGACTCCTTTGCGGAAGCTGAGGTGGACCGCCTGCTGGCCAAGCTG
CACTACATGCGCACAGGGTTGAACTGTGACGTAATCATTCTGGACCACATCTCAATCGTAGTGTCTGCCTCGGAGG
AATCCGATGAGCGCAAGATGATTGACCGACTCATGACCAAGCTGAAAGGGTTCGCTAAGTCAACCGGAGTGGTAC
TTATTGTTATTTGCCACCTGAAGAACCCGGAGAAAGGTAAAGCTCATGAAGAAGGACGTGCTGTTTCCATTACTGA
```

Figure 13(e)

```
CCTGCGTGGGTCTGGGTCTCTGCGCCAGCTCTCTGATACTATCATTGCACTTGAGCGTAATCAGCAAGGGGATATG
CCTAATCTTGTCCTCCTTCGTATTCTCAAGTGCCGCTTTAATGGTATTGGCGTTGGCATTGCGGGGTACATGGAGTA
CAACGAAAAGACAGGACTCCTTGAACCGTCTAGCTACACTGGCGGAGAAGGAGAGGGAGATACTGGCTGGGAAG
GCCACGAAGAAGACGATTACTAAACGTAAATGCAATGGGGCGTACTGCTGGTGCGCCTTTGACCCTGATTATCAA
TAACGGAAGGAGAGCCATCATGTTTAAACTTATCGAAGCATTAGGCCGTCTGGTCATCGCACTGTACGTACGTGAA
GCCAAGGCACTGGACAAAGCGTCCAAGGTGGAAGCGAAAGCAGCCGCTAAGCTGGCTAAGGCAGCCGACAAGG
CACGTCAGGCATCTCTGGATGCAACCGCAGAGGCAGCTAAAGTTGCCGCTAAAGCTCAGAAACTTAAGGAGTTCT
TCTAATGACTACCAAAGTTAAATTCCCCGGCAATACCATTCAGCTGTCCGACACCGTTGACCAGTGGGGACGCAAG
GTTCACATCAACGTTCGCAACGACAAGGTCACTCTGGTCTACCGCTGGAAGGCCAAGAGCGATAATCGTGCGCAT
ACTCAGCGTGTGACCCTCGACGACACACAGGCAGCTCGGCTGCTGGCGTCCGTAGCTGTAGCCGCTACTGTGGCC
ATAGGTGAGGACAAAGTGCGTGAGGCAATCCTGAGCAAAGAGGTTGGCGAAACGTCCGTGCGTCTGGCCGAAGC
GTCAGAAGTTAAGTGATAAACTCAAGGTCATTACTATATGTAGTGGCCTTTATGATTATACACAACATATTGAG
AGGACATTACCATGCGTAAACCTGAAGAGATTCGTAAAGAGATTGAAGCGCTGAACAAAGAGCTGGCTGAGGCC
AAGACCTATGAGGCTAAGCGTGACGCTGCTGTGCACATTCTGGAGAACTTAGGGTGGACCCACAGTGGCCACAAG
GGCTGGCAGAAGCCTTCGCAAAAGTGGAGCGACTATAAGGCTCCCCTGAAGGCTGGTGAGCTGGCAACTTGGGA
CGACAAGGTACTAGGTGGGATAGTGTACATACGCAGTGTGGGCGATAAGTACGCTCAGGTGTCCCACGTTCGTGG
TGTTAGTAGACTGGGAGCTGATGTACTGAACAGTAGCTTTGCTGTCGAGAAGAGTAAGTTAACCGTGCGTCCTCG
TGAGTATTTCATCGGGCGTCGTTAAGCAACAGGAGACCACTATGTTAGTAACCGATATCGAGGCGAACAACCTCTT
AGAGAAAGTCACTCAGTTCCACTGTGGTGTCATTTATGACTACAGTACGGACGAGTACGTATCGTATCGACCTTGG
GACTTCTCAGCGTATCTCGATGCGTTGGAAGCTGAGGTGGCTCGTGGTGGTCTCATCGTATTCCACAACGGTCACA
AGTACGATGCCCCAGTGTTAACCAAGCTGGCCAAGCTCCAGTTAAACCGAGAGTTCCACCTGCCGCGTGAGAACG
TAGTGGACACGTTGGTGCTCAGTCGTTTACTGTTTGCGAACATTAAGGACTCCGACATGGCCCTGCTGCGTTCCGG
TAAGTTACCCGGTAAGCGCTATGGGTCTCACGCTCTGGAGGCGTGGGGTTACCGCTTGGGCGAGATGAAGGGTG
AGTACAAGGACGACTTCAAGAAGCTACTTGAGGAACAGGGAGAGGACTATGTTGACGGTGCTGAGTGGATTAGC
TTCAACGAGCCGATGATGGCGTATAACGTTCAGGACGTTGTGGTGACCAAGGCTCTCTTAGAGAAGCTGCTGAGC
GACAAGCACTACTTCCCACTGTTTGGTAGTAACACCATAGAGTTCTACACCTCAGCGTACTGCTTGAGGTTCTGGG
AGGAGGCTTGTGAGGCCGTCTGGTTGGAACATCGGGCCGCTTGGTTACTCGCTAAGCAGGAGCGCAACGGATTCC
CGTTCAACACCAAGGCCATTGAGGAGTTGTACGTTGAACTCGCTGGTCGTCGTTCTGAACTCCTTCAGACACTTACC
GACACTTTCGGAACTTGGTACCAACCTAAAGGCGGCACTGAGTTATTCCTGCACCCGCGCACTGGTAAACCTCTGG
GTAAATACCCACGAGTGAAGTACCCGAAACAGGGTGGTATCTACAAGAAACCCAAGAACAAAGCTCAACGAGAG
GGTCGTGAACCCTGTGAGCTGGACACTCGGGATTACGTAGAGGGTGCTCCATACACACCAGTAGAGCACGTTGTG
TTCAACCCAAGTAGCCGAGACCACATTGCGCTCAAGCTGAAGGAAGCCGGATGGGTACCCACAGAGTTCACCGAA
AAGGGTGCACCTAAGGTAGACGACGAGGTCCTTGAGCATGTTCGTGTGGGGACCCTGAGAAGCAGCGCTGTAT
CGACCTCATCAAAGAGTACCTGATGATACAGAAGCGTATCGGTCAGGCGGCTGAGGGCGACAAAGCGTGGCTAC
GTTACGTTCAAGAGGATGGTAAAATCCATGGAAGTGTTAACCCTAATGGTGCAGTTACAGGGCGAGCAACGCATA
GCTTCCCTAACCTTGGTCAAGTTCCGGGCGTTCGTTCGCCGTATGGTGAGCCTTGTCGAGCAGCGTTCGGCGCAGA
GCATCACTTGGACGGACTTACCGGACAGCCTTGGGTTCAAGCAGGCATCGACGCCAGCGGACTCGAACTCCGTTG
TCTGGCACACTTCATGTCTAAGTACGACGACGGGGCATATGCGGATGTCATTCTCAACGGTGATATACACACAGTC
AACCAAACGGCGGCTGAGTTGCCAACACGTGATAACGCCAAGACATTCATCTACGGTTTCCTCTATGGTGCTGGAG
ACGAAAAGATTGGACAGATTGTGGGCGCAGGTAAGGAACGCGGAAAGGAACTCAAGAAGAAATTCCTTGAGAAC
ACCCCAGCAATCGCAGCCCTGCGTGAAGGAATCCAGCAGACCCTCGTCGAGTCATCCCGATGGGTTGCCGGAGAG
CAGAAGGTCAAGTGGAAACGACGCTGGATTAAGGGACTGGATGGAAGAAAGGTACACGTTCGGTCACCACATGC
CGCGCTCAACACGTTGCTTCAGTCAGCGGGTGCGCTCATTTGTAAGCTGTGGATTGTCGAGACTGAAGAGTTGCTT
```

Figure 13(f)

```
CTTAAGGCAGGATTGAAGCACGGATGGGATGGCGACTTCGCCTACATGGCGTGGGTTCACGATGAAATACAAGT
GGCCTGCCGGACCTCAGAGATTGCACAGCAGGTGATTGACATAGCGCAGCAAGCTATGCGTAACGTGGGAGACC
ACTTTAAGTTCCGTTGCCGTCTGGACACAGAAGGTAAGATGGGTCCGAACTGGGCCGTATGTCACTAATAATACA
GGAGATTTATCATGGGTATTAACAAACAGTTTCGCGTAACGTTCGATGTAACGGCTACTATGAGTGATGACCAAGA
GCGGGAGTTCCTTGAGGACCTACTATCTCTTGCGTATGGCGTGGACGACAAACGTCAGGCGCACATTGTAACCGA
AGCAATCACCAAAGGTCATGAGGCGGCACTGGCATTCGTCATGCAGAGTGGTCTGCGGGAAGCTATTAAGGACAT
CGGTAAGGAGCTGAGCTGCTCCGCTGTGACAGTACGCTTCTCTCCGGCAACCGTGAGGGTGACTAAGTGAGCGAG
TACCTCAAAGTTCTGGCGGCCCTCAAGGGCTGCCCTAAGTCCTTCCAGTCGAACTACGTGCGGAACAACGCCGCGT
TAGTCGCTGAGGCTGCGAGCCGTGGTCACATTTCATGTCTGACCATGAGTGGTCGTAACGGTGGCGCTTGGGAAA
TTACCAGTGCCGGAGTGAAATTCCTTAAGGCCCATGGAGGTTGTCTATGAAAGACTTTTTAGGTAACGATATCGAG
ATTGGCGACACCATTGTGTATGCTGACGCTGGTGGCCGTGGAGGCTCTTCGGGTCTTAACAAGACAGTAGTTACCC
GAATGACTGATAAACAGGTCATGGTGTACGAATCAACGTGGTCAAAACTGTGGCGTCCGTTTGACCGTGTTGTGG
TTGTTGCTAAGGGAGGTTCCCAATGAAGCACACATTGTTATCCTTCAGTGACTACCGGGCAACCCAGAAGATTGCC
AAGGGTGTCCTTGTGATGGATGGTGACTGGTTGGTATTCCAAGCCATGAGTGCCGCTGAGTTCGATGCCTCGTGG
GAGGAGGAGATTTGGCACCGTTGCTGTGACCACGCTAAGGCCCGAGAGATTCTGGAGAACTCCATCGAGTCCTAC
AAGGGCCGCAAGAAGGCGTGGAAGAATGCAGACGTTGTCCTAGCGTTCACTGACCGTGTCAACTGGCGCAAGCT
GCTTGTGGACCCGACGTACAAAGAGAACCGCGCAGTCGTCAAGAAACCTGTGGGTTACTTTGAGTTCCTTGAGTA
CGTCTTTGAGTCCTACACATGTGTCCTTGAGCCTCAGCTCGAAGGTGATGACGTGATGGGTATCATCGGGTCTAAC
CCTCTCGTGTACAACTACGAGAAGGCCGTGCTGGTCTCCTGCGACAAGGACTTTAAGACCATCCCGGATTGTGATT
TCCTGTGGTGCACGACTGGTAACATCCTCGTTCAGACTCAGGAGACAGCCGACTACTGGCACCTCTTCCAGACTAT
CAAGGGTGACATCACCGATGGTTACGGTGGGATTCCCGGATGGGGAGATACCGCTGAGGACTTCCTCAAGGAAC
CCTTCATTGTGGAGCCTGTAACGTCCGTGCTGAAGTCCGGTAAGAACAAGGGCCAAGAGGTAACCAAGTGGGTG
AAACGCGCTCCTGAGCCGGGAGAGACGCTCTGGGACTGCATTAAGTCCATTGGTGCCAAAGCAGGGATGACCGA
AGCGGAAGTAATTAAGCAGGGCCAGATGGCTCGCATCCTCCGTTCTGATGAGTACAACATCGAGACTGGGGAGAT
TACTCTATGGCAACCGGGCAGCTGATTCTCATCGTCCTGACCATGGGCTTAGTTGCTCGTGGTCTCTGGATGTTGG
CCTTGATTATCAAGCAGATAGTCGAGCATAAAGCAGAGTGATAAACTCATGGGCACAATTAGGACCCACTATAGG
GAAGTGCCCATTATGATTATTACTTAAAGATTACTTAGAGAGGAGACTCAAATGTTAAAACCTATAGAGCACATCC
TTAACAATCCTAATGACCTTCCTGACGTACCGCGAGCTGTCAAGGAGTACCTACAGTCTCGCTTCAATGCTGACTTC
CTGTATCAGTCAGAGGTCCGTAAGCTGCGTGAGGCTGGCCACAGTGAGGAGTTCATCTCCGGTGTACTGTATGGT
CACTACATGGCTTCTCGTGTCCTTGACGAGATGGAGGGCCGCCAGCGTGCACTCAAAGAAGGAGATTGATTATGT
GTTTCTCACCTAAGATGAAAGCACCTAAGGTCGACACAACGACTGTCCCTGAGCCAGCTCCGCTCACTGAGGAACC
TAAGGGTATCCAGTACGGTGGCGACGAAGACTCAAACAGCACCACTCCTGAGGTGTCAGGGCGTAAGTCACTCAA
GGTGACCAAGACGACCGAGCCCACAGGGTCAGTCAGTAAAATCCGTAAGTCAGCTTTAGGAGGCTAACATGGGA
CTGTTCAAGAAAATCAAGAAGGCTATCTCCAAGGTAGTCAAGGCACCACTCAAGGCCGTGGGTCTAGCAGCAGAT
GCGCCTAACGTGCAGACAGCCGCTGAGACACCTGTGGCAGCACCTCAGGAAGCACCGAAAGAGGTCGTGGAGGA
CGTTGAGTCTTCAGCAGACACCGAGTCTGGTAAGAAGAAATCCCGAGCGTCTGGTAAGAAGTCCCTCTCAGTTTCC
CGCAGCTCAGGCGGTGGGATTAACTTATGATTGGTTACGGGGAGGGCTAACAAATGGCAGAAGTTAAACTCGAA
GGCTTCGCAGAGGAGGGAGCCAAGGCGGTGTATGACCGTCTGAAGAACGACCGACAACCTTACGAGACACGAGC
AGAGTCCTGTGCGCAGTACACGATTCCATCACTGTTCCCTAAGGACTCCGATAACGCATCAACAGATTACACGACT
CCGTGGCAATCCGTAGGTGCTCGCGGCCTGAACAACCTAGCGTCCAAGCTGATGTTGGCCCTGTTCCCGATGCAGT
CATGGATGAAGTTGACCATTAGTGAATACGAAGCGAAGAACCTTCTGGGTGACGCTGAGGGTCTCGCTAAGGTCG
ATGAGGGCCTATCAATGGTAGAGCGAATCATCATGAACTACATCGAGTCCAACAGTTACCGAGTGACTCTCTTCGA
GTGCTTGAAGCAACTGTGTGTGGCCGGGAACGCATTGCTGTACTTACCGGAGCCTGAGGGTTACACCCCGATGAA
```

Figure 13(g)

```
GCTCTATCGCCTGAACTCGTATGTGGTCCAGCGAGACGCTTTCGGTAACGTACTCCAGATTGTCACTCTCGACAAG
ATTGCGTTCAACGCTCTCCCTGAGGATGTCCGCAGCCAAGTGGAAGCAGCCCAAGGTGAGCAGAAGGAAGACGC
TGAGGTTGACGTCTACACCCACGTGTACCTGAACGAATCCGGGGATGGCTACTCGAAGTACGAAGAGGTTGCCGA
AGCAGTAGTACCGGGCAGCGAGGCTGAATACCCGCTCGAAGAGTGTCCGTACATTCCGGTCCGCATGGTCCGCAT
CGACGGTGAATCCTACGGTCGTTCCTACGTGGAAGAGTATCTGGGTGACCTCAAGTCCCTAGAGAACCTCCAAGA
GTCCATCGTGAAGATGGCGATGATTACCGCGAAGGTCATCGGTCTGGTAGACCCGGCAGGTATCACTCAGGTCCG
CCGACTCACGGCAGCACAGTCTGGTGCGTTCGTACCGGGCCGTAAGCAGGACATTGAGTTCCTCCAGCTGGAGAA
GTCCGGTGACTTTACCGTAGCGAAGAACGTAAGCGACACCATTGAGGCTCGCCTATCGTATGCCTTTATGCTCAAC
AGTGCGGTACAACGTACAGGCGAGCGAGTCACAGCCGAAGAGATTCGGTACGTGGCGTCAGAGCTGGAAGATAC
CCTAGGCGGTGTCTACTCGATTCTATCGCAGGAACTCCAGCTGCCTCTGGTAAGAGTGCTCTTGAAGCAACTACAA
GCCACGCAGCAAATCCGGAGTTACCTAAAGAGGCCGTCGAGCCAACTATCAGCACTGGCCTTGAGGCTATCGGA
CGTGGTCAGGACCTTGACAAGCTGGAGCGGTGCATTGCCGCATGGTCAGCCCTTAAGGCCCTCGAAGGTGATGAC
GACCTCAACTTGGCTAACCTCAAGTTACGTATCGCTAACGCTATTGGACTCGACACTGCTGGTATGCTTCTCACTCA
GGAGCAGAAGAACGCCCTTATGGCACAGCAAGGTGCTCAGATTGCCACACAGCAAGGGGCCGCAGCGCTGGGTC
AAGGGATGGCCGCACAGGCTACTGCAAGTCCTGAAGCGATGGCCGCAGCAGCTGATTCAGTAGGTATGCAACCG
GGCATGTAATTAGGGCACACTATAGGGAGACCGATTGGTTTCCCTCTTAGTCTTAACTTTAAGGAGATTGAAATGG
CTGGCGAATCTAACGCAGACGTATACGCATCCTTCGGTGTTAACAGTGCTGTACTGACTGGTAGTACACCTGAGGA
GCACCAAGAAACATGTTGGCTCTTGATGTTGCTGCCCGTGATGGCGATGATGCAATCGAGCTGAACACAAACAG
TGATGACCCGTATGGTTCCGATGTGGACCCGTTCGGTGAACCTGAAGAGGGCCGTATGCAGGTCCGTATCTCCGC
TGACGGTTCAGACGAACAGGACGGCGAAGAGGGTCAGGGTGACGAAGAACAGCAGGGCGACGAAGAGAGTCA
GCCGGAGGAAGTAACCGATGAAGGTGAACCTGAAGAGTTCAAACCTATTGGTGAAACTCCGGCTGACATCAACG
AAGCCTCTCAGCAGCTGGAAGAACACGAAGCTGGCTTTAACGACATGGTTGCTACTGCAATCGAACGCGGTCTCT
CACAGGATGCTGTGACCCGTATTCAGCAGGAGTACCAGAACGAGGACAGTTTGTCCGACGAGTCTTACCGAGAGC
TGGCCGAGGCGGGCTACAGTAAGGCGTTCGTCGATGCGTACATTCGCGGTCAGGAGGCTCTGGTCAACCAGTAC
GTTGAGAAAGTGATGGACTTCGTGGGAGGCCGTGAGCGATTCCAGCAGGTCTACAGTCACATGCAGACCAATAAC
CCTGAGGGTGCCGAGGCGCTCATCAAGGCTTTTGAGTCTCGTGATGTAGCCACCATGAAGACGATTCTGAACCTA
GCGGGACAGTCTCGTGATAAAACCTTTGGTAAGAAAGCTGAGCGCTCTATTGCCAAGCGTGCAACCCCAGCGAAA
CCTGCTCCCCGCAAGGCTGTAGGCTTCGAGTCTCAAGCTGAGATGATTAAGGCGATGTCCGACCCGCGCTACCGC
ACCGACTCTAAGTATCGTCGTGAAGTAGAGCAAAAGGTAATCGACTCAACGTTCTAATGAATTAGGGCACACTATA
GGGAGACCATCAGACTGAACACGGTGACGTCCACTGGCTCCCTTCGAGTTACACAATGAGTATCACCTCGTTTCAA
GTAGTAACTGACGCGACCTTAGGGCAAGACCTTATGATAGGCGCGGAGAATCACCCCAAGAGCTTGGCAACGATA
GGCCCGTTTGGTCAGCGTAATGACTAATTCTATTCGTAAACAACATAAGGAGATTCAACATGGCTAACATGCAAGG
TGGACAGCAGCTCGGTACTAACCAAGGTAAAGGTCAATCCGCAGCAGACAAGCTGGCGCTATTCCTGAAAGTATT
CGGCGGTGAAGTCCTGACCGCATTCGCTCGTACCTCTGTGACCACCAACCGTCACATGCAGCGTCAAATCAGCTCC
GGTAAGTCCGCACAGTTCCCTGTGATTGGCCGCACCAAGGCTGCTTACCTGCAACCGGGCGAGTCTCTGGATGAC
AAACGTAAAGACATCAAGCACACCGAGAAGACCATTAACATTGATGGCCTGCTGACCGCTGACGTGCTGATTTAC
GACATCGAAGACGCGATGAACCACTATGACGTGCGCTCCGAGTACACCTCTCAGATTGGTGAATCTCTGGCGATG
GCGGCGGATGGTGCGGTTCTGGCTGAGCTGGCTGGTCTGGTTAACCTCGCTGATTCCGTCAACGAGAACATCGCG
GGTCTGGGCAAACCGTCCCTGCTGGAAGTTGGTGCTAAGGCTGACCTGACCGACCCGGTTAAACTGGGCCAAGCG
GTTATCGCACAGCTGACCATTGCTCGTGCGGCCCTGACCAAGAACTACGTCCCGGCGAACGACCGTACGTTCTACA
CCACCCCGGACGTGTACTCTGCGATTCTGGCGGCTCTGATGCCTAACGCTGCGAACTATGCGGCTCTGATTGACCC
TGAGCGTGGCTCTATCCGTAACGTGATGGGCTTCGAAGTCGTAGAGGTTCCGCACCTGACCGCTGGTGGTGCTGG
TGATGACCGCCCGGACGAAGGCGCAGAAGCGACCAACCAGAAGCACGCCTTCCCGGCAACTGGCGGTAAAGTCA
```

Figure 13(h)

ACAAAGAGAACGTTGTGGGCCTGTTCCAGCACCGTTCCGCTGTCGGCACCGTTAAACTGAAAGACCTGGCTCTGG
AGCGTGCTCGTCGTACTGAGTATCAGGCTGACCAGATTGTTGCCAAGTACGCGATGGGTCATGGTGGTCTGCGTC
CAGAATCTGCTGGTGCGCTGGTTTTCACAGCAGCCAAGCGTAAATACCTTTAGTGCTCGGACGGTAACTCCGTCT
GAGTATGAGGTACAGACTGTGGCCATTACTGGTGATTCACTTAAGGTGACACTTGGTGGGCTGGAGGGAGTAAC
GGACTGGTCAACACTTGAGGTAACTTATGGTACTTCCGGGATTGCCAGCCACACTCGCCGGACCAACACGCTGTAC
TTCAAAGGAATCGCTGTGGGCGAAACTCTAGTGACTGTCAGCTTTGACGGGTCTGAAAGGAAGTCCTTTAAGCTG
GTCGTGACTAATTAAAACTAAGCCAAACCCCTTGGGGACCACTCACGGTCTCTGAGGGGTTTTTTCGTTAGGAGCT
TACATTATGAACATGCAAGATGCTTACTTTGGGTCTGCCGCTGAGCTGGATGCTATCAACGAGATGCTCGCAGCTA
TCGGTGAATCCCCGGTGACCACCCTTGACGAAGATGGTAGCGCAGACGTAGCTAACGCTCGTCGTATCCTCAACA
GGATTAACCGCCAGATTCAGTCTAAAGGTTGGGCCTTCAACATCAACGAGTCGGCCACGCTGACCCCTGACGCGG
ACACTGGGCTTATCCCGTTCCGTCCGGCCTACCTGTCCATCCTTGGTGGCCAGTACGTCAACCGTGGTGGTTGGGT
GTACGACAAGTCCACAGAGACGGATACCTTCTCTGGGGCAATCACAGTGACCCTAATCACACTTCAGGACTACGAC
GAGATGCCTGAGTGTTTCCGCCAGTGGATTGTCACCAAGGCCAGCCGTCAGTTCAACTCTCGGTTCTTCGGAGCGG
AGGACGTAGAGAACTCTCTGGCACAGGAAGAGATGGAAGCGCGTATGGCATGCAACGAGTACGAGATGGACTTC
GGTCAGTACAACATGCTTGACGGCGACGCATACGTGCAGGGTCTCATCGGTCGTTAATAGGAGGTATACAATGGT
CTTCACACTCGAAGATTTCGTTGGGGACTGGCGACAGACAGCCGGCTACAACCTGGACCAAGTCCTTGAACAGGG
AGGTGTGTCCAGTTTGTTTCAGAATCTCGGGGTGTCCGTAACTCCGATCCAAAGGATTGTCCTGAGCGGTGAAAAT
GGGCTGAAGATCGACATCCATGTCATCATCCCGTATGAAGGTCTGAGCGGCGACCAAATGGGCCAGATCGAAAAA
ATTTTTAAGGTGGTGTACCCTGTGGATGATCATCACTTTAAGGTGATCCTGCACTATGGCACACTGGTAATCGACG
GGGTTACGCCGAACATGATCGACTATTTCGGACGGCCGTATGAAGGCATCGCCGTGTTCGACGGCAAAAAGATCA
CTGTAACAGGGACCCTGTGGAACGGCAACAAAATTATCGACGAGCGCCTGATCAACCCCGACGGCTCCCTGCTGT
TCCGAGTAACCATCAACGGAGTGACCGGCTGGCGGCTGTGCGAACGCATTCTGGCGTAATCAGAAACTTAAGGAG
GACCAAATGGCTCTCGTATCACAATCAATCAAGAACCTCAAGGGAGGCATTAGCCAGCAGCCTGAAATCCTACGG
TACCCAGAGCAGGGTACACTTCAGGTCAACGGTTGGTCCTCCGAGACTGAGGGTCTCCAGAAGCGACCACCTATG
GTGTTCATCAAGTCCCTTGGACCTAGGGGCTACTTGGGGGAAGACCCGTACATTCACCTCATCAACCGAGATGAAT
ACGAGCAGTATTACGCAGTGTTCACTGGGAACGATGTTCGGGTATTCGACCTGTCCGGCTATGAGTACCAAGTAA
GAGGTGACCGCTCGTATATCTCAGTAGTCAACCCTAAGGATAACTTGCGGATGATAACCGTGGCCGACTACACGTT
CATCGTTAACCGTACCCGACAGGTCCGCGAGAACCAGAACGTGACCAACGGTGGTACCTTCAGGGACAACGTGGA
CGGTATTGTCAACGTCCGTGGTGGCCAGTATGGTCGTAAGCTCGAAGTGAACATTAACGGTGTATGGGTCAGCCA
CCAGCTGCCTCCGGGTGACAACGCTAAGGATGACCCGCCCAAGGTTGACGCACAGGCCATTGCGGCTGCACTCGC
TGACCTACTTCGTGTGGCCCACCCAACGTGGACATTCAACGTGGGGACTGGTTATATCCACTGCATCGCACCAGCT
GGGGTAACTCTTGATGAGTTCCAGACGAGGGACGGTTACGCGGACCAGCTGATTAACCCGGTGACCCACTACGTT
CAGAGCTTCTCTAAGTTGCCACTTAACGCGCCTGACGGGTACATGGTGAAGATTGTCGGGGACACGTCCAAGACT
GCTGACCAGTATTACGTGAAGTATGACGCTTCTCAGAAGGTCTGGAAGGAAACCGTGGGCTGGAACATCTCGGTC
GGCCTTGAGTATCACACGATGCCTTGGACTCTGGTGCGTGCAGCTGACGGTAACTTTGACCTCGGGTATCACGAGT
GGAGGGACCGCCGTGCTGGTGACGACGACACTAACCCTCAGCCGTCCTTTGTTAACTCAACGATAACCGATGTGTT
CTTCTTCAGGAACCGCTTAGGGTTCATCTCTGGGGAGAACATCGTGCTTTCCCGCACCAGTAAATACTTTGAGTTCT
ACCCGCCGTCAGTGGCCAACTATACGGACGATGACCCGCTAGATGTTGCCGTGAGTCATAACCGTGTGTCGGTCCT
TAAGTACGCTGTGAGCTTCGCTGAGGAGCTTCTGCTGTGGTCCGATGAGGCTCAGTTCGTCCTGTCGGCCAACGGT
GTGTTATCCGCTAAGACTGCACAGCTGGACCTGACCACTCAGTTCGATGTGTCAGACCGTGCGCGTCCTTACGGTA
TCGGCAGGAACATCTACTATGCGTCTCCTCGAAGCTCCTTTACGTCCATCATGCGCTACTACGCGGTACAGGATGT
AAGCTCTGTGAAGAACGCAGAGGACATGACGGCCCACGTCCCGAACTACATCCCGAACGGTGTGTACAGTATCAA
CGGGTCCGGTACTGAGAACTTCGCGTGTGTGCTGACCAAGGGTGCTCCCAGCAAGGTGTTCATCTACAAGTTCCTC

Figure 13(i)

```
TACATGGACGAGAACATTCGACAGCAGTCATGGTCCCACTGGGACTTCGGAGATGGTGTGGAGGTGATGGCTGC
AAACTGCATCAACTCAACGATGTACCTGCTGATGCGGAACGCCTACAACGTGTGGATAGCTGCTGTGGACTTTAAG
AAGGAGTCGACTGACTTCCCGTTCGAGCCTTACAGGTTCCACGTGGATGCCAAGCGGTCATATCACATCTCAGAGA
CTGCGTACGACATCGAGACCAACCAGACGGTAGTGAACGTCAAGGACATCTACGGTGCGTCGTTCTCCAATGGTA
CGGTGGCAATCTGCGAGAGTGACGGCAAAATCACCGAGTATGAGCCGATGGGTGACTCTTGGGATTCAACCCCA
GACATCCGCATTAGCGGTGACATCTCTGGCAAGGATATCGTCATTGGGTTCCTGTACGACTTCCAATATGTGTTCA
GTCGGTTCCTCATCAAGCAGGAGCAGAACGATGGCACAACGTCCACAGAGGACGCCGGACGCCTACAACTTCGGA
GAGCGTGGGTGAACTATCAGGACACTGGTGCGTTCACTGTGAGTGTCGAGAATGGCAACCGTGAGTTCAACTATC
TGGTCAACGCCAGAGTAGGCTCCACGGGTCTACGTCTTGGCCAGAAGGCAACGACCACTGGTCAGTATCGCTTCC
CGGTGACAGGTAACGCCTTGTACCAGAAGGTGTCCCTGAGTTCCTTCAACGCTTCCCCGGTGTCAATCATTGGGTG
CGGCTGGGAAGGTAACTACAGCAGACGAGCCAACGGCATTTAACTGAAGGAATCCTTATGGTGTGCTCAATTAGG
GCACACTATAGGGAGACCACACTAAGAGGGGACTTAAAGCATGTACATAAGACAATCCACTAAAACTGACCTATT
TGTGTTCAAGCCGTCCCGTGACGATAGACTTGAGGCAGCAGCCTTGGGTATAGCTCCGGGATTCCCACCGCATACC
GAATGTGTCTCACTGGTTACCGATGGTGACATAGAGGGCACATACAACCTTCTGGCTATTGGAGGCAACGTGGGT
GACCAAGTGTGGTTCGTAACGGACCAGAAGGTATCACGCTTGACCAGAGAGGAGCGTTTAGAGTTTCGTAAGAAC
ATTATCGAATACCGCGACAGGTTACACGAGAAGTACCCAATCCTCTGGAACTACGTGTGGGTAGGTAACAAGTCG
CACATTCGGTTCCTGAAGACAATTGGTGCTGTATTCGAGAATGATTTTACACTCAACGGCACCTTCCAACTGTTCAC
CATAACGAGGAGGTAACTATGTGCTGGATGGCAGCTATTCCTATCGCAATGACGGCGGTGCAGGCCATCGGCCAG
TCACGCAATGAAGCCAAGATGATTGGCCTTCAGAATGACCAGATGCGCCGACAGTCTGCCCAGATGATTAAAGAG
TCAAACATTCAGAACGCTAACGCCAGCCTTGAGCAGAAGCAGAAGCTGGAAGAAGCCAGTTCGGACCTGACCGCT
AAGAATCTCGATAAGGTTCAGGCCATGGGTACAATCCGTGCAGCAATCGGAGAGGGAAACCTTGAGGGTGCCAG
CATGGACCGTATCAGTCGAATCGAGGAGGGCAAGTTCATTCGGGAGGCCAACGCGGTCACCGATAACTACCGTCG
AGACTATGCGTCACTGTTCGCTCAGCAGCTGGGCAACTCAGAGTCAACTATTGACCAAGTTAAGTCCATGCAGAAG
GCTGAGGGCAAAGGTAAGTCTAAGCTGGAACAGGTGCTGGACCCGCTGGCATTGATGACCTCACAAGGCGCATC
CGCATATTCGTCAGGTGCGTTCGACAGTAAGGGAACCAAGGCACCAATTAGTCAGGCCCAAGGTACTAAGGTAGG
AGGTAAGTAATGGCCAGTAAATTAGAACAAGCATTAAGCCAACTGCCGCAGGCCGGGTCTACCCGCATCCGTGGT
GGCTCAGCGTCCATGCAGTATCGCCCAGTAACCATCCAACAGGAAGGGTTCCGTCAGTCCAACCTCGTGCAGTCCT
TGGCGAAGTTTGGTACTGCGGTGGGTGAGGCAGCGGATGCCTACGACAAGCGCCAACGGGACAAGGCCGATGA
GCGGTCCGACGAGATTATCCGCAAGTTGACCCCAGAGCAGCGCCGGGAGGCAATCAAGAACGGGACCCTGCTGT
ATCAGGATGACCCGTACGCTATGGAGGCCCTACGGTTCAAGACTGGTCGTAACGCAGCGTTCCTCATTGACGACG
AAGTGGCACAGCGTGTTCAGAACGGTGAGTTCCGTACCCGTGCTGAGATGGAAGAGTACCGCCACAAACGGTTG
ACCGAAGGTGCCAACGAGTTCGCTGAACAGTTCATGATTAACCCTGAGGACTCTGAGTTCCAGAGAGGGTTCAAC
GCGAACATCACTGAGCGCAACATCTCGCTGTACGGTAAGCACGATACGTTCCTGAGCGAGCAGGCCCAGAAGGGT
GCCATACTGGCCTCGAAGGTGGAGCTGTCAGGTGTGCTCAAAGACCCTGCCGTTCTGGCCCGTCCAGAGTCCGGT
GAGTTCTTCCAGCGCTACATCGACAACGCACTTAAGACTGGGAGTATCCCTAGCGACGCTCAGGCACAGCAGGTC
ATCATCGGGTCCCTTAACGACGTCATTCAGCGTCCGGGTGCTACCAACTTCCTCCAGAGCCTTGAGGGCCGCCCAG
TCACCCTTAATGGGAAGACCACGACCTATAAGGAGCTGATGGGAGAGGAGCAATGGAACGCCCTGATGGTCAAG
GCCCAGTCAACTCAGTTCGACAATGACGCTAAGTTGTCTGAAGGTTTCCGCCTTGGGATTACCAGCGCGTTGAACC
AAGACGATACCAGCAAGGGCTGGAGATGCTTCAGGGTGCCAAAGCGGAACTTGACCGCCTGCAACCCGGTGAG
CAGATGACCCCAGAGCGTGAGCGCTTGATTCAGGCTGAGGAGCAGATGCAGGCCCGTTTCCGTCAGGAGGCCCA
AGCCGCAGCCAAGGAGATGGACAAGCGTCAGAAGACCATCAACAAGAATCAGGTCATCGACCAGCAGTTCACCA
AGCGTATCAACGGTCAGTACGTGTCCACCAGCTACAAGGACATGCCGACCAATGAGAACACCGGAGAGTTCACGC
ACAGTGACATGGTGAACTACGCTAACGGTAAGCTGGCCGAGATTGACCAGATGCAGCTCACGGAGCAACAGAAG
```

Figure 13(j)

```
GACCGCATGAAGCTGAGCTACCTCCGGGCAGACTCAGAGGGTGGAGCCTTCCGTACCGTTGTGGGCCAGTTGGTA
ACCGACGCCGGGTCTGAATGGTCTGCCGCTGTGATTAACGGTAAGTTACCGGAGGACACCACAGCGTTGAACAAA
CTGCGCACCATGCGTAACACCGACCCGGACCTCTTCGCTGCACTGTACCCGGACAAGGCTGACTTGTTCCTGACGA
TGGACATGATGGATAAGCAGGGCATTGACCCGCAGATTCTCATCGACGCTGACCGTTCTCGCCGCAGTCTCACCAA
GGAGATGCAGTACGAGGACGATAAGGCGTGGGCGTCCCTGAAGAACAACTCAGAGTCCCCAGAGCTGTCCCGCA
TTCCGGCTAGTCTGGATGGTATGGCCCGTAAGATTTACGACAGCGTCAAGTACCGTACAGGCAACAGCGACATGG
CGATGCAGCAGACCGACAAGTTCCTCAAGGAATCCACTGTGACCTTCAAGGGTGATGACGTGGATGGCGATACCA
TTGGTATTATCCCGAAGAACATCCTACAGGTCAGTGATGACCCTAAGAGCTGGGAGCAGGGCCGAGACATCCTCG
AAGAAGCCCGTAAGGGAATCATTGCGGCTAACCCTTGGGTGACCAACAAGCAGCTGACGATGTACCAGCAGGGT
GACTCTATCTACATGATGGACACCACTGGCACTGTGCGAATCCGCTACGACAAGGAGCTACTGACTCGCACTTATC
AGGAACAGCAGCAGCGTCTGGCCAAGGAAGCCGAAGAGAAGGCACTGAAGGAAGCAACCAAGCGTGCACCTAT
CGCCGCAGCCACTCAGGCCCGTAAGGCCGCTGGTGAGCGTGTCCGTGCGAAACGTAAAGCCACTCCGAAGTTCAT
CTATGGAGGTGGTGACCAATAATCATTAAGGAGACAACATGAGCTACGATAAGTCCAAACCTAGCGATTACGATG
GCATCTTTCAGAAGGCAGCAGACTCTCATGGGGTCTCCTATGACCTCCTGCGTAAGTTATCGTTTAACGAATCATCC
TTCAACCCTAAGGCCGTCTCTAAGACTGGCCCTAAGGGAATCATGCAGTTCACCCGCAACACGGCCCGAGCGATG
GGCCTTAACGTGACAGATGGTGACGACGATGGGCGCTACAACCCTGAGTTAGCCATTGACGCTGGCGCTAAGCTG
CTTGCGAGCCTCGTTAAGAAGTACAATGGGGATGAGCTTAAAGCGGCCCTAGCGTACAACCAAGGGGAAGGCCC
AGCAGGTGCCCCTCAGCTCCAAGCGTACGACAAGGGAGACTTCGGGTCTATCTCGGAGGAAGGGCGTAACTACAT
GCGCAAGCTGCTGGATGTGGCCAAGAGTCCGAACTCAGGCGCACTGGAGGCGTTCGGTGGCATCACCCCAAAGG
GTAAAGGGATTCCCGCAGAGGATGCCTTCAAGGGCATCGCTAAGGCTGGAAAGGTTGGTACCGAACTGCCGGAG
TCCCATGGGTTCGACATTGAGGGTGTAGCGCAGGAAGCACCAAACACTCCATACGCTAAGGACTTCTGGGAGAAG
ACCGGGACTACTCTCGATGAGTATAACTCTCGGTCAACCTTCTTCGGGTTCGGGGACGCTGCTGAGGCTCAGATTC
AGAACTCCACATTAGGTGTGGCCTTCCGTGCTGCGCGGGCTGACGATGGGTACGATGTGTTCAAGGACACGATGA
CCCCGACTCGCTGGAACTCTTATGTTCCCTCCAAGGAAGACCTACAGAAGCTGCGCGACTCTGGGCTACCTCCGAG
CTACTACGGTGTGGTGACTGGTGGTGACGGTGAGAACTGGGATGCACTCATCAAGCTGGCCAAGGATAACTTCGA
GGCTGACCAACGGGCCGCTGAGGCTGGTACTGGGGCGAAACTCGCTGCTGGTATCGTTGGGGCTGGTGTAGACC
CACTCAGCTATGTACCTCTGGTCGGTGTGGCCGGGAAGGGACTCAAGGTTGTCAATAAGGCCCTGCTAGTAGGCG
CACAGGCTGGGGCACTCAGTGTTGCCTCTGAGGGAATCCGTACGTCAGTGGCTGGTGGCGAGGCTCACTACGCTG
ATGCGGCACTCGGTGGGTTACTGTTTGGCGCTGGTATGTCGGCTCTCAGTGATGCTGTGGCGGCTGGTATCCGTA
AGGCCCGTGGAGTCGATTCTGTGAATGAGTTCGCTGGACCAGCACTCCGTATGGAAGCGCGAGAGACTGCCATCA
ACACTGGTGGTCATGACACCTCGACGCTACCTCCAGAGAACTTCTCGTTCGAGCAGGACCACAGAGGCGTTCCGTT
TGCTGACCACCCGACCGAAGAGGGAGCAGTGGTTCTGGCCAATGGTTCCATCCTGAGCGATACCAACCCGCTTAA
CCCAAGGACTCAACGTGACTTCGCAGAGATTGACCCAGAGCGTGCAGCTCCCGGTATCAAACTCGGTGGGTTCAC
TGAGATTGGCCTGAAGACCTTAGGGTCCAAGGATGCTGGTGTACGTGCAATCGCTCAGGACCTCGTGCGCTCTCC
CACAGGGATGCAATCAGGGTCTAGTGGTAAGTTCGGTGCGACCGCTTCGGACATCCACGAGCGACTCCATGCGAC
TGACCAACGGATGTATAACCAACTGTATGACGCTGTTGACCGTGCCATGAAGGACCCAGAGTTCTCCGTGGGCGA
GCAGAAGATGTCACGCAGAGCCATCCGTCAGGAAGTCTACAAGCGTGCCTCATTGGCGATTGAGCGCCCAGAGTT
ACAGGCTGATTTGACCAAAGGTGAACGTGAGGTGATGGACCTGCTGAAAGAGCACTTCGACACCAAGCGTGAACT
GATGGAACAGCCGGGTATCTTCGGTAACGCTAACGCCGTGAGCATCTTCCCCGGTAGTCGACACAAGGGTACTTA
CGTGCCTAACGTGTACGACAGGGGTGCCAAGGAACTGATGATGCAGAAGCTGGGCGGACCTGAAGGACTCCAAC
AGGCAATCGCTCAGAGCTGGCTTACCAGTTACCGAGTGCGACCTGAGGTCAAGGCGCGTGTTGACGAGTACCTGA
TGGAACTCAACGGCTACAAGTCGGTAGACCAAGTGACACCTGAGGTGGTCCAGAAGCACGCTATGGATAAGGCG
TACGGTATCAGCCACACTGAGGACTTCACAGCGTCCAGTGTCATTGACGACAACATCACAGGTCTGGTCGGTATCG
```

Figure 13(k)

```
AGAACAACTCGTTCCTTGAGGCCCGTAACATGTTCGACAGCGACCTCCCGGTTACCTTACCGGATGGGTCAACCTT
CAGCGTCAACGACCTGAGGGACTTCGACATGGCACGGATTATCCCAGCGTACGACCGTCGAGTTAACGGTGATAT
CTCCATCATGGGCGGTAGCGGTAAGACCACGCAGCAGCTCAAGGACGAAATCATGGCGTTAGACAAGCGGGCTG
AGCGTAAGGGACAGCTGAAGGGCGAAGTGGAAGCACTGAAGGACACCGTTAAGATTCTCACGGGGCGTGCTCGT
CGTAACAACGATACAGCCTTTGAGACCGCCATGCGTACCCTGAACGACCTAGCGTTCTTCGCTAAGAACTTCTACA
TGGGTCCGCAGAACCTCACAGAGATTGCTGGGATGTTGGCTAAGGGTAACGTTAAGGCGATGCTCCACGGTATCC
CGACGTTGCGTGACCTAGCCACCAGAACCTCTCCGGTGTCCGGTAGTGAACTCCGCGAACTCCATGGGGCGCTGTT
CGGTAAGGAACTCGACCAGTTAATCCGTCCGGGGCGTGAGGATATCGTACAGCGAATCCGCGAGGCTTCCGATAC
CAGTGGGGCCATGGCGTCAGTCATTGGCACCATCAAGTTCGGTACTCAGGAGCTGTCGGCTCGTTCTCCTTGGACC
AAGATGCTGAACGGTACGGCTAACTACATTCTGGACACTGCCCGTCAGGGTGTGCTCGGTGATGTGGCTGGTGCG
GCCCTAGGCGGTAAGGGTTCCAAGTTTGGCAAAGAGAACTTCCTCAAAGCTGCCTCTATCAGTCCTGAGCAGTGG
AAGGGAATCAAGCAACTCTTTGTCGACCACGCAACTCGTGACGCTAACGGCCAGTTCACCATCAAGGACAAGAAG
GCTTTCAGTCAGGACCCGAGAGCGATGGACCTGTGGCGTCTTGCCGATAAGGTTGCCGACGAGACCATGCTGCGC
CCTCACAAGGTATCCCAGCAGGATTCCAAGGCGTACGGTGCTGGTGTCAAGATGGCTATGCAGTTCAAGAACTTC
ACCATCAAGTCACTCAATGCCAAGTTCATTCGGTCCTTCTACGAGGGCTACAAGAACAACCGCGCTATCGACATGG
CGTTGACACACGTGTTGTCTCTGGGTATCGCCGGGACTTACTTTGCGATGCAGGCCCACGTGAAGGCTTACGGCCT
CCAAGAGTCCCAACGTAAGGACTACCTGAAGAAAGCCCTGAACCCGACCATGCTGGGCTACGCAGCGTTGACTCG
AAGTTCCCACACTGGTGCCCCGCTGTCCATCGTTTCGATGATGGCTGGTGCCGCTGGGTTCCAAGACGCCAACATG
CTGCGCTCCACCATCTTACCTAAGGAGGAACAATTCCAGAAGAAAGATGGAGCGTCCAAAGGTCGAGCCGAGTCG
AGCAACCTTGCGGGTAACTTAGGGTCTCAGGTCCCAGCTCTGGGTTACGTAGGGAACGTCATTGCTACCGCCAAG
AACGCCTACGGTGTTGCTACAGCACCCAACAAGCCGACTGAGCGTGACTACATGACTGGCCTGATGAACTCCACCA
AGGAGCTTGTTCCGAACGACCCACTGACCCAGCAGCTCATCATGAAAATCTATGAAGCCAACGGGGTCACCATCA
AGCAGCAGCCGAAGCCTAACTAATTAGGACACACTATAGGGAGACCGATTGGTTTCCCCCCTTCTCATTCAACTAA
AGGAGGTCACAATGGACCAAGACATTAAAACAGTCATTCAGTACCCAGTAGGGGCCACTGAGTTCGACATCCCGT
TCGACTACCTGTCCCGTAAGTTTGTCCGTGTGTCGCTGGCAGCTGACGACAACCGCAGACTGCTGAGTAACATCAC
TGAGTACCGCTACGTGTCTAAGACCAGAGTGAAGCTCCTTGTGGAAACTACCGGGTTCGACCGTGTGGAAATCCG
CAGATTCACCTCAGCGTCTGAGCGTATTGTTGACTTCAGCGACGGCTCCGTACTGCGGGCAACAGACCTTAACGTT
TCTCAGATTCAGTCTGCCCATATCGCAGAGGAAGCACGTGATTCAGCACTGTTGGCTATGCCGCAGGATGATGCTG
GCAACCTTGATGCCCGTAACCGCAGAATCGTTCGGCTGGCTCCGGGTGTCGAAGGTACGGATGCAATCAACAAGA
ACCAGCTGGACACCACCTTAGGTGAAGCTGGTGGCATCCTGTCGGAAATCAAACAGACCGAGAAGGACATTCAGG
ATTACATCGAGAACTTTGCAGATGACACCACGTCTCTCAAGGGAATCAACTGGGTGTATAACAATGGGTCGGCCA
ATGGTGGCGAGACCTCCATCCTGATTACCCGCGAGGGGCCAGTGTTCGCTGTGCCTACCATTTACATCAATGGGGA
CAGACAGTCTGTTGGTTACCACTACTCTTACGACTCCGGTGATAAGACCATTCACCTAGTTAAGCCGCTAACTGCTG
GAGACTTTGTGGAATGTGTTACCTCTGAGGGCGTACTGCCGCTGTCTAATCTTCTGTCGACACCAGACGGGGCCAG
TCAGATTGGCACTAAAAGCGGCCTGACTGTGCAAGACTACCTTAACGGCGTGAAGTCCGCTACCATCCTGCGCAAC
ATTGAGCCAGTCATTGATGGACAGCGCATCGTCCTCTCTGAGATTAGCCCTACTTTGGGGCCTAAGTCTGGAGGTA
CCTTGGTGTACGACCAGTCTGATACATCCTCTGTGGACGACGGGTACACTGTTTTCGTGACAGCTGGCGGTAAACG
GTGGAAGCGAGAAGAGTCCTACATTGACGTAGCGTGGTTCGGTCCTAACTTTGGCCTTGCCTTACAGACCGCTGTT
AACCTCGTTGACAACTACGTGAGAACTGTCGGTTTCTACAGTCGCAAGACCATCTACATTGCAGCTGGTACCTATA
CGACAGACCGTCAGGTGGACATTCCATCTTATGTCTCTGTGGTGGCCATAGGTAACGTTAGCATCAATGGTTCTGG
GCTTCCAGTAAACTCCTACGTACTCCGCATAACGAACAAGGTTGGTGGCATTGTCACAACCCACCACTCAGGGTGG
AACCTCGGGGCCGTAGGTGGGACCCTTCGTCTTGTAGGAAACGGCAACACCGGGCAAGTGGATGGGCTTTATGT
GGGCGGTGCGACTTCTATGAGCGACGTACGGAACGTTAGCCTTTACGCTGTGTCAACTTCGGGTGTTCGCTATGG
```

Figure 13(I)

```
GCTAACATTTGGTAGCACCAACACTTACCTCTTCACGGCAACCAAATGCCACTTTGAGACGTCTCTTGTAAACCTGT
ACATTCCGGGCACCACAAGCTCTAACTCAGGGGAGAAGATGGTATTCAATGATACTGTGTTCGGTGGCTCATCTAG
GAACCATGTAGAGGTAAGCACCCCAGGCATGGACCTCACGTTCAATAACTGCTCTTTCGACTTCACAAGCGGTAGC
GTCCTGTACGGGACAGAGACTTGGGGCTATGCGAAAGTAGGCATGAATAATTGCCACTTCGAGGGGTTCAATAGT
TTGTGGATAAAGGTGGATGCCCCGCAAGGTGGATTCATTGGGTCAAACCGAGCGATAACCGTATCAAACGCCACA
GTCCTTCCTAGGCTTCGCTCCAACACTGCTGGAACAAACTCGGCGAGCCGTATGCACATTGATGCCAAGTCTACCC
CGGTGTATATCAGTGGGCTGGACCTACGGCACGAGGTCGTACCATACACCGAGGAAATCTTCATGGCTTCAGCTG
AAACTACCCTGTCTCTGCAAGGATATCTTAAGGACCCGCATTTCCAGATTCCAAGTGCTGCGCACATTCAGAACCGT
GGGTGGAACATCGCTGACGAAACAACTGGAACTGTTGTGAACAGCCCCGCAACCTTGGATTCCCTTACGCGATTTA
CATGCACCGAGAGGAACGCGATGTCTGCGGCTGTGGTCGATGGTGGAACTTCTGGTAAGCTCTTAGCAATGACTG
GAGCGGGTGGGTATTTCACTCTGGTCACTAAAGGATTCATTCCGGTGAGTACGTTCCAACGGATTGGCGGAGCAA
TGTCGATTCAGGCAGCAGCAAGTACCGGAAACATCCAGTGCACGCTTGGTGTCCAGTGGTTCGACTACGATGGTA
ACCTAATCGGGACAGACCAAGCCTTTGCGATTAACATGCGTGAGGTGTTCAACAACTCTTCTCTACCTAACTTCGCC
GAAGGCAACAACCGCTTCATCTCTACATCTGCGAGAACATTCCGTGCGCCAGCGGGGGCCGCTAAGTGTAAACCA
TTGTGGCGAATCTCTGGTCATACTGGCGTTGTGAACATCTCGAGATTAGCATCATTTGTTTTATAAGGAGACAACAT
GCTGAATGATTTAAACCAACCACGAGGCTCGACGCTGGGCCTCTTTACTCCAAACCTTCCGTTGAAGAAGCGGTTG
GACACCTTACCAAACATTTTAGATTTTGATTCAGACAGCCTTAACGATGATAGCACTCGGTTTCAAAAGGCTATTAC
AGCTGGTGTGAAATCTTTATACGTCCCAGAACCTCAGTTCTTTGGCAACAATAAGCCTCTTAAAATTGCTAACGTTG
ACATTGTGACCAATATGCACATCTACGGGAACGGCTCAGCGGGATACCGTCAGGTTGGCGGGGCCATCACCATCC
TAGATGGAGCGGACTATGGGTTTAAACTGGCTGGTGTCGACTCTCAGACGCGAAACATTGGAGGCCGCATTGACG
GTCTCTCGTTCCAAGGTGAGTTCCCAACGACCGTGGCCGACGCCATCCGGTGCCAATCTGCCAGTAGCTTCGCGCT
GGTCAACCTCTCGTTCAGGAACCTCTCCGGGTCCGCTCTGGACCTGCGTGACTTCATGGAGAGCCACATTGAGCAC
TGCTACTTTAACTCAGTAGGTTCCGACACAAAGAACCCAATCAACATCGGGGACTTCGTCGGGTCGGCTCCTTGGA
ACGTCAACAACCTGCACATTGAGAACAACACCTTCGGGTCATGTAGTGGGAACATTATCAACATTAGTGACTCAGC
TAACGCCGACCTCATTTGGATTCTCAACAATAAATTCGAATGGGACTCGACCCCAGTAAGCCCCAACGTTTCCAACA
AGGCGGTGGCATACATCGGGCGAGCCGAGCGTGTAAATGTGTCCGGTAACGGCTTCGTGTACTACTACCCGGCCC
ACAACAAGTACGATGCCCTTATCCGAGTTTCCGATAAGTCGGCCTATGGTAACTTGTTCTCTGATAATACCGCTTGG
GGCTGTACGCCTCCTTCAGGTAGTGACCTCACTCCAGCGTTCTATTGGGACATTGCTGGTGGGTCGTCTGCGGGGT
CTAACAACAAGGCTAACACAAACCTCCCTACGCGCTGCACCAGTATCCACTCTCAGGATATCGACGAGCCGCTGGT
AAGGACTACTCCGGGTAACCGACCAAACCTCCAGAGCATCGGGGCAATGTCTCCCGGATATCTCTCTGCGCACTCC
TTAGGTGGGGCTAACGCTTCCAACTTCTTTGTGCCAGACACTGGTGCTACCAAGTACGGTACGGTGCTAGAGGCTC
AAACTGGTGGTGAGGTTCGCCGCTTGTTCATTCCTAAGGACATTGTTAGCCAGCGTGCTTGCGTTCGAGTTCAGGC
CAGAGTGATGCCGTCGCCGACAGCTGATGCCCTTGTGGGCTGACCTGTGACGGCTCCATTGTTTCCACCACAATC
CAAGGCGCAACCCAAGACTACCATACGGTGGCGGCTGGTGGCGGCTGGCAGATTGTCGAGTGGCTCATCCCGGC
GTCTAGTTACACTGCGGGCCAGTTAATCTTCACGAACCGTAGTGACACCGTCAAGTTCAAACTTGATGGCGTCCGT
GTGTCACGTGCAGACTTCGTAGATGTGACGATTGCATGGAGTCCGACCCCAATCTCCGCAGGGTCTGTGGTAAAC
ACCACTGCATCAATCACTCGCGTAAGTTCCCACGTGGTCGGCACTAGTGGTCTGAAGACAGACGGTACGTTAGGT
GGCGCTGTTAGTAGCTCTTATTTCAACCGTGGGGCCAATACCTTAGTGGTACAGCTGGCAGCACTCACAGCAGCCA
CTCCGTCAATCACTCAGGTTACGGTTAGGCTGTTCCTTAACTAAGGAGGTAACATGTTGTCCCTAGACTTCAACAAC
GAAGTTATCAAGGCGGCTCCCATTGCGGGGTCGCTGGGGCCGATGGTGTAGCGAGGCTCTTCTGGGGCCTCTCA
CTCAACGAGTGGTTCTACGTCGCGGCAATCGCCTACACAGTGGTTCAGATTGGTGCCAAGGTAGTCGACAAAATC
ATTGACTGGAAGAAAGCAAATAAGGAGTAACATATGGACCTGATTAAGTTCCTCGAAATGTTAGATACTGAGATG
GCTCAGCAGATGCTCATGGACCTGAAGAATCCCGAGAAGCGAACCCCTCAGCTGTACAACGCCATTGGTAAACTA
```

Figure 13(m)

```
CTGGAGCGCCATAAGTTCCAAATCTCTAAGCTGACCCCTGACGTTAACATCTTGGGCGGACTGGCTGAGGGTCTG
GAGGCTTACAACTCCAAGGTGGGCGCCGATGGTCTGACAGACGACGATACGTTCACCCTACAGTGATATACTCAA
GGTACTACTATATGTAGTGCCTTTATGGATGTCATTGCACTACGCTAGGCGTTCCTACGTGAAATCTGAGAAACAA
CGGGAGGCATTATGCTGGAGTTCACAAAGAGAATCGTCCCGTATCTTGTGGCTATCATGGTGTTTGCCTTCGGGTG
GCACTTGGGGTCTCAATCTACGGACGCTAAATGGAAGGAGGTAGTACAGCATGAATACGTTAAGAAGCAAACGG
CTAGAGCTGAAACTCAGAAAGCGATTGACGCAATATCGGCTAAGTACCAAGCAGACCTTGAGGGGCTGGAGGGC
AGCACTGATAGGGTTATTGCTGATTTGCGTAGCGACAATAAGCGGCTGCGCGTCAGAGTCAAACCTACCAGTGTC
GCCGCAGGACCAGACGGTCGATGCCTCGTTGATGGTTCCGTCGAACTACACGAAGCAACTGCTCGAAGTCTTATC
GCAATAACCCAGAAGGCCGACCTCAAAGAGAAGGCCCTACAGGACACTATTCGCAAGCTACAGCGGAAAGGAGG
TGAACATTGAGTAACTCTCAGCAAGCCAAGAACGCCTTAATCATTGCGCAACTGAAGGGTGACTTTGTCGCCTTTC
TCTTCGTGCTCTGGAAGGCCCTGAACCTGCCGGAACCAACCAAGTGTCAAATCGACATGGCCAAGTGTCTGGCGA
ACCCAAAGAACAAGAAGTTTATCCTTCAGGCTTTCCGTGGTATCGGGAAGTCATTCATCACGTGTGCGTTCGTAGT
GTGGACCCTGTGGCGTGACCCTCAGTTAAAGATACTGATTGTCTCGGCCTCAAAGGAACGTGCGGACGCTAACTC
CATCTTCATCAAGAACATCATCGACTTGTTGCCTTTCCTGAGTGAGCTTAAGCCCCGCCCCGGTCAGCGTGACTCCG
TGATTAGCTTTGATGTAGGCCCTGCCAAGCCAGACCACAGCCCGTCAGTTAAGTCTGTGGGTATTACTGGTCAGCT
TACTGGTAGCCGTGCTGATATCATCATTGCGGATGACGTGGAGATTCCCGGTAACTCTGCAACCCAAGGCGCTCGT
GAGAAACTCTGGACGCTGGTTCAGGAGTTCGCCGCACTGTTGAAACCTCTGCCGACTAGCCGTGTTATCTATCTGG
GTACACCTCAGACCGAGATGACGCTCTACAAGGAACTTGAGGACAACCGTGGGTACTCCACCATTATCTGGCCTGC
ACAGTATCCTCGCTCCAAAGAGGAGGACCTGTACTATGGCGACCGACTGGCCCCGATGCTCCGTAGTGAGTACGA
TGAGGACAAAGAGGGCCTCAGCAGTCAGCCTACTGACCCGGTTCGATTCGACTCCATGGACCTTCAGGAACGTGA
GGTGGAATACGGCAAGGCTGGCTATACGCTTCAGTTCATGCTCAACCCGAACCTCAGTGACGCCGAGAAGTACCC
GCTACGCCTCCGTGACGCTATCGTGTGCGGTCTACAGATGGACAAGGCCCCAATGCATTACCAGTGGTTGCCGAA
CCGTCAGAACCGCAATGAGGAGCTTCCTAACGTGGGCATGAAGGGTGACGAGATTTACTCCTTCCATACAGCCTC
AAGTAACACTGGCGCGTATCAGGGTAAGATTCTGGTCATTGACCCCAGCGGTCGCGGTAAGGATGAGACTGGCTG
GTGCGTACTGTACACCCTCAACGGTTACATCTACTTGATGGACGCTGGCGGTACTCGTGGGTACGAAGAGAAGTC
CCTTGAGTTCCTCGCTAAGAAAGCCAAACAGTGGCAGGTTCAGACTGTGGTCTTCGAGAGCAACTTCGGTGACGG
TATGTTCGGTAACGTGTTCCAGCCTGTGCTCCTGAAGCATCACCCAGCGCAACTCAAGAGATTCGTGCTCGTGGT
ATGAAAGAGGTCCGTATCTGCGATACCCTTGAGCCTGTACTGGCAAGTCACCGCTTGGTCATCCGTGATGAGGTTA
TCCGACAGGACTACCAGACGGCACGTGATGCAGACGGTAAGCACGCTCTGAAGTACAGTCTGTTCTACCAGATGA
CCCGTATGAGCCGTGAGAAGGGCGCGGTGGCACACGATGACCGACTTGATGCGTTAGCATTGGGTGTCGAGTTCC
TACGCTCTACGATGCAGCAGGACGCTGTGAAGATAGAGGCTGAGGTACTTCAGGAGTTCTTGGAGCACCACATGG
AGAAGCCCCTGAGTAACATCTCCCAGTTCCGGGCCACCAGTAGCAACGGTGTGGACATCCGATGGGAAGACGATG
GGGATGACACTATGTTCATCGCATGGTGATTATGCAGGGATTGTGCATAAGGATTCATTAGGCCACGGAAGGCCA
CTTTGAGGAAACTCCATGTATAACAGACACTTGGAATTAGGACCCACTATAGGGAGAGACCCTTGAAGACTTACTA
TAAGACAACTTAAAGATTCATTCATATAGTTATTCACTTTAAGTCTCCTTAAAGGCAGAGGGTAGTGATGATAATAT
CACCCTCTCACTATAAGACACTAAGAGCCAACATAAGGAGGACCTATGCGCTTATTGTTAACCTTACTGCCCATA
GGGCTACTTGGCGATTTCTGCTGGTACTTGCTGGTGCCCTTGGGGCTTCACTGGTTACTCAGCAGCAACTCAGTGG
ACTGGAGACTCTCGTGTGCTCTCTACTCACTTGTAGCGATTAGGGTCTTCCTGACGCGCTAGGGATTCCGTAGTGA
TGCTTATCAGCATACACCACTCCATCCCTCTACAGTCAATACTTAAAGTTAACCTTAGGTGATTCACTGGGTCTACCT
ACGGGTCTATGCAATGACCTGAGGAGTACCTGAGGTTACCTTTAAGAATTTTACATAAAGTTCTGAGTGTACATCT
CACAGTTTACACTTTTGGTTATCCCCCGGTACCCTCCAGTTCACCCAAAGTAACCTAGGGTACCCTCTTTACCTTT
GGTTTAACCTTGGGTGGTACCTTGGGAATCCCTTAGGTGATACCATATGTTGGGGTAATGGTGACCTGAGGACACT
ATATGTTGATGTCTCTGTGTCCCTTTAATTAA
```

Figure 14(a)

>DLPECO3_T7 semi-synthesis (SEQ ID NO: 2)

TCTCACAGTGTACGGACCTAAAGTTCCCCCATAGGGGGTACCTAAAGCCCAGCCAATCACCTAAAGTC
AACCTTCGGTTGACCTTGAGGGTTCCCTAAGGGTTGGGGATGACCCTTGGGTTTGTCTTTGGGTGTTAC
CTTGAGTGTCTCTCTGTGTCCCTATCTGTTACAGTCTCCTAAAGTATCCTCCTAAAGTCACCTCCTAACG
TCCATCCTAAAGCCAACACCTAAAGCCTACACCTAAAGACCCATCAAGTCAACGCCTATCTTAAAGTT
TAAACATAAAGACCAGACCTAAAGACCAGACCTAAAGACACTACATAAAGACCAGACCTAAAGACGC
CTTGTTGTTAGCCATAAAGTGATAACCTTTAATCATTGTCTTTATTAATACAACTCACTATAAGGAGAG
ACAACTTAAAGAGACTTAAAAGATTAATTTAAAATTTATCAAAAGAGTATTGACTTAAAGTCTAACC
TATAGGATACTTACAGCCATCGAGAGGGACACGGCGAATAGCCATCCCAATCGACACCGGGGTCAAC
CGGATAAGTAGACAGCCTGATAAGTCGCACGAAAAACAGGTATTGACAACATGAAGTAACATGCAGT
AAGATACAAATCGCTAGGTAACACTAGCAGCGTCAACCGGGCGCACAGTGCCTTCTAGGTGACTTAAG
CGCACCACGGCACATAAGGTGAAACAAAACGGTTGACAACATGAAGTAAACACGGTACGATGTACCA
CATGAAACGACAGTGAGTCACCACACTGAAAGGTGATGCGGTCTAACGAAACCTGACCTAAGACGCT
CTTTAACAATCTGGTAAATAGCTCTTGAGTGCATGACTAGCGGATAACTCAAGGGTATCGCAAGGTGC
CCTTTATGATATTCACTAATAACTGCACGAGGTAACACAAGATGGCTATGTCTAACATGACTTACAAC
AACGTTTTCGACCACGCTTACGAAATGCTGAAAGAAAACATCCGTTATGATGACATCCGTGACACTGA
TGACCTGCACGATGCTATTCACATGGCTGCCGATAATGCAGTTCCGCACTACTACGCTGACATCTTTAG
CGTAATGGCAAGTGAGGGCATTGACCTTGAGTTCGAAGACTCTGGTCTGATGCCTGACACCAAGGACG
TAATCCGCATCCTGCAAGCGCGTATCTATGAGCAATTAACGATTGACCTCTGGGAAGACGCAGAAGAC
TTGCTCAATGAATACTTGGAGGAAGTCGAGGAGTACGAGGAGGATGAAGAGTAATGTCTACTACCAA
CGTGCAATACGGTCTGACCGCTCAAACTGTACTTTTCTATAGCGACATGGTGCGCTGTGGCTTTAACTG
GTCACTCGCAATGGCACAGCTCAAAGAACTGTACGAAAACAACAAGGCAATAGCTTTAGAATCTGCTG
AGTGATAGACTCAAGGTCGCTCCTAGCGAGTGGCCTTTATGATTATCACTTTACTTATGAGGGAGTAAT
GTATATGCTTACTATCGGTCTACTCACCGCTCTAGGTCTAGCTGTAGGTGCATCCTTTGGGAAGGCTTT
AGGTGTAGCTGTAGGTTCCTACTTTACCGCTTGCATCATCATAGGAATCATCAAAGGGGCACTACGCA
AATGATGAAGCACTACGTTATGCCAATCCACACGTCCAACGGGGCAACCGTATGTACACCTGATGGGT
TCGCAATGAAACAACGAATCGAACGCCTTAAGCGTGAACTCCGCATTAACCGCAAGATTAACAAGAT
AGGTTCCGGCTATGACAGAACGCACTGATGGCTTAAAGAAAGGTTATATGCCCAATGGCACACTATAC
GCTGCAAATCGGCGAATAGTGAGAACTTGGCGAGAGAACAACCTCGAACGCCGCAAGGACAAGAGAG
GGCGGCGTGGCATAGACGAAAGGAAAAGGTTAAAGCCAAGAAACTCGCCGCACTTGAACAGGCACTA
GCCAACACACTGAACGCTATCTCATAACGAACATAAAGGACACAATGCAATGAACATTACCGACATC
ATGAACGCTATCGACGCAATCAAAGCACTGCCAATCTGTGAACTTGACAAGCGTCAAGGTATGCTTAT
CGACTTACTGGTCGAGATGGTCAACAGCGAGACGTGTGATGGCGAGCTAACCGAACTAAATCAGGCA
CTTGAGCATCAAGATTGGTGGACTACCTTGAAGTGTCTCACGGCTGACGCAGGGTTCAAGATGCTCGG
TAATGGTCACTTCTCGGCTGCTTATAGTCACCCGCTGCTACCTAACAGAGTGATTAAGGTGGGCTTTAA
GAAAGAGGATTCAGGCGCAGCCTATACCGCATTCTGCCGCATGTATCAGGGTCGTCCTGGTATCCCTA
ACGTCTACGATGTACAGCGCCACGCTGGATGCTATACGGTGGTACTTGACGCACTTAAGGATTGCGAG
CGTTTCAACAATGATGCCCATTATAAATACGCTGAGATTGCAAGCGACATCATTGATTGCAATTCGGA
TGAGCATGATGAGTTAACTGGATGGGATGGTGAGTTTGTTGAAACTTGTAAACTAATCCGCAAGTTCT
TTGAGGGCATCGCCTCATTCGACATGCATAGCGGGAACATCATGTTCTCAAATGGAGACGTACCATAC
ATCACCGACCCGGTATCATTCTCGCAGAAGAAAGACGGTGGCGCATTCAGCATCGACCCTGAGGAACT
CATCAAGGAAGTCGAGGAAGTCGCACGACAGAAAGAAATTGACCGCGCTAAGGCCCGTAAAGAACGT
CACGAGGGGCGCTTAGAGGCACGCAGATTCAAACGTCGCAACCGCAAGGCACGTAAAGCACACAAAG
CTAAGCGCGAAGAATGCTTGCTGCGTGGCGATGGGCTGAACGTCAAGAACGGCGTAACCATGAGGT
AGCTGTAGATGTACTAGGAAGAACCAATAACGCTATGCTCTGGGTCAACATGTTCTCTGGGGACTTTA
AGGCGCTTGAGGAACGAATCGCGCTGCACTGGCGTAATGCTGACCGGATGGCTATCGCTAATGGTCTT
ACGCTCAACATTGATAAGCAACTTGACGCAATGTTAATGGGCTGATAGTCTTATCTTACAGGTCATCTG

Figure 14(b)

```
CGGGTGGCCTGAATAGGTACGATTTACTAACTGGAAGAGGCACTAAATGAACACGATTAACATCGCTA
AGAACGACTTCTCTGACATCGAACTGGCTGCTATCCCGTTCAACACTCTGGCTGACCATTACGGTGAGC
GTTTAGCTCGCGAACAGTTGGCCCTTGAGCATGAGTCTTACGAGATGGGTGAAGCACGCTTCCGCAAG
ATGTTTGAGCGTCAACTTAAAGCTGGTGAGGTTGCGGATAACGCTGCCGCCAAGCCTCTCATCACTAC
CCTACTCCCTAAGATGATTGCACGCATCAACGACTGGTTTGAGGAAGTGAAAGCTAAGCGCGGCAAGC
GCCCGACAGCCTTCCAGTTCCTGCAAGAAATCAAGCCGGAAGCCGTAGCGTACATCACCATTAAGACC
ACTCTGGCTTGCCTAACCAGTGCTGACAATACAACCGTTCAGGCTGTAGCAAGCGCAATCGGTCGGGC
CATTGAGGACGAGGCTCGCTTCGGTCGTATCCGTGACCTTGAAGCTAAGCACTTCAAGAAAAACGTTG
AGGAACAACTCAACAAGCGCGTAGGGCACGTCTACAAGAAAGCATTTATGCAAGTTGTCGAGGCTGA
CATGCTCTCTAAGGGTCTACTCGGTGGCGAGGCGTGGTCTTCGTGGCATAAGGAAGACTCTATTCATGT
AGGAGTACGCTGCATCGAGATGCTCATTGAGTCAACCGGAATGGTTAGCTTACACCGCCAAAATGCTG
GCGTAGTAGGTCAAGACTCTGAGACTATCGAACTCGCACCTGAATACGCTGAGGCTATCGCAACCCGT
GCAGGTGCGCTGGCTGGCATCTCTCCGATGTTCCAACCTTGCGTAGTTCCTCCTAAGCCGTGGACTGGC
ATTACTGGTGGTGGCTATTGGGCTAACGGTCGTCGTCCTCTGGCGCTGGTGCGTACTCACAGTAAGAA
AGCACTGATGCGCTACGAAGACGTTTACATGCCTGAGGTGTACAAAGCGATTAACATTGCGCAAAACA
CCGCATGGAAAATCAACAAGAAAGTCCTAGCGGTCGCCAACGTAATCACCAAGTGGAAGCATTGTCC
GGTCGAGGACATCCCTGCGATTGAGCGTGAAGAACTCCCGATGAAACCGGAAGACATCGACATGAAT
CCTGAGGCTCTCACCGCGTGGAAACGTGCTGCCGCTGCTGTGTACCGCAAGGACAAGGCTCGCAAGTC
TCGCCGTATCAGCCTTGAGTTCATGCTTGAGCAAGCCAATAAGTTTGCTAACCATAAGGCCATCTGGTT
CCCTTACAACATGGACTGGCGCGGTCGTGTTTACGCTGTGTCAATGTTCAACCCGCAAGGTAACGATA
TGACCAAAGGACTGCTTACGCTGGCGAAAGGTAAACCAATCGGTAAGGAAGGTTACTACTGGCTGAA
AATCCACGGTGCAAACTGTGCGGGTGTCGATAAGGTTCCGTTCCCTGAGCGCATCAAGTTCATTGAGG
AAAACCACGAGAACATCATGGCTTGCGCTAAGTCTCCACTGGAGAACACTTGGTGGGCTGAGCAAGAT
TCTCCGTTCTGCTTCCTTGCGTTCTGCTTTGAGTACGCTGGGGTACAGCACCACGGCCTGAGCTATAAC
TGCTCCCTTCCGCTGGCGTTTGACGGGTCTTGCTCTGGCATCCAGCACTTCTCCGCGATGCTCCGAGAT
GAGGTAGGTGGTCGCGCGGTTAACTTGCTTCCTAGTGAAACCGTTCAGGACATCTACGGGATTGTTGC
TAAGAAAGTCAACGAGATTCTACAAGCAGACGCAATCAATGGGACCGATAACGAAGTAGTTACCGTG
ACCGATGAGAACACTGGTGAAATCTCTGAGAAAGTCAAGCTGGGCACTAAGGCACTGGCTGGTCAAT
GGCTGGCTTACGGTGTTACTCGCAGTGTGACTAAGCGTTCAGTCATGACGCTGGCTTACGGGTCCAAA
GAGTTCGGCTTCCGTCAACAAGTGCTGGAAGATACCATTCAGCCAGCTATTGATTCCGGCAAGGGTCT
GATGTTCACTCAGCCGAATCAGGCTGCTGGATACATGGCTAAGCTGATTTGGGAATCTGTGAGCGTGA
CGGTGGTAGCTGCGGTTGAAGCAATGAACTGGCTTAAGTCTGCTGCTAAGCTGCTGGCTGCTGAGGTC
AAAGATAAGAAGACTGGAGAGATTCTTCGCAAGCGTTGCGCTGTGCATTGGGTAACTCCTGATGGTTT
CCCTGTGTGGCAGGAATACAAGAAGCCTATTCAGACGCGCTTGAACCTGATGTTCCTCGGTCAGTTCC
GCTTACAGCCTACCATTAACACCAACAAAGATAGCGAGATTGATGCACACAAACAGGAGTCTGGTATC
GCTCCTAACTTTGTACACAGCCAAGACGGTAGCCACCTTCGTAAGACTGTAGTGTGGGCACACGAGAA
GTACGGAATCGAATCTTTTGCACTGATTCACGACTCCTTCGGTACCATTCCGGCTGACGCTGCGAACCT
GTTCAAAGCAGTGCGCGAAACTATGGTTGACACATATGAGTCTTGTGATGTACTGGCTGATTTCTACG
ACCAGTTCGCTGACCAGTTGCACGAGTCTCAATTGGACAAAATGCCAGCACTTCCGGCTAAAGGTAAC
TTGAACCTCCGTGACATCTTAGAGTCGGACTTCGCGTTCGCGTAACGCCAAATCAATACGACTCACTAT
AGAGGGACAAACTCAAGGTCATTCGCAAGAGTGGCCTTTATGATTGACCTTCTTCCGGTTAATACGAC
TCACTATAGGAGAACCTTAAGGTTTAACTTTAAGACCCTTAAGTGTTAATTAGAGATTTAAATTAAAG
AATTACTAAGAGAGGACTTTAAGTATGCGTAACTTCGAAAAGATGACCAAACGTTCTAACCGTAATGC
TCGTGACTTCGAGGCAACCAAAGGTCGCAAGTTGAATAAGACTAAGCGTGACCGCTCTCACAAGCGTA
GCTGGGAGGGTCAGTAAGATGGGACGTTTATATAGTGGTAATCTGGCAGCATTCAAGGCAGCAACAA
ACAAGCTGTTCCAGTTAGACTTAGCGGTCATTTATGATGACTGGTATGATGCCTATACAAGAAAAGAT
TGCATACGGTTACGTATTGAGGACAGGAGTGGAAACCTGATTGATACTAGCACCTTCTACCACCACGA
CGAGGACGTTCTGTTCAATATGTGTACTGATTGGTTGAACCATATGTATGACCAGTTGAAGGACTGGA
AGTAATACGACTCAGTATAGGGACAATGCTTAAGGTCGCTCTCTAGGAGTGGCCTTAGTCATTTAACC
AATAGGAGATAAACATTATGATGAACATTAAGACTAACCCGTTTAAAGCCGTGTCTTTCGTAGAGTCT
```

Figure 14(c)

```
GCCATTAAGAAGGCTCTGGATAACGCTGGGTATCTTATCGCTGAAATCAAGTACGATGGTGTACGCGG
GAACATCTGCGTAGACAATACTGCTAACAGTTACTGGCTCTCTCGTGTATCTAAAACGATTCCGGCACT
GGAGCACTTAAACGGGTTTGATGTTCGCTGGAAGCGTCTACTGAACGATGACCGTTGCTTCTACAAAG
ATGGCTTTATGCTTGATGGGGAACTCATGGTCAAGGGCGTAGACTTTAACACAGGGTCCGGCCTACTG
CGTACCAAATGGACTGACACGAAGAACCAAGAGTTCCATGAAGAGTTATTCGTTGAACCAATCCGTAA
GAAAGATAAAGTTCCCTTTAAGCTGCACACTGGACACCTTCACATAAAACTGTACGCTATCCTCCCGCT
GCACATCGTGGAGTCTGGAGAAGACTGTGATGTCATGACGTTGCTCATGCAGGAACACGTTAAGAACA
TGCTGCCTCTGCTACAGGAATACTTCCCTGAAATCGAATGGCAAGCGGCTGAATCTTACGAGGTCTAC
GATATGGTAGAACTACAGCAACTGTACGAGCAGAAGCGAGCAGAAGGCCATGAGGGTCTCATTGTGA
AGACCCGATGTGTATCTATAAGCGCGGTAAGAAATCGGCTGGTGGAAAATGAAACCTGAGAACGA
AGCTGACGGTATCATTCAGGGTCTGGTATGGGGTACAAAAGGTCTGGCTAATGAAGGTAAAGTGATTG
GTTTTGAGGTGCTTCTTGAGAGTGGTCGTTTAGTTAACGCCACGAATATCTCTCGCGCCTTAATGGATG
AGTTCACTGAGACAGTAAAAGAGGCCACCCTAAGTCAATGGGGATTCTTTAGCCCATACGGTATTGGC
GACAACGATGCTTGTACTATTAACCCTTACGATGGCTGGGCGTGTCAAATTAGCTACATGGAGGAAAC
ACCTGATGGCTCTTTGCGGCACCCATCGTTCGTAATGTTCCGTGGCACCGAGGACAACCCTCAAGAGA
AAATGTAATCACACTGGCTCACCTTCGGGTGGGCCTTTCTGCGTTTATAAGGAGACACTTTATGTTTAA
GAAGGTTGGTAAATTCCTTGCGGCTTTGGCAGCTATCCTGACGCTTGCGTATATTCTTGCGGTATACCC
TCAAGTAGCACTAGTAGTAGTTGGCGCTTGTTACTTAGCGGCAGTGTGTGCTTGCGTGTGGAGTATAGT
TAACTGGTAATACGACTCACTAAAGGAGGTACACACCATGATGTACTTAATGCCATTACTCATCGTCA
TTGTAGGATGCCTTGCGCTCCACTGTAGCGATGATGATATGCCAGATGGTCACGCTTAATACGACTCAC
TAAAGGAGACACTATATGTTTCGACTTCATTACAACAAAAGCGTTAAGAATTTCACGGTTCGCCGTGC
TGACCGTTCAATCGTATGTGCGAGCGAGCGCCGAGCTAAGATACCTCTTATTGGTAACACAGTTCCTTT
GGCACCGAGCGTCCACATCATTATCACCCGTGGTGACTTTGAGAAAGCAATAGACAAGAAACGTCCGG
TTCTTAGTGTGGCAGTGACCCGCTTCCCGTTCGTCCGTCTGTTACTCAAACGAATCAAGGAGGTGTTCT
GATGGGACTGTTAGATGGTGAAGCCTGGGAAAAAGAAAACCCGCCAGTACAAGCAACTGGGTGTATA
GCTTGCTTAGAGAAAGATGACCGTTATCCACACACCTGTAACAAAGGAGCTAACGATATGACCGAACG
TGAACAAGAGATGATCATTAAGTTGATAGACAATAATGAAGGTCGCCCAGATGATTTGAATGGCTGCG
GTATTCTCTGCTCCAATGTCCCTTGCCACCTCTGCCCCGCAAATAACGATCAAAAGATAACCTTAGGTG
AAATCCGAGCGATGGACCCACGTAAACCACATCTGAATAAACCTGAGGTAACTCCTACAGATGACCA
GCCTTCCGCTGAGACAATCGAAGGTGTCACTAAGCCTTCCCACTACATGCTGTTTGACGACATTGAGG
CTATCGAAGTGATTGCTCGTTCAATGACCGTTGAGCAGTTCAAGGGATACTGCTTCGGTAACATCTTAA
AGTACAGACTACGTGCTGGTAAGAAGTCAGAGTTAGCGTACTTAGAGAAAGACCTAGCGAAAGCAGA
CTTCTATAAAGAACTCTTTGAGAAACATAAGGATAAATGTTATGCATAACTTCAAGTCAACCCCACCT
GCCGACAGCCTATCTGATGACTTCACATCTTGCTCAGAGTGGTGCCGAAAGATGTGGGAAGAGACATT
CGACGATGCGTACATCAAGCTGTATGAACTTTGGAAATCGAGAGGTCAATGACTATGTCAAACGTAAA
TACAGGTTCACTTAGTGTGGACAATAAGAAGTTTTGGGCTACCGTAGAGTCCTCGGAGCATTCCTTCG
AGGTTCCAATCTACGCTGAGACCCTAGACGAAGCTCTGGAGTTAGCCGAATGGCAATACGTTCCGGCT
GGCTTTGAGGTTACTCGTGTGCGTCCTTGTGTAGCACCGAAGTAATACGACTCACTATTAGGGAAGAC
TCCCTCTGAGAAACCAAACGAAACCTAAAGGAGATTAACATTATGGCTAAGAAGATTTTCACCTCTGC
GCTGGGTACCGCTGAACCTTACGCTTACATCGCCAAGCCGGACTACGGCAACGAAGAGCGTGGCTTTG
GGAACCCTCGTGGTGTCTATAAAGTTGACCTGACTATTCCCAACAAAGACCCGCGCTGCCAGCGTATG
GTCGATGAAATCGTGAAGTGTCACGAAGAGGCTTATGCTGCTGCCGTTGAGGAATACGAAGCTAATCC
ACCTGCTGTAGCTCGTGGTAAGAAACCGCTGAAACCGTATGAGGGTGACATGCCGTTCTTCGATAACG
GTGACGGTACGACTACCTTTAAGTTCAAATGCTACGCGTCTTTCCAAGACAAGAAGACCAAAGAGACC
AAGCACATCAATCTGGTTGTGGTTGACTCAAAAGGTAAGAAGATGGAAGACGTTCCGATTATCGGTGG
TGGCTCTAAGCTGAAAGTTAAATATTCTCTGGTTCCATACAAGTGGAACACTGCTGTAGGTGCGAGCG
TTAAGCTGCAACTGGAATCCGTGATGCTGGTCGAACTGGCTACCTTTGGTGGCGGTGAAGACGATTGG
GCTGACGAAGTTGAAGAGAACGGCTATGTTGCCTCTGGTTCTGCCAAAGCGAGCAAACCACGCGACG
AAGAAAGCTGGGACGAAGACGACGAAGAGTCCGAGGAAGCAGACGAAGACGGAGACTTCTAAGTGG
AACTGCGGGAGAAAATCCTTGAGCGAATCAAGGTGACTTCCTCTGGGTGTTGGGAGTGGCAGGGCGCT
```

Figure 14(d)

```
ACGAACAATAAAGGGTACGGGCAGGTGTGGTGCAGCAATACCGGAAAGGTTGTCTACTGTCATCGCG
TAATGTCTAATGCTCCGAAAGGTTCTACCGTCCTGCACTCCTGTGATAATCCATTATGTTGTAACCCTG
AACACCTATCCATAGGAACTCCAAAAGAGAACTCCACTGACATGGTAAATAAGGGTCGCTCACACAA
GGGGTATAAACTTTCAGACGAAGACGTAATGGCAATCATGGAGTCCAGCGAGTCCAATGTATCCTTAG
CTCGCACCTATGGTGTCTCCCAACAGACTATTTGTGATATACGCAAAGGGAGGCGACATGGCAGGTTA
CGGCGCTAAAGGAATCCGAAAGGTTGGAGCGTTTCGCTCTGGCCTAGAGGACAAGGTTTCAAAGCAGT
TGGAATCAAAAGGTATTAAATTCGAGTATGAAGAGTGGAAAGTGCCTTATGTAATTCCGGCGAGCAAT
CACACTTACACTCCAGACTTCTTACTTCCAAACGGTATATTCGTTGAGACAAAGGGTCTGTGGGAAAG
CGATGATAGAAAGAAGCACTTATTAATTAGGGAGCAGCACCCCGAGCTAGACATCCGTATTGTCTTCT
CAAGCTCACGTACTAAGTTATACAAAGGTTCTCCAACGTCTTATGGAGAGTTCTGCGAAAAGCATGGT
ATTAAGTTCGCTGATAAACTGATACCTGCTGAGTGGATAAAGGAACCCAAGAAGGAGGTCCCCTTTGA
TAGATTAAAAAGGAAAGGAGGAAAGAAATAATGGCTCGTGTACAGTTTAAACAACGTGAATCTACTG
ACGCAATCTTTGTTCACTGCTCGGCTACCAAGCCAAGTCAGAATGTTGGTGTCCGTGAGATTCGCCAGT
GGCACAAAGAGCAGGGTTGGCTCGATGTGGGATACCACTTTATCATCAAGCGAGACGGTACTGTGGA
GGCAGGACGAGATGAGATGGCTGTAGGCTCTCACGCTAAGGGTTACAACCACAACTCTATCGGCGTCT
GCCTTGTTGGTGGTATCGACGATAAAGGTAAGTTCGACGCTAACTTTACGCCAGCCCAAATGCAATCC
CTTCGCTCACTGCTTGTCACACTGCTGGCTAAGTACGAAGGCGCTGTGCTTCGCGCCCATCATGAGGTG
GCGCCGAAGGCTTGCCCTTCGTTCGACCTTAAGCGTTGGTGGGAGAAGAACGAACTGGTCACTTCTGA
CCGTGGATAATTAATTGAACTCACTAAAGGGAGACCACAGCGGTTTCCCTTTGTTCGCATTGGAGGTC
AAATAATGCGCAAGTCTTATAAACAATTCTATAAGGCTCCGAGGAGGCATATCCAAGTGTGGGAGGCA
GCCAATGGGCCTATACCAAAAGGTTATTATATAGACCACATTGACGGCAATCCACTCAACGACGCCTT
AGACAATCTCCGTCTGGCTCTCCCAAAAGAAAACTCATGGAACATGAAGACTCCAAAGAGCAATACCT
CAGGACTAAAGGGACTGAGTTGGAGCAAGGAAAGGGAGATGTGGAGAGGCACTGTAACAGCTGAGG
GTAAACAGCATAACTTTCGTAGTAGAGATCTATTGGAAGTCGTTGCGTGGATTTATAGAACTAGGAGG
GAATTGCATGGACAATTCGCACGATTCCGATAGTGTATTTCTTTACCACATTCCTTGTGACAACTGTGG
GAGTAGTGATGGGAACTCGCTGTTCTCTGACGGACACACGTTCTGCTACGTATGCGAGAAGTGGACTG
CTGGTAATGAAGACACTAAAGAGAGGGCTTCAAAACGGAAACCCTCAGGAGGTAAACCAATGACTTA
CAACGTGTGGAACTTCGGGGAATCCAATGGACGCTACTCCGCGTTAACTGCGAGAGGAATCTCCAAGG
AAACCTGTCAGAAGGCTGGCTACTGGATTGCCAAAGTAGACGGTGTGATGTACCAAGTGGCTGACTAT
CGGGACCAGAACGGCAACATTGTGAGTCAGAAGGTTCGAGATAAAGATAAGAACTTTAAGACCACTG
GTAGTCACAAGAGTGACGCTCTGTTCGGGAAGCACTTGTGGAATGGTGGTAAGAAGATTGTCGTTACA
GAAGGTGAAATCGACATGCTTACCGTGATGGAACTTCAAGACTGTAAGTATCCTGTAGTGTCGTTGGG
TCACGGTGCCTCTGCCGCTAAGAAGACATGCGCTGCCAACTACGAATACTTTGACCAGTTCGAACAGA
TTATCTTAATGTTCGATATGGACGAAGCAGGGCGCAAAGCAGTCGAAGAGGCTGCACAGGTTCTACCT
GCTGGTAAGGTACGAGTGGCAGTTCTTCCGTGTAAGGATGCAAACGAGTGTCACCTAAATGGTCACGA
CCGTGAAATCATGGAGCAAGTGTGGAATGCTGGTCCTTGGATTCCTGATGGTGTGGTATCGGCTCTTTC
GTTACGTGAACGAATCCGTGAGCACCTATCGTCCGAGGAATCAGTAGGTTTACTTTCAGTGGCTGCA
CTGGTATCAACGATAAGACCTTAGGTGCCCGTGGTGGTGAAGTCATTATGGTCACTTCCGGTTCCGGTA
TGGGTAAGTCAACGTTCGTCCGTCAACAAGCTCTACAATGGGGCACAGCGATGGGCAAGAAGGTAGG
CTTAGCGATGCTTGAGGAGTCCGTTGAGGAGACCGCTGAGGACCTTATAGGTCTACACAACCGTGTCC
GACTGAGACAATCCGACTCACTAAAGAGAGATTATTGAGAACGGTAAGTTCGACCAATGGTTCGAT
GAACTGTTCGGCAACGATACGTTCCATCTATATGACTCATTCGCCGAGGCTGAGACGGATAGACTGCT
CGCTAAGCTGGCCTACATGCGCTCAGGCTTGGGCTGTGACGTAATCATTCTAGACCACATCTCAATCGT
CGTATCCGCTTCTGGTGAATCCGATGAGCGTAAGATGATTGACAACCTGATGACCAAGCTCAAAGGGT
TCGCTAAGTCAACTGGGGTGGTGCTGGTCGTAATTTGTCACCTTAAGAACCCAGACAAAGGTAAAGCA
CATGAGGAAGGTCGCCCCGTTTCTATTACTGACCTACGTGGTTCTGGCGCACTACGCCAACTATCTGAT
ACTATTATTGCCCTTGAGCGTAATCAGCAAGGCGATATGCCTAACCTTGTCCTCGTTCGTATTCTCAAG
TGCCGCTTTACTGGTGATACTGGTATCGCTGGCTACATGGAATACAACAAGGAAACCGGATGGCTTGA
ACCATCAAGTTACTCAGGGGAAGAAGAGTCACACTCAGAGTCAACAGACTGGTCCAACGACACTGAC
TTCTGACAGGATTCTTGATGACTTTCCAGACGACTACGAGAAGTTTCGCTGGAGAGTCCCATTCTAATA
```

Figure 14(e)

CGACTCACTAAAGGAGACACACCATGTTCAAACTGATTAAGAAGTTAGGCCAACTGCTGGTTCGTATG
TACAACGTGGAAGCCAAGCGACTGAACAGAGGAGATATACAATGGTCTTCACACTCGAAGATTTCGTT
GGGGACTGGCGACAGACAGCCGGCTACAACCTGGACCAAGTCCTTGAACAGGGAGGTGTGTCCAGTT
TGTTTCAGAATCTCGGGGTGTCCGTAACTCCGATCCAAAGGATTGTCCTGAGCGGTGAAAATGGGCTG
AAGATCGACATCCATGTCATCATCCCGTATGAAGGTCTGAGCGGCGACCAAATGGGCCAGATCGAAA
AAATTTTTAAGGTGGTGTACCCTGTGGATGATCATCACTTTAAGGTGATCCTGCACTATGGCACACTGG
TAATCGACGGGGTTACGCCGAACATGATCGACTATTTCGGACGGCCGTATGAAGGCATCGCCGTGTTC
GACGGCAAAAGATCACTGTAACAGGGACCCTGTGGAACGGCAACAAAATTATCGACGAGCGCCTGA
TCAACCCCGACGGCTCCCTGCTGTTCCGAGTAACCATCAACGGAGTGACCGGCTGGCGGCTGTGCGAA
CGCATTCTGGCGTAAGATGAGGCTCGTAAAGAGGCCACACAGTCACGCGCTCTGGCGATTCGCTCCAA
CGAACTGGCTGACAGTGCATCCACTAAAGTTACCGAGGCTGCCCGTGTGGCAAACCAAGCTCAACAGC
TTTCCAAATTCTTTGAGTAATCAAACAGGAGAAACCATTATGTCTAACGTAGCTGAAACTATCCGTCTA
TCCGATACAGCTGACCAGTGGAACCGTCGAGTCCACATCAACGTTCGCAACGGTAAGGCGACTATGGT
TTACCGCTGGAAGGACTCTAAGTCCTCTAAGAATCACACTCAGCGTATGACGTTGACAGATGAGCAAG
CACTGCGTCTGGTCAATGCGCTTACCAAAGCTGCCGTGACAGCAATTCATGAAGCTGGTCGCGTCAAT
GAAGCTATGGCTATCCTCGACAAGATTGATAACTAAGAGTGGTATCCTCAAGGTCGCCAAAGTGGTGG
CCTTCATGAATACTATTCGACTCACTATAGGAGATATTACCATGCGTGACCCTAAAGTTATCCAAGCAG
AAATCGCTAAACTGGAAGCTGAACTGGAGGACGTTAAGTACCATGAAGCTAAGACTCGCTCCGCTGTT
CACATCTTGAAGAACTTAGGCTGGACTTGGACAAGACAGACTGGCTGGAAGAAACCAGAAGTTACCA
AGCTGAGTCATAAGGTGTTCGATAAGGACACTATGACCCACATCAAGGCTGGTGATTGGGTTAAGGTT
GACATGGGAGTTGTTGGTGGATACGGCTACGTCCGCTCAGTTAGTGGCAAATATGCACAAGTGTCATA
CATCACAGGTGTTACTCCACGCGGTGCAATCGTTGCCGATAAGACCAACATGATTCACACAGGTTTCTT
GACAGTTGTTTCATATGAAGAGATTGTTAAGTCACGATAATCAATAGGAGAAATCAATATGATCGTTT
CTGACATCGAAGCTAACGCCCTCTTAGAGAGCGTCACTAAGTTCCACTGCGGGGTTATCTACGACTAC
TCCACCGCTGAGTACGTAAGCTACCGTCCGAGTGACTTCGGTGCGTATCTGGATGCGCTGGAAGCCGA
GGTTGCACGAGGCGGTCTTATTGTGTTCCACAACGGTCACAAGTATGACGTTCCTGCATTGACCAAACT
GGCAAAGTTGCAATTGAACCGAGAGTTCCACCTTCCTCGTGAGAACTGTATTGACACCCTTGTGTTGTC
ACGTTTGATTCATTCCAACCTCAAGGACACCGATATGGGTCTTCTGCGTTCCGGCAAGTTGCCCGGAAA
ACGCTTTGGGTCTCACGCTTTGGAGGCGTGGGGTTATCGCTTAGGCGAGATGAAGGGTGAATACAAAG
ACGACTTTAAGCGTATGCTTGAAGAGCAGGGTGAAGAATACGTTGACGGAATGGAGTGGTGGAACTT
CAACGAAGAGATGATGGACTATAACGTTCAGGACGTTGTGGTAACTAAAGCTCTCCTTGAGAAGCTAC
TCTCTGACAAACATTACTTCCCTCCTGAGATTGACTTTACGGACGTAGGATACACTACGTTCTGGTCAG
AATCCCTTGAGGCCGTTGACATTGAACATCGTGCTGCATGGCTGCTCGCTAAACAAGAGCGCAACGGG
TTCCCGTTTGACACAAAAGCAATCGAAGAGTTGTACGTAGAGTTAGCTGCTCGCCGCTCTGAGTTGCTC
CGTAAATTGACCGAAACGTTCGGCTCGTGGTATCAGCCTAAAGGTGGCACTGAGATGTTCTGCCATCC
GCGAACAGGTAAGCCACTACCTAAATACCCTCGCATTAAGACACCTAAAGTTGGTGGTATCTTTAAGA
AGCCTAAGAACAAGGCACAGCGAGAAGGCCGTGAGCCTTGCGAACTTGATACCCGCGAGTACGTTGC
TGGTGCTCCTTACACCCCAGTTGAACATGTTGTGTTTAACCCTTCGTCTCGTGACCACATTCAGAAGAA
ACTCCAAGAGGCTGGGTGGGTCCCGACCAAGTACACCGATAAGGGTGCTCCTGTGGTGGACGATGAG
GTACTCGAAGGAGTACGTGTAGATGACCCTGAGAAGCAAGCCGCTATCGACCTCATTAAAGAGTACTT
GATGATTCAGAAGCGAATCGGACAGTCTGCTGAGGGAGACAAAGCATGGCTTCGTTATGTTGCTGAGG
ATGGTAAGATTCATGGTTCTGTTAACCCTAATGGAGCAGTTACGGGTCGTGCGACCCATGCGTTCCCA
AACCTTGCGCAAATTCCGGGTGTACGTTCTCCTTATGGAGAGCAGTGTCGCGCTGCTTTTGGCGCTGAG
CACCATTTGGATGGGATAACTGGTAAGCCTTGGGTTCAGGCTGGCATCGACGCATCCGGTCTTGAGCT
ACGCTGCTTGGCTCACTTCATGGCTCGCTTTGATAACGGCGAGTACGCTCACGAGATTCTTAACGGCGA
CATCCACACTAAGAACCAGATAGCTGCTGAACTACCTACCCGAGATAACGCTAAGACGTTCATCTATG
GGTTCCTCTATGGTGCTGGTGATGAGAAGATTGGACAGATTGTTGGTGCTGGTAAAGAGCGCGGTAAG
GAACTCAAGAAGAAATTCCTTGAGAACACCCCCGCGATTGCAGCACTCCGCGAGTCTATCCAACAGAC
ACTTGTCGAGTCCTCTCAATGGGTAGCTGGTGAGCAACAAGTCAAGTGGAAACGCCGCTGGATTAAAG
GTCTGGATGGTCGTAAGGTACACGTTCGTAGTCCTCACGCTGCCTTGAATACCCTACTGCAATCTGCTG

Figure 14(f)

```
GTGCTCTCATCTGCAAACTGTGGATTATCAAGACCGAAGAGATGCTCGTAGAGAAAGGCTTGAAGCAT
GGCTGGGATGGGGACTTTGCGTACATGGCATGGGTACATGATGAAATCCAAGTAGGCTGCCGTACCGA
AGAGATTGCTCAGGTGGTCATTGAGACCGCACAAGAAGCGATGCGCTGGGTTGGAGACCACTGGAAC
TTCCGGTGTCTTCTGGATACCGAAGGTAAGATGGGTCCTAATTGGGCGATTTGCCACTGATACAGGAG
GCTACTCATGAACGAAAGACACTTAACAGGTGCTGCTTCTGAAATGCTAGTAGCCTACAAATTTACCA
AAGCTGGGTACACTGTCTATTACCCTATGCTGACTCAGAGTAAAGAGGACTTGGTTGTATGTAAGGAT
GGTAAATTTAGTAAGGTTCAGGTTAAAACAGCCACAACGGTTCAAACCAACACAGGAGATGCCAAGC
AGGTTAGGCTAGGTGGATGCGGTAGGTCCGAATATAAGGATGGAGACTTTGACATTCTTGCGGTTGTG
GTTGACGAAGATGTGCTTATTTTCACATGGGACGAAGTAAAAGGTAAGACATCCATGTGTGTCGGCAA
GAGAAACAAAGGCATAAAACTATAGGAGAAATTATTATGGCTATGACAAAGAAATTTAAAGTGTCCT
TCGACGTTACCGCAAAGATGTCGTCTGACGTTCAGGCAATCTTAGAGAAAGATATGCTGCATCTATGT
AAGCAGGTCGGCTCAGGTGCGATTGTCCCCAATGGTAAACAGAAGGAAATGATTGTCCAGTTCCTGAC
ACACGGTATGGAAGGATTGATGACATTCGTAGTACGTACATCATTTCGTGAGGCCATTAAGGACATGC
ACGAAGAGTATGCAGATAAGGACTCTTTCAAACAATCTCCTGCAACAGTACGGGAGGTGTTCTGATGT
CTGACTACCTGAAAGTGCTGCAAGCAATCAAAAGTTGCCCTAAGACTTTCCAGTCCAACTATGTACGG
AACAATGCGAGCCTCGTAGCGGAGGCCGCTTCCCGTGGTCACATCTCGTGCCTGACTACTAGTGGACG
TAACGGTGGCGCTTGGGAAATCACTGCTTCCGGTACTCGCTTTCTGAAACGAATGGGAGGATGTGTCT
AATGTCTCGTGACCTTGTGACTATTCCACGCGATGTGTGGAACGATATACAGGGCTACATCGACTCTCT
GGAACGTGAGAACGATAGCCTTAAGAATCAACTAATGGAAGCTGACGAATACGTAGCGGAACTAGAG
GAGAAACTTAATGGCACTTCTTGACCTTAAACAATTCTATGAGTTACGTGAAGGCTGCGACGACAAGG
GTATCCTTGTGATGGACGGCGACTGGCTGGTCTTCCAAGCTATGAGTGCTGCTGAGTTTGATGCCTCTT
GGGAGGAAGAGATTTGGCACCGATGCTGTGACCACGCTAAGGCCCGTCAGATTCTTGAGGATTCCATT
AAGTCCTACGAGACCCGTAAGAAGGCTTGGGCAGGTGCTCCAATTGTCCTTGCGTTCACCGATAGTGT
TAACTGGCGTAAAGAACTGGTTGACCCGAACTATAAGGCTAACCGTAAGGCCGTGAAGAAACCTGTA
GGGTACTTTGAGTTCCTTGATGCTCTCTTTGAGCGCGAAGAGTTCTATTGCATCCGTGAGCCTATGCTT
GAGGGTGATGACGTTATGGGAGTTATTGCTTCCAATCCGTCTGCCTTCGGTGCTCGTAAGGCTGTAATC
ATCTCTTGCGATAAGGACTTTAAGACCATCCCTAACTGTGACTTCCTGTGGTGTACCACTGGTAACATC
CTGACTCAGACCGAAGAGTCCGCTGACTGGTGGCACCTCTTCCAGACCATCAAGGGTGACATCACTGA
TGGTTACTCAGGGATTGCTGGATGGGGTGATACCGCCGAGGACTTCTTGAATAACCCGTTCATAACCG
AGCCTAAAACGTCTGTGCTTAAGTCCGGTAAGAACAAAGGCCAAGAGGTTACTAAATGGTTAAACG
CGACCCTGAGCCTCATGAGACGCTTTGGGACTGCATTAAGTCCATTGGCGCGAAGGCTGGTATGACCG
AAGAGGATATTATCAAGCAGGGCCAAATGGCTCGAATCCTACGGTTCAACGAGTACAACTTTATTGAC
AAGGAGATTTACCTGTGGAGACCGTAGCGTATATTGGTCTGGGTCTTTGTGTTCTCGGAGTGTGCCTCA
TTTCGTGGGGCCTTTGGGACTTAGCCAGAATAATCAAGTCGTTACACGACACTAAGTGATAAACTCAA
GGTCCCTAAATTAATACGACTCACTATAGGGAGATAGGGGCCTTTACGATTATTACTTTAAGATTTAAC
TCTAAGAGGAATCTTTATTATGTTAACACCTATTAACCAATTACTTAAGAACCCTAACGATATTCCAGA
TGTACCTCGTGCAACCGCTGAGTATCTACAGGTTCGATTCAACTATGCGTACCTCGAAGCGTCTGGTCA
TATAGGACTTATGCGTGCTAATGGTTGTAGTGAGGCCCACATCTTGGGTTTCATTCAGGGCCTACAGTA
TGCCTCTAACGTCATTGACGAGATTGAGTTACGCAAGGAACAACTAAGAGATGATGGGGAGGATTGA
CACTATGTGTTTCTCACCGAAAATTAAAACTCCGAAGATGGATACCAATCAGATTCGAGCCGTTGAGC
CAGCGCCTCTGACCCAAGAAGTGTCAAGCGTGGAGTTCGGTGGGTCTTCTGATGAGACGGATACCGAG
GGCACCGAAGTGTCTGGACGCAAAGGCCTCAAGGTCGAACGTGATGATTCCGTAGCGAAGTCTAAAG
CCAGCGGCAATGGCTCCGCTCGTATGAAATCTTCCATCCGTAAGTCCGCATTTGGAGGTAAGAAGTGA
TGTCTGAGTTCACATGTGTGGAGGCTAAGAGTCGCTTCCGTGCAATCCGGTGGACTGTGGAACACCTT
GGGTTGCCTAAAGGATTCGAAGGACACTTTGTGGGCTACAGCCTCTACGTAGACGAAGTGATGGACAT
GTCTGGTTGCCGTGAAGAGTACATTCTGGACTCTACCGGAAAACATGTAGCGTACTTCGCGTGGTGCG
TAAGCTGTGACATTCACCACAAAGGAGACATTCTGGATGTAACGTCCGTTGTCATTAATCCTGAGGCA
GACTCTAAGGGCTTACAGCGATTCCTAGCGAAACGCTTTAAGTACCTTGCGGAACTCCACGATTGCGA
TTGGGTGTCTCGTTGTAAGCATGAAGGCGAGACAATGCGTGTATACTTTAAGGAGGTATAAGTTATGG
GTAAGAAAGTTAAGAAGGCCGTGAAGAAAGTCACCAAGTCCGTTAAGAAAGTCGTTAAGGAAGGGGC
```

Figure 14(g)

```
TCGTCCGGTTAAACAGGTTGCTGGCGGTCTAGCTGGTCTGGCTGGTGGTACTGGTGAAGCACAGATGG
TGGAAGTACCACAAGCTGCCGCACAGATTGTTGACGTACCTGAGAAAGAGGTTTCCACTGAGGACGA
AGCACAGACAGAAAGCGGACGCAAGAAAGCTCGTGCTGGCGGTAAGAAATCCTTGAGTGTAGCCCGT
AGCTCCGGTGGCGGTATCAACATTTAATCAGGAGGTTATCGTGGAAGACTGCATTGAATGGACCGGAG
GTGTCAACTCTAAGGGTTATGGTCGTAAGTGGGTTAATGGTAAACTTGTGACTCCACATAGGCACATC
TATGAGGAGACATATGGTCCAGTTCCAACAGGAATTGTGGTGATGCATATCTGCGATAACCCTAGGTG
CTATAACATAAAGCACCTTACGCTTGGAACTCCAAAGGATAATTCCGAGGACATGGTTACCAAAGGTA
GACAGGCTAAAGGAGAGGAACTAAGCAAGAAACTTACAGAGTCAGACGTTCTCGCTATACGCTCTTC
AACCTTAAGCCACCGCTCCTTAGGAGAACTGTATGGAGTCAGTCAATCAACCATAACGCGAATACTAC
AGCGTAAGACATGGAGACACATTTAATGGCTGAGAAACGAACAGGACTTGCGGAGGATGGCGCAAAG
TCTGTCTATGAGCGTTTAAAGAACGACCGTGCTCCCTATGAGACACGCGCTCAGAATTGCGCTCAATA
TACCATCCCATCATTGTTCCCTAAGGACTCCGATAACGCCTCTACAGATTATCAAACTCCGTGGCAAGC
CGTGGGCGCTCGTGGTCTGAACAATCTAGCCTCTAAGCTCATGCTGGCTCTATTCCCTATGCAGACTTG
GATGCGACTTACTATATCTGAATATGAAGCAAAGCAGTTACTGAGCGACCCCGATGGACTCGCTAAGG
TCGATGAGGGCCTCTCGATGGTAGAGCGTATCATCATGAACTACATTGAGTCTAACAGTTACCGCGTG
ACTCTCTTTGAGGCTCTCAAACAGTTAGTCGTAGCTGGTAACGTCCTGCTGTACCTACCGGAACCGGAA
GGGTCAAACTATAATCCCATGAAGCTGTACCGATTGTCTTCTTATGTGGTCCAACGAGACGCATTCGGC
AACGTTCTGCAAATGGTGACTCGTGACCAGATAGCTTTTGGTGCTCTCCCTGAGGACATCCGTAAGGCT
GTAGAAGGTCAAGGTGGTGAGAAGAAAGCTGATGAGACAATCGACGTGTACACTCACATCTATCTGG
ATGAGGACTCAGGTGAATACCTCCGATACGAAGAGGTCGAGGGTATGGAAGTCCAAGGCTCCGATGG
GACTTATCCTAAAGAGGCTTGCCCATACATCCCGATTCGGATGGTCAGACTAGATGGTGAATCCTACG
GTCGTTCGTACATTGAGGAATACTTAGGTGACTTACGGTCCCTTGAAAATCTCCAAGAGGCTATCGTCA
AGATGTCCATGATTAGCTCTAAGGTTATCGGCTTAGTGAATCCTGCTGGTATCACCCAGCCACGCCGAC
TGACCAAAGCTCAGACTGGTGACTTCGTTACTGGTCGTCCAGAAGACATCTCGTTCCTCCAACTGGAG
AAGCAAGCAGACTTTACTGTAGCTAAAGCCGTAAGTGACGCTATCGAGGCTCGCCTTTCGTTTGCCTTT
ATGTTGAACTCTGCGGTTCAGCGTACAGGTGAACGTGTGACCGCCGAAGAGATTCGGTATGTAGCTTC
TGAACTTGAAGATACTTTAGGTGGTGTCTACTCTATCCTTTCTCAAGAATTACAATTGCCTCTGGTACG
AGTGCTCTTGAAGCAACTACAAGCCACGCAACAGATTCCTGAGTTACCTAAGGAAGCCGTAGAGCCAA
CCATTAGTACAGGTCTGGAAGCAATTGGTCGAGGACAAGACCTTGATAAGCTGGAGCGGTGTGTCACT
GCGTGGGCTGCACTGGCACCTATGCGGGACGACCCTGATATTAACCTTGCGATGATTAAGTTACGTAT
TGCCAACGCTATCGGTATTGACACTTCTGGTATTCTACTCACCGAAGAACAGAAGCAACAGAAGATGG
CCCAACAGTCTATGCAAATGGGTATGGATAATGGTGCTGCTGCGCTGGCTCAAGGTATGGCTGCACAA
GCTACAGCTTCACCTGAGGCTATGGCTGCTGCCGCTGATTCCGTAGGTTTACAGCCGGGAATTTAATAC
GACTCACTATAGGGAGACCTCATCTTTGAAATGAGCGATGACAAGAGGTTGGAGTCCTCGGTCTTCCT
GTAGTTCAACTTTAAGGAGACAATAATAATGGCTGAATCAATGCAGACGTATATGCATCTTTTGGCG
TGAACTCCGCTGTGATGTCTGGTGGTTCCGTTGAGGAACATGAGCAGAACATGCTGGCTCTTGATGTTG
CTGCCCGTGATGGCGATGATGCAATCGAGTTAGCGTCAGACGAAGTGGAAACAGAACGTGACCTGTAT
GACAACTCTGACCCGTTCGGTCAAGAGGATGACGAAGGCCGCATTCAGGTTCGTATCGGTGATGGCTC
TGAGCCGACCGATGTGGACACTGGAGAAGAAGGCGTTGAGGGCACCGAAGGTTCCGAAGAGTTTACC
CCACTGGGCGAGACTCCAGAAGAACTGGTAGCTGCCTCTGAGCAACTTGGTGAGCACGAAGAGGGCT
TCCAAGAGATGATTAACATTGCTGCTGAGCGTGGCATGAGTGTCGAGACCATTGAGGCTATCCAGCGT
GAGTACGAGGAGAACGAAGAGTTGTCCGCCGAGTCCTACGCTAAGCTGGCTGAAATTGGCTACACGA
AGGCTTTCATTGACTCGTATATCCGTGGTCAAGAAGCTCTGGTGGAGCAGTACGTAAACAGTGTCATT
GAGTACGCTGGTGGTCGTGAACGTTTTGATGCACTGTATAACCACCTTGAGACGCACAACCCTGAGGC
TGCACAGTCGCTGGATAATGCGTTGACCAATCGTGACTTAGCGACCGTTAAGGCTATCATCAACTTGG
CTGGTGAGTCTCGCGCTAAGGCGTTCGGTCGTAAGCCAACTCGTAGTGTGACTAATCGTGCTATTCCGG
CTAAACCTCAGGCTACCAAGCGTGAAGGCTTTGCGGACCGTAGCGAGATGATTAAAGCTATGAGTGAC
CCTCGGTATCGCACAGATGCCAACTATCGTCGTCAAGTCGAACAGAAAGTAATCGATTCGAACTTCTG
ATAGACTTCGAAATTAATACGACTCACTATAGGGAGACCACAACGGTTTCCCTCTAGAAATAATTTTG
TTTAACTTTAAGAAGGAGATATACATATGGCTAGCATGACTGGTGGACAGCAAATGGGTACTAACCAA
```

Figure 14(h)

```
GGTAAAGGTGTAGTTGCTGCTGGAGATAAACTGGCGTTGTTCTTGAAGGTATTTGGCGGTGAAGTCCT
GACTGCGTTCGCTCGTACCTCCGTGACCACTTCTCGCCACATGGTACGTTCCATCTCCAGCGGTAAATC
CGCTCAGTTCCCTGTTCTGGGTCGCACTCAGGCAGCGTATCTGGCTCCGGGCGAGAACCTCGACGATA
AACGTAAGGACATCAAACACACCGAGAAGGTAATCACCATTGACGGTCTCCTGACGGCTGACGTTCTG
ATTTATGATATTGAGGACGCGATGAACCACTACGACGTTCGCTCTGAGTATACCTCTCAGTTGGGTGA
ATCTCTGGCGATGGCTGCGGATGGTGCGGTTCTGGCTGAGATTGCCGGTCTGTGTAACGTGGAAAGCA
AATATAATGAGAACATCGAGGGCTTAGGTACTGCTACCGTAATTGAGACCACTCAGAACAAGGCCGC
ACTTACCGACCAAGTTGCGCTGGGTAAGGAGATTATTGCGGCTCTGACTAAGGCTCGTGCGGCTCTGA
CCAAGAACTATGTTCCGGCTGCTGACCGTGTGTTCTACTGTGACCCAGATAGCTACTCTGCGATTCTGG
CAGCACTGATGCCGAACGCAGCAAACTACGCTGCTCTGATTGACCCTGAGAAGGGTTCTATCCGCAAC
GTTATGGGCTTTGAGGTTGTAGAAGTTCCGCACCTCACCGCTGGTGGTGCTGGTACCGCTCGTGAGGG
CACTACTGGTCAGAAGCACGTCTTCCCTGCCAATAAAGGTGAGGGTAATGTCAAGGTTGCTAAGGACA
ACGTTATCGGCCTGTTCATGCACCGCTCTGCGGTAGGTACTGTTAAGCTGCGTGACTTGGCTCTGGAGC
GCGCTCGCCGTGCTAACTTCCAAGCGGACCAGATTATCGCTAAGTACGCAATGGGCCACGGTGGTCTT
CGCCCAGAAGCTGCTGGTGCAGTGGTTTTCAAAGTGGAGTAATGCTGGGGGTGGCCTCAACGGTCGCT
GCTAGTCCCGAAGAGGCGAGTGTTACTTCAACAGAAGAAACCTTAACGCCAGCACAGGAGGCCGCAC
GCACCCGCGCTGCTAACAAAGCCCGAAAGGAAGCTGAGTTGGCTGCTGCCACCGCTGAGCAATAACT
AGCATAACCCCTTGGGGCCTCTAAACGGGTCTTGAGGGGTTTTTTGCTGAAAGGAGGAACTATATGCG
CTCATACGATATGAACGTTGAGACTGCCGCTGAGTTATCAGCTGTGAACGACATTCTGGCGTCTATCG
GTGAACCTCCGGTATCAACGCTGGAAGGTGACGCTAACGCAGATGCAGCGAACGCTCGGCGTATTCTC
AACAAGATTAACCGACAGATTCAATCTCGTGGATGGACGTTCAACATTGAGGAAGGCATAACGCTACT
ACCTGATGTTTACTCCAACCTGATTGTATACAGTGACGACTATTTATCCCTAATGTCTACTTCCGGTCA
ATCCATCTACGTTAACCGAGGTGGCTATGTGTATGACCGAACGAGTCAATCAGACCGCTTTGACTCTG
GTATTACTGTGAACATTATTCGTCTCCGCGACTACGATGAGATGCCTGAGTGCTTCCGTTACTGGATTG
TCACCAAGGCTTCCCGTCAGTTCAACAACCGATTCTTTGGGGCACCGGAAGTAGAGGGTGTACTCCAA
GAAGAGGAAGATGAGGCTAGACGTCTCTGCATGGAGTATGAGATGGACTACGGTGGGTACAATATGC
TGGATGGAGATGCGTTCACTTCTGGTCTACTGACTCGCTAACATTAATAAATAAGGAGGCTCTAATGG
CACTCATTAGCCAATCAATCAAGAACTTGAAGGGTGGTATCAGCCAACAGCCTGACATCCTTCGTTAT
CCAGACCAAGGGTCACGCCAAGTTAACGGTTGGTCTTCGGAGACCGAGGGCCTCCAAAAGCGTCCACC
TCTTGTTTTCTTAAATACACTTGGAGACAACGGTGCGTTAGGTCAAGCTCCGTACATCCACCTGATTAA
CCGAGATGAGCACGAACAGTATTACGCTGTGTTCACTGGTAGCGGAATCCGAGTGTTCGACCTTTCTG
GTAACGAGAAGCAAGTTAGGTATCCTAACGGTTCCAACTACATCAAGACCGCTAATCCACGTAACGAC
CTGCGAATGGTTACTGTAGCAGACTATACGTTCATCGTTAACCGTAACGTTGTTGCACAGAAGAACAC
AAAGTCTGTCAACTTACCGAATTACAACCCTAATCAAGACGGATTGATTAACGTTCGTGGTGGTCAGT
ATGGTAGGGAACTAATTGTACACATTAACGGTAAAGACGTTGCGAAGTATAAGATACCAGATGGTAGT
CAACCTGAACACGTAAACAATACGGATGCCCAATGGTTAGCTGAAGAGTTAGCCAAGCAGATGCGCA
CTAACTTGTCTGATTGGACTGTAAATGTAGGGCAAGGGTTCATCCATGTGACCGCACCTAGTGGTCAA
CAGATTGACTCCTTCACGACTAAAGATGGCTACGCAGACCAGTTGATTAACCCTGTGACCCACTACGC
TCAGTCGTTCTCTAAGCTGCCACCTAATGCTCCTAACGGCTACATGGTGAAAATCGTAGGGGACGCCT
CTAAGTCTGCCGACCAGTATTACGTTCGGTATGACGCTGAGCGGAAAGTTTGGACTGAGACTTTAGGT
TGGAACACTGAGGACCAAGTTCTATGGGAAACCATGCCACACGCTCTTGTGCGAGCCGCTGACGGTAA
TTTCGACTTCAAGTGGCTTGAGTGGTCTCCTAAGTCTTGTGGTGACGTTGACACCAACCCTTGGCCTTC
TTTTGTTGGTTCAAGTATTAACGATGTGTTCTTCTTCCGTAACCGCTTAGGATTCCTTAGTGGGGAGAA
CATCATATTGAGTCGTACAGCCAAATACTTCAACTTCTACCCTGCGTCCATTGCGAACCTTAGTGATGA
CGACCCTATAGACGTAGCTGTGAGTACCAACCGAATAGCAATCCTTAAGTACGCCGTTCCGTTCTCAG
AAGAGTTACTCATCTGGTCCGATGAAGCACAATTCGTCCTGACTGCCTCGGGTACTCTCACATCTAAGT
CGGTTGAGTTGAACCTAACGACCCAGTTTGACGTACAGGACCGAGCGAGACCTTTTGGGATTGGGCGT
AATGTCTACTTTGCTAGTCCGAGGTCCAGCTTCACGTCCATCCACAGGTACTACGCTGTGCAGGATGTC
AGTTCCGTTAAGAATGCTGAGGACATTACATCACACGTTCCTAACTACATCCCTAATGGTGTGTTCAGT
ATTTGCGGAAGTGGTACGGAAAACTTCTGTTCGGTACTATCTCACGGGGACCCTAGTAAAATCTTCAT
```

Figure 14(i)

```
GTACAAATTCCTGTACCTGAACGAAGAGTTAAGGCAACAGTCGTGGTCTCATTGGGACTTTGGGGAAA
ACGTACAGGTTCTAGCTTGTCAGAGTATCAGCTCAGATATGTATGTGATTCTTCGCAATGAGTTCAATA
CGTTCCTAGCTAGAATCTCTTTCACTAAGAACGCCATTGACTTACAGGGAGAACCCTATCGTGCCTTTA
TGGACATGAAGATTCGATACACGATTCCTAGTGGAACATACAACGATGACACATTCACTACCTCTATT
CATATTCCAACAATTTATGGTGCAAACTTCGGGAGGGGCAAAATCACTGTATTGGAGCCTGATGGTAA
GATAACCGTGTTTGAGCAACCTACGGCTGGGTGGAATAGCGACCCTTGGCTGAGACTCAGCGGTAACT
TGGAGGGACGCATGGTGTACATTGGGTTCAACATTAACTTCGTATATGAGTTCTCTAAGTTCCTCATCA
AGCAGACTGCCGACGACGGGTCTACCTCCACGGAAGACATTGGGCGCTTACAGTTACGCCGAGCGTGG
GTTAACTACGAGAACTCTGGTACGTTTGACATTTATGTTGAGAACCAATCGTCTAACTGGAAGTACAC
AATGGCTGGTGCCCGATTAGGCTCTAACACTCTGAGGGCTGGGAGACTGAACTTAGGGACCGGACAAT
ATCGATTCCCTGTGGTTGGTAACGCCAAGTTCAACACTGTATACATCTTGTCAGATGAGACTACCCCTC
TGAACATCATTGGGTGTGGCTGGGAAGGTAACTACTTACGGAGAAGTTCCGGTATTTAATTAAATATT
CTCCCTGTGGTGGCTCGAAATTAATACGACTCACTATAGGGAGAACAATACGACTACGGGAGGGTTTT
CTTATGATGACTATAAGACCTACTAAAAGTACAGACTTTGAGGTATTCACTCCGGCTCACCATGACATT
CTTGAAGCTAAGGCTGCTGGTATTGAGCCGAGTTTCCCTGATGCTTCCGAGTGTGTCACGTTGAGCCTC
TATGGGTTCCCTCTAGCTATCGGTGGTAACTGCGGGACCAGTGCTGGTTCGTTACGAGCGACCAAGT
GTGGCGACTTAGTGGAAAGGCTAAGCGAAAGTTCCGTAAGTTAATCATGGAGTATCGCGATAAGATGC
TTGAGAAGTATGATACTCTTTGGAATTACGTATGGGTAGGCAATACGTCCCACATTCGTTTCCTCAAGA
CTATCGGTGCGGTATTCCATGAAGAGTACACACGAGATGGTCAATTTCAGTTATTTACAATCACGAAA
GGAGGATAACCATATGTGTTGGGCAGCCGCAATACCTATCGCTATATCTGGCGCTCAGGCTATCAGTG
GTCAGAACGCTCAGGCCAAAATGATTGCCGCTCAGACCGCTGCTGGTCGTCGTCAAGCTATGGAAATC
ATGAGGCAGACGAACATCCAGAATGCTGACCTATCGTTGCAAGCTCGAAGTAAACTTGAGGAAGCGT
CCGCCGAGTTGACCTCACAGAACATGCAGAAGGTCCAAGCTATTGGGTCTATCCGAGCGGCTATCGGA
GAGAGTATGCTTGAAGGTTCCTCAATGGACCGCATTAAGCGAGTCACAGAAGGACAGTTCATTCGGGA
AGCCAATATGGTAACTGAGAACTATCGCCGTGACTACCAAGCAATCTTCGCACAGCAACTTGGTGGTA
CTCAAAGTGCTGCAAGTCAGATTGACGAAATCTATAAGAGCGAACAGAAACAGAAGAGTAAGCTACA
GATGGTTCTGGACCCACTGGCTATCATGGGGTCTTCCGCTGCGAGTGCTTACGCATCCGGTGCGTTCGA
CTCTAAGTCCACAACTAAGGCACCTATTGTTGCCGCTAAAGGAACCAAGACGGGGAGGTAATGAGCTA
TGAGTAAAATTGAATCTGCCCTTCAAGCGGCACAACCGGGACTCTCTCGGTTACGTGGTGGTGCTGGA
GGTATGGGCTATCGTGCAGCAACCACTCAGGCCGAACAGCCAAGGTCAAGCCTATTGGACACCATTGG
TCGGTTCGCTAAGGCTGGTGCCGATATGTATACCGCTAAGGAACAACGAGCACGAGACCTAGCTGATG
AACGCTCTAACGAGATTATCCGTAAGCTGACCCCTGAGCAACGTCGAGAAGCTCTCAACAACGGGACC
CTTCTGTATCAGGATGACCCATACGCTATGGAAGCACTCCGAGTCAAGACTGGTCGTAACGCTGCGTA
TCTTGTGGACGATGACGTTATGCAGAAGATAAAAGAGGGTGTCTTCCGTACTCGCGAAGAGATGGAAG
AGTATCGCCATAGTCGCCTTCAAGAGGGCGCTAAGGTATACGCTGAGCAGTTCGGCATCGACCCTGAG
GACGTTGATTATCAGCGTGGTTTCAACGGGGACATTACCGAGCGTAACATCTCGCTGTATGGTGCGCA
TGATAACTTCTTGAGCCAGCAAGCTCAGAAGGGCGCTATCATGAACAGCCGAGTGGAACTCAACGGTG
TCCTTCAAGACCCTGATATGCTGCGTCGTCCAGACTCTGCTGACTTCTTTGAGAAGTATATCGACAACG
GTCTGGTTACTGGCGCAATCCCATCTGATGCTCAAGCCACACAGCTTATAAGCCAAGCGTTCAGTGAC
GCTTCTAGCCGTGCTGGTGGTGCTGACTTCCTGATGCGAGTCGGTGACAAGAAGGTAACACTTAACGG
AGCCACTACGACTTACCGAGAGTTGATTGGTGAGGAACAGTGGAACGCTCTCATGGTCACAGCACAAC
GTTCTCAGTTTGAGACTGACGCGAAGCTGAACGAGCAGTATCGCTTGAAGATTAACTCTGCGCTGAAC
CAAGAGGACCCAAGGACAGCTTGGGAGATGCTTCAAGGTATCAAGGCTGAACTAGATAAGGTCCAAC
CTGATGAGCAGATGACACCACAACGTGAGTGGCTAATCTCCGCACAGGAACAAGTTCAGAATCAGAT
GAACGCATGGACGAAAGCTCAGGCCAAGGCTCTGGACGATTCCATGAAGTCAATGAACAAACTTGAC
GTAATCGACAAGCAATTCCAGAAGCGAATCAACGGTGAGTGGGTCTCAACGGATTTTAAGGATATGCC
AGTCAACGAGAACACTGGTGAGTTCAAGCATAGCGATATGGTTAACTACGCCAATAAGAAGCTCGCTG
AGATTGACAGTATGGACATTCCAGACGGTGCCAAGGATGCTATGAAGTTGAAGTACCTTCAAGCGGAC
TCTAAGGACGGAGCATTCCGTACAGCCATCGGAACCATGGTCACTGACGCTGGTCAAGAGTGGTCTGC
CGCTGTGATTAACGGTAAGTTACCAGAACGAACCCCAGCTATGGATGCTCTGCGCAGAATCCGCAATG
```

Figure 14(j)

```
CTGACCCTCAGTTGATTGCTGCGCTATACCCAGACCAAGCTGAGCTATTCCTGACGATGGACATGATG
GACAAGCAGGGTATTGACCCTCAGGTTATTCTTGATGCCGACCGACTGACTGTTAAGCGGTCCAAAGA
GCAACGCTTTGAGGATGATAAAGCATTCGAGTCTGCACTGAATGCATCTAAGGCTCCTGAGATTGCCC
GTATGCCAGCGTCACTGCGCGAATCTGCACGTAAGATTTATGACTCCGTTAAGTATCGCTCGGGGAAC
GAAAGCATGGCTATGGAGCAGATGACCAAGTTCCTTAAGGAATCTACCTACACGTTCACTGGTGATGA
TGTTGACGGTGATACCGTTGGTGTGATTCCTAAGAATATGATGCAGGTTAACTCTGACCCGAAATCAT
GGGAGCAAGGTCGGGATATTCTGGAGGAAGCACGTAAGGGAATCATTGCGAGCAACCCTTGGATAAC
CAATAAGCAACTGACCATGTATTCTCAAGGTGACTCCATTTACCTTATGGACACCACAGGTCAAGTCA
GAGTCCGATACGACAAAGAGTTACTCTCGAAGGTCTGGAGTGAGAACCAGAAGAAACTCGAAGAGAA
AGCTCGTGAGAAGGCTCTGGCTGATGTGAACAAGCGAGCACCTATAGTTGCCGCTACGAAGGCCCGTG
AAGCTGCTGCTAAACGAGTCCGAGAGAAACGTAAACAGACTCCTAAGTTCATCTACGGACGTAAGGA
GTAACTAAAGGCTACATAAGGAGGCCCTAAATGGATAAGTACGATAAGAACGTACCAAGTGATTATG
ATGGTCTGTTCCAAAAGGCTGCTGATGCCAACGGGGTCTCTTATGACCTTTTACGTAAAGTCGCTTGGA
CAGAATCACGATTTGTGCCTACAGCAAAATCTAAGACTGGACCATTAGGCATGATGCAATTTACCAAG
GCAACCGCTAAGGCCCTCGGTCTGCGAGTTACCGATGGTCCAGACGACGACCGACTGAACCCTGAGTT
AGCTATTAATGCTGCCGCTAAGCAACTTGCAGGTCTGGTAGGGAAGTTTGATGGCGATGAACTCAAAG
CTGCCCTTGCGTACAACCAAGGCGAGGGACGCTTGGGTAATCCACAACTTGAGGCGTACTCTAAGGGA
GACTTCGCATCAATCTCTGAGGAGGGACGTAACTACATGCGTAACCTTCTGGATGTTGCTAAGTCACCT
ATGGCTGGACAGTTGGAAACTTTTGGTGGCATAACCCCAAAGGGTAAAGGCATTCCGGCTGAGGTAGG
ATTGGCTGGAATTGGTCACAAGCAGAAAGTAACACAGGAACTTCCTGAGTCCACAAGTTTTGACGTTA
AGGGTATCGAACAGGAGGCTACGGCGAAACCATTCGCCAAGGACTTTTGGGAGACCCACGGAGAAAC
ACTTGACGAGTACAACAGTCGTTCAACCTTCTTCGGATTCAAAAATGCTGCCGAAGCTGAACTCTCCA
ACTCAGTCGCTGGGATGGCTTTCCGTGCTGGTCGTCTCGATAATGGTTTTGATGTGTTTAAAGACACCA
TTACGCCGACTCGCTGGAACTCTCACATCTGGACTCCAGAGGAGTTAGAGAAGATTCGAACAGAGGTT
AAGAACCCTGCGTACATCAACGTTGTAACTGGTGGTTCCCCTGAGAACCTCGATGACCTCATTAAATT
GGCTAACGAGAACTTTGAGAATGACTCCCGCGCTGCCGAGGCTGGCCTAGGTGCCAAACTGAGTGCTG
GTATTATTGGTGCTGGTGTGGACCCGCTTAGCTATGTTCCTATGGTCGGTGTCACTGGTAAGGGCTTTA
AGTTAATCAATAAGGCTCTTGTAGTTGGTGCCGAAAGTGCTGCTCTGAACGTTGCATCCGAAGGTCTCC
GTACCTCCGTAGCTGGTGGTGACGCAGACTATGCGGGTGCTGCCTTAGGTGGCTTTGTGTTTGGCGCAG
GCATGTCTGCAATCAGTGACGCTGTAGCTGCTGGACTGAAACGCAGTAAACCAGAAGCTGAGTTCGAC
AATGAGTTCATCGGTCCTATGATGCGATTGGAAGCCCGTGAGACAGCACGAAACGCCAACTCTGCGGA
CCTCTCTCGGATGAACACTGAGAACATGAAGTTTGAAGGTGAACATAATGGTGTCCCTTATGAGGACT
TACCAACAGAGAGAGGTGCCGTGGTGTTACATGATGGCTCCGTTCTAAGTGCAAGCAACCCAATCAAC
CCTAAGACTCTAAAAGAGTTCTCCGAGGTTGACCCTGAGAAGGCTGCGCGAGGAATCAAACTGGCTGG
GTTCACCGAGATTGGCTTGAAGACCTTGGGGTCTGACGATGCTGACATCCGTAGAGTGGCTATCGACC
TCGTTCGCTCTCCTACTGGTATGCAGTCTGGTGCCTCAGGTAAGTTCGGTGCAACAGCTTCTGACATCC
ATGAGAGACTTCATGGTACTGACCAGCGTACTTATAATGACTTGTACAAAGCAATGTCTGACGCTATG
AAAGACCCTGAGTTCTCTACTGGCGGCGCTAAGATGTCCCGTGAAGAAACTCGATACACTATCTACCG
TAGAGCGGCACTAGCTATTGAGCGTCCAGAACTACAGAAGGCACTCACTCCGTCTGAGAGAATCGTTA
TGGACATCATTAAGCGTCACTTTGACACCAAGCGTGAACTTATGGAAAACCCAGCAATATTCGGTAAC
ACAAAGGCTGTGAGTATCTTCCCTGAGAGTCGCCACAAAGGTACTTACGTTCCTCACGTATATGACCG
TCATGCCAAGGCGCTGATGATTCAACGCTACGGTGCCGAAGGTTTGCAGGAAGGGATTGCCCGCTCAT
GGATGAACAGCTACGTCTCCAGACCTGAGGTCAAGGCCAGAGTCGATGAGATGCTTAAGGAATTACA
CGGGGTGAAGGAAGTAACACCAGAGATGGTAGAGAAGTACGCTATGGATAAGGCTTATGGTATCTCC
CACTCAGACCAGTTCACCAACAGTTCCATAATAGAAGAGAACATTGAGGGCTTAGTAGGTATCGAGAA
TAACTCATTCCTTGAGGCACGTAACTTGTTTGATTCGGACCTATCCATCACTATGCCAGACGGACAGCA
ATTCTCAGTGAATGACCTAAGGGACTTCGATATGTTCCGCATCATGCCAGCGTATGACGCCGTGTCA
ATGGTGACATCGCCATCATGGGGTCTACTGGTAAAACCACTAAGGAACTTAAGGATGAGATTTTGGCT
CTCAAAGCGAAAGCTGAGGGAGACGGTAAGAAGACTGGCGAGGTACATGCTTTAATGGATACCGTTA
AGATTCTTACTGGTCGTGCTAGACGCAATCAGGACACTGTGTGGGAAACCTCACTGCGTGCCATCAAT
```

Figure 14(k)

GACCTAGGGTTCTTCGCTAAGAACGCCTACATGGGTGCTCAGAACATTACGGAGATTGCTGGGATGAT
TGTCACTGGTAACGTTCGTGCTCTAGGGCATGGTATCCCAATTCTGCGTGATACACTCTACAAGTCTAA
ACCAGTTTCAGCTAAGGAACTCAAGGAACTCCATGCGTCTCTGTTCGGGAAGGAGGTGGACCAGTTGA
TTCGGCCTAAACGTGCTGACATTGTGCAGCGCCTAAGGGAAGCAACTGATACCGGACCTGCCGTGGCG
AACATCGTAGGGACCTTGAAGTATTCAACACAGGAACTGGCTGCTCGCTCTCCGTGGACTAAGCTACT
GAACGGAACCACTAACTACCTTCTGGATGCTGCGCGTCAAGGTATGCTTGGGGATGTTATTAGTGCCA
CCCTAACAGGTAAGACTACCCGCTGGGAGAAAGAAGGCTTCCTTCGTGGTGCCTCCGTAACTCCTGAG
CAGATGGCTGGCATCAAGTCTCTCATCAAGGAACATATGGTACGCGGTGAGGACGGGAAGTTTACCGT
TAAGGACAAGCAAGCGTTCTCTATGGACCCACGGGCTATGGACTTATGGAGACTGGCTGACAAGGTAG
CTGATGAGGCAATGCTGCGTCCACATAAGGTGTCCTTACAGGATTCCCATGCGTTCGGAGCACTAGGT
AAGATGGTTATGCAGTTTAAGTCTTTCACTATCAAGTCCCTTAACTCTAAGTTCCTGCGAACCTTCTAT
GATGGATACAAGAACAACCGAGCGATTGACGCTGCGCTGAGCATCATCACCTCTATGGGTCTCGCTGG
TGGTTTCTATGCTATGGCTGCACACGTCAAAGCATACGCTCTGCCTAAGGAGAAACGTAAGGAGTACT
TGGAGCGTGCACTGGACCCAACCATGATTGCCCACGCTGCGTTATCTCGTAGTTCTCAATTGGGTGCTC
CTTTGGCTATGGTTGACCTAGTTGGTGGTGTTTTAGGGTTCGAGTCCTCCAAGATGGCTCGCTCTACGA
TTCTACCTAAGGACACCGTGAAGGAACGTGACCCAAACAAACCGTACACCTCTAGAGAGGTAATGGG
CGCTATGGGTTCAAACCTTCTGGAACAGATGCCTTCGGCTGGCTTTGTGGCTAACGTAGGGGCTACCTT
AATGAATGCTGCTGGCGTGGTCAACTCACCTAATAAAGCAACCGAGCAGGACTTCATGACTGGTCTTA
TGAACTCCACAAAAGAGTTAGTACCGAACGACCCATTGACTCAACAGCTTGTGTTGAAGATTTATGAG
GCGAACGGTGTTAACTTGAGGGAGCGTAGGAAATAATACGACTCACTATAGGGAGAGGCGAAATAAT
CTTCTCCCTGTAGTCTCTTAGATTTACTTTAAGGAGGTCAAATGGCTAACGTAATTAAAACCGTTTTGA
CTTACCAGTTAGATGGCTCCAATCGTGATTTTAATATCCCGTTTGAGTATCTAGCCCGTAAGTTCGTAG
TGGTAACTCTTATTGGTGTAGACCGAAAGGTCCTTACGATTAATACAGACTATCGCTTTGCTACACGTA
CTACTATCTCTCTGACAAAGGCTTGGGGTCCAGCCGATGGCTACACGACCATCGAGTTACGTCGAGTA
ACCTCCACTACCGACCGATTGGTTGACTTTACGGATGGTTCAATCCTCCGCGCGTATGACCTTAACGTC
GCTCAGATTCAAACGATGCACGTAGCGGAAGAGGCCCGTGACCTCACTACGGATACTATCGGTGTCAA
TAACGATGGTCACTTGGATGCTCGTGGTCGTCGAATTGTGAACCTAGCGAACGCCGTGGATGACCGCG
ATGCTGTTCCGTTTGGTCAACTAAAGACCATGAACCAGAACTCATGGCAAGCACGTAATGAAGCCTTA
CAGTTCCGTAATGAGGCTGAGACTTTCAGAAACCAAGCGGAGGGCTTTAAGAACGAGTCCAGTACCA
ACGCTACGAACACAAAGCAGTGGCGCGATGAGACCAAGGGTTTCCGAGACGAAGCCAAGCGGTTCAA
GAATACGGCTGGTCAATACGCTACATCTGCTGGGAACTCTGCTTCCGCTGCGCATCAATCTGAGGTAA
ACGCTGAGAACTCTGCCACAGCATCCGCTAACTCTGCTCATTTGGCAGAACAGCAAGCAGACCGTGCG
GAACGTGAGGCAGACAAGCTGGAAAATTACAATGGATTGGCTGGTGCAATTGATAAGGTAGATGGAA
CCAATGTGTACTGGAAAGGAAATATTCACGCTAACGGGCGCCTTTACATGACCACAAACGGTTTTGAC
TGTGGCCAGTATCAACAGTTCTTTGGTGGTGTCACTAATCGTTACTCTGTCATGGAGTGGGGAGATGAG
AACGGATGGCTGATGTATGTTCAACGTAGAGAGTGGACAACAGCGATAGGCGGTAACATCCAGTTAG
TAGTAAACGGACAGATCATCACCCAAGGTGGAGCCATGACCGGTCAGCTAAAATTGCAGAATGGGCA
TGTTCTTCAATTAGAGTCCGCATCCGACAAGGCGCACTATATTCTATCTAAAGATGGTAACAGGAATA
ACTGGTACATTGGTAGAGGGTCAGATAACAACAATGACTGTACCTTCCACTCCTATGTACATGGTACG
ACCTTAACACTCAAGCAGGACTATGCAGTAGTTAACAAACACTTCCACGTAGGTCAGGCCGTTGTGGC
CACTGATGGTAATATTCAAGGTACTAAGTGGGGAGGTAAATGGCTGGATGCTTACCTACGTGACAGCT
TCGTTGCGAAGTCCAAGGCGTGGACTCAGGTGTGGTCTGGTAGTGCTGGCGGTGGGTAAGTGTGACT
GTTTCACAGGATCTCCGCTTCCGCAATATCTGGATTAAGTGTGCCAACAACTCTTGGAACTTCTTCCGT
ACTGGCCCCGATGGAATCTACTTCATAGCCTCTGATGGTGGATGGTTACGATTCCAAATACACTCCAAC
GGTCTCGGATTCAAGAATATTGCAGACAGTCGTTCAGTACCTAATGCAATCATGGTGGAGAACGAGTA
ATTGGTAAATCACAAGGAAAGACGTGTAGTCCACGGATGGACTCTCAAGGAGGTACAAGGTGCTATC
ATTAGACTTTAACAACGAATTGATTAAGGCTGCTCCAATTGTTGGGACGGGTGTAGCAGATGTTAGTG
CTCGACTGTTCTTTGGGTTAAGCCTTAACGAATGGTTCTACGTTGCTGCTATCGCCTACACAGTGGTTC
AGATTGGTGCCAAGGTAGTCGATAAGATGATTGACTGGAAGAAAGCCAATAAGGAGTGATATGTATG
GAAAAGGATAAGAGCCTTATTACATTCTTAGAGATGTTGGACACTGCGATGGCTCAGCGTATGCTTGC

Figure 14(I)

GGACCTTTCGGACCATGAGCGTCGCTCTCCGCAACTCTATAATGCTATTAACAAACTGTTAGACCGCCA
CAAGTTCCAGATTGGTAAGTTGCAGCCGGATGTTCACATCTTAGGTGGCCTTGCTGGTGCTCTTGAAGA
GTACAAAGAGAAAGTCGGTGATAACGGTCTTACGGATGATGATATTTACACATTACAGTGATATACTC
AAGGCCACTACAGATAGTGGTCTTTATGGATGTCATTGTCTATACGAGATGCTCCTACGTGAAATCTGA
AAGTTAACGGGAGGCATTATGCTAGAATTTTTACGTAAGCTAATCCCTTGGGTTCTCGCTGGGATGCTA
TTCGGGTTAGGATGGCATCTAGGGTCAGACTAATGGACGCTAAATGGAAACAGGAGGTACACAATG
AGTACGTTAAGAGAGTTGAGGCTGCGAAGAGCACTCAAAGAGCAATCGATGCGGTATCTGCTAAGTA
TCAAGAAGACCTTGCCGCGCTGGAAGGGAGCACTGATAGGATTATTTCTGATTTGCGTAGCGACAATA
AGCGGTTGCGCGTCAGAGTCAAAACTACCGGAACCTCCGATGGTCAGTGTGGATTCGAGCCTGATGGT
CGAGCCGAACTTGACGACCGAGATGCTAAACGTATTCTCGCAGTGACCCAGAAGGGTGACGCATGGA
TTCGTGCGTTACAGGATACTATTCGTGAACTGCAACGTAAGTAGGAAATCAAGTAAGGAGGCAATGTG
TCTACTCAATCCAATCGTAATGCGCTCGTAGTGGCGCAACTGAAAGGAGACTTCGTGGCGTTCCTATTC
GTCTTATGGAAGGCGCTAAACCTACCGGTGCCCACTAAGTGTCAGATTGACATGGCTAAGGTGCTGGC
GAATGGAGACAACAAGAAGTTCATCTTACAGGCTTTCCGTGGTATCGGTAAGTCGTTCATCACATGTG
CGTTCGTTGTGTGGTCCTTATGGAGAGACCCTCAGTTGAAGATACTTATCGTATCAGCCTCTAAGGAGC
GTGCAGACGCTAACTCCATCTTTATTAAGAACATCATTGACCTGCTGCCATTCCTATCTGAGTTAAAGC
CAAGACCCGGACAGCGTGACTCGGTAATCAGCTTTGATGTAGGCCCAGCCAATCCTGACCACTCTCCT
AGTGTGAAATCAGTAGGTATCACTGGTCAGTTAACTGGTAGCCGTGCTGACATTATCATTGCGGATGA
CGTTGAGATTCCGTCTAACAGCGCAACTATGGGTGCCCGTGAGAAGCTATGGACTCTGGTTCAGGAGT
TCGCTGCGTTACTTAAACCGCTGCCTTCCTCTCGCGTTATCTACCTTGGTACACCTCAGACAGAGATGA
CTCTCTATAAGGAACTTGAGGATAACCGTGGGTACACAACCATTATCTGGCCTGCTCTGTACCCAAGG
ACACGTGAAGAGAACCTCTATTACTCACAGCGTCTTGCTCCTATGTTACGCGCTGAGTACGATGAGAA
CCCTGAGGCACTTGCTGGGACTCCAACAGACCCAGTGCGCTTTGACCGTGATGACCTGCGCGAGCGTG
AGTTGGAATACGGTAAGGCTGGCTTTACGCTACAGTTCATGCTTAACCCTAACCTTAGTGATGCCGAG
AAGTACCCGCTGAGGCTTCGTGACGCTATCGTAGCGGCCTTAGACTTAGAGAAGGCCCCAATGCATTA
CCAGTGGCTTCCGAACCGTCAGAACATCATTGAGGACCTTCCTAACGTTGGCCTTAAGGGTGATGACC
TGCATACGTACCACGATTGTTCCAACAACTCAGGTCAGTACCAACAGAAGATTCTGGTCATTGACCCT
AGTGGTCGCGGTAAGGACGAAACAGGTTACGCTGTGCTGTACACACTGAACGGTTACATCTACCTTAT
GGAAGCTGGAGGTTTCCGTGATGGCTACTCCGATAAGACCCTTGAGTTACTCGCTAAGAAGGCAAAGC
AATGGGGAGTCCAGACGGTTGTCTACGAGAGTAACTTCGGTGACGGTATGTTCGGTAAGGTATTCAGT
CCTATCCTTCTTAAACACCACAACTGTGCGATGGAAGAGATTCGTGCCCGTGGTATGAAAGAGATGCG
TATTTGCGATACCCTTGAGCCAGTCATGCAGACTCACCGCCTTGTAATTCGTGATGAGGTCATTAGGGC
CGACTACCAGTCCGCTCGTGACGTAGACGGTAAGCATGACGTTAAGTACTCGTTGTTCTACCAGATGA
CCCGTATCACTCGTGAGAAAGGCGCTCTGGCTCATGATGACCGATTGGATGCCCTTGCGTTAGGCATT
GAGTATCTCCGTGAGTCCATGCAGTTGGATTCCGTTAAGGTCGAGGGTGAAGTACTTGCTGACTTCCTT
GAGGAACACATGATGCGTCCTACGGTTGCTGCTACGCATATCATTGAGATGTCTGTGGGAGGAGTTGA
TGTGTACTCTGAGGACGATGAGGGTTACGGTACGTCTTTCATTGAGTGGTGATTTATGCATTAGGACTG
CATAGGGATGCACTATAGACCACGGATGGTCAGTTCTTTAAGTTACTGAAAAGACACGATAAATTAAT
ACGACTCACTATAGGGAGAGGAGGGACGAAAGGTTACTATATAGATACTGAATGAATACTTATAGAG
TGCATAAAGTATGCATAATGGTGTACCTAGAGTGACCTCTAAGAATGGTGATTATATTGTATTAGTATC
ACCTTAACTTAAGGACCAACATAAAGGGAGGAGACTCATGTTCCGCTTATTGTTGAACCTACTGCGGC
ATAGAGTCACCTACCGATTTCTTGTGGTACTTTGTGCTGCCCTTGGGTACGCATCTCTTACTGGAGACC
TCAGTTCACTGGAGTCTGTCGTTTGCTCTATACTCACTTGTAGCGATTAGGGTCTTCCTGACCGACTGA
TGGCTCACCGAGGGATTCAGCGGTATGATTGCATCACACCACTTCATCCCTATAGAGTCAAGTCCTAA
GGTATACCCATAAAGAGCCTCTAATGGTCTATCCTAAGGTCTATACCTAAAGATAGGCCATCCTATCA
GTGTCACCTAAAGAGGGTCTTAGAGAGGGCCTATGGAGTTCCTATAGGGTCCTTTAAAATATACCATA
AAAATCTGAGTGACTATCTCACAGTGTACGGACCTAAAGTTCCCCCATAGGGGGTACCTAAAGCCCAG
CCAATCACCTAAAGTCAACCTTCGGTTGACCTTGAGGGTTCCCTAAGGGTTGGGGATGACCCTTGGGTT
TGTCTTTGGGTGTTACCTTGAGTGTCTCTCTGTGTCCCT

BACTERIOPHAGE ENGINEERING VIA SEMI-SYNTHESIS

CROSS-REFERENCE TO RELATED APPLICATIONS

This application claims the benefit of and priority to U.S. Provisional Patent Application No. 62/542,609, filed Aug. 8, 2017, the entire contents of which are incorporated herein by reference.

SEQUENCE LISTING

The instant application contains a Sequence Listing which has been filed electronically in ASCII format and is hereby incorporated by reference in its entirety. Said ASCII copy, created on Aug. 30, 2018, is named 102590-0646_SL.txt and is 114,955 bytes in size.

TECHNICAL FIELD

The present technology relates generally to methods and kits for generating recombinant bacteriophage genomes via semi-synthesis. In particular, the present technology relates to methods of integrating a heterologous nucleic acid sequence into a bacteriophage genome, and isolating recombinant bacteriophages that express the heterologous nucleic acid sequence.

BACKGROUND

The following description of the background of the present technology is provided simply as an aid in understanding the present technology and is not admitted to describe or constitute prior art to the present technology.

Model phages have been engineered using molecular biology techniques to deliver heterologous protein products to bacterial cells. E.g., US 2009/0155215; M. J. Loessner et. al., *Applied and Environmental Microbiology*, Vol. 62, No. 4, pp. 1133-40 (1996)). The natural host range of model phage engineered to date is limited. Methods for creating variations in phage genomes and engineering new phage genomes may lead to the identification of phages with varied properties (e.g., varied host ranges) that are useful for diagnostic and therapeutic purposes.

Engineering diverse phage is generally made more difficult by the properties of phage genomes. For example, phage genomes have relatively few restriction sites and are heavily modified, making use of traditional cloning techniques with phage challenging. Phages also have compact genomes with very little non-coding DNA, which can make it challenging to find sites within the genome that are compatible with traditional engineering. Many existing phage engineering technologies that rely on in vitro strategies are generally inefficient and challenging to scale up. Further, engineering phages within bacteria can be problematic due to toxicity of phages to bacteria as well as the difficulty in maintaining the stability of large engineered genomes.

SUMMARY OF THE PRESENT TECHNOLOGY

In one aspect, the present disclosure provides a method for generating a recombinant bacteriophage genome comprising: (a) generating a plurality of amplicons from a template comprising a first bacteriophage DNA genome, wherein the plurality of amplicons collectively span the entire length of the first bacteriophage DNA genome, wherein at least one end of each amplicon comprises a sequence that is homologous to an opposite end of another amplicon and wherein each amplicon is no more than 15 kilobases in length; and (b) recombining in vitro the plurality of amplicons with a heterologous nucleic acid in the presence of a recombination system under conditions to produce a recombinant bacteriophage genome. In some embodiments, the heterologous nucleic acid comprises a 3' flanking region that is homologous to the 5' end of an amplicon. Additionally or alternatively, in some embodiments, the heterologous nucleic acid comprises a 5' flanking region that is homologous to the 3' end of an amplicon. In certain embodiments, the method further comprises propagating the recombinant bacteriophage genome in a non-natural or natural bacterial host. The first bacteriophage DNA genome may be recombinant or non-recombinant.

In certain embodiments, the first bacteriophage DNA genome corresponds to a bacteriophage family or order selected from the group consisting of Myoviridae, Styloviridae, Siphoviridae, Pedoviridae, Tectiviridae, Leviviridae, Podoviridae, and Plasmaviridae. In some embodiments, the first bacteriophage DNA genome is derived from a bacteriophage genus selected from the group consisting of T7-like phage, phiKMV-like phage, LUZ24-like phage, phiKZ-like phage, PB1-like phage, Felix-O1-like phage, T4-like phage, phi92-like phage, rV5-like phage, SP6-like phage, N4-like phage, phiEco32-like phage, T5-like phage, KP34-like phage, KP15-like phage, GAP227-like phage, AP22-like phage, phiFel-like phage, Sap6-like phage, Silvia-like phage, Kay-like phage, Twort-like phage, P68-like phage, and phiETA-like phage.

Additionally or alternatively, in some embodiments, the first bacteriophage DNA genome corresponds to *Klebsiella* phage K11, lambda phage, *Enterobacteria* phage T2, *Enterobacteria* phage T1, *Enterobacteria* phage T7, *Enterobacteria* phage T5, *Enterobacteria* phage P1, *Enterobacteria* phage PRD1, K1E phage, K1-5 phage, RB49 phage, RB16 phage, KP15 phage, KP27 phage, Miro phage, Matisse phage, phiEap-3 phage, ECP3 phage, EFDG1 phage, EFLK1 phage, vB_Efae230P-4 phage, vB_EfaP_IME195 phage, SA11 phage, Stau2 phage, K phage, G1 phage, SA12 phage, 812 phage, P68 phage, SAP-2 phage, 44AHJD phage, or SA97 phage.

Additionally or alternatively, in some embodiments of the method, the recombination system comprises a 5'-3' exonuclease, a DNA polymerase, and a DNA ligase. In one embodiment, the 5'-3' exonuclease is T5 exonuclease, the DNA polymerase is Phusion® DNA polymerase (Thermo Fisher Scientific, Waltham, MA), and the DNA ligase is Taq ligase. In other embodiments, the recombination system comprises a 3'-5' exonuclease, a DNA polymerase, and a DNA ligase.

In any of the above embodiments, the heterologous nucleic acid comprises an open reading frame that encodes a bioluminescent protein, a fluorescent protein, a chemiluminescent protein, a phage protein that modifies host range, or any combination thereof. In certain embodiments, the open reading frame of the heterologous nucleic acid is operably linked to an expression control sequence that is capable of directing expression of the bioluminescent protein, the fluorescent protein, the chemiluminescent protein, the phage protein that modifies host range, or any combination thereof. In some embodiments, the expression control sequence is an inducible promoter or a constitutive promoter. The heterologous nucleic acid can be about 100-500 base pairs in length, about 500-1000 base pairs in length, 1000-1500 base pairs in length, about 1500-2000 base pairs in length, 2000-2500 base pairs in length, about 2500-3000 base pairs in length, 3000-3500 base pairs in length, or about 3500-4000 base pairs in length.

Examples of bioluminescent protein include, but are not limited to, Aequorin, firefly luciferase, *Renilla* luciferase, red luciferase, luxAB, and nanoluciferase. Examples of chemiluminescent protein include β-galactosidase, horseradish peroxidase (HRP), and alkaline phosphatase. Examples of fluorescent protein include, but are not limited to, TagBFP, Azurite, EBFP2, mKalama1, Sirius, Sapphire, T-Sapphire, ECFP, Cerulean, SCFP3A, mTurquoise, monomeric Midoriishi-Cyan, TagCFP, mTFP1, GFP, EGFP, Emerald, Superfolder GFP, Monomeric Azami Green, TagGFP2, mUKG, mWasabi, EYFP, Citrine, Venus, SYFP2, TagYFP, Monomeric Kusabira-Orange, mKOκ, mKO2, mOrange, mOrange2, mRaspberry, mCherry, dsRed, mStrawberry, mTangerine, tdTomato, TagRFP, TagRFP-T, mApple, mRuby, mPlum, HcRed-Tandem, mKate2, mNeptune, NirFP, TagRFP657, IFP1.4, iRFP, mKeima Red, LSS-mKate1, LSS-mKate2, PA-GFP, PAmCherry1, PATagRFP, Kaede (green), Kaede (red), KikGR1 (green), KikGR1 (red), PS-CFP2, PS-CFP2, mEos2 (green), mEos2 (red), PSmOrange, or Dronpa.

Additionally or alternatively, in some embodiments, the phage protein that modifies host range is a tail spike protein (e.g., gp11, gp12, and gp17), a structural phage virion protein involved with bacterial cell attachment, or a structural phage virion protein involved with degradation of bacterial cell wall components.

In some embodiments, the recombinant bacteriophage genome is a recombinant *Klebsiella* phage K11 comprising the nucleic acid sequence of SEQ ID NO: 1 and the plurality of amplicons were generated using one or more primer pairs selected from the group consisting of SEQ ID NO: 3 and SEQ ID NO: 4; SEQ ID NO: 5 and SEQ ID NO: 6; SEQ ID NO: 7 and SEQ ID NO: 8; SEQ ID NO: 9 and SEQ ID NO: 10; and SEQ ID NO: 11 and SEQ ID NO: 12.

In other embodiments, the recombinant bacteriophage genome is a recombinant *Enterobacteria* phage T7 comprising the nucleic acid sequence of SEQ ID NO: 2 and the plurality of amplicons were generated using one or more primer pairs selected from the group consisting of SEQ ID NO: 15 and SEQ ID NO: 16; SEQ ID NO: 17 and SEQ ID NO: 18; SEQ ID NO: 19 and SEQ ID NO: 20; and SEQ ID NO: 21 and SEQ ID NO: 22.

In another aspect, the present disclosure provides a method for generating a semi-synthetic recombinant bacteriophage genome from a bacteriophage DNA template comprising a first genomic region and a second genomic region comprising: (a) generating a first plurality of amplicons, wherein the first plurality of amplicons collectively span the entire length of the first genomic region of the bacteriophage DNA template, wherein at least one end of each amplicon of the first plurality of amplicons comprises a sequence that is homologous to an opposite end of another amplicon of the first plurality of amplicons and wherein each amplicon of the first plurality of amplicons is no more than 15 kilobases in length; (b) recombining the first plurality of amplicons and a heterologous nucleic acid in vitro in the presence of a recombination system under conditions to produce a first recombinant bacteriophage genomic fragment; and (c) introducing the first recombinant bacteriophage genomic fragment into a first expression vector to produce a first circular phage expression vector. In some embodiments, the heterologous nucleic acid comprises a 3' flanking region that is homologous to the 5' end of an amplicon. Additionally or alternatively, in some embodiments, the heterologous nucleic acid comprises a 5' flanking region that is homologous to the 3' end of an amplicon. In some embodiments, the first genomic region has a length of 75,000 bases-150,000 bases and the second genomic region has a length of 75,000 bases-150,000 bases.

In certain embodiments, the method further comprises (a) generating a second plurality of amplicons, wherein the second plurality of amplicons collectively span the entire length of the second genomic region of the bacteriophage DNA template, wherein at least one end of each amplicon of the second plurality of amplicons comprises a sequence that is homologous to an opposite end of another amplicon of the second plurality of amplicons and wherein each amplicon of the second plurality of amplicons is no more than 15 kilobases in length; (b) recombining the second plurality of amplicons in vitro in the presence of a recombination system under conditions to produce a second bacteriophage genomic fragment; and (c) introducing the second bacteriophage genomic fragment into a second expression vector to produce a second circular phage expression vector. In certain embodiments, the method further comprises transforming a non-natural or natural bacterial host cell with the first circular phage expression vector and/or the second circular phage expression vector.

Additionally or alternatively, in some embodiments of the method, the in vitro recombination system comprises a 5'-3' exonuclease, a DNA polymerase, and a DNA ligase. In one embodiment, the 5'-3' exonuclease is T5 exonuclease, the DNA polymerase is Phusion® DNA polymerase (Thermo Fisher Scientific, Waltham, MA), and the DNA ligase is Taq ligase. In other embodiments, the recombination system comprises a 3'-5' exonuclease, a DNA polymerase, and a DNA ligase.

Additionally or alternatively, in some embodiments of the method, the first circular phage expression vector comprises a first unique restriction enzyme recognition sequence that is located 3' to the first recombinant bacteriophage genomic fragment and the second circular phage expression vector comprises a second unique restriction enzyme recognition sequence that is located 5' to the second bacteriophage genomic fragment. In other embodiments, the first circular phage expression vector comprises a first unique restriction enzyme recognition sequence that is located 5' to the first recombinant bacteriophage genomic fragment and the second circular phage expression vector comprises a second unique restriction enzyme recognition sequence that is located 3' to the second bacteriophage genomic fragment.

Additionally or alternatively, in some embodiments, the method further comprises cleaving the first circular phage expression vector with a first restriction enzyme that recognizes the first unique restriction enzyme recognition sequence to produce a first linear phage expression vector, and/or cleaving the second circular phage expression vector with a second restriction enzyme that recognizes the second unique restriction enzyme recognition sequence to produce a second linear phage expression vector. The first restriction enzyme may cleave within the first unique restriction enzyme recognition sequence or at a position near the first unique restriction enzyme recognition sequence. Likewise, the second restriction enzyme may cleave within the second unique restriction enzyme recognition sequence or at a position near the second unique restriction enzyme recognition sequence. The first restriction enzyme and second restriction enzyme may be identical or distinct.

Additionally or alternatively, in some embodiments, the method further comprises transforming a non-natural or natural bacterial host cell with the first linear phage expression vector and/or the second linear phage expression vector. The non-natural or natural bacterial host cell may comprise a non-endogenous inducible recombination system. In some embodiments, the non-endogenous inducible recombination system comprises lambda Red proteins Gam, Exo, and Beta operably linked to an inducible promoter. In certain embodiments, the inducible promoter is araB and the non-endogenous inducible recombination system is induced by the addition of arabinose.

In one aspect, the present disclosure provides a method for generating a plurality of semi-synthetic recombinant bacteriophage genomes comprising: (a) generating a plurality of amplicons from a template comprising a first bacteriophage DNA genome, wherein the plurality of amplicons collectively span the entire length of the first bacteriophage DNA genome, wherein at least one end of each amplicon comprises a sequence that is homologous to an opposite end of another amplicon and wherein each amplicon is no more than 15 kilobases in length; (b) recombining in vitro the plurality of amplicons with a heterologous nucleic acid in the presence of a recombination system under conditions to produce a recombinant linear bacteriophage genome; (c) recombining in vitro the recombinant linear bacteriophage genome with a DNA bridge in the presence of a recombination system under conditions to produce a recombinant circular bacteriophage genome; and (d) amplifying the recombinant circular bacteriophage genome using rolling circle amplification to generate a plurality of semi-synthetic recombinant bacteriophage genomes. Rolling circle amplification may involve contacting the recombinant circular bacteriophage genome with phi29 DNA polymerase. In some embodiments, the heterologous nucleic acid comprises a 3' flanking region that is homologous to the 5' end of an amplicon. Additionally or alternatively, in some embodiments, the heterologous nucleic acid comprises a 5' flanking region that is homologous to the 3' end of an amplicon.

The DNA bridge comprises a 3' flanking region that is homologous to the 5' end of the recombinant linear bacteriophage genome, and a 5' flanking region that is homologous to the 3' end of the recombinant linear bacteriophage genome. In some embodiments, the length of the DNA bridge is at least 50 base pairs.

Additionally or alternatively, in some embodiments, the plurality of semi-synthetic recombinant bacteriophage genomes are further subjected to in vitro homologous recombination so as to seal subgenomic replication products.

Additionally or alternatively, in some embodiments, the method further comprises propagating the plurality of semi-synthetic recombinant bacteriophage genomes in a non-natural or natural bacterial host cell. The non-natural or natural bacterial host cell may comprise a non-endogenous inducible recombination system. In some embodiments, the non-endogenous inducible recombination system comprises lambda Red proteins Gam, Exo, and Beta operably linked to an inducible promoter. In certain embodiments, the inducible promoter is araB and the non-endogenous inducible recombination system is induced by the addition of arabinose.

In any of the above embodiments of the methods disclosed herein, the heterologous nucleic acid comprises an open reading frame that encodes a bioluminescent protein, a fluorescent protein, a chemiluminescent protein, a phage protein that modifies host range, or any combination thereof. In certain embodiments, the open reading frame of the heterologous nucleic acid is operably linked to an expression control sequence that is capable of directing expression of the bioluminescent protein, the fluorescent protein, the chemiluminescent protein, the phage protein that modifies host range, or any combination thereof. In some embodiments, the expression control sequence is an inducible promoter or a constitutive promoter. The heterologous nucleic acid can be about 100-500 base pairs in length, about 500-1000 base pairs in length, 1000-1500 base pairs in length, about 1500-2000 base pairs in length, 2000-2500 base pairs in length, about 2500-3000 base pairs in length, 3000-3500 base pairs in length, or about 3500-4000 base pairs in length.

Examples of bioluminescent protein include, but are not limited to, Aequorin, firefly luciferase, *Renilla* luciferase, red luciferase, luxAB, and nanoluciferase. Examples of chemiluminescent protein include β-galactosidase, horseradish peroxidase (HRP), and alkaline phosphatase. Examples of fluorescent protein include, but are not limited to, TagBFP, Azurite, EBFP2, mKalama1, Sirius, Sapphire, T-Sapphire, ECFP, Cerulean, SCFP3A, mTurquoise, monomeric Midoriishi-Cyan, TagCFP, mTFP1, GFP, EGFP, Emerald, Superfolder GFP, Monomeric Azami Green, TagGFP2, mUKG, mWasabi, EYFP, Citrine, Venus, SYFP2, TagYFP, Monomeric Kusabira-Orange, mKOκ, mKO2, mOrange, mOrange2, mRaspberry, mCherry, dsRed, mStrawberry, mTangerine, tdTomato, TagRFP, TagRFP-T, mApple, mRuby, mPlum, HcRed-Tandem, mKate2, mNeptune, NirFP, TagRFP657, IFP1.4, iRFP, mKeima Red, LSS-mKate1, LSS-mKate2, PA-GFP, PAmCherry1, PATagRFP, Kaede (green), Kaede (red), KikGR1 (green), KikGR1 (red), PS-CFP2, PS-CFP2, mEos2 (green), mEos2 (red), PSmOrange, or Dronpa. Additionally or alternatively, in some embodiments, the phage protein that modifies host range is a tail spike protein (e.g., gp11, gp12, and gp17), a structural phage virion protein involved with bacterial cell attachment, or a structural phage virion protein involved with degradation of bacterial cell wall components.

Also disclosed herein are kits for integrating a heterologous nucleic acid sequence into a bacteriophage genome.

BRIEF DESCRIPTION OF THE DRAWINGS

FIG. 6 discloses SEQ ID NO: 23.

Figure 8A:
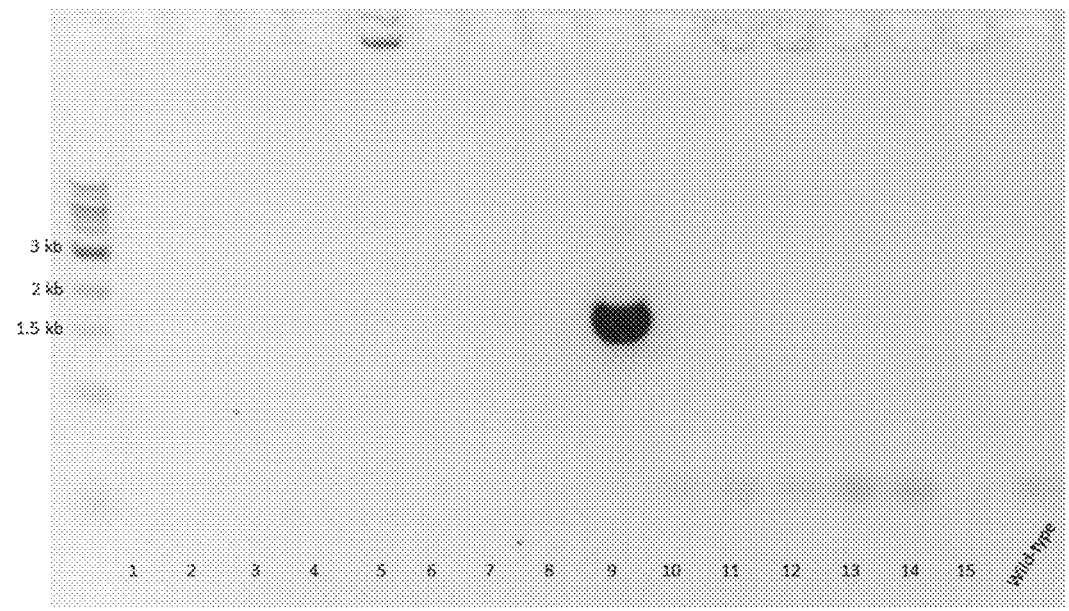
Figure 8B:
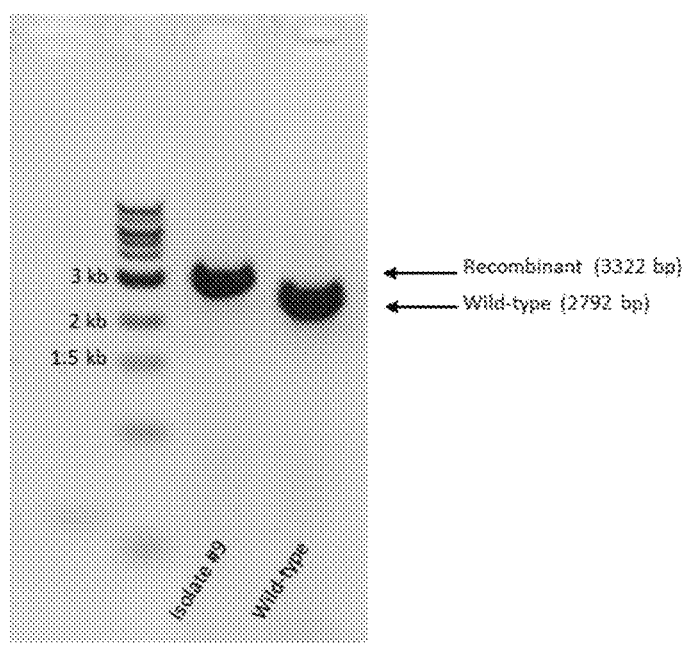

FIGS. 8(a)-8(b) shows the recovery of recombinant T7 bacteriophage containing a heterologous nanoluciferase nucleic acid sequence using the methods of the present technology. FIG. 8(a) shows the results of a junctional PCR screen of 15 potential T7-nanoluciferase plaques, and a wild-type control plaque. The primer pair spans from inside the nanoluciferase gene to a location in the T7 genome. Amplification of a recombinant phage produces an 1856 bp PCR product, whereas wild-type phage which lacks one of the primer binding sites will not form a product. Of the 15 isolates screened, only isolate #9 produces a junctional PCR product of the expected size. FIG. 8(b) shows the analysis of T7-nanoluciferase isolate #9 via flanking PCR screening. A primer pair that spans the intended nanoluciferase insertion site produces a 2792 bp amplicon in wild-type T7 phage and a 3322 bp amplicon in recombinant nanoluciferase T7 phage.

Figure 9:
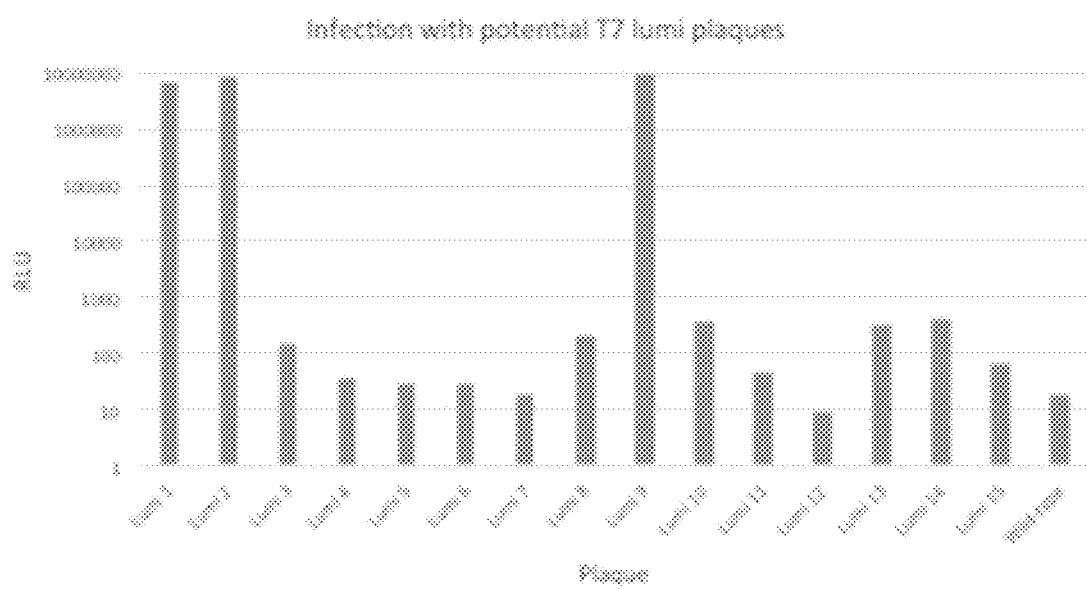

FIG. 9 shows the phenotypic analysis of 15 potential T7-nanoluciferase phage plaques. Plaques were picked into 20 µl of 10 mM Tris-HCl with 10 mM MgSO$_4$. 5 µl of each of these 'pickates' was used to infect 5 mL cultures of mid-log phase NEB10β cells for 1.5 hours. Relative luminescence units (RLU) are substantially higher for isolates 1, 2, and 9, indicating a luminescent phenotype.

FIG. 10 shows the design of the K11 chimeric guide RNA expression construct used in the Break and Recombine 3.0 (BAR 3.0) experiments. FIG. 10 discloses SEQ ID NO: 24.

Figure 11:

FIG. 11 shows a representative gel image of K11 genomic DNA after cleavage with the Cas9/sgRNA 4.5 complex.

Figure 12:
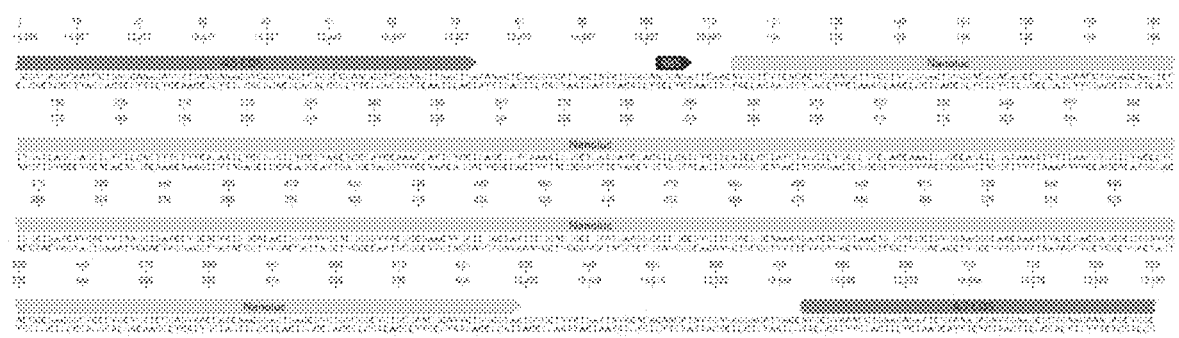

FIG. 12 shows the synthetic DNA construct used to introduce the nanoluciferase gene into the cleaved K11 genome via BAR 3.0. FIG. 12 discloses SEQ ID NO: 25.

FIGS. 13(a)-13(m) show the complete genome sequence of the recombinant NanoLuc® K11 phage that was generated using the methods of the present technology (SEQ ID NO: 1).

FIGS. 14(a)-14(l) show the complete genome sequence of the recombinant NanoLuc® T7 phage that was generated using the methods of the present technology (SEQ ID NO: 2).

DETAILED DESCRIPTION

It is to be appreciated that certain aspects, modes, embodiments, variations and features of the present methods are described below in various levels of detail in order to provide a substantial understanding of the present technology.

Manipulating phage genomes is more difficult compared to manipulating bacterial hosts. In vitro synthesis and assembly of phage genomes is inefficient and relies on the delivery of large DNA molecules across the cell membranes of a bacterial host. Some bacterial strains are recalcitrant to large DNA transformation across the membrane. Classic in vivo recombination strategies are also inefficient and are complicated by the fact that lytic phage genomes have a comparatively short residence time in a host before lysis.

One of the most commonly used and well-established methods for engineering phage genomes is homologous recombination in their bacterial hosts, which can occur between two homologous DNA sequences as short as 23 bp (Alberts B et al., MOLECULAR BIOLOGY OF THE CELL, 5th ed. Garland Science, New York, NY (2007); Snyder L et al., MOLECULAR GENETICS OF BACTERIA, 4th ed. ASM Press, Washington, DC (2013)). Homologous recombination occurs between the plasmid and the phage genome, allowing the heterologous gene to be integrated into the phage genome and eventually packaged within the phage particle. However, homologous recombination only yields a small fraction of recombinant progeny phage. Reported recombination rates range from $10^{-10}$ to $10^{-4}$ (Loessner M. et al., Appl Environ Microbiol 62:1133-1140 (1996); Le S. et al., PLoS One 8:e68562 (2013); Mahichi F. et al., FEMS Microbiol Lett 295:211-217 (2009)). One of the major challenges of generating recombinant bacteriophages is that the recombinant processes used to create such bacteriophages are inefficient, and often result in a low yield of recombinant bacteriophage genomes. Transformation of large bacteriophage genomes (e.g., about or greater than 40-48 kb) is prohibitive in many bacterial strains and species, making it difficult to isolate viable bacteriophage particles post-transformation. See e.g., Chauthaiwale et al., Microbiological Reviews 56 (4): 577-592 (1992); see also Vaughan et al., Nature Biotechnology 14:309-314 (1996). Thus, finding the desired clone using conventional phage screening methods is labor-intensive and unpredictable.

The present disclosure provides methods for integrating a heterologous nucleic acid sequence into a bacteriophage genome, and isolating recombinant bacteriophages that express the heterologous nucleic acid sequence. The methods disclosed herein permit higher recovery of recombinant bacteriophage genomes that express the phenotypic properties associated with the heterologous nucleic acid sequence relative to that observed with other phage engineering methods, such as Break and Recombine 3.0 (BAR 3.0). For example, the overall yield of recombinant bacteriophage genomes obtained using the methods of the present technology was about 20-100% (3 out of 15 isolates for recombinant T7 phage; 6 out of 6 isolates for recombinant K11 phage). In contrast, no recombinant bacteriophages were generated using BAR 3.0 (i.e., 0% recovery of recombinant bacteriophage genomes).

In practicing the present methods, many conventional techniques in molecular biology, protein biochemistry, cell biology, microbiology and recombinant DNA are used. See, e.g., Sambrook and Russell eds. (2001) Molecular Cloning: A Laboratory Manual, 3rd edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5th edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology.

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, "bacteriophage" or "phage" refers to a virus that infects bacteria. Bacteriophages are obligate intracellular parasites that multiply inside bacteria by co-opting some or all of the host biosynthetic machinery (i.e., viruses that infect bacteria). Though different bacteriophages may contain different materials, they all contain nucleic acid and protein, and can under certain circumstances be encapsulated in a lipid membrane. Depending upon the phage, the nucleic acid can be either DNA or RNA (but not both) and can exist in various forms.

The term "control sequences" is intended to encompass, at a minimum, any component whose presence is essential for expression, and can also encompass an additional component whose presence is advantageous, for example, leader sequences.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, an "expression control sequence" refers to polynucleotide sequences which are necessary to affect the expression of coding sequences to which they are operably linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence.

As used herein, "heterologous nucleic acid sequence" is any sequence placed at a location in the genome where it does not normally occur. A heterologous nucleic acid sequence may comprise a sequence that does not naturally occur in a bacteriophage, or it may comprise only sequences naturally found in the bacteriophage, but placed at a non-normally occurring location in the genome. In some embodiments, the heterologous nucleic acid sequence is not a natural phage sequence. In certain embodiments, the heterologous nucleic acid sequence is a natural phage sequence that is derived from a different phage. In other embodiments, the heterologous nucleic acid sequence is a sequence that occurs naturally in the genome of a wild-type phage but is then relocated to another site where it does not naturally occur, rendering it a heterologous sequence at that new site.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same nucleobase or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences.

This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+SwissProtein+SPupdate+PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

As used herein, a "host cell" is a bacterial cell that can be infected by a phage to yield progeny phage particles. A host cell can form phage particles from a particular type of phage genomic DNA. In some embodiments, the phage genomic DNA is introduced into the host cell by infecting the host cell with a phage. In some embodiments, the phage genomic DNA is introduced into the host cell using transformation, electroporation, or any other suitable technique. In some embodiments, the phage genomic DNA is substantially pure when introduced into the host cell. In some embodiments, the phage genomic DNA is present in a vector when introduced into the host cell. The definition of host cell can vary from one phage to another. For example, *E. coli* may be the natural host cell for a particular type of phage, but *Klebsiella pneumoniae* is not.

As used herein, the term "isolated" refers to a substance or entity that has been separated from at least some of the components with which it was associated when initially produced (whether in nature or in an experimental setting). Isolated substances and/or entities may be separated from at least about 10%, about 20%, about 30%, about 40%, about 50%, about 60%, about 70%, about 80%, about 90%, or more of the other components with which they were initially associated. In some embodiments, isolated substances and/ or entities are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

As used herein, "operably linked" means that expression control sequences are positioned relative to the nucleic acid of interest to initiate, regulate or otherwise control transcription of the nucleic acid of interest.

As used herein, a "phage genome" includes naturally occurring phage genomes and derivatives thereof. Generally, the derivatives possess the ability to propagate in the same hosts as the naturally occurring phage. In some embodiments, the only difference between a naturally occurring phage genome and a derivative phage genome is at least one of a deletion and an addition of nucleotides from at least one end of the phage genome (if the genome is linear) or at least one point in the genome (if the genome is circular).

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, for example, recombinant cells express genes that are not found within the native (non-recombinant) form of the cell or express native genes that are otherwise abnormally expressed, under expressed or not expressed at all.

As used herein, an endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous to the organism (originating from the same organism or progeny thereof) or exogenous (originating from a different organism or progeny thereof). By way of example, a promoter sequence can be substituted (e.g., by homologous recombination) for the native promoter of a gene in the genome of an organism, such that this gene has an altered expression pattern. This gene would be "recombinant" because it is separated from at least some of the sequences that naturally flank it.

A nucleic acid is also considered "recombinant" if it contains any modifications that do not naturally occur in the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, a "recombinant bacteriophage genome" is a bacteriophage genome that has been genetically modified by the insertion of a heterologous nucleic acid sequence into the bacteriophage genome.

A "recombinant bacteriophage" means a bacteriophage that comprises a recombinant bacteriophage genome. In some embodiments, the bacteriophage genome is modified by recombinant DNA technology to introduce a heterologous nucleic acid sequence into the genome at a defined site. In some embodiments, the heterologous nucleic acid sequence is introduced with no corresponding loss of endogenous phage genomic nucleotides. In other words, if bases N1 and N2 are adjacent in the wild-type bacteriophage genome, the heterologous nucleic acid sequence is inserted between N1 and N2. Thus, in the resulting recombinant bacteriophage genome, the heterologous nucleic acid sequence is flanked by nucleotides N1 and N2. In some embodiments, endogenous phage nucleotides are removed or replaced during the insertion of the heterologous nucleic acid sequence. For example, in some embodiments, the heterologous nucleic acid sequence is inserted in place of some or all of the endogenous phage sequence which is removed. In some embodiments, endogenous phage sequences are removed from a position in the phage genome distant from the site(s) of insertion of the heterologous nucleic acid sequences.

As used herein, the term "sample" refers to clinical samples obtained from a subject or isolated microorganisms. In certain embodiments, a sample is obtained from a biological source (i.e., a "biological sample"), such as tissue, bodily fluid, or microorganisms collected from a subject. Sample sources include, but are not limited to, mucus, sputum, bronchial alveolar lavage (BAL), bronchial wash (BW), whole blood, bodily fluids, cerebrospinal fluid (CSF), urine, plasma, serum, or tissue.

As used herein, "transformation of" or "transforming" bacterial cells refers to the process by which bacterial cells take up naked DNA molecules. If the exogenous DNA to be transformed has an origin of replication recognized by the host cell DNA polymerases, the bacteria will replicate the exogenous DNA along with its own endogenous DNA.

Bacteriophage

Bacteriophage are obligate intracellular parasites that multiply inside bacteria by co-opting some or all of the host biosynthetic machinery. Phages contain nucleic acid and protein, and may be enveloped by a lipid membrane. Depending upon the phage, the nucleic acid genome can be either DNA or RNA but not both, and can exist in either circular or linear forms. The size of the phage genome varies depending upon the phage. The simplest phages have genomes that are only a few thousand nucleotides in size, while the more complex phages may contain more than 100,000 nucleotides in their genome, and in rare instances less than 500,000 nucleotides. The number and amount of individual types of protein in phage particles will vary depending upon the phage. The proteins function in infection and to protect the nucleic acid genome from environmental nucleases.

Phage genomes come in a variety of sizes and shapes (e.g., linear or circular). Most phages range in size from 24-200 nm in diameter. The capsid is composed of many copies of one or more phage proteins, and acts as a protective envelope around the phage genome. Many phages have tails attached to the phage capsid. The tail is a hollow tube through which the phage nucleic acid passes during infection. The size of the tail can vary and some phages do not even have a tail structure. In the more complex phages, the tail is surrounded by a contractile sheath which contracts during infection of the bacterial host cell. At the end of the tail, phages have a base plate and one or more tail fibers attached to it. The base plate and tail fibers are involved in the binding of the phage to the host cell.

Lytic or virulent phages are phages which can only multiply in bacteria and lyse the bacterial host cell at the end of the life cycle of the phage. The lifecycle of a lytic phage begins with an eclipse period. During the eclipse phase, no infectious phage particles can be found either inside or outside the host cell. The phage nucleic acid takes over the host biosynthetic machinery and phage specific mRNAs and proteins are produced. Early phage mRNAs code for early proteins that are needed for phage DNA synthesis and for shutting off host DNA, RNA and protein biosynthesis. In some cases, the early proteins actually degrade the host chromosome. After phage DNA is made late mRNAs and late proteins are made. The late proteins are the structural proteins that comprise the phage as well as the proteins needed for lysis of the bacterial cell. In the next phase, the phage nucleic acid and structural proteins are assembled and infectious phage particles accumulate within the cell. The bacteria begin to lyse due to the accumulation of the phage lysis protein, leading to the release of intracellular phage particles. The number of particles released per infected cell can be as high as 1000 or more. Lytic phage may be enumerated by a plaque assay. The assay is performed at a low enough concentration of phage such that each plaque arises from a single infectious phage. The infectious particle that gives rise to a plaque is called a PFU (plaque forming unit).

Lysogenic phages are those that can either multiply via the lytic cycle or enter a quiescent state in the host cell. In the quiescent state, the phage genome exists as a prophage (i.e., it has the potential to produce phage). In most cases, the phage DNA actually integrates into the host chromosome and is replicated along with the host chromosome and passed on to the daughter cells. The host cell harboring a prophage is not adversely affected by the presence of the prophage and the lysogenic state may persist indefinitely. The lysogenic state can be terminated upon exposure to adverse conditions. Conditions which favor the termination of the lysogenic state include: desiccation, exposure to UV or ionizing radiation, exposure to mutagenic chemicals, etc. Adverse conditions lead to the production of proteases (rec A protein), the expression of the phage genes, reversal of the integration process, and lytic multiplication.

In some embodiments, a phage genome comprises at least 5 kilobases (kb), at least 10 kb, at least 15 kb, at least 20 kb, at least 25 kb, at least 30 kb, at least 35 kb, at least 40 kb, at least 45 kb, at least 50 kb, at least 55 kb, at least 60 kb, at least 65 kb, at least 70 kb, at least 75 kb, at least 80 kb, at least 85 kb, at least 90 kb, at least 95 kb, at least 100 kb, at least 105 kb, at least 110 kb, at least 115 kb, at least 120 kb, at least 125 kb, at least 130 kb, at least 135 kb, at least 140 kb, at least 145 kb, at least 150 kb, at least 175 kb, at least 200 kb, at least 225 kb, at least 250 kb, at least 275 kb, at least 300 kb, at least 325 kb, at least 350 kb, at least 375 kb, at least 400 kb, at least 425 kb, at least 450 kb, at least 475 kb, or at least 500 kb of nucleic acids.

In one aspect, bacteriophage DNA genomes can be engineered using the methods disclosed herein. In certain embodiments, the bacteriophage DNA genome corresponds to a bacteriophage family or order selected from the group consisting of Myoviridae, Styloviridae, Siphoviridae, Pedoviridae, Tectiviridae, Leviviridae, Podoviridae, and Plasmaviridae. In some embodiments, the bacteriophage DNA genome is derived from one or more bacteriophage genuses (or genera) selected from the group consisting of T7-like phage, phiKMV-like phage, LUZ24-like phage, phiKZ-like phage, PB1-like phage, Felix-O1-like phage, T4-like phage, phi92-like phage, rV5-like phage, SP6-like phage, N4-like phage, phiEco32-like phage, T5-like phage, KP34-like phage, KP15-like phage, GAP227-like phage, AP22-like phage, phiFel-like phage, Sap6-like phage, Silvia-like phage, Kay-like phage, Twort-like phage, P68-like phage, and phiETA-like phage.

Examples of bacteriophage genomes that can be engineered using the methods of the present technology include *Klebsiella* phage K11, lambda phage, *Enterobacteria* phage T2, *Enterobacteria* phage T1, *Enterobacteria* phage T7, *Enterobacteria* phage T5, *Enterobacteria* phage P1, *Enterobacteria* phage PRD1, K1E phage, K1-5 phage, RB49 phage, RB16 phage, KP15 phage, KP27 phage, Miro phage, Matisse phage, phiEap-3 phage, ECP3 phage, EFDG1 phage, EFLK1 phage, vB_Efae230P-4 phage, vB_EfaP_IME195 phage, SA11 phage, Stau2 phage, K phage, G1 phage, SA12 phage, 812 phage, P68 phage, SAP-2 phage, 44AHJD phage, or SA97 phage.

Phage Engineering Methods of the Present Technology

FIGS. 1-4 describe various schemes for integrating a heterologous nucleic acid sequence into a bacteriophage genome via semi-synthesis.

In one aspect, the present disclosure provides a method for generating a recombinant bacteriophage genome comprising: (a) generating a plurality of amplicons from a template comprising a first bacteriophage DNA genome, wherein the plurality of amplicons collectively span the entire length of the first bacteriophage DNA genome, wherein at least one end of each amplicon comprises a sequence that is homologous to an opposite end of another amplicon and wherein each amplicon is no more than 15 kilobases in length; and (b) recombining in vitro the plurality of amplicons with a heterologous nucleic acid in the presence of a recombination system under conditions to produce a recombinant bacteriophage genome. In some embodiments, the heterologous nucleic acid comprises a 3' flanking region that is homologous to the 5' end of an amplicon. Additionally or alternatively, in some embodiments, the heterologous nucleic acid comprises a 5' flanking region that is homologous to the 3' end of an amplicon. In certain embodiments, the method further comprises propagating the recombinant bacteriophage genome in a non-natural or natural bacterial host cell. The first bacteriophage DNA genome may be recombinant or non-recombinant. See FIG. 1.

In certain embodiments, the first bacteriophage DNA genome corresponds to a bacteriophage family or order selected from the group consisting of Myoviridae, Styloviridae, Siphoviridae, Pedoviridae, Tectiviridae, Leviviridae, Podoviridae, and Plasmaviridae. In some embodiments, the first bacteriophage DNA genome is derived from a bacteriophage genus selected from the group consisting of T7-like phage, phiKMV-like phage, LUZ24-like phage, phiKZ-like phage, PB1-like phage, Felix-O1-like phage, T4-like phage, phi92-like phage, rV5-like phage, SP6-like phage, N4-like phage, phiEco32-like phage, T5-like phage, KP34-like phage, KP15-like phage, GAP227-like phage, AP22-like phage, phiFel-like phage, Sap6-like phage, Silvia-like phage, Kay-like phage, Twort-like phage, P68-like phage, and phiETA-like phage.

Additionally or alternatively, in some embodiments, the first bacteriophage DNA genome corresponds to *Klebsiella* phage K11, lambda phage, *Enterobacteria* phage T2, *Enterobacteria* phage T1, *Enterobacteria* phage T7, *Enterobacteria* phage T5, *Enterobacteria* phage P1, *Enterobacteria* phage PRD1, K1E phage, K1-5 phage, RB49 phage, RB16 phage, KP15 phage, KP27 phage, Miro phage, Matisse phage, phiEap-3 phage, ECP3 phage, EFDG1 phage, EFLK1 phage, vB_Efae230P-4 phage, vB_EfaP_IME195 phage, SA11 phage, Stau2 phage, K phage, G1 phage, SA12 phage, 812 phage, P68 phage, SAP-2 phage, 44AHJD phage, or SA97 phage.

In some embodiments, the recombinant bacteriophage genome is a recombinant *Klebsiella* phage K11 comprising the nucleic acid sequence of SEQ ID NO: 1 and the plurality of amplicons were generated using one or more primer pairs selected from the group consisting of SEQ ID NO: 3 and SEQ ID NO: 4; SEQ ID NO: 5 and SEQ ID NO: 6; SEQ ID NO: 7 and SEQ ID NO: 8; SEQ ID NO: 9 and SEQ ID NO: 10; and SEQ ID NO: 11 and SEQ ID NO: 12.

In other embodiments, the recombinant bacteriophage genome is a recombinant *Enterobacteria* phage T7 comprising the nucleic acid sequence of SEQ ID NO: 2 and the plurality of amplicons were generated using one or more primer pairs selected from the group consisting of SEQ ID NO: 15 and SEQ ID NO: 16; SEQ ID NO: 17 and SEQ ID NO: 18; SEQ ID NO: 19 and SEQ ID NO: 20; and SEQ ID NO: 21 and SEQ ID NO: 22.

In another aspect, the present disclosure provides a method for generating a semi-synthetic recombinant bacteriophage genome from a bacteriophage DNA template comprising a first genomic region and a second genomic region comprising: (a) generating a first plurality of amplicons, wherein the first plurality of amplicons collectively span the entire length of the first genomic region of the bacteriophage DNA template, wherein at least one end of each amplicon of the first plurality of amplicons comprises a sequence that is homologous to an opposite end of another amplicon of the first plurality of amplicons and wherein each amplicon of the first plurality of amplicons is no more than 15 kilobases in length; (b) recombining the first plurality of amplicons and a heterologous nucleic acid in vitro in the presence of a recombination system under conditions to produce a first recombinant bacteriophage genomic fragment; and (c) introducing the first recombinant bacteriophage genomic fragment into a first expression vector to produce a first circular phage expression vector. In some embodiments, the heterologous nucleic acid comprises a 3' flanking region that is homologous to the 5' end of an amplicon. Additionally or alternatively, in some embodiments, the heterologous nucleic acid comprises a 5' flanking region that is homologous to the 3' end of an amplicon. In some embodiments, the first genomic region has a length of 75,000 bases-150,000 bases and the second genomic region has a length of 75,000 bases-150,000 bases. The bacteriophage DNA template may be recombinant or non-recombinant.

In certain embodiments, the method further comprises (a) generating a second plurality of amplicons, wherein the second plurality of amplicons collectively span the entire length of the second genomic region of the bacteriophage DNA template, wherein at least one end of each amplicon of the second plurality of amplicons comprises a sequence that is homologous to an opposite end of another amplicon of the second plurality of amplicons and wherein each amplicon of the second plurality of amplicons is no more than 15 kilobases in length; (b) recombining the second plurality of amplicons in vitro in the presence of a recombination system under conditions to produce a second bacteriophage genomic fragment; and (c) introducing the second bacteriophage genomic fragment into a second expression vector to produce a second circular phage expression vector. In certain embodiments, the method further comprises transforming a non-natural or natural bacterial host cell with the first circular phage expression vector and/or the second circular phage expression vector. See FIG. 2.

Additionally or alternatively, in some embodiments of the method, the first circular phage expression vector comprises a first unique restriction enzyme recognition sequence that is located 3' to the first recombinant bacteriophage genomic fragment and the second circular phage expression vector comprises a second unique restriction enzyme recognition sequence that is located 5' to the second bacteriophage genomic fragment. In other embodiments, the first circular phage expression vector comprises a first unique restriction enzyme recognition sequence that is located 5' to the first recombinant bacteriophage genomic fragment and the second circular phage expression vector comprises a second unique restriction enzyme recognition sequence that is located 3' to the second bacteriophage genomic fragment.

Additionally or alternatively, in some embodiments, the method further comprises cleaving the first circular phage expression vector with a first restriction enzyme that recognizes the first unique restriction enzyme recognition sequence to produce a first linear phage expression vector, and/or cleaving the second circular phage expression vector with a second restriction enzyme that recognizes the second unique restriction enzyme recognition sequence to produce a second linear phage expression vector. The first restriction enzyme may cleave within the first unique restriction enzyme recognition sequence or at a position near the first unique restriction enzyme recognition sequence. Likewise, the second restriction enzyme may cleave within the second unique restriction enzyme recognition sequence or at a position near the second unique restriction enzyme recognition sequence. The first restriction enzyme and second restriction enzyme may be identical or distinct. The first restriction enzyme and/or second restriction enzyme may be selected from the group consisting of AclI, HindIII, SspI, MluCI Tsp509I, PciI, AgeI, BspMI, BfuAI, SexAI, MluI, BceAI, HpyCH4IV, HpyCH4III, BaeI, BsaXI, AflIII, SpeI, BsrI, BmrI, BglII, AfeI, AluI, StuI, ScaI, ClaI, BspDI, PI-SceI, NsiI, AseI, SwaI, CspCI, MfeI, BssSI, BssSαI, Nb.BssSI, BmgBI, PmlI, DraIII, AleI, EcoP15I, PvuII, AlwNI, BtsIMutI, TspRI, NdeI, NlaIII, CviAII, FatI, MslI, FspEI, XcmI, BstXI, PflMI, BccI, NcoI, BseYI, FauI, SmaI, XmaI, TspMI, Nt.CviPII, LpnPI, AciI, SacII, BsrBI, MspI, HpaII, ScrFI, BssKI, StyD4I, BsaJI, BslI, BtgI, NciI, AvrII, MnlI, BbvCI, Nb.BbvCI, Nt.BbvCI, SbfI, Bpu10I, Bsu36I, EcoNI, HpyAV, BstNI, PspGI, StyI, BcgI, PvuI, BstUI, EagI, RsrII, BsiEI, BsiWI, BsmBI, Hpy99I, MspA1I, MspJI, SgrAI, BfaI, BspCNI, XhoI, PaeR7I, TliI, EarI, AcuI, PstI, BpmI, DdeI, SfcI, AflIII, BpuEI, Sm1I, AvaI, BsoBI, MboII, BbsI, XmnI, BsmI, Nb.BsmI, EcoRI, HgaI, AatII, ZraI, Tth111I, PflFI, PshAI, AhdI, DrdI, Eco53kI, SacI, BseRI, PleI, Nt.BstNBI, MlyI, HinfI, EcoRV, MboI, Sau3AI, DpnII, BfuCI, DpnI, BsaBI, TfiI, BsrDI, Nb.BsrDI, BbvI, BtsI, BtsαI, Nb.BtsI, BstAPI, SfaNI, SphI, SrfI, NmeAIII, NaeI, NgoMIV, BglI, AsiSI, BtgZI, HinP1I, HhaI, BssHII, NotI, Fnu4HI, Cac8I, MwoI, NheI, BmtI, SapI, BspQI, Nt.BspQI, BlpI, TseI, ApeKI, Bsp1286I, AlwI, Nt.AlwI, BamHI, FokI, BtsCI, HaeIII, PhoI, FseI, SfiI, NarI, KasI, SfoI, PluTI, AscI, EciI, BsmFI, ApaI, PspOMI, Sau96I, NlaIV, KpnI, Acc65I, BsaI, HphI, BstEII, AvaII, BanI, BaeGI, BsaHI, BanII, RsaI, CviQI, BstZ17I, BciVI, SalI, Nt.BsmAI, BsmAI, BcoDI, ApaLI, BsgI, AccI, Hpy166II, Tsp45I, HpaI, PmeI, HincII, BsiHKAI, ApoI, NspI, BsrFI, BsrFαI, BstYI, HaeII, CviKI-1, EcoO109I, PpuMI, I-CeuI, SnaBI, I-SceI, BspHI, BspEI, MmeI, TaqαI, NruI, Hpy188I, Hpy188III, XbaI, BclI, HpyCH4V, FspI, PI-PspI, MscI, BsrGI, MseI, PacI, PsiI, BstBI, DraI, PspXI, BsaWI, BsaAI, and EaeI.

Additionally or alternatively, in some embodiments, the method further comprises transforming a non-natural or natural bacterial host cell with the first linear phage expression vector and/or the second linear phage expression vector.

In one aspect, the present disclosure provides a method for generating a plurality of semi-synthetic recombinant bacteriophage genomes comprising: (a) generating a plurality of amplicons from a template comprising a first bacteriophage DNA genome, wherein the plurality of amplicons collectively span the entire length of the first bacteriophage DNA genome, wherein at least one end of each amplicon comprises a sequence that is homologous to an opposite end of another amplicon and wherein each amplicon is no more than 15 kilobases in length; (b) recombining in vitro the plurality of amplicons with a heterologous nucleic acid in the presence of a recombination system under conditions to produce a recombinant linear bacteriophage genome; (c) recombining in vitro the recombinant linear bacteriophage genome with a DNA bridge in the presence of a recombination system under conditions to produce a recombinant circular bacteriophage genome; and (d) amplifying the recombinant circular bacteriophage genome using rolling circle amplification to generate a plurality of semi-synthetic recombinant bacteriophage genomes. See FIG. 3. Rolling circle amplification may involve contacting the recombinant circular bacteriophage genome with phi29 DNA polymerase. In some embodiments, the heterologous nucleic acid comprises a 3' flanking region that is homologous to the 5' end of an amplicon. Additionally or alternatively, in some embodiments, the heterologous nucleic acid comprises a 5' flanking region that is homologous to the 3' end of an amplicon. The first bacteriophage DNA genome may be recombinant or non-recombinant.

The DNA bridge comprises a 3' flanking region that is homologous to the 5' end of the recombinant linear bacteriophage genome, and a 5' flanking region that is homologous to the 3' end of the recombinant linear bacteriophage genome. In some embodiments, the length of the DNA bridge is at least 50 base pairs (bps). In certain embodiments, the length of the DNA bridge is about 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Figure 1:
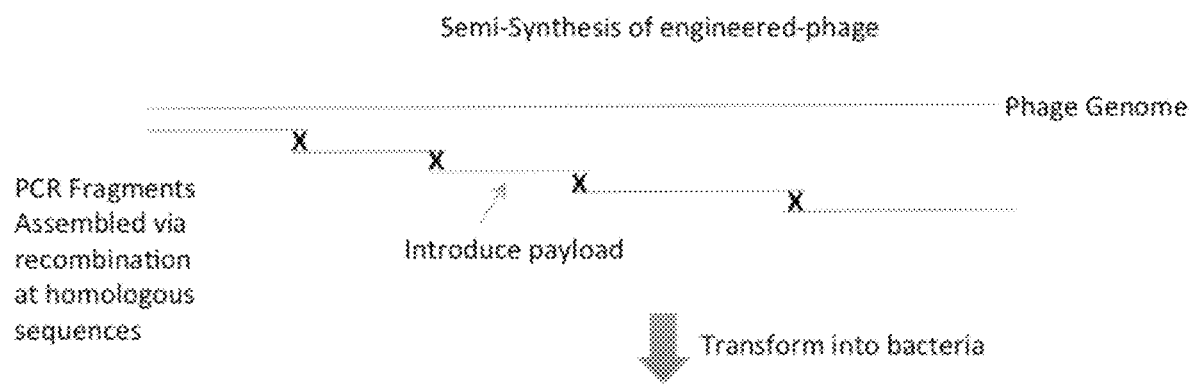
FIG. 1 shows a scheme for integrating a heterologous nucleic acid sequence into a bacteriophage genome via semi-synthesis.
Figure 2:
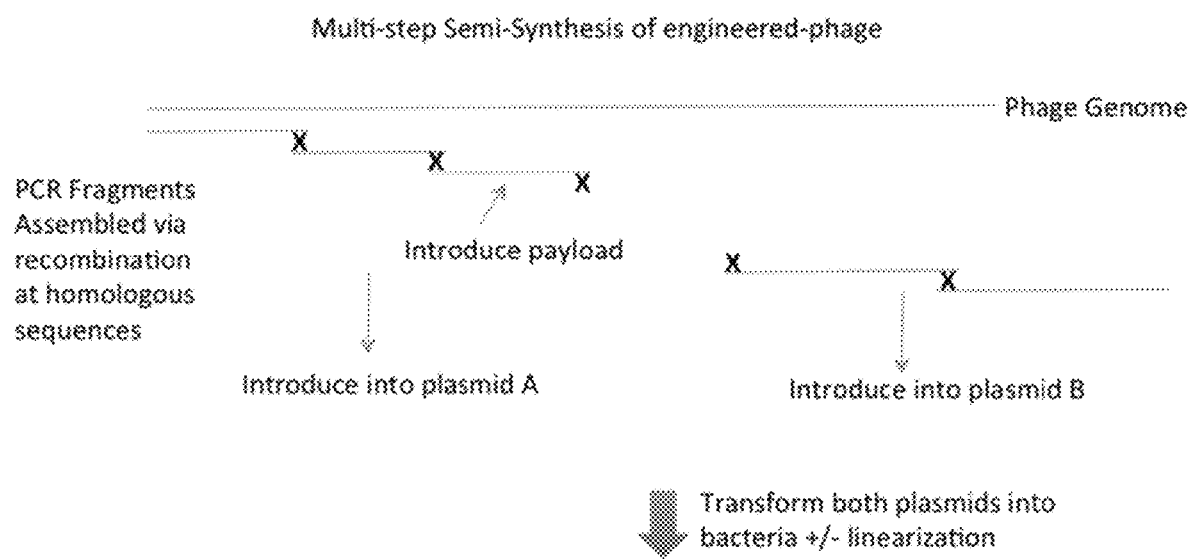
FIG. 2 shows a scheme for integrating a heterologous nucleic acid sequence into a bacteriophage genome via semi-synthesis.
Figure 3:
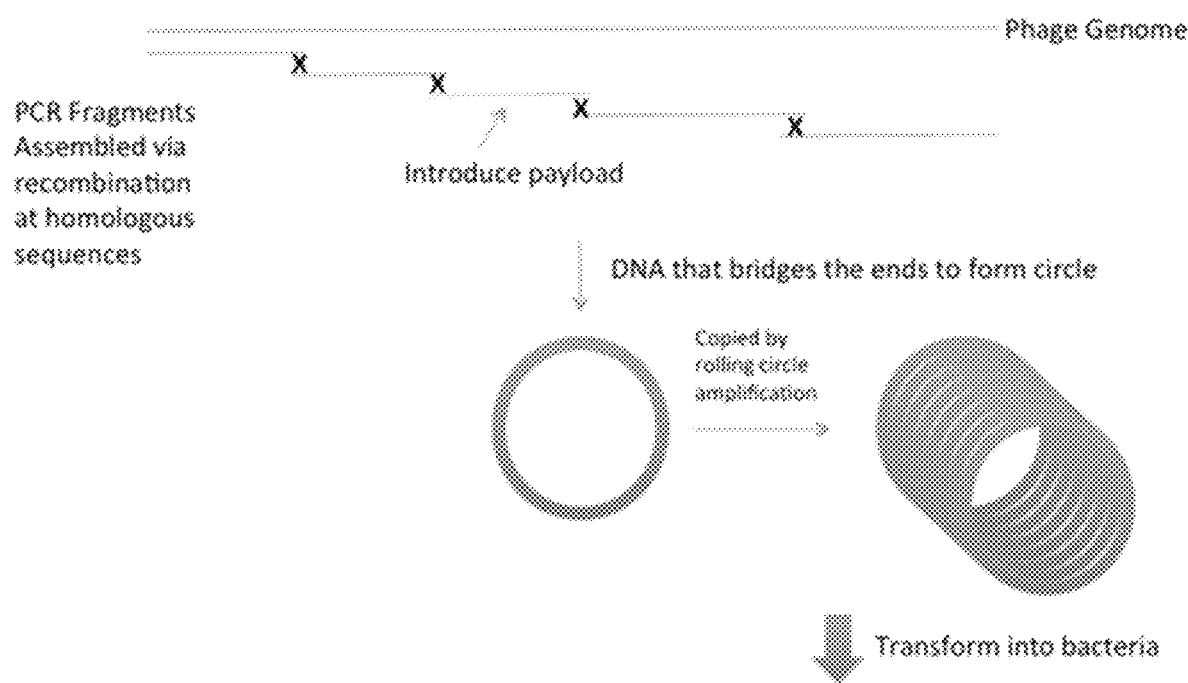
FIG. 3 shows a scheme for integrating a heterologous nucleic acid sequence into a bacteriophage genome via semi-synthesis.
Figure 4:
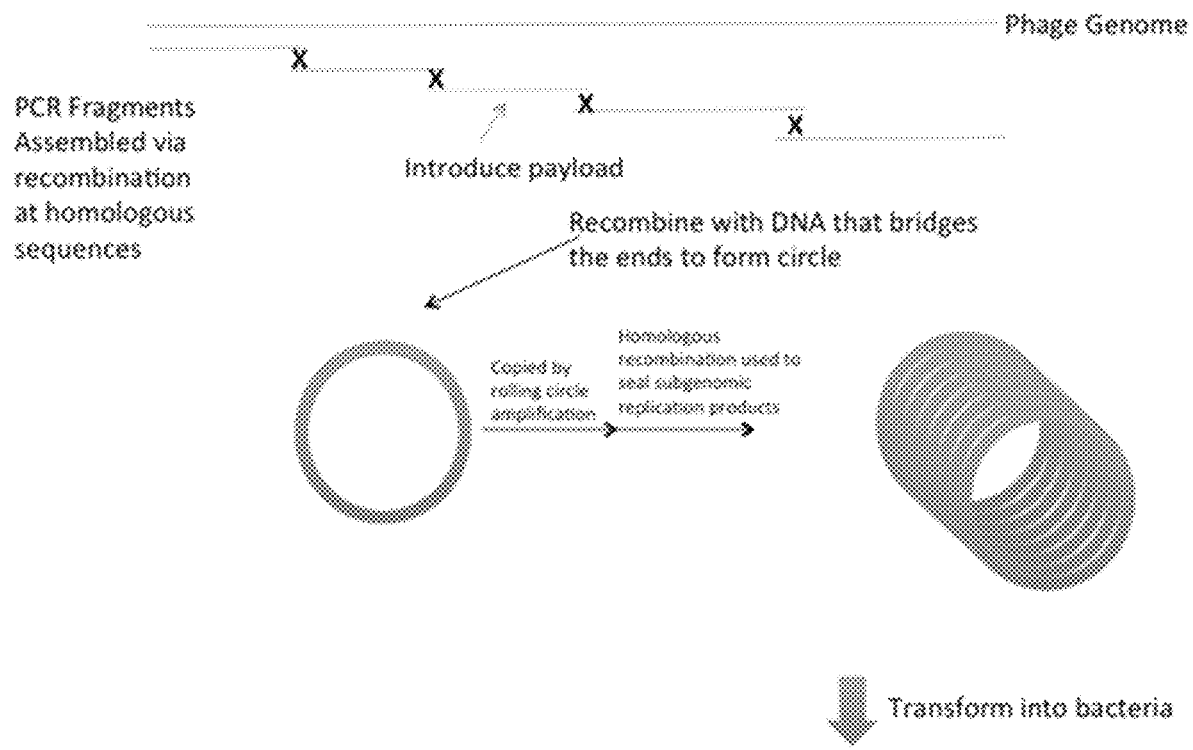
FIG. 4 shows a scheme for integrating a heterologous nucleic acid sequence into a bacteriophage genome via semi-synthesis.

Additionally or alternatively, in some embodiments, the plurality of semi-synthetic recombinant bacteriophage genomes are further subjected to in vitro homologous recombination so as to seal subgenomic replication products (See FIG. 4). In some embodiments, the method further comprises propagating the plurality of semi-synthetic recombinant bacteriophage genomes in a non-natural or natural bacterial host cell.

In any of the above embodiments of the methods disclosed herein, the homologous 5' flanking region of the heterologous nucleic acid has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Additionally or alternatively, in any of the above embodiments of the methods disclosed herein, the homologous 3' flanking region of the heterologous nucleic acid has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Additionally or alternatively, in any of the above embodiments of the methods disclosed herein, the in vitro recombination system comprises a 5'-3' exonuclease, a DNA polymerase, and a DNA ligase. In one embodiment, the 5'-3' exonuclease is T5 exonuclease, the DNA polymerase is Phusion® DNA polymerase (Thermo Fisher Scientific, Waltham, MA), and the DNA ligase is Taq ligase. In other embodiments, the in vitro recombination system comprises a 3'-5' exonuclease, a DNA polymerase, and a DNA ligase.

Additionally or alternatively, in any of the above embodiments of the methods disclosed herein, the non-natural or natural bacterial host cell may comprise a non-endogenous inducible recombination system. In some embodiments of the methods disclosed herein, the non-endogenous inducible recombination system comprises lambda Red proteins Gam, Exo, and Beta operably linked to an inducible promoter, RecET (RecE, RecT) operons operably linked to an inducible promoter, or RecA recombinase or a RecA gain-of-function variant operably linked to an inducible promoter. Additionally or alternatively, in certain embodiments of the methods disclosed herein, the inducible promoter is araB and the non-endogenous inducible recombination system is induced by the addition of arabinose.

Accurate identification of bacterial species within a biological sample informs the selection of suitable therapies for treating bacterial infections. Recombinant bacteriophage generated using the methods disclosed herein, may be used to identify bacteria present within a biological sample (e.g., whole blood, plasma, serum). Such methods entail contacting the biological sample with a recombinant bacteriophage generated using the methods disclosed herein, and detecting the presence of bacterial host cells infected by the recombinant phage, wherein the recombinant phage comprises a heterologous nucleic acid that encodes a detectable gene product, thereby leading to the identification of bacteria present within the biological sample.

Additionally or alternatively, recombinant bacteriophage generated using the methods disclosed herein, may be used in methods for profiling antibiotic susceptibility of bacteria present within a biological sample (e.g., whole blood, plasma, serum). These methods include (a) contacting the biological sample with an antibiotic and a recombinant bacteriophage generated using the methods disclosed herein, (b) detecting the presence of bacterial host cells infected by the recombinant phage, wherein the recombinant phage comprises a heterologous nucleic acid that encodes a detectable gene product, and (c) determining that the antibiotic is effective in inhibiting the bacteria present in the biological sample when the number of recombinant phage infected bacterial host cells is reduced relative to that observed in an untreated control sample.

Heterologous Nucleic Acids

In any of the above embodiments of the methods disclosed herein, the heterologous nucleic acid comprises an open reading frame that encodes a bioluminescent protein, a fluorescent protein, a chemiluminescent protein, a phage protein that modifies host range, or any combination thereof. In some embodiments, the encoded gene product(s) produces a detectable signal upon exposure to the appropriate stimuli, and the resulting signal permits detection of bacterial host cells infected by the recombinant phage. In certain embodiments, the open reading frame encodes a protein that serves as a marker that can be identified by screening bacterial host cells infected by a recombinant phage comprising a heterologous nucleic acid sequence comprising the open reading frame. Examples of such markers include by way of example and without limitation: a fluorescent label, a luminescent label, a chemiluminescence label, or an enzymatic label. In some embodiments, the heterologous nucleic acid sequence further comprises sequences naturally found in the bacteriophage, but placed at a non-normally occurring location in the genome. Additionally or alternatively, in some embodiments, the phage protein that modifies host range is a tail spike protein (e.g., gp11, gp12, and gp17) or a structural phage virion protein that is involved with bacterial cell attachment or degradation of bacterial cell wall components.

In some embodiments of the methods disclosed herein, the length of the heterologous nucleic acid sequence is at least 100 bases, at least 200 bases, at least 300 bases, at least 400 bases, at least 500 bases, at least 600 bases, at least 700 bases, at least 800 bases, at least 900 bases, at least 1 kilobase (kb), at least 1.1 kb, at least 1.2 kb, at least 1.3 kb, at least 1.4 kb, at least 1.5 kb, at least 1.6 kb, at least 1.7 kb, at least 1.8 kb, at least 1.9 kb, at least 2.0 kb, at least 2.1 kb, at least 2.2 kb, at least 2.3 kb, at least 2.4 kb, at least 2.5 kb, at least 2.6 kb, at least 2.7 kb, at least 2.8 kb, at least 2.9 kb, at least 3.0 kb, at least 3.1 kb, at least 3.2 kb, at least 3.3 kb, at least 3.4 kb, at least 3.5 kb, at least 3.6 kb, at least 3.7 kb, at least 3.8 kb, at least 3.9 kb, at least 4.0 kb, at least 4.5 kb, at least 5.0 kb, at least 5.5 kb, at least 6.0 kb, at least 6.5 kb, at least 7.0 kb, at least 7.5 kb, at least 8.0 kb, at least 8.5 kb, at least 9.0 kb, at least 9.5 kb, at least 10 kb, or more. In certain embodiments, the heterologous nucleic acid sequence comprises a length that is less than or equal to a length selected from the group consisting of 1 kb, 2 kb, 3 kb, 4 kb, 5 kb, 6 kb, 7 kb, 8 kb, 9 kb, and 10 kb. In some embodiments, the heterologous nucleic acid sequence comprises a length that is less than or equal to the maximum length of heterologous nucleic acid sequence that can be packaged into a phage particle comprising the phage genome.

In some embodiments, the length of the heterologous nucleic acid sequence is from 100 to 500 bases, from 200 to 1,000 bases, from 500 to 1,000 bases, from 500 to 1,500 bases, from 1 kb to 2 kb, from 1.5 kb to 2.5 kb, from 2.0 kb to 3.0 kb, from 2.5 kb to 3.5 kb, from 3.0 kb to 4.0 kb, from 3.5 kb to 4.5 kb, from 4.0 kb to 5.0 kb, from 4.5 kb to 5.5 kb, from 5.0 kb to 6.0 kb, from 5.5 kb to 6.5 kb, from 6.0 kb to 7.0 kb, from 6.5 kb to 7.5 kb, from 7.0 kb to 8.0 kb, from 7.5 kb to 8.5 kb, from 8.0 kb to 9.0 kb, from 8.5 kb to 9.5 kb, or from 9.0 kb to 10.0 kb.

In some embodiments, the heterologous nucleic acid sequence is inserted into the phage genome with no loss of endogenous phage genomic sequence. In some embodiments, the heterologous nucleic acid sequence replaces an endogenous phage genomic sequence. In some embodiments, the heterologous nucleic acid sequence includes an endogenous phage genomic sequence that was previously excised from the phage genome.

In certain embodiments, the heterologous nucleic acid sequence replaces an endogenous phage genomic sequence that is less than the length of the heterologous nucleic acid sequence. Accordingly, in some embodiments, the length of the recombinant phage genome is longer than the length of the wild-type phage genome. In some embodiments, the heterologous nucleic acid sequence replaces an endogenous phage genomic sequence that is greater than the length of the heterologous nucleic acid sequence. Thus, in some embodiments, the length of the recombinant phage genome is shorter than the length of the wild-type phage genome. In certain embodiments, the heterologous nucleic acid sequence replaces an endogenous phage genomic sequence that is equal to the length of the heterologous nucleic acid sequence.

In certain embodiments, the open reading frame of the heterologous nucleic acid encodes a protein that confers a phenotype of interest on a host cell infected by a recombinant phage expressing the heterologous nucleic acid. In some embodiments, the phenotype of interest is the expression and/or activity of the gene product encoded by the open reading frame of the heterologous nucleic acid.

In certain embodiments, the open reading frame of the heterologous nucleic acid is operably linked to an expression control sequence that is capable of directing expression of the open reading frame, wherein the open reading frame encodes a bioluminescent protein, a fluorescent protein, a chemiluminescent protein, a phage protein that modifies host range, or any combination thereof. In some embodiments, the expression control sequence is located within the heterologous nucleic acid sequence. In other embodiments, the expression control sequence is located in the endogenous phage genome sequence. For example, the open reading frame may be inserted into the phage genome downstream of or in the place of an endogenous phage open reading frame sequence. In some embodiments, the expression control sequence is an inducible promoter or a constitutive promoter (e.g., sarA promoter or lpp promoter). See e.g., Djordjevic & Klaenhammer, *Methods in Cell Science* 20(1): 119-126 (1998). The inducible promoter or constitutive promoter may be an endogenous phage promoter sequence, a non-endogenous phage promoter sequence, or a bacterial host promoter sequence. Additionally or alternatively, in some embodiments, the inducible promoter is a pH-sensitive promoter, or a temperature sensitive promoter.

In some embodiments, the heterologous nucleic acid sequence comprises a first open reading frame and at least one supplemental open reading frame. In certain embodiments, the first and the at least one supplemental open reading frames are operably linked to the same expression control sequences. In some embodiments, the first and the at least one supplemental open reading frames are operably linked to different expression control sequences.

Fluorescent proteins include but are not limited to blue/UV fluorescent proteins (for example, TagBFP, Azurite, EBFP2, mKalama1, Sirius, Sapphire, and T-Sapphire), cyan fluorescent proteins (for example, ECFP, Cerulean, SCFP3A, mTurquoise, monomeric Midoriishi-Cyan, TagCFP, and mTFP1), green fluorescent proteins (for example, EGFP, Emerald, Superfolder GFP, Monomeric Azami Green, TagGFP2, mUKG, and mWasabi), yellow fluorescent proteins (for example, EYFP, Citrine, Venus, SYFP2, and TagYFP), orange fluorescent proteins (for example, Monomeric Kusabira-Orange, mKOκ, mKO2, mOrange, and mOrange2), red fluorescent proteins (for example, mRaspberry, mCherry, dsRed, mStrawberry, mTangerine, tdTomato, TagRFP, TagRFP-T, mApple, and mRuby), far-red fluorescent proteins (for example, mPlum, HcRed-Tandem, mKate2, mNeptune, and NirFP), near-IR fluorescent proteins (for example, TagRFP657, IFP1.4, and iRFP), long stokes-shift proteins (for example, mKeima Red, LSS-mKate1, and LSS-mKate2), photoactivatable fluorescent proteins (for example, PA-GFP, PAmCherry1, and PATagRFP), photoconvertible fluorescent proteins (for example, Kaede (green), Kaede (red), KikGR1 (green), KikGR1 (red), PS-CFP2, PS-CFP2, mEos2 (green), mEos2 (red), PSmOrange, and PSmOrange), fluorescein, rhodamine, and photoswitchable fluorescent proteins (for example, Dronpa).

Examples of bioluminescent proteins are aequorin (derived from the jellyfish *Aequorea victoria*) and luciferases (including luciferases derived from firefly and *Renilla*, nano-luciferase, red luciferase, luxAB, and the like). These proteins have also been genetically separated into two distinct functional domains that will generate light only when the protein domains are closely co-localized. A variety of emission spectrum-shifted mutant derivatives of both of these proteins have been generated over the past decade and have been used for multi-color imaging and co-localization within a living cell.

Examples of chemiluminescent protein include β-galactosidase, horseradish peroxidase (HRP), and alkaline phosphatase. Peroxidases generate peroxide that oxidizes luminol in a reaction that generates light, whereas alkaline phosphatases remove a phosphate from a substrate molecule, destabilizing it and initiating a cascade that results in the emission of light.

In some embodiments, the open reading frame of the heterologous nucleic acid comprises an epitope that can be detected with an antibody or other binding molecule. For example, an antibody that recognizes the epitope may be directly linked to a signal generating moiety (such as by covalent attachment of a chemiluminescent or fluorescent protein), or can be detected using at least one additional binding reagent such as a secondary antibody, directly linked to a signal generating moiety. In some embodiments, the epitope is absent in wild-type bacteriophage and the bacterial host cell. Accordingly, detection of the epitope in a sample demonstrates the presence of a bacterial host cell infected by a recombinant phage comprising a heterologous nucleic acid, wherein the open reading frame of the heterologous nucleic acid comprises the epitope.

In other embodiments, the open reading frame of the heterologous nucleic acid comprises a polypeptide tag sequence, such that the expression product of the open reading frame comprises the tag fused to a polypeptide or protein encoded by the open reading frame (e.g., poly-histidine, FLAG, Glutathione S-transferase (GST) etc.).

In some embodiments, the open reading frame of the heterologous nucleic acid sequence comprises a biotin binding protein such as avidin, streptavidin, or neutrAvidin that can be detected with a biotin molecule conjugated to an enzyme (e.g., β-galactosidase, horseradish peroxidase (HRP), and alkaline phosphatase) or an antibody. In some embodiments, the antibody conjugated to a biotin molecule may be directly linked to a signal generating moiety (such as by covalent attachment of a chemiluminescent or fluorescent protein), or can be detected using at least one additional binding reagent such as a secondary antibody, directly linked to a signal generating moiety.

Kits

The present technology provides kits for integrating a heterologous nucleic acid sequence into a bacteriophage genome.

In one aspect, the kits of the present technology comprise (a) one or more coded/labeled vials that contain a plurality of bacteriophage genomes, (b) a plurality of primer pairs that are useful for producing a plurality of amplicons that collectively span the entire length of a bacteriophage genome, wherein each amplicon is no more than 15 kilobases in length and (c) a non-endogenous recombination system.

In some embodiments of the kits, each coded/labeled vial containing a plurality of bacteriophage genomes corresponds to a different bacteriophage type. In other embodiments, each coded/labeled vial containing a plurality of bacteriophage genomes corresponds to the same bacteriophage type. In some embodiments, each phage vial is assigned a unique code that identifies the bacteriophage in the phage vial, or the types of bacteria that the bacteriophage strain infects. The unique code can be encoded by a machine discernible pattern, such as a bar code, a QR code, an alphanumeric string, or any other pattern that can be discerned by a reader. Each unique code may be shown as, for example, a bar code sticker on a vial or container storing a corresponding phage sample. In some embodiments, the kit is stored under conditions that permit the preservation of the bacteriophage genomes for extended periods, such as under bacteriophage-specific, controlled temperature, moisture, and pH conditions.

Additionally or alternatively, in some embodiments of the kits disclosed herein, the plurality of primer pairs may comprise one or more of SEQ ID NO: 3 and SEQ ID NO: 4; SEQ ID NO: 5 and SEQ ID NO: 6; SEQ ID NO: 7 and SEQ ID NO: 8; SEQ ID NO: 9 and SEQ ID NO: 10; SEQ ID NO: 11 and SEQ ID NO: 12; SEQ ID NO: 15 and SEQ ID NO: 16; SEQ ID NO: 17 and SEQ ID NO: 18; SEQ ID NO: 19 and SEQ ID NO: 20; and SEQ ID NO: 21 and SEQ ID NO: 22.

Additionally or alternatively, in some embodiments, the kits comprise a non-endogenous recombination system that includes a 5'-3' exonuclease, a DNA polymerase, and a DNA ligase. For example, in one embodiment, the 5'-3' exonuclease is T5 exonuclease, the DNA polymerase is Phusion® DNA polymerase (Thermo Fisher Scientific, Waltham, MA), and the DNA ligase is Taq ligase. In other embodiments, the kits comprise a non-endogenous recombination system that includes a 3'-5' exonuclease, a DNA polymerase, and a DNA ligase.

Additionally or alternatively, in some embodiments, the kits further comprise vials containing natural or non-natural bacterial host cells. In some embodiments, the bacterial host cells are E. coli. In certain embodiments, the bacterial host cells are E. coli strain DH10β.

In some embodiments, the kits further comprise positive control heterologous nucleic acid sequences to correct for any variability in the recombination systems between experimental runs. The kits may also comprise instructions for use, software for automated analysis, containers, packages such as packaging intended for commercial sale and the like.

The kit may further comprise one or more of: wash buffers and/or reagents, hybridization buffers and/or reagents, labeling buffers and/or reagents, and detection means. The buffers and/or reagents are usually optimized for the particular detection technique for which the kit is intended. Protocols for using these buffers and reagents for performing different steps of the procedure may also be included in the kit. Further optional components of the kits may include expression media for gene products encoded by the heterologous nucleic acids disclosed herein, such as a medium containing nutrients and cofactors for bioluminescence, devices such as a lamp configured to illuminate at specific wavelengths of light to detect biofluorescence, and devices for measuring the extent of heterologous nucleic acid expression, such as a photometer or photodetector.

Additionally or alternatively, the kits disclosed herein may also include coded and labeled vials that contain a plurality of antibiotics.

EXAMPLES

Example 1: Phage Engineering Methods of the Present Technology in *Klebsiella* Bacteriophage K11

This Example demonstrates that the methods of the present technology are useful for integrating a heterologous nucleic acid into a bacteriophage genome (e.g., *Klebsiella* bacteriophage K11) and for isolating recombinant bacteriophages that express the heterologous nucleic acid sequence.

Semisynthesis of *Klebsiella pneumoniae* Phage K11.

A culture of *Klebsiella pneumoniae* 390 was inoculated with K11 phage, and allowed to lyse. K11 phage gDNA was purified from the phage lysate using the ZR Viral DNA/RNA Kit™ (Zymo Research Corp., Irvine, CA), and was used as a template for semi-synthesis of the recombinant nanoluciferase K11 phage.

Design of the Semi-Synthetic K11-nanoluciferase Heterologous Nucleic Acid Insert.

A construct comprising a Shine Dalgarno site and the nanoluciferase gene was designed such that it would be inserted downstream of ORF11, at position 23,431 of the K11 phage genome. PCR was used to generate 5 DNA fragments, which were subsequently fused via Gibson assembly. The oligonucleotides that were used are listed below.

| Oligonucleotide Sequences | Identity of Individual Fragments |
|---|---|
| Fragment 1 (13,567 bp)<br>MTR50: 5'<br>GTTGATGTCTCTGTGTCCCTTTAATTAATCT<br>CACAGTTTACACTTTTGGT 3' (SEQ ID NO: 3)<br>MTR53: 5'<br>TAATGTCCTCTCAATATGTTGTGTGT 3'<br>(SEQ ID NO: 4) | Fragment 1: (K11 genome bp 41,162 to bp 41,181) +<br>(PacI site) + (K11 genome bp 1 to bp 13,539) |
| Fragment 2 (9,974 bp)<br>MTR54: 5'<br>AACTCAAGGTCATTACTATATGTAGT 3'<br>(SEQ ID NO: 5)<br>MTR68: 5'<br>ATTGTATACCTCCTATTAACGACCGATGAG<br>ACCCTG 3' (SEQ ID NO: 6) | Fragment 2: (K11 genome bp 13,473 to bp 23,431) +<br>(RBS) + (Nanoluc bp 1 to bp 2) |
| Fragment 3 (559 bp: luciferase insert)<br>MTR69: 5'<br>CTCATCGGTCGTTAATAGGAGGTATACAAT<br>GGTCTTCACAC 3' (SEQ ID NO: 7)<br>MTR70: 5'<br>TCCTTAAGTTTCTGATTACGCCAGAATGCG<br>TTCGC 3' (SEQ ID NO: 8) | Fragment 3: (K11 genome bp 23,416 to bp 23,431) +<br>(RBS) + (NanoLuc ®) + (K11 genome bp 23,428 to bp 23,445) |
| Fragment 4 (9,807 bp)<br>MTR71: 5'<br>CGCATTCTGGCGTAATCAGAAACTTAAGGA<br>GGACCA 3' (SEQ ID NO: 9)<br>MTR57: GTGACCTCCTTTAGTTGAATGAGA<br>(SEQ ID NO: 10) | Fragment 4: (NanoLuc ® bp 515-529) + (K11 genome bp 23,431 to bp 33,451) |
| Fragment 5 (8020 bp)<br>MTR58: 5' AGGACACACTATAGGGAGAC3'<br>(SEQ ID NO: 11)<br>MTR59: 5' AGGGACACAGAGACATCAACA<br>3' (SEQ ID NO: 12) | Fragment 5: (K11 genome bp 33,162 to bp 41,181) |

The PCR fragments were produced using Q5® Hot Start High-Fidelity 2X Mastermix (NEB, Ipswich, MA) according to the manufacturer's protocol. The PCR thermocycling conditions are provided below:

| Component | 25 µl Reaction | Final Concentration |
|---|---|---|
| Q5 High-Fidelity 2X Master Mix | 12.5 µl | 1X |
| 10 µM Forward Primer | 1.25 µl | 0.5 µM |
| 10 µM Reverse Primer | 1.25 µl | 0.5 µM |
| Template DNA | Variable (~1 ng) | variable |
| Nuclease-Free Water | to 25 µl | |
| Initial Denaturation | 98° C. | 30 seconds |
| 30 Cycles | 98° C. | 10 seconds |
| | 52°-72° gradient | 15 seconds |
| | 72° C. | 45 seconds/kb |
| Final Extension | 72° C. | 2 minutes |

Figure 5:
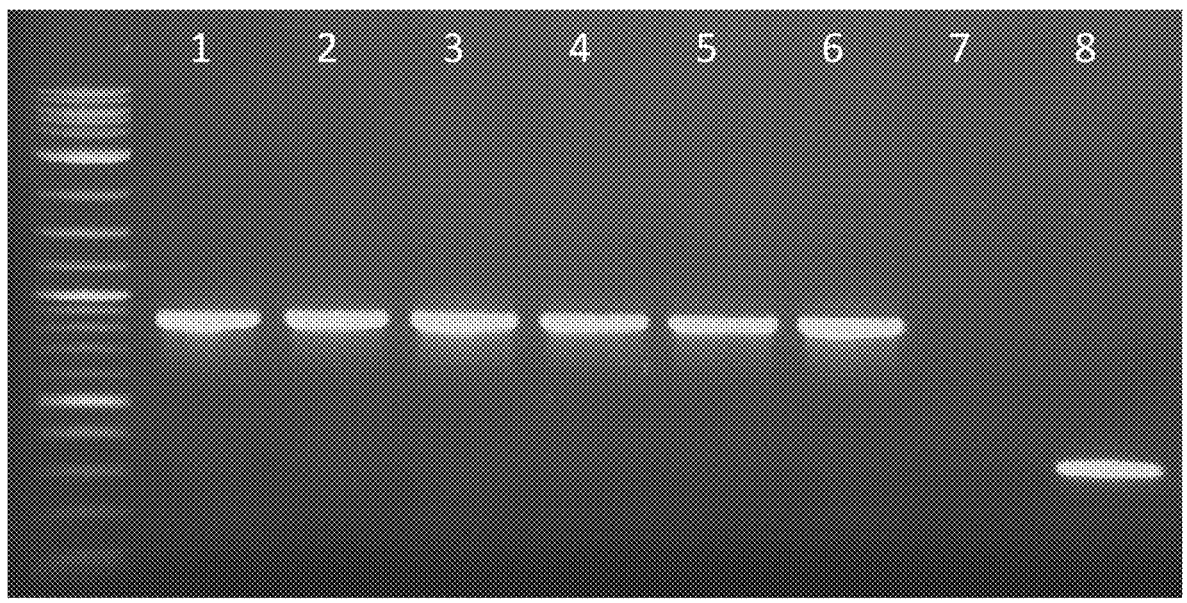
FIG. 5 shows the recovery of recombinant K11 bacteriophage containing a heterologous nanoluciferase nucleic acid sequence using the methods of the present technology. PCR screening was conducted using primers that flank the location of the nanoluciferase insertion. Lanes 1-6 correspond to recombinant nanoluciferase K11 phage which yield a 865 base pair (bp) amplicon, whereas the wild-type phage yield a 336 bp amplicon (lane 8). Lane 7 corresponds to *K. pneumoniae* 390 (no phage template control).

The expected fragment mass was verified by agarose gel electrophoresis through a 0.7% (w/v) agarose gel in 0.5× TBE at 200V for 2 hours, alongside HindIII-digested phage lambda DNA ladder or 1 kb DNA ladder where appropriate (FIG. 5). The PCR fragments were purified by phenol:chloroform:isopropyl alcohol extraction, and quantified by Nanodrop. The fragments (0.1 pmol each) were assembled using the NEB HiFi Assembly kit (NEB, Ipswich, MA), according to the manufacturer's instructions. The reactions were performed in triplicate. The reactions were then pooled, purified by phenol:chloroform:isopropyl alcohol extraction and quantified. Commercially available competent cells NEB10β (NEB, Ipswich, MA) were transformed by electroporation with 2 µg assembled phage DNA and 5 µg salmon sperm competitor DNA. Cells (50 µl) were transformed in a 2-mm cuvette at 2.4 kV, 600 Ω, 25 µF, and were allowed to recover in SOC media for 2 hours at 37° C. with shaking. The cells were then pelleted by centrifugation, and the supernatant was recovered. The supernatant was added to 3 ml top agar with 100 µl of an overnight culture of *K. pneumoniae* 390, and poured onto an LB plate. The plates were incubated overnight.

Characterization of Recombinant K11-nanoluciferase Phage.

The next day, six plaques were picked from the plates and tested for the presence of the nanoluciferase gene using primers that flank the nanoluciferase insertion site, compared with wild-type K11 phage. Flanking forward primer: 5' GAGATGCCTGAGTGTTTCCG 3' (SEQ ID NO: 13); Flanking reverse primer: 5' GACCAACCGTTGACCTGAAG 3' (SEQ ID NO: 14).

Results.

Figure 6:
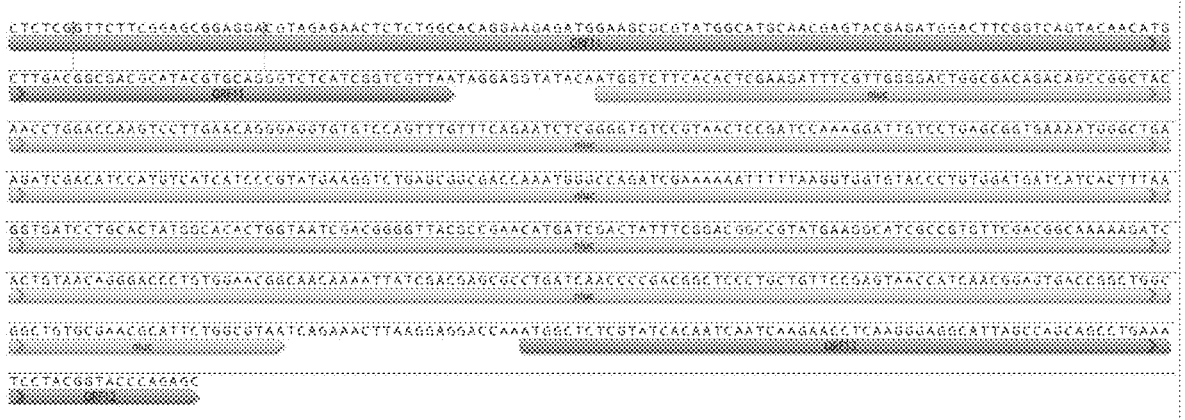
FIG. 6 shows the sequence corresponding to the nanoluciferase insertion within a recombinant K11 phage genome.

The PCR products from the recombinant phage templates displayed the expected increase in amplicon size to account for the additional nanoluciferase gene insertion (FIG. 5), whereas the wild-type fragment had a lower amplicon size. One of the recombinant K11 phages was selected for further testing, and the presence of the nanoluciferase gene along with the flanking regions was verified by sequencing (FIG. 6). FIGS. 13(a)-13(m) show the complete genome sequence of the recombinant NanoLuc® K11 phage.

Figure 7:
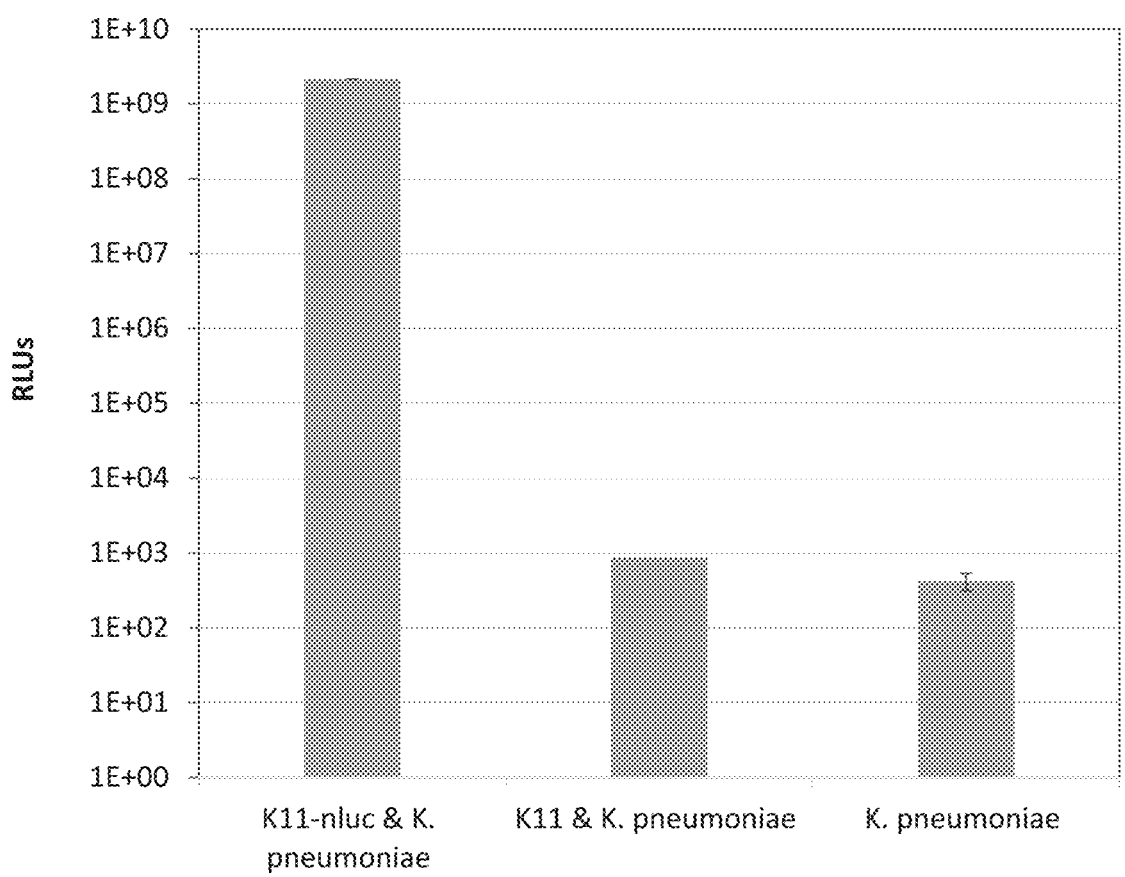
FIG. 7 shows the luminescence activity profile of a recombinant nanoluciferase K11 phage. *K. pneumoniae* 390 was inoculated with recombinant K11-nanoluciferase phage, wild-type K11 phage, or no phage, and luminescence was assessed. Relative luminescence units (RLUs) were plotted on a log scale.

To assess luminescence production of the recombinant K11 phage, *K. pneumoniae* 390 was inoculated with the selected recombinant phage, wild-type K11 phage, or a phage-free control supernatant, and was grown for 1 hour. Luminescence was measured using the Promega luciferase kit (Promega, Madison, WI). As shown in FIG. 7, only bacterial samples infected with recombinant nanoluciferase K11 phage were able to produce luminescence.

These results demonstrate that the methods of the present technology permit the efficient recovery of recombinant bacteriophage genomes that (a) contain a heterologous nucleic acid sequence of interest, and (b) express the phenotypic properties associated with the heterologous nucleic acid sequence of interest. Accordingly, the methods disclosed herein are useful for integrating heterologous nucleic acids into bacteriophage genomes to generate recombinant bacteriophage genomes.

Example 2: Phage Engineering Methods of the Present Technology in T7 Phage

This Example demonstrates that the methods of the present technology are useful for integrating a heterologous nucleic acid into a bacteriophage genome (e.g., *E. coli* bacteriophage T7) and for isolating recombinant bacteriophages that express the heterologous nucleic acid sequence.

T7 is a 39,937 bp, terminally redundant, lytic bacteriophage that infects numerous strains of *E. coli*. As a demonstration of the semi-synthesis methodology disclosed herein, the NanoLuc® luciferase gene was inserted into the non-essential gene 4.3 of the T7 genome.

Purified T7 genomic DNA was used as a template for semi-synthesis of the recombinant nanoluciferase T7 phage. The NanoLuc® gene with an upstream ribosome binding site was chemically synthesized by Integrated DNA Technologies (Coralville, IA). PCR was used to generate 4 DNA fragments, which were subsequently fused via Gibson assembly. The oligonucleotides that were used are listed below.

| Oligonucleotide Sequences | Identity of Individual Fragments |
|---|---|
| Fragment 1(13,436 bp) GA CM Frag 1 F: 5' TCTCACAGTGTACGGACCT 3' (SEQ ID NO: 15) 4.3 lumi Frag 2 R: 5' GTATATCTCCTCTGTTCAGTCGCTTGGCTTC CA 3' (SEQ ID NO: 16) | Fragment 1: (T7 genome bp 1 to bp 13,423) + (RBS bp 1 to bp 13) |
| Fragment 2 (556 bp: luciferase insert) 4.3 lumi F: 5' CAAGCGACTGAACAGAGGAGATATACAAT GGTCTTCACA 3' (SEQ ID NO: 17) 4.3 lumi R: 5' TACGAGCCTCATCTTACCATTCGCCATTCA GGCT 3' (SEQ ID NO: 18) | Fragment 2: (T7 genome bp 13,411 to bp 13,423) + (RBS) + (NanoLuc ®) + (T7 genome bp 13,423 to bp 13,436) The overlaps between pieces of the T7 genome and the RBS/NanoLuc ® insert were installed using primers that contained the desired 5' overhangs. |

| Oligonucleotide Sequences | Identity of Individual Fragments |
|---|---|
| Fragment 3 (13,268 bp)<br>4.3 lumi Frag 3 F: 5' TGGCGAATGGTAAGATGAGGCTCGTAAAG AGGCC 3' (SEQ ID NO: 19)<br>GA CM Frag 4 R: 5' TGAATGTGTCATCGTTGTATGTTCCACTAG GAATCGTG 3' (SEQ ID NO: 20) | Fragment 3: (NanoLuc ® bp 504 to bp 516) + (T7 genome bp 13,424 to bp 26,678)<br>The overlaps between pieces of the T7 genome and the RBS/NanoLuc ® insert were installed using primers that contained the desired 5' overhangs. |
| Fragment 4 (13,285 bp)<br>GA CM Frag 5 F: 5' TGGAACATACAACGATGACACATTCACTAC CTCT 3' (SEQ ID NO: 21)<br>GA CM Frag 6 R: 5' AGGGACACAGAGAGACACTCA 3' (SEQ ID NO: 22) | Fragment 4: (T7 genome bp 26,653 to bp 39,937) |

The PCR fragments were produced using Q5® Hot Start High-Fidelity 2X Mastermix (NEB, Ipswich, MA) according to the manufacturer's protocol. The PCR thermocycling conditions are provided below:

| Component | 25 µl Reaction | Final Concentration |
|---|---|---|
| Q5 High-Fidelity 2X Master Mix | 12.5 µl | 1X |
| 10 µM Forward Primer | 1.25 µl | 0.5 µM |
| 10 µM Reverse Primer | 1.25 µl | 0.5 µM |
| Template DNA | Variable (~1 ng) | variable |
| Nuclease-Free Water | to 25 µl | |
| Initial Denaturation | 98° C. | 30 seconds |
| 30 Cycles | 98° C. | 10 seconds |
| | 52°-72° gradient | 15 seconds |
| | 72° C. | 45 seconds/kb |
| Final Extension | 72° C. | 2 minutes |

The PCR products were purified by phenol: chloroform: isoamyl alcohol extraction followed by ethanol precipitation. The four fragments (0.125 pmol each) were added to an NEBuilder HiFi DNA Assembly Reaction (NEB, Ipswich, MA) and were incubated for 1 hour at 50° C. This Gibson assembly reaction uses an exonuclease to resect back the 5' end of DNA to expose compatible (sticky) ends found in the overlap regions. Next, a polymerase fills in any gaps and a ligase covalently joins the fragments.

The Gibson assembly reaction was purified by phenol: chloroform: isoamyl alcohol extraction followed by ethanol precipitation. A total of 1 µg of purified assembled DNA plus 5 µg of salmon sperm competitor DNA was transformed into NEB® 10-beta Electrocompetent E. coli via electroporation (2.4 kV, 200 Ω, 25 µF) and recovered in 950 µl of SOC for approximately 2 hours at 37° C. The cells were then pelleted by centrifugation, and the supernatant was recovered. Next, 100 µl of supernatant was plated on 3 mL of 0.65% LB top agar containing an overnight culture of E. coli and incubated at 37° C. overnight.

Characterization of Recombinant K11-nanoluciferase Phage.

Junctional PCR screening and flanking PCR screening of 15 potential T7-NanoLuc® plaques were carried out using a primer pair that spans from inside the nanoluciferase gene to a location in the T7 genome and a primer pair that spans the intended NanoLuc® insertion site, respectively. Amplification of a recombinant phage during junctional PCR screening produces an 1856 bp PCR product, whereas wild-type phage which lacks one of the primer binding sites will not form a product. Amplification of a recombinant phage during flanking PCR screening yields a 2792 bp amplicon in wild-type T7 phage and a 3322 bp amplicon in recombinant nanoluciferase T7 phage. For phenotypic analysis, plaques were picked into 20 µl of 10 mM Tris-HCl with 10 mM MgSO$_4$. 5 µl of each of these 'pickates' was used to infect 5 mL cultures of mid-log phase NEB10β cells for 1.5 hours. Luminescence was measured using the Promega luciferase kit (Promega, Madison, WI).

Results.

Out of 15 isolated plaques, isolates 1, 2, and 9 exhibited a luminescent phenotype. See FIG. 9. As shown in FIGS. 8(a) and 8(b), isolate #9 yielded a 1856 bp amplicon during junctional PCR, and a 3322 bp amplicon during flanking PCR, which is indicative of a recombinant NanoLuc® T7 phage. FIGS. 14(a)-14(l) show the complete genome sequence of the recombinant NanoLuc® T7 phage.

These results demonstrate that the methods of the present technology permit the efficient recovery of recombinant bacteriophage genomes that (a) contain a heterologous nucleic acid sequence of interest, and (b) express the phenotypic properties associated with the heterologous nucleic acid sequence of interest. Accordingly, the methods disclosed herein are useful for integrating heterologous nucleic acids into bacteriophage genomes to generate recombinant bacteriophage genomes.

Example 3: Comparison Against BAR 3.0 Phage Engineering Method

This Example demonstrates that the methods of the present technology are useful for integrating a heterologous nucleic acid into a bacteriophage genome (e.g., Klebsiella bacteriophage K11) and for isolating recombinant bacteriophages that express the heterologous nucleic acid sequence. Moreover, this Example demonstrates that the methods disclosed herein show superior efficiency with respect to recovering recombinant phage genomes compared to other phage engineering techniques, such as BAR 3.0.

The CRISPR/Cas system was used to cleave the K11 phage genome after gene 4.5 to create an insertion site for a nanoluciferase reporter sequence into the phage genome. The desired chimeric guide sequence was placed under the control of a T7 promoter (FIG. 10) and was transcribed using the NEB HiScribe T7 High Yield RNA Synthesis Kit (NEB E2040, Ipswich, MA). The resulting RNA product was purified using the Qiagen RNeasy Mini Kit (Qiagen 74104, Hilden Germany).

The Cas9 endonuclease from New England Biolabs (NEB M0386, Ipswich, MA) was complexed with the sgRNA using a modified protocol. Briefly, in a 27 μL volume, 30 nM of sgRNA was incubated with 30 nM of Cas9 endonuclease. NEBuffer 3.1 was used instead of the included Cas9 Nuclease Reaction buffer. After a 10 minute preincubation at 25° C., 2.3 μg of K11 genomic DNA was added to the reaction to achieve a final concentration of 3 nM target DNA. The reaction was then incubated at 37° C. for 1 hr before adding an additional 3 nM Cas9 endonuclease. After incubation for another hour, 10 Units of RNase A (ThermoFisher EN0351, Waltham, MA) was added to the reaction mixture to degrade any remaining RNA.

After cleavage, the DNA was purified using phenol/chloroform precipitation. Cleavage of the K11 genomic DNA was verified using gel imaging. See FIG. 11.

A synthetic DNA construct containing 60 bp of homology to the K11 genome around the gene 4.5 cleavage site surrounding a nanoluciferase gene (FIG. 12) was introduced into the cleaved K11 phage genome using NEBuilder HiFi DNA assembly mix (NEB E5520, Ipswich, MA) according to the manufacturer's protocol. Briefly, 4 μg of cleaved K11 DNA was mixed with 90 ng of the NanoLuc®/K11 homology construct. The reaction was incubated at 50° C. for 60 minutes.

The reaction was subsequently purified using phenol/chloroform precipitation and 1 μg of the reaction product was electroporated into competent *Klebsiella pneumoniae* Sp 390 using the following electroporation settings: 200Ω resistance, 25 μF capacitance, and 2.4 kV. After electroporation, 400 μl of SOC broth was added to the cultures and cells were allowed to recover for one hour at 37° C. with shaking. Cells were then plated on a 0.65% soft agar overlay on an LB plate and incubated overnight at 37° C. Plaque formation was evaluated the following day. As shown in the Table below, no recombinant K11 bacteriophage were recovered using the BAR 3.0 protocol.

| | Electroplaquing Results for Cas9 cleaved K11 and recombined K11/nanoluciferase | | |
|---|---|---|---|
| | 60 ng K11 DNA (uncleaved control) | 60 ng cleaved K11 DNA | 1 μg recombinant K11 phage with nanoluciferase insert |
| Pfu/ml | 2.00E+08 | 0 | 0 |

These results demonstrate that the methods disclosed herein show superior efficiency with respect to recovering recombinant phage genomes compared to other phage engineering techniques, such as BAR 3.0. These results demonstrate that the methods of the present technology permit the efficient recovery of recombinant bacteriophage genomes that (a) contain a heterologous nucleic acid sequence of interest, and (b) express the phenotypic properties associated with the heterologous nucleic acid sequence of interest. Accordingly, the methods disclosed herein are useful for integrating heterologous nucleic acids into bacteriophage genomes to generate recombinant bacteriophage genomes.

Example 4: Variations of Semi-Synthetic Phage Generation Methods

The complete recombinant genome of *Klebsiella pneumoniae* phage K11 DNA will be generated via semi-synthesis using the oligonucleotides and PCR conditions provided in Example 1.

In one example, the recombinant linear bacteriophage genome will be recombined in vitro with a DNA bridge in the presence of a recombination system under conditions to produce a recombinant circular bacteriophage genome (e.g., NEB HiFi Assembly kit (NEB, Ipswich, MA) according to the manufacturer's instructions). The recombinant circular bacteriophage genome will be amplified using rolling circle amplification to generate a plurality of semi-synthetic recombinant bacteriophage genomes, which will then be transformed by electroporation into competent bacterial host cells. Alternatively, the plurality of semi-synthetic recombinant bacteriophage genomes may be further subjected to in vitro homologous recombination (e.g., NEB HiFi Assembly kit (NEB, Ipswich, MA) according to the manufacturer's instructions) so as to seal subgenomic replication products prior to transforming the same into competent bacterial host cells.

Accordingly, the methods disclosed herein are useful for integrating heterologous nucleic acids into bacteriophage genomes to generate recombinant bacteriophage genomes.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A method for generating a recombinant *Klebsiella* phage K11 bacteriophage genome comprising:
   (a) generating a plurality of PCR fragments that are no more than 15 kilobases in length from a template comprising a first *Klebsiella* phage K11 bacteriophage DNA genome using polymerase chain reaction (PCR), wherein the plurality of PCR fragments collectively span the entire length of the first *Klebsiella* phage K11 bacteriophage DNA genome, wherein at least one end of each PCR fragment comprises a sequence that is homologous to an opposite end of another PCR fragment and wherein each PCR fragment is no more than 15 kilobases in length; and
   (b) recombining in vitro the plurality of PCR fragments with a heterologous nucleic acid in the presence of a recombination system under conditions to produce a recombinant *Klebsiella* phage K11 bacteriophage genome, wherein the recombinant *Klebsiella* phage K11 bacteriophage genome comprises the nucleic acid sequence of SEQ ID NO: 23.

2. The method of claim 1, wherein the plurality of PCR fragments were generated using one or more primer pairs selected from the group consisting of SEQ ID NO: 3 and SEQ ID NO: 4; SEQ ID NO: 5 and SEQ ID NO: 6; SEQ ID NO: 7 and SEQ ID NO: 8; SEQ ID NO: 9 and SEQ ID NO: 10; and SEQ ID NO: 11 and SEQ ID NO: 12.

3. A method for generating a recombinant *Enterobacteria* phage T7 bacteriophage genome comprising:
   (a) generating a plurality of PCR fragments that are no more than 15 kilobases in length from a template comprising a first *Enterobacteria* phage T7 bacteriophage DNA genome using polymerase chain reaction (PCR), wherein the plurality of PCR fragments collectively span the entire length of the first *Enterobacteria* phage T7 bacteriophage DNA genome, wherein at least one end of each PCR fragment comprises a sequence that is homologous to an opposite end of another PCR fragment and wherein each PCR fragment is no more than 15 kilobases in length; and
   (b) recombining in vitro the plurality of PCR fragments with a heterologous nucleic acid in the presence of a recombination system under conditions to produce a recombinant *Enterobacteria* phage T7 bacteriophage genome, wherein the recombinant *Enterobacteria* phage T7 bacteriophage genome comprises the nucleic acid sequence of SEQ ID NO: 2.

4. The method of claim 3, wherein the plurality of PCR fragments were generated using one or more primer pairs selected from the group consisting of SEQ ID NO: 15 and SEQ ID NO: 16; SEQ ID NO: 17 and SEQ ID NO: 18; SEQ ID NO: 19 and SEQ ID NO: 20; and SEQ ID NO: 21 and SEQ ID NO: 22.

5. The method of claim 3, wherein the heterologous nucleic acid comprises a 3' flanking region that is homologous to the 5' end of one PCR fragment from the plurality of PCR fragments and a 5' flanking region that is homologous to the 3' end of another PCR fragment from the plurality of PCR fragments.

6. The method of claim 3, further comprising propagating the recombinant bacteriophage genome in a non-natural or natural bacterial host.

7. The method of claim 1, wherein the heterologous nucleic acid comprises a 3' flanking region that is homologous to the 5' end of one PCR fragment from the plurality of PCR fragments and a 5' flanking region that is homologous to the 3' end of another PCR fragment from the plurality of PCR fragments.

8. The method of claim 1, further comprising propagating the recombinant bacteriophage genome in a non-natural or natural bacterial host.

\* \* \* \* \*

SEQUENCE LISTING

<160> NUMBER OF SEQ ID NOS: 25

<210> SEQ ID NO 1
<211> LENGTH: 41718
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

| | | | | | |
|---|---|---|---|---|---|
| tctcacagtt | tacacttttg | gttatccccc | cggtaccctc | cagttcaccc | aaagtaacct | 60 |
| agggtacccc | tctttacctt | tggtttaacc | ttgggtggta | ccttgggaat | cccttaggtg | 120 |
| ataccatatg | ttggggtaat | ggtgacctga | ggacactata | tgttgatgtc | tctgtgtccc | 180 |
| tatctgttgg | tactcattaa | gtcacacctc | aagtcgccac | ctgaggttag | accagaggta | 240 |
| accacctgag | gttatacctg | agaccatata | cctaaggtga | gctgactgct | cacgaggttc | 300 |
| accgtttgac | taacgtttag | cagtgactgt | tagtaggtca | cattaagaga | gtcggtgcta | 360 |
| ttagtaatag | cggtaagtat | ctcgtttagc | agtccctgag | acactgagag | cgggacaaga | 420 |
| gggtatcggt | gagtcatcac | tataagggct | attggtggtc | agtgtcaaca | ccataatcaa | 480 |
| ttaggacaca | ctatagggag | acacttaaag | tattactatg | agaccatcac | cataaagatc | 540 |
| actatcacta | taggtctaac | taaaagttta | actttaagtg | ttgacattca | gattccttta | 600 |
| tgagacatta | gcaaccgttg | agagacacaa | cgtcaccaac | gaccagacaa | taccacgagt | 660 |
| tatctggtta | gactgagggt | ctcaagtagt | catcaaccgg | acatacgaaa | gtggttgact | 720 |
| caacgatgaa | caagtagtaa | gatgtaccac | agattcacga | agcaccgctc | tttaacaata | 780 |
| tggattagtc | gctgatatgt | acaccatgac | attagtgttt | aactagtggt | tacattcagg | 840 |
| tctctggcaa | ggtacgtcct | gtcaccctga | gagtagccac | gatgataacc | actaacatcg | 900 |
| aggatacaca | gcatggaaat | cgtaatgcag | gcactgaacc | acggggtcat | tatgacgaca | 960 |
| gcacgggact | acaccggggc | caccaaatac | atggtgcaat | acggcttaca | gttcacggtg | 1020 |
| tttgactcgt | tccgtgaggc | actgcaagat | tacacagatt | tgcgtcaccc | atttcgcaag | 1080 |
| agtgtgggga | ctagcggtta | acgacaggtc | atccaagcgg | tggcctgaaa | gataaccact | 1140 |
| aactgaagga | tatacacgat | gattttcact | aaagagccag | caaataaagc | cttcgtattc | 1200 |
| gtaaccgctt | accgtggcta | tgagtcgctc | gaagttaacg | agaaggtcct | caagggtctc | 1260 |
| atccgcacca | ttaagaccta | tccgggtgct | tacggtaaca | tccgcgatga | gaatgttgtg | 1320 |
| ggatgcttca | aagaggctgg | catggagtac | gcaacggaag | agcgcacgct | caaggttgaa | 1380 |
| tgcaccgtta | acaagcggc | tgaactggcg | tggctggcat | gtaagaccta | ccatcaagac | 1440 |
| gctgtactag | tggttaactc | acagacccac | acagcctcct | tatggtctat | tgagaacgta | 1500 |
| ggggagtatc | ctcaggtata | cccacgcttg | aaagaggtgt | ctttaggtgg | tacgctgcaa | 1560 |
| caagttgatg | cacctaaggg | tgaatgctat | tcagtcatcg | acgggcaata | ctgggaggtg | 1620 |
| gcgtgatggt | tgactatggt | ctcacacaag | aacacttgaa | gttataccgc | acggccatgg | 1680 |
| catatggtgc | atcgttcggt | tactgtatgg | cccaactggc | ccagacctac | cgcacacgca | 1740 |
| aggtgatgta | tggtaaccct | gttcgtaatt | agtgtgtacg | ccctgattgt | cctgtacttt | 1800 |
| gtgcgggact | ttcgcaaggg | cctcaaggtg | cacaaagcat | cattcagtta | catgaagtgg | 1860 |
| ggcgtgttac | ctcgctttac | tgtacggcta | cctaatggcc | gctttaaggc | taacaaggta | 1920 |
| ggtatttct | atatcgcaac | ccattaacac | atcgcacata | aggaaacaac | caaatgaact | 1980 |

```
acaccgacat gcaagagcgc ttagacgtcg tccgtaacct gccaatctgt gaactcgaca    2040
agcgccagcc gctgctggta gcactcatgg cggacattgt gaacgctgag acgtccgatg    2100
gtgacgatac ggatagcggt tggggtctgg aacgtcagga ctactggcaa accctgaaga    2160
ttaaggccaa agatgctggg tttaacctgc tgggcaacgg tcacttcagc gcagcgttta    2220
agcacgagct gctaccgggt agggccatta aggttggctt taagaaagag gactcagggg    2280
ccgcatacgt ggcttctgc cggatgcacc aaggacgggg agggataccct aacgtctatc     2340 acgtagcgcg tcacgctggg tgctacacgg tggtacttga tgagctggaa ccgtgccagc    2400
gcagtgggaa cgatgagcac gagcactacg cagacctagc gtattacttt gtcgaaggtg    2460
aatcggaccc agcggactac tcggagggcg accagccgtt tattgagacg tgccaaatga    2520
ttcgcaagtt cttctacggg attgcgtcct ttgatatgca cagcggtaac atcatgttca    2580
ccaaggacgg caagccagtg attaccgacc cggtgtcatt ctcagcggac cgggaccggg    2640
agcctttctc actggaacct gaggacctgc tcgcagagat tgagcagata gcgcacgaca    2700
agatgatcga acgctgtaag cgcaacaagg ctaagcgtga cccgaacgga gagctgcgca    2760
tcgcacgccg taaggccaat aaggaacgtc gagcacgccg taaggcacac gctcggtggc    2820
gtaaggagcg cgagcgtatt aacgctgatg ccttaaagtt tgaccttgct aaaatcgagg    2880
agcgggtact agcgtggcaa atgggaccag gcctggcgat acaaatgggc aagccgttac    2940
cactcgacaa ctaccttcag ggtagactta tgggttaacg aggtgtatct taggtgtctc    3000
cgaacggtga ggcacccata gataaacttt atccacaaag aggcacacaa tgaacgcatt    3060
aaacattgca cgtaatgact tctccgagat tgaacttgct gctattccgt acaacatcct    3120
cagcgagcac tacggggaca agctggcacg tgagcagtta gcactggagc atgaagcgta    3180
cgagcttggc gaacaacgtt tcctgaagat gttagaacgt caggtgaaag ctggtgagtt    3240
cgctgacaac gcggccgcta agccgctggt cttaacgttg cacccacagc tgaccaagcg    3300
cattgacgac tggaaggagg agcaagcaaa cgctcgcgt aagaagcctc gcgcatacta     3360
cccgattaag cacggcgtcg cctcaaagtt agctgttagc atgggcgctg aggtgctaaa    3420
agagaagcgc ggagtgtcca gtgaggcaat cgcactgctg accattaagg tcgtcttggg    3480
gacgctcaca gacgcctcaa aggccacaat ccagcaggta tcctctcagt taggcaaggc    3540
tcttgaggat gaggcccgct tcggtcgtat ccgtgagcag gaagccgcat acttcaagaa    3600
gaacgtagcg gaccagctgg acaagcgagt aggccacgtg tacaagaagg ctttcatgca    3660
ggtagtcgag gccgatatga tatccaaagg gatgctgggc ggcgacaact gggcgagctg    3720
gaaaactgac gagcagatgc acgtagggac caagctgctg gagctactca ttgagggaac    3780
tggtctggtg gaaatgacca agaacaagat ggccgatggc tccgatgatg taaccagtat    3840
gcagatggtc cagctggctc cggcctttgt ggaactcctg agcaaacggg caggcgcact    3900
cgcgggtatc agcccgatgc accagccgtg cgtagtccct ccgaaacctt gggtggagac    3960
cgtaggcggt ggctactggt cagtcggtcg ccgtccgctg gcactggtgc gtacccactc    4020
caagaaggcg ctgcgccgct acgctgacgt gcacatgcca gaggtataca aggcggtaaa    4080
cctcgcgcaa aacacgccgt ggaaggtgaa caagaaggtg ctggcggtag tcaacgagat    4140
tgtcaactgg aagcactgcc cggtaggtga cgtcccagcg attgaacgcg aagagttacc    4200
gccgcgcccg gacgatattg acaccaacga ggtggcacgt aaggcatggc gcaaggaggc    4260
cgcagcggtc taccgtaagg acaaggcccg ccagtctcgc cgtttgtcga tggagttcat    4320
ggtcgcacag gctaacaagt tcgctaacca caaggccatt tggttcccgt acaacatgga    4380
```

-continued

```
ctggcgcggg cgtgtgtacg ctgtgagcat gttcaaccca cagggtaacg atatgaccaa   4440
ggggatgctg acgctggcca agggtaagcc aattggtctc gacgggttct actggctgaa   4500
gattcacggc gcaaactgtg caggtgtcga caaggttccc ttccctgagc gcatcaagtt   4560
catcgaagag aacgagggca acattctggc gagcgcagcg gacccgctga ataacacttg   4620
gtggacccag caagattcgc cgttctgttt cttagcgttc tgcttcgagt acgcaggtgt   4680
taagcatcac ggcctgaatt acaactgctc gctgccgctg gcgttcgatg ggtcctgctc   4740
tgggattcag cacttcagcg cgatgctccg agattccatc ggtggtcgtg cggttaacct   4800
gctgccttct gataccgtgc aggatatcta caagattgtg gccgacaagg tgaacgaagt   4860
gctccaccag cacgccgtca acgggtctca gaccgtggtc gagcagattg ctgacaaaga   4920
gactggcgag tttcacgaga aggtgactct gggcgagtcc gtactggctg cgcagtggtt   4980
gcaatatggt gtgacccgca aggtgactaa gcgttcggtc atgacgctgg catacggttc   5040
caaagagttt ggcttccgcc agcaggttct tgaggacacc attcagcctg ctattgacaa   5100
cggcgagggc ctgatgttta cgcaccctaa ccaagcagct ggctacatgg ctaagctgat   5160 ttggacgct gtgaccgtga ccgtagtggc cgctgtcgag gcaatgaact ggctgaagtc   5220
tgccgctaag ctgctggctg ctgaagtcaa ggacaagaag accaaagagg tgctgcgtaa   5280
gcgctgcgca atccactggg taacacccga tggcttcccg gtgtggcagg agtaccgcaa   5340
gcagaaccaa gcgcgcctga agctggtctt cctcgggcag gccaacgtca agatgacgta   5400
taacactggg aaggactccg agattgatgc ccacaagcag gaatccggca tcgctcctaa   5460 cttttgttcac tcacaggatg gcagtcacct gcgcatgact gtagtacacg ccaacgaggt   5520
ctacgggatt gactccttcg cactcattca cgactccttt gggaccattc cggctgacgc   5580
tgggaatctc tttaaggcag tccgcgagac gatggtcaag acctacgagg acaacgatgt   5640
aattgcagac ttctacgacc agtttgccga ccagctgcac gagtctcaac tggacaagat   5700
gcctgcggtt ccggccaaag gtgacctgaa tctgcgcgat atcttggagt ctgacttcgc   5760
gtttgcgtaa ggtctcaggc aattagggca cactataggg aaccttcgaa tgaccgaggg   5820
ttccattact taaagtctta acttaaagaa tacttaaaga ggcacgctat gacttactca   5880
atcgttgtaa ccatcttgtt aatcatcacc cttacgctcc tcattaacac catacgcaat   5940
tcactacgca gcgaggagcg gctggggcgc aaggtccaag aggccaactc cgcgtttagc   6000
agtgagtcct gcaaggtcct gcgtctggca gacagggctg actcgctcag tagacaggtt   6060
cgttacttag agggtgagct tgagagcgag aaacagaagg tgcgcgatgt gaacgaactt   6120
cgagagcacc agcgggaacg catgaagttt cttcgtaagt ccctgaagga agcacaagac   6180
gagctgatga tggtctccga cctgattcac gttaagttca ccgcagtgtt gccagacggt   6240
acccactcta agacgatctt taagttagga ctcgggccgt gtggtctgca cgttaagtcc   6300
ctgcgctgga ccgagctgga cgaccgctat ctgatagacc agctgtgcac caacggtgag   6360
cgcaagcagt tcgtctacta caagagcgaa gtagtagggc gcatcgagtt ccgccacggt   6420
aagctgtaat taggacccac tatcaggaac atactcaagg tcatcattcg gtggccttca   6480
tgaatgtccc ttactatcac aatcaggagc aacaccatgt atcagaacac aatcaatttc   6540
gagcgcaacc gtgaacgtca gcagactgag ggttatatcc ctaagggccg caagctgaac   6600
aagacgaagc gcgcggtgg cgtgaagggt tccttccgta acgctaaggg tgacagcgtt   6660
gttaaccaag agaaatactt cgtaggagcg taacaaatgg ctacgaaaaa aagatggctc   6720
```

```
ttcgatggaa gcacctcaca atggtctcgt ttaggagcag cggagcgtag actactagat    6780
acgacaggcc tgcacgtggt catgcttgac gacccattca ctaacaccgt gctgttcaac    6840
gtattcgagc cacgcgggtc acttctaata agtaagcggt tcagccactg gtcgattgac    6900
tcagcgtcag actggctggc aaaactcacc gcagactact cgagctggaa gtaattagga    6960
cacactatag gcagactcaa ggtcatcgga ttccggcggc ctttatgatt gcttattgca    7020
cactaaatga acactacact tcggagacat catcatgatg aacattaaga ctaatccatt    7080
taaggccgta tcgttcgttc gctctgctat cgagaaggcg ctggagactt ccggttacct    7140
catcgcagac actaagcatg atggtgtacg cgggaacatt tgcgtagaca cacggctaa    7200 ctcatcgtgg ctcagccggg tctccaagac cattccggcc cttgagcacc tcaacggttt    7260
cgaccagcgc tggcagaagt tactgaaaga tgaccgctgg attttcccgg atggcttcat    7320
gcttgatggt gaactcatgg tcaaaggcgt ggacttcaac accgggtctg gcctgctgcg    7380
caccaagtgg ctcaaagaga ccaactggat gtactccagc aaggatggag tggtgaaggg    7440
caagaaggaa cctttcgagc tggataccaa gcaactaaaa gttgtcctct atgatatcat    7500
tccgcttgac attatcgagt ccggtgatga ctacaacgtg atgaccctcc tccgccttga    7560
gcatgtcaag gtagccttac cagtcctgca agaccacttc cctgaagtcg agtggtgcct    7620
ctcggagtcc catgaagttt acgacatgga cgaactcgaa gcgctgtacc gacagaaacg    7680
tgaagaaggt cacgaaggtc tggtggtcaa ggaccctcag gcatctacta agcgtggtaa    7740
gaagtccggc tggtggaaga tgaagccaga gaatgaagct gacggtgtag ttgtgggact    7800
caactgggga actcccggtc ttgccaacga gggcaaggtg attggcttcg aggtcctcct    7860
tgagtctggt cgcgtggtat ccgccaacaa catctctcag gcacttatgg aggagttcac    7920
agccaaagtt aaggcccaca ccatgtgcgc caatggttgc cggatgtcta aggatgtcgg    7980
tatggataat cactcctgcg ctggcaagtg tgcttacgac caacaccgt cgaataaccc    8040 ttatgagggc tgggcgtgcc aaatcaagta catggaggaa actccagacg gctccctgcg    8100
tcacccgacc gttcgacaaa tggcgtggca ctgaggctga cccgaccatc aagatgtaat    8160
taggacccac tataggagac accaaatgtc tatcaacctg attctaatca tcgtgctcat    8220
cctcgcggct atcgtgtggt caatgaatga cgagccacct aaaggagcat aaaccatgcg    8280
cttacacttc aataaatcca acggtatctt ctcggttcgc cgggaggacc gcagcactgt    8340
agcggccacc gagcgccacg gtaagattcc acgtatcggc gacaccttcg agctggcacc    8400
tagcgttcac atcttggtta ctcgcggtct ctacgaattg gctcagacca agagccgtcc    8460
tttcgtaccc gttgtggtaa ccaagtggcc acgccttcgt ctgttctggg agcgcatcaa    8520
ggaggtggtc aatgactgaa cgtgaaattc aagttgtgga ccttctggtt gggcaaaaca    8580
ctgaccgccc agactccaca acgtgcgctg atggcgtcat atgctacaag gtatcgtgta    8640
gcgagtgtcc gctaaacgtc aaaggtacga ccattgggga ggtccgtaca atgaaggaca    8700
gcaaaggctc cgcccacttc ccggagtgca agatatggaa cggcgctggt cagtgtacct    8760
gcgagccgac ccgagacgac ggtgttaagc agccgagcca ctaccagctg ttcgacggtg    8820
tcgaggccat cgaggtgatt gctcgcagca tgacccaaga gatgtttaag gggtactgcc    8880
tcgggaacat cctcaagtac cgccttcggg ccgggaagaa gtccgagctg ctaccttag    8940 agaaagacat ggcgaaggcc gctttctatc tggagctgta caccaagcac aagggtctgt    9000
gttatgacgc caagtgagtg ggcaagaaag atgtacgaga gacgctcga ccctgcgtac    9060 atcaccctgt ataacatgtg gaaggagcga gaagatgcaa aagttcgtcg taacggtcga    9120
```

```
gacagctaac gcatcgtacg aactcccggt acacgctggg tctcttgatg aggccctcga   9180
agttgccgag gcggagtacg aagagttagg ccaagtgact cgggtacgcc cggatagtca   9240
ttaggacaca ctatagggac acaggttgtc cctctttctg ttataaacca aaggagattc   9300
accatggcat tcgctaagaa gaaaatttac accaccaaga ttggtacctg tgagccgtac   9360
gcttacttca acaagccgga ctatggcggt gagggttttg agaacccacg tggtacctac   9420
aaaggttacg taacgttcaa gaacgaagac tgtcaggagc tggtagacct catcgttaag   9480
acccatgagg aaaactacgc cgctcgtctg gaagcgcacg aagcgaaccc gcctaaggtt   9540
cagaagggta agaaacctct gaagccgtat gaaggcgaca tgccgttctt cgataacggt   9600
gacggcacca ccacgttcaa cttcaagtgc tacggttcgt acgaggacaa gaagactggc   9660
gagaccaaga agattgttct gggcgtagta gacgcgaagg gcaagcgcat tcaggacgtt   9720
ccgattatcg gtggcggctc caaagtgaag attcgcttct cgctggtacc gtacggctgg   9780
tctgcggtag ctggcgcttc cgttaagttg cagctggaag gcgtgatgct ggtcgaactg   9840
gctacctttg gtggtggcga agacgactgg gctgacgaag ccgtagaagg cggttacgaa   9900
gcggacgaat ctcgcagccg taaacctcag gaagacccgg aagactggtc tggtgaggaa   9960
gctgacgagg gcgaagccga agaagacgat gacttctaat ggcgggctat ggggccaaag  10020
ggattcggaa ggtgggtgcc ttccggtctg gccttgagga caaggtgtcc aagcagttag  10080
aagcaaaggg cgtcacgttc gattacgaat tgtggcgcat cccttacgtt attcctgcga  10140
gtgaccacct ttacactcca gacttcttgt tacccaacgg tatcttcgtg gagactaagg  10200
gtctctggga agccgaggac cgcaagaagc acctactgat tcgtgagcag cacccggagt  10260
tagacatccg gttagtgttc tcttcgagtc gcactaagat ttacaaaggg tcaccaacca  10320
gttacgctga gtggtgtgag aagcataaca tcttgtttgc cgacaaactg attcccgtag  10380
actggctgaa ggagccgaag cgtgatgtac cgttcggcaa gttcaagcag aagaaaggag  10440
caaagtaagt atgccaaggt tcaattcac taagcgacag gagacctctc agattttcgt  10500
tcactgttcc gccaccaagg caaacatgga cgtaggcgtc cgtgagattc gccagtggca  10560
caaagagcag ggctggctgg atgtagggta tcacttcatc atccgtcgtg acggtaccgt  10620
tgaggcgggc cgcgaccaag acgctgtggg ttcacacgtc aagggataca actcgacctc  10680
tgtcggtgtg tgtctggtag gtggtatcga cgccaagggt aaccccgagg caaacttcac  10740
gcctcagcag atgagcgcac tgaatgggtt gctgcacgag ctgaggggga cctaccccaa  10800
ggctgtcatt atgcgcacc acgatgtagc gccgaaggct tgtcctagct tcgacctgca  10860
acgttgggta aagactggcg agctggtcac ttctgaccgt gggtaaacat tagggcacac  10920
tacagggaga caattacgtt tccctgttgt cacacattct gtacaaatta tggtcaggct  10980
aaggtgcact tggcgtagcg ctgcgttttca ttcgggttcg attcccggac tgaccacacc  11040
aacggagatt actttatgaa caagttcaaa gaacactttg ctgactcatg ccactgtat   11100 gtgtacgcat cggcattcat cattggcgca ctgcgagtgt tgctcccatg agttacgggg  11160
acagtcgaga agacggtcag gaaagtatct tcctgttcca cgctccgtgc gaaaactgtg  11220
gttcttctga tggtaactca gtgtactctg acgggcatga gtattgcttc gtgtgtcaac  11280
accgggttcc cggctcagag gaacgtaccg aaaagttatc atcgagaaga cccaaaggag  11340
ggaattacgg gatgaataca caaggctcag gactactggt attcggcgag agtgacggtc  11400
ggtacactga cctgactgct cgtggtatct caaaggcgac atgccagaag gctggctatt  11460
```

```
gggtcgccaa ggtcagagga accgcctatc aggtggccga ctatcgtgac cagaatggct    11520
ccatcgtctc ccagaagctg agggacaagg agaagaactt ctctacccga gggtcccaca    11580
aaggggatgc actgtttggt aagcacctat ggaatggtgg taagaagatt gtcatcaccg    11640
agggtgaaat cgacatgcta accgtgatgc aactacagga ctgtaagtgg cctgtggttt    11700
ctctcggtca cggtgcgtca gccgctaaga aaacttgtag tgcaaactac gagtattttg    11760
atagcttcga ccagattatc ctgatgttcg acatggatga ccccggtcgg gcagctgtag    11820
aggaagccgc tcaggttctc cctcccggta aggtgcacgt agctgtgctg accgagaagg    11880
atgccaacga gtgtttactc aaaggtaagg gaaaggaggt tctcgaccag atatggaacg    11940
cggcaccttg ggtacctgat ggtgtcatcg gtgcgatgtc catgaaggac cgagtgcgtg    12000
aggccatgac cagcgaacaa agcgtaggat accttttctc gggatgcccg ggactgaatg    12060
accgaacctt gggtgcacgt ggtggcgaag tcatcatggt cacttctggg tcaggaatgg    12120
gtaagtctac gttcgttcgt cagcaggctc tagggttcgc cagagggcaa ggactgaggg    12180
taggcatggc gatgcttgag gagtccgtag aggagaccat ggaggatgtc ctagggattg    12240
ctaacggaat ccgcttacgg cagcagcctc gggagttcaa gcagaaactc attgaggatg    12300
gtacgtacga tgagtggttc gatgagctgt atggctccga ccagttccat ctctacgact    12360
cctttgcgga agctgaggtg gaccgcctgc tggccaagct gcactacatg cgcacagggt    12420
tgaactgtga cgtaatcatt ctggaccaca tctcaatcgt agtgtctgcc tcggaggaat    12480
ccgatgagcg caagatgatt gaccgactca tgaccaagct gaaagggttc gctaagtcaa    12540
ccggagtggt acttattgtt atttgccacc tgaagaaccc ggagaaaggt aaagctcatg    12600
aagaaggacg tgctgtttcc attactgacc tgcgtgggtc tgggtctctg cgccagctct    12660
ctgatactat cattgcactt gagcgtaatc agcaagggga tatgcctaat cttgtcctcc    12720
ttcgtattct caagtgccgc tttaatggta ttggcgttgg cattgcgggg tacatggagt    12780
acaacgaaaa gacaggactc cttgaaccgt ctagctacac tggcggagaa ggagagggag    12840
atactggctg ggaaggccac gaagaagacg attactaaac gtaaatgcaa tggggcgtac    12900
tgctggtgcg ccttttgaccc tgattatcaa taacggaagg agagccatca tgtttaaact    12960
tatcgaagca ttaggccgtc tggtcatcgc actgtacgta cgtgaagcca aggcactgga    13020
caaagcgtcc aaggtggaag cgaaagcagc cgctaagctg gctaaggcag ccgacaaggc    13080
acgtcaggca tctctggatg caaccgcaga ggcagctaaa gttgccgcta agctcagaa    13140 acttaaggag ttcttctaat gactaccaaa gttaaattcc ccggcaatac cattcagctg    13200
tccgacaccg ttgaccagtg gggacgcaag gttcacatca acgttcgcaa cgacaaggtc    13260
actctggtct accgctggaa ggccaagagc gataatcgtg cgcatactca gcgtgtgacc    13320
ctcgacgaca cacaggcagc tcggctgctg gcgtccgtag ctgtagccgc tactgtggcc    13380
ataggtgagg acaaagtgcg tgaggcaatc ctgagcaaag aggttggcga aacgtccgtg    13440
cgtctggccg aagcgtcaga agttaagtga taaactcaag gtcattacta tatgtagtgg    13500
cctttatgat tatacacaca acatattgag aggacattac catgcgtaaa cctgaagaga    13560
ttcgtaaaga gattgaagcg ctgaacaaag agctggctga ggccaagacc tatgaggcta    13620
agcgtgacgc tgctgtgcac attctggaga acttagggtg gacccacagt ggccacaagg    13680
gctggcagaa gccttcgcaa aagtggagcg actataaggc tcccctgaag gctggtgagc    13740
tggcaacttg ggacgacaag gtactaggtg ggatagtgta catacgcagt gtgggcgata    13800
agtacgctca ggtgtcccac gttcgtggtg ttagtagact gggagctgat gtactgaaca    13860
```

```
gtagctttgc tgtcgagaag agtaagttaa ccgtgcgtcc tcgtgagtat ttcatcgggc   13920
gtcgttaagc aacaggagac cactatgtta gtaaccgata tcgaggcgaa caacctctta   13980
gagaaagtca ctcagttcca ctgtggtgtc atttatgact acagtacgga cgagtacgta   14040
tcgtatcgac cttgggactt ctcagcgtat ctcgatgcgt tggaagctga ggtggctcgt   14100
ggtggtctca tcgtattcca caacggtcac aagtacgatg ccccagtgtt aaccaagctg   14160
gccaagctcc agttaaaccg agagttccac ctgccgcgtg agaacgtagt ggacacgttg   14220
gtgctcagtc gtttactgtt tgcgaacatt aaggactccg acatggccct gctgcgttcc   14280
ggtaagttac ccgtaagcg ctatgggtct cacgctctgg aggcgtgggg ttaccgcttg   14340
ggcgagatga agggtgagta caaggacgac ttcaagaagc tacttgagga acaggagag   14400 gactatgttg acgtgctga gtggattagc ttcaacgagc cgatgatggc gtataacgtt   14460
caggacgttg tggtgaccaa ggctctctta gagaagctgc tgagcgacaa gcactacttc   14520
ccactgtttg gtagtaacac catagagttc tacacctcag cgtactgctt gaggttctgg   14580
gaggaggctt gtgaggccgt ctggttggaa catcgggccg cttggttact cgctaagcag   14640
gagcgcaacg gattcccgtt caacaccaag gccattgagg agttgtacgt tgaactcgct   14700
ggtcgtcgtt ctgaactcct tcagacactt accgacactt tcggaacttg gtaccaacct   14760
aaaggcggca ctgagttatt cctgcacccg cgcactggta aacctctggg taaataccca   14820
cgagtgaagt acccgaaaca gggtggtatc tacaagaaac ccaagaacaa agctcaacga   14880
gagggtcgtg aaccctgtga gctggacact cgggattacg tagagggtgc tccatacaca   14940
ccagtagagc acgttgtgtt caacccaagt agccgagacc acattgcgct caagctgaag   15000
gaagccggat gggtacccac agagttcacc gaaaagggtg cacctaaggt agacgacgag   15060
gtccttgagc atgttcgtgt gggggaccct gagaagcagc gctgtatcga cctcatcaaa   15120
gagtacctga tgatacagaa gcgtatcggt caggcggctg agggcgacaa agcgtggcta   15180
cgttacgttc aagaggatgg taaaatccat ggaagtgtta accctaatgg tgcagttaca   15240
gggcgagcaa cgcatagctt ccctaacctt ggtcaagttc cgggcgttcg ttcgccgtat   15300
ggtgagcctt gtcgagcagc gttcggcgca gagcatcact tggacggact taccggacag   15360
ccttgggttc aagcaggcat cgacgccagc ggactcgaac tccgttgtct ggcacacttc   15420
atgtctaagt acgacgacgg ggcatatgcg gatgtcattc tcaacggtga tatacacaca   15480
gtcaaccaaa cggcggctga gttgccaaca cgtgataacg ccaagacatt catctacggt   15540
ttcctctatg gtgctggaga cgaaaagatt ggacagattg tgggcgcagg taaggaacgc   15600
ggaaaggaac tcaagaagaa attccttgag aacaccccag caatcgcagc cctgcgtgaa   15660
ggaatccagc agaccctcgt cgagtcatcc cgatgggttg ccggagagca gaaggtcaag   15720
tggaaacgac gctggattaa gggactggat ggaagaaagg tacacgttcg gtcaccacat   15780
gccgcgctca acacgttgct tcagtcagcg ggtgcgctca tttgtaagct gtggattgtc   15840
gagactgaag agttgcttct taaggcagga ttgaagcacg gatgggatgg cgacttcgcc   15900
tacatggcgt gggttcacga tgaaatacaa gtggcctgcc ggacctcaga gattgcacag   15960
caggtgattg acatagcgca gcaagctatg cgtaacgtgg agaccacttt aagttccgt   16020 tgccgtctgg acacagaagg taagatgggt ccgaactggg ccgtatgtca ctaataatac   16080
aggagattta tcatgggtat taacaaacag tttcgcgtaa cgttcgatgt aacggctact   16140
atgagtgatg accaagagcg ggagttcctt gaggacctac tatctcttgc gtatggcgtg   16200
```

```
gacgacaaac gtcaggcgca cattgtaacc gaagcaatca ccaaaggtca tgaggcggca    16260
ctggcattcg tcatgcagag tggtctgcgg gaagctatta aggacatcgg taaggagctg    16320
agctgctccg ctgtgacagt acgcttctct ccggcaaccg tgagggtgac taagtgagcg    16380
agtacctcaa agttctggcg gccctcaagg gctgccctaa gtccttccag tcgaactacg    16440
tgcggaacaa cgccgcgtta gtcgctgagg ctgcgagccg tggtcacatt tcatgtctga    16500
ccatgagtgg tcgtaacggt ggcgcttggg aaattaccag tgccggagtg aaattcctta    16560
aggcccatgg aggttgtcta tgaaagactt tttaggtaac gatatcgaga ttggcgacac    16620
cattgtgtat gctgacgctg gtggccgtgg aggctcttcg ggtcttaaca agacagtagt    16680
tacccgaatg actgataaac aggtcatggt gtacgaatca acgtggtcaa aactgtggcg    16740
tccgtttgac cgtgttgtgg ttgttgctaa gggaggttcc caatgaagca cacattgtta    16800
tccttcagtg actaccgggc aacccagaag attgccaagg gtgtccttgt gatggatggt    16860
gactggttgg tattccaagc catgagtgcc gctgagttcg atgcctcgtg ggaggaggag    16920
atttggcacc gttgctgtga ccacgctaag gcccgagaga ttctggagaa ctccatcgag    16980
tcctacaagg gccgcaagaa ggcgtggaag aatgcagacg ttgtcctagc gttcactgac    17040
cgtgtcaact ggcgcaagct gcttgtggac ccgacgtaca agagaaccg cgcagtcgtc    17100 aagaaacctg tgggttactt tgagttcctt gagtacgtct ttgagtccta cacatgtgtc    17160
cttgagcctc agctcgaagg tgatgacgtg atgggtatca tcgggtctaa ccctctcgtg    17220
tacaactacg agaaggccgt gctggtctcc tgcgacaagg actttaagac catcccggat    17280
tgtgatttcc tgtggtgcac gactggtaac atcctcgttc agactcagga gacagccgac    17340
tactggcacc tcttccagac tatcaagggt gacatcaccg atggttacgg tgggattccc    17400
ggatggggag ataccgctga ggacttcctc aaggaaccct tcattgtgga gcctgtaacg    17460
tccgtgctga gtccggtaa gaacaagggc caagaggtaa ccaagtgggt gaaacgcgct    17520
cctgagccgg gagagacgct ctgggactgc attaagtcca ttggtgccaa agcagggatg    17580
accgaagcgg aagtaattaa gcagggccag atggctcgca tcctccgttc tgatgagtac    17640
aacatcgaga ctgggagat tactctatgg caaccgggca gctgattctc atcgtcctga    17700
ccatgggctt agttgctcgt ggtctctgga tgttggcctt gattatcaag cagatagtcg    17760
agcataaagc agagtgataa actcatgggc acaattagga cccactatag ggaagtgccc    17820
attatgatta ttacttaaag attacttaga gaggagactc aaatgttaaa acctatagag    17880
cacatcctta acaatcctaa tgaccttcct gacgtaccgc gagctgtcaa ggagtaccta    17940
cagtctcgct tcaatgctga cttcctgtat cagtcagagg tccgtaagct gcgtgaggct    18000
ggccacagtg aggagttcat ctccggtgta ctgtatggtc actacatggc ttctcgtgtc    18060
cttgacgaga tggagggccg ccagcgtgca ctcaaagaag gagattgatt atgtgtttct    18120
cacctaagat gaaagcacct aaggtcgaca caacgactgt ccctgagcca gctccgctca    18180
ctgaggaacc taagggtatc cagtacggtg gcgacgaaga ctcaaacagc accactcctg    18240
aggtgtcagg gcgtaagtca ctcaaggtga ccaagacgac cgagcccaca gggtcagtca    18300
gtaaaatccg taagtcagct ttaggaggct aacatggac tgttcaagaa aatcaagaag    18360
gctatctcca aggtagtcaa ggcaccactc aaggccgtgg gtctagcagc agatgcgcct    18420
aacgtgcaga cagccgctga gacacctgtg gcagcacctc aggaagcacc gaaagaggtc    18480
gtggaggacg ttgagtcttc agcagacacc gagtctggta agaagaaatc ccgagcgtct    18540
ggtaagaagt ccctctcagt ttcccgcagc tcaggcggtg ggattaactt atgattggtt    18600
```

```
acggggaggg ctaacaaatg gcagaagtta aactcgaagg cttcgcagag gagggagcca   18660
aggcggtgta tgaccgtctg aagaacgacc gacaacctta cgagacacga gcagagtcct   18720
gtgcgcagta cacgattcca tcactgttcc ctaaggactc cgataacgca tcaacagatt   18780
acacgactcc gtggcaatcc gtaggtgctc gcggcctgaa caacctagcg tccaagctga   18840
tgttggccct gttcccgatg cagtcatgga tgaagttgac cattagtgaa tacgaagcga   18900
agaaccttct gggtgacgct gagggtctcg ctaaggtcga tgagggccta tcaatggtag   18960
agcgaatcat catgaactac atcgagtcca acagttaccg agtgactctc ttcgagtgct   19020
tgaagcaact gtgtgtggcc gggaacgcat tgctgtactt accggagcct gagggttaca   19080
ccccgatgaa gctctatcgc ctgaactcgt atgtggtcca gcgagacgct ttcggtaacg   19140
tactccagat tgtcactctc gacaagattg cgttcaacgc tctccctgag gatgtccgca   19200
gccaagtgga agcagcccaa ggtgagcaga aggaagacgc tgaggttgac gtctacaccc   19260
acgtgtacct gaacgaatcc ggggatggct actcgaagta cgaagaggtt gccgaagcag   19320
tagtaccggg cagcgaggct gaatacccgc tcgaagagtg tccgtacatt ccggtccgca   19380
tggtccgcat cgacggtgaa tcctacggtc gttcctacgt ggaagagtat ctgggtgacc   19440
tcaagtccct agagaacctc caagagtcca tcgtgaagat ggcgatgatt accgcgaagg   19500
tcatcggtct ggtagacccg gcaggtatca ctcaggtccg ccgactcacg gcagcacagt   19560
ctggtgcgtt cgtaccgggc cgtaagcagg acattgagtt cctccagctg gagaagtccg   19620
gtgactttac cgtagcgaag aacgtaagcg acaccattga ggctcgccta tcgtatgcct   19680
ttatgctcaa cagtgcggta caacgtacag gcgagcgagt cacagccgaa gagattcggt   19740
acgtggcgtc agagctggaa gatacctag gcggtgtcta ctcgattcta tcgcaggaac   19800
tccagctgcc tctggtaaga gtgctcttga agcaactaca agccacgcag caaatcccgg   19860
agttacctaa agaggccgtc gagccaacta tcagcactgg ccttgaggct atcggacgtg   19920
gtcaggacct tgacaagctg gagcggtgca ttgccgcatg gtcagcccctt aaggccctcg   19980
aaggtgatga cgacctcaac ttggctaacc tcaagttacg tatcgctaac gctattggac   20040
tcgacactgc tggtatgctt ctcactcagg agcagaagaa cgcccttatg gcacagcaag   20100
gtgctcagat tgccacacag caaggggccg cagcgctggg tcaagggatg gccgcacagg   20160
ctactgcaag tcctgaagcg atggccgcag cagctgattc agtaggtatg caaccgggca   20220
tgtaattagg gcacactata gggagaccga ttggtttccc tcttagtctt aactttaagg   20280
agattgaaat ggctggcgaa tctaacgcag acgtatacgc atccttcggt gttaacagtg   20340
ctgtactgac tggtagtaca cctgaggagc accagaaaaa catgttggct cttgatgttg   20400
ctgcccgtga tggcgatgat gcaatcgagc tgaacacaaa cagtgatgac ccgtatggtt   20460
ccgatgtgga cccgttcggt gaacctgaag agggccgtat gcaggtccgt atctccgctg   20520
acggttcaga cgaacaggac ggcgaagagg gtcagggtga cgaagaacag cagggcgacg   20580
aagagagtca gccggaggaa gtaaccgatg aaggtgaacc tgaagagttc aaacctattg   20640
gtgaaactcc ggctgacatc aacgaagcct ctcagcagct ggaagaacac gaagctggct   20700
ttaacgacat ggttgctact gcaatcgaac gcggtctctc acaggatgct gtgaccgtta   20760
ttcagcagga gtaccagaac gaggacagtt tgtccgacga gtcttaccga gagctggccg   20820
aggcgggcta cagtaaggcg ttcgtcgatg cgtacattcg cggtcaggag gctctggtca   20880
accagtacgt tgagaaagtg atggacttcg tgggaggccg tgagcgattc cagcaggtct   20940
```

```
acagtcacat gcagaccaat aaccctgagg gtgccgaggc gctcatcaag gcttttgagt    21000
ctcgtgatgt agccaccatg aagacgattc tgaacctagc gggacagtct cgtgataaaa    21060
cctttggtaa gaaagctgag cgctctattg ccaagcgtgc aaccccagcg aaacctgctc    21120
cccgcaaggc tgtaggcttc gagtctcaag ctgagatgat taaggcgatg tccgacccgc    21180
gctaccgcac cgactctaag tatcgtcgtg aagtagagca aaaggtaatc gactcaacgt    21240
tctaatgaat tagggcacac tagggagacc catcagact gaacacggtg acgtccactg    21300
gctcccttcg agttacacaa tgagtatcac ctcgtttcaa gtagtaactg acgcgacctt    21360
agggcaagac cttatgatag gcgcggagaa tcaccccaag agcttggcaa cgataggccc    21420
gtttggtcag cgtaatgact aattctattc gtaaacaaca taaggagatt caacatggct    21480
aacatgcaag gtggacagca gctcggtact aaccaaggta aaggtcaatc cgcagcagac    21540
aagctggcgc tattcctgaa agtattcggc ggtgaagtcc tgaccgcatt cgctcgtacc    21600
tctgtgacca ccaaccgtca catgcagcgt caaatcagct ccggtaagtc cgcacagttc    21660
cctgtgattg gccgcaccaa ggctgcttac ctgcaaccgg gcgagtctct ggatgacaaa    21720
cgtaaagaca tcaagcacac cgagaagacc attaacattg atggcctgct gaccgctgac    21780
gtgctgattt acgacatcga agacgcgatg aaccactatg acgtgcgctc cgagtacacc    21840
tctcagattg gtgaatctct ggcgatggcg gcggatggtg cggttctggc tgagctggct    21900
ggtctggtta acctcgctga ttccgtcaac gagaacatcg cgggtctggg caaaccgtcc    21960
ctgctggaag ttggtgctaa ggctgacctg accgacccgg ttaaactggg ccaagcggtt    22020
atcgcacagc tgaccattgc tcgtgcggcc ctgaccaaga actacgtccc ggcgaacgac    22080
cgtacgttct acaccacccc ggacgtgtac tctgcgattc tggcggctct gatgcctaac    22140
gctgcgaact atgcggctct gattgaccct gagcgtggct ctatccgtaa cgtgatgggc    22200
ttcgaagtcg tagaggttcc gcacctgacc gctggtggtg ctggtgatga ccgcccggac    22260
gaaggcgcag aagcgaccaa ccagaagcac gccttcccgg caactggcgg taaagtcaac    22320
aaagagaacg ttgtgggcct gttccagcac cgttccgctg tcggcaccgt taaactgaaa    22380
gacctggctc tggagcgtgc tcgtcgtact gagtatcagg ctgaccagat tgttgccaag    22440
tacgcgatgg gtcatggtgg tctgcgtcca gaatctgctg gtgcgctggt tttcacagca    22500
gcctaagcgt aaataccttt agtgctcgga cggtaactcc gtctgagtat gaggtacaga    22560
ctgtggccat tactggtgat tcacttaagg tgacacttgg tgggctggag ggagtaacgg    22620
actggtcaac acttgaggta acttatggta cttccgggat tgccagccac actcgccgga    22680
ccaacacgct gtacttcaaa ggaatcgctg tgggcgaaac tctagtgact gtcagctttg    22740
acgggtctga aaggaagtcc tttaagctgg tcgtgactaa ttaaaactaa gccaaacccc    22800
ttggggacca ctcacggtct ctgaggggtt ttttcgttag gagcttacat tatgaacatg    22860
caagatgctt actttgggtc tgccgctgag ctggatgcta tcaacgagat gctcgcagct    22920
atcggtgaat ccccggtgac caccttgac gaagatggta gcgcagacgt agctaacgct    22980
cgtcgtatcc tcaacaggat taaccgccag attcagtcta aaggttgggc cttcaacatc    23040
aacgagtcgg ccacgctgac ccctgacgcg gacactgggc ttatcccgtt ccgtccggcc    23100
tacctgtcca tccttggtgg ccagtacgtc aaccgtggtg gttgggtgta cgacaagtcc    23160
acagagacgg ataccttctc tggggcaatc acagtgaccc taatcacact tcaggactac    23220
gacgagatgc ctgagtgttt ccgccagtgg attgtcacca aggccagccg tcagttcaac    23280
tctcggttct tcggagcgga ggacgtagag aactctctgg cacaggaaga gatggaagcg    23340
```

```
cgtatggcat gcaacgagta cgagatggac ttcggtcagt acaacatgct tgacggcgac   23400
gcatacgtgc agggtctcat cggtcgttaa taggaggtat acaatggtct tcacactcga   23460
agatttcgtt ggggactggc gacagacagc cggctacaac ctggaccaag tccttgaaca   23520
gggaggtgtg tccagtttgt ttcagaatct cggggtgtcc gtaactccga tccaaaggat   23580
tgtcctgagc ggtgaaaatg ggctgaagat cgacatccat gtcatcatcc cgtatgaagg   23640
tctgagcggc gaccaaatgg gccagatcga aaaaatttt aaggtggtgt accctgtgga   23700
tgatcatcac tttaaggtga tcctgcacta tggcacactg gtaatcgacg gggttacgcc   23760
gaacatgatc gactatttcg gacggccgta tgaaggcatc gccgtgttcg acggcaaaaa   23820
gatcactgta acagggaccc tgtggaacgg caacaaaatt atcgacgagc gcctgatcaa   23880
ccccgacggc tccctgctgt tccgagtaac catcaacgga gtgaccggct ggcggctgtg   23940
cgaacgcatt ctggcgtaat cagaaactta aggaggacca aatggctctc gtatcacaat   24000
caatcaagaa cctcaaggga ggcattagcc agcagcctga atcctacgg tacccagagc   24060 agggtacact tcaggtcaac ggttggtcct ccgagactga gggtctccag aagcgaccac   24120
ctatggtgtt catcaagtcc cttggaccta ggggctactt gggggaagac ccgtacattc   24180
acctcatcaa ccgagatgaa tacgagcagt attacgcagt gttcactggg aacgatgttc   24240
gggtattcga cctgtccggc tatgagtacc aagtaagagg tgaccgctcg tatatctcag   24300
tagtcaaccc taaggataac ttgcggatga taaccgtggc cgactacacg ttcatcgtta   24360
accgtacccg acaggtccgc gagaaccaga acgtgaccaa cggtggtacc ttcagggaca   24420
acgtggacgg tattgtcaac gtccgtggtg ccagtatgg tcgtaagctc gaagtgaaca   24480
ttaacggtgt atgggtcagc caccagctgc ctccgggtga caacgctaag gatgacccgc   24540
ccaaggttga cgcacaggcc attgcggctg cactcgctga cctacttcgt gtggcccacc   24600
caacgtggac attcaacgtg gggactggtt atatccactg catcgcacca gctggggtaa   24660
ctcttgatga gttccagacg agggacggtt acgcggacca gctgattaac ccggtgaccc   24720
actacgttca gagcttctct aagttgccac ttaacgcgcc tgacgggtac atggtgaaga   24780
ttgtcgggga cacgtccaag actgctgacc agtattacgt gaagtatgac gcttctcaga   24840
aggtctggaa ggaaaccgtg ggctggaaca tctcggtcgg ccttgagtat cacacgatgc   24900
cttggactct ggtgcgtgca gctgacggta actttgacct cgggtatcac gagtggaggg   24960
accgccgtgc tggtgacgac gacactaacc ctcagccgtc ctttgttaac tcaacgataa   25020
ccgatgtgtt cttcttcagg aaccgcttag ggttcatctc tggggagaac atcgtgcttt   25080
cccgcaccag taaatacttt gagttctacc cgccgtcagt ggccaactat acggacgatg   25140
acccgctaga tgttgccgtg agtcataacc gtgtgtcggt ccttaagtac gctgtgagct   25200
tcgctgagga gcttctgctg tggtccgatg aggctcagtt cgtcctgtcg gccaacggtg   25260
tgttatccgc taagactgca cagctggacc tgaccactca gttcgatgtg tcagaccgtg   25320
cgcgtcctta cggtatcggc aggaacatct actatgcgtc tcctcgaagc tcctttacgt   25380
ccatcatgcg ctactacgcg gtacaggatg taagctctgt gaagaacgca gaggacatga   25440
cggcccacgt cccgaactac atcccgaacg gtgtgtacag tatcaacggg tccggtactg   25500
agaacttcgc gtgtgtgctg accaaggggtg ctcccagcaa ggtgttcatc tacaagttcc   25560
tctacatgga cgagaacatt cgacagcagt catggtccca ctgggacttc ggagatggtg   25620
tggaggtgat ggctgcaaac tgcatcaact caacgatgta cctgctgatg cggaacgcct   25680
```

-continued

```
acaacgtgtg gatagctgct gtggacttta agaaggagtc gactgacttc ccgttcgagc   25740
cttacaggtt ccacgtggat gccaagcggt catatcacat ctcagagact gcgtacgaca   25800
tcgagaccaa ccagacggta gtgaacgtca aggacatcta cggtgcgtcg ttctccaatg   25860
gtacggtggc aatctgcgag agtgacggca aaatcaccga gtatgagccg atgggtgact   25920
cttgggattc aaccccagac atccgcatta gcggtgacat ctctggcaag gatatcgtca   25980
ttgggttcct gtacgacttc caatatgtgt tcagtcggtt cctcatcaag caggagcaga   26040
acgatggcac aacgtccaca gaggacgccg gacgcctaca acttcggaga gcgtgggtga   26100
actatcagga cactggtgcg ttcactgtga gtgtcgagaa tggcaaccgt gagttcaact   26160
atctggtcaa cgccagagta ggctccacgg gtctacgtct tggccagaag gcaacgacca   26220
ctggtcagta tcgcttcccg gtgacaggta acgccttgta ccagaaggtg tccctgagtt   26280
ccttcaacgc ttccccggtg tcaatcattg ggtgcggctg ggaaggtaac tacagcagac   26340
gagccaacgg catttaactg aaggaatcct tatggtgtgc tcaattaggg cacactatag   26400
ggagaccaca ctaagagggg acttaaagca tgtacataag acaatccact aaaactgacc   26460
tatttgtgtt caagccgtcc cgtgacgata gacttgaggc agcagccttg ggtatagctc   26520
cgggattccc accgcatacc gaatgtgtct cactggttac cgatggtgac atagagggca   26580
catacaacct tctggctatt ggaggcaacg tgggtgacca agtgtggttc gtaacggacc   26640
agaaggtatc acgcttgacc agagaggagc gtttagagtt tcgtaagaac attatcgaat   26700
accgcgacag gttacacgag aagtacccaa tcctctggaa ctacgtgtgg gtaggtaaca   26760
agtcgcacat tcggttcctg aagacaattg gtgctgtatt cgagaatgat tttacactca   26820
acggcacctt ccaactgttc accataacga ggaggtaact atgtgctgga tggcagctat   26880
tcctatcgca atgacggcgg tgcaggccat cggccagtca cgcaatgaag ccaagatgat   26940
tggccttcag aatgaccaga tgcgccgaca gtctgcccag atgattaaag agtcaaacat   27000
tcagaacgct aacgccagcc ttgagcagaa gcagaagctg gaagaagcca gttcggacct   27060
gaccgctaag aatctcgata aggttcaggc catgggtaca atccgtgcag caatcggaga   27120
gggaaacctt gagggtgcca gcatggaccg tatcagtcga atcgaggagg gcaagttcat   27180
tcgggaggcc aacgcggtca ccgataacta ccgtcgagac tatgcgtcac tgttcgctca   27240
gcagctgggc aactcagagt caactattga ccaagttaag tccatgcaga aggctgaggg   27300
caaaggtaag tctaagctgg aacaggtgct ggacccgctg gcattgatga cctcacaagg   27360
cgcatccgca tattcgtcag gtgcgttcga cagtaaggga accaaggcac caattagtca   27420
ggcccaaggt actaaggtag gaggtaagta atggccagta aattagaaca agcattaagc   27480
caactgccgc aggccgggtc tacccgcatc cgtggtggct cagcgtccat gcagtatcgc   27540
ccagtaacca tccaacagga agggttccgt cagtccaacc tcgtgcagtc cttggcgaag   27600
tttggtactg cggtgggtga ggcagcggat gcctacgaca agcgccaacg ggacaaggcc   27660
gatgagcggt ccgacgagat tatccgcaag ttgaccccag agcagcgccg ggaggcaatc   27720
aagaacggga ccctgctgta tcaggatgac ccgtacgcta tggaggccct acggttcaag   27780
actggtcgta acgcagcgtt cctcattgac gacgaagtgg cacagcgtgt tcagaacggt   27840
gagttccgta cccgtgctga gatggaagag taccgccaca acggttgac cgaaggtgcc   27900
aacgagttcg ctgaacagtt catgattaac cctgaggact ctgagttcca gagagggttc   27960
aacgcgaaca tcactgagcg caacatcctc ctgtacggta agcacgatac gttcctgagc   28020
gagcaggccc agaagggtgc catactggcc tcgaaggtgg agctgtcagg tgtgctcaaa   28080
```

```
gaccctgccg ttctggcccg tccagagtcc ggtgagttct tccagcgcta catcgacaac   28140
gcacttaaga ctgggagtat ccctagcgac gctcaggcac agcaggtcat catcgggtcc   28200
cttaacgacg tcattcagcg tccgggtgct accaacttcc tccagagcct tgagggccgc   28260
ccagtcaccc ttaatgggaa gaccacgacc tataaggagc tgatgggaga ggagcaatgg   28320
aacgccctga tggtcaaggc ccagtcaact cagttcgaca atgacgctaa gttgtctgaa   28380
ggtttccgcc ttgggattac cagcgcgttg aaccaagacg ataccagcaa gggctgggag   28440
atgcttcagg gtgccaaagc ggaacttgac cgcctgcaac ccggtgagca gatgacccca   28500
gagcgtgagc gcttgattca ggctgaggag cagatgcagg cccgtttccg tcaggaggcc   28560
caagccgcag ccaaggagat ggacaagcgt cagaagacca tcaacaagaa tcaggtcatc   28620
gaccagcagt tcaccaagcg tatcaacggt cagtacgtgt ccaccagcta caaggacatg   28680
ccgaccaatg agaacaccgg agagttcacg cacagtgaca tggtgaacta cgctaacggt   28740
aagctggccg agattgacca gatgcagctc acggagcaac agaaggaccg catgaagctg   28800
agctacctcc gggcagactc agagggtgga gccttccgta ccgttgtggg ccagttggta   28860
accgacgccg ggtctgaatg gtctgccgct gtgattaacg gtaagttacc ggaggacacc   28920
acagcgttga caaactgcg caccatgcgt aacaccgacc cggacctctt cgctgcactg   28980
tacccggaca aggctgactt gttcctgacg atggacatga tggataagca gggcattgac   29040
ccgcagattc tcatcgacgc tgaccgttct cgccgcagtc tcaccaagga gatgcagtac   29100
gaggacgata aggcgtgggc gtccctgaag aacaactcag agtccccaga gctgtcccgc   29160
attccggcta gtctggatgg tatggcccgt aagatttacg acagcgtcaa gtaccgtaca   29220
ggcaacagcg acatggcgat gcagcagacc gacaagttcc tcaaggaatc cactgtgacc   29280
ttcaagggtg atgacgtgga tggcgatacc attggtatta tcccgaagaa catcctacag   29340
gtcagtgatg accctaagag ctgggagcag ggccgagaca tcctcgaaga agcccgtaag   29400
ggaatcattg cggctaaccc cttgggtgac aacaagcagc tgacgatgta ccagcagggt   29460
gactctatct acatgatgga caccactggc actgtgcgaa tccgctacga caaggagcta   29520
ctgactcgca cttatcagga acagcagcag cgtctggcca aggaagccga agagaaggca   29580
ctgaaggaag caaccaagcg tgcacctatc gccgcagcca ctcaggcccg taaggccgct   29640
ggtgagcgtg tccgtgcgaa acgtaaagcc actccgaagt tcatctatgg aggtggtgac   29700
caataatcat taaggagaca acatgagcta cgataagtcc aaacctagcg attacgatgg   29760
catctttcag aaggcagcag actctcatgg ggtctcctat gacctcctgc gtaagttatc   29820
gtttaacgaa tcatccttca accctaaggc cgtctctaag actggcccta agggaatcat   29880
gcagttcacc cgcaacacgg cccgagcgat gggccttaac gtgacagatg gtgacgacga   29940
tgggcgctac aaccctgagt tagccattga cgctggcgct aagctgcttg cgagcctcgt   30000
taagaagtac aatgggatga gcttaaagc ggccctagcg tacaaccaag gggaaggcc    30060 agcaggtgcc cctcagctcc aagcgtacga caagggagac ttcgggtcta tctcggagga   30120
agggcgtaac tacatgcgca agctgctgga tgtggccaag agtccgaact caggcgcact   30180
ggaggcgttc ggtggcatca ccccaaaggg taaagggatt cccgcagagg atgccttcaa   30240
gggcatcgct aaggctggaa aggttggtac cgaactgccg gagtcccatg ggttcgacat   30300
tgagggtgta gcgcaggaag caccaaacac tccatacgct aaggacttct gggagaagac   30360
cgggactact ctcgatgagt ataactctcg gtcaaccttc ttcgggttcg gggacgctgc   30420
```

-continued

```
tgaggctcag attcagaact ccacattagg tgtggccttc cgtgctgcgc gggctgacga    30480
tgggtacgat gtgttcaagg acacgatgac cccgactcgc tggaactctt atgttccctc    30540
caaggaagac ctacagaagc tgcgcgactc tgggctacct ccgagctact acggtgtggt    30600
gactggtggt gacggtgaga actgggatgc actcatcaag ctggccaagg ataacttcga    30660
ggctgaccaa cgggccgctg aggctggtac tggggcgaaa ctcgctgctg gtatcgttgg    30720
ggctggtgta gacccactca gctatgtacc tctggtcggt gtggccggga agggactcaa    30780
ggttgtcaat aaggccctgc tagtaggcgc acaggctggg gcactcagtg ttgcctctga    30840
gggaatccgt acgtcagtgg ctggtggcga ggctcactac gctgatgcgg cactcggtgg    30900
gttactgttt ggcgctggta tgtcggctct cagtgatgct gtggcggctg gtatccgtaa    30960
ggcccgtgga gtcgattctg tgaatgagtt cgctggacca gcactcccta tggaagcgcg    31020
agagactgcc atcaacactg gtggtcatga cacctcgacg ctacctccag agaacttctc    31080
gttcgagcag gaccacagag gcgttccgtt tgctgaccac ccgaccgaag agggagcagt    31140
ggttctggcc aatggttcca tcctgagcga taccaacccg cttaacccaa ggactcaacg    31200
tgacttcgca gagattgacc cagagcgtgc agctcccggt atcaaactcg gtgggttcac    31260
tgagattggc ctgaagacct tagggtccaa ggatgctggt gtacgtgcaa tcgctcagga    31320
cctcgtgcgc tctcccacag ggatgcaatc agggtctagt ggtaagttcg gtgcgaccgc    31380
ttcggacatc cacgagcgac tccatgcgac tgaccaacgg atgtataacc aactgtatga    31440
cgctgttgac cgtgccatga aggacccaga gttctccgtg ggcgagcaga agatgtcacg    31500
cagagccatc cgtcaggaag tctacaagcg tgcctcattg gcgattgagc gcccagagtt    31560
acaggctgat ttgaccaaag gtgaacgtga ggtgatggac ctgctgaaag agcacttcga    31620
caccaagcgt gaactgatgg aacagccggg tatcttcggt aacgctaacg ccgtgagcat    31680
cttccccggt agtcgacaca agggtactta cgtgcctaac gtgtacgaca ggggtgccaa    31740
ggaactgatg atgcagaagc tgggcggacc tgaaggactc caacaggcaa tcgctcagag    31800
ctggcttacc agttaccgag tgcgacctga ggtcaaggcg cgtgttgacg agtacctgat    31860
ggaactcaac ggctacaagt cggtagacca agtgacacct gaggtggtcc agaagcacgc    31920
tatggataag gcgtacggta tcagccacac tgaggacttc acagcgtcca gtgtcattga    31980
cgacaacatc acaggtctgg tcggtatcga gaacaactcg ttccttgagg cccgtaacat    32040
gttcgacagc gacctcccgg ttaccttacc ggatgggtca accttcagcg tcaacgacct    32100
gagggacttc gacatggcac ggattatccc agcgtacgac cgtcgagtta acggtgatat    32160
ctccatcatg ggcggtagcg gtaagaccac gcagcagctc aaggacgaaa tcatggcgtt    32220
agacaagcgg gctgagcgta agggacagct gaagggcgaa gtggaagcac tgaaggacac    32280
cgttaagatt ctcacggggc gtgctcgtcg taacaacgat acagcctttg agaccgccat    32340
gcgtaccctg aacgacctag cgttcttcgc taagaacttc tacatgggtc cgcagaacct    32400
cacagagatt gctgggatgt tggctaaggg taacgttaag gcgatgctcc acggtatccc    32460
gacgttgcgt gacctagcca ccagaacctc tccggtgtcc ggtagtgaac tccgcgaact    32520
ccatggggcg ctgttcggta aggaactcga ccagttaatc cgtccgggc gtgaggatat    32580 cgtacagcga atccgcgagg cttccgatac cagtggggcc atggcgtcag tcattggcac    32640
catcaagttc ggtactcagg agctgtcggc tcgttctcct tggaccaaga tgctgaacgg    32700
tacggctaac tacattctgg acactgcccg tcagggtgtg ctcggtgatg tggctggtgc    32760
ggccctaggc ggtaagggtt ccaagtttgg caaagagaac ttcctcaaag ctgcctctat    32820
```

```
cagtcctgag cagtggaagg gaatcaagca actctttgtc gaccacgcaa ctcgtgacgc   32880
taacggccag ttcaccatca aggacaagaa ggctttcagt caggacccga gagcgatgga   32940
cctgtggcgt cttgccgata aggttgccga cgagaccatg ctgcgccctc acaaggtatc   33000
ccagcaggat tccaaggcgt acggtgctgg tgtcaagatg gctatgcagt tcaagaactt   33060
caccatcaag tcactcaatg ccaagttcat tcggtccttc tacgagggct acaagaacaa   33120
ccgcgctatc gacatggcgt tgacacacgt gttgtctctg ggtatcgccg ggacttactt   33180
tgcgatgcag gcccacgtga aggcttacgg cctccaagag tcccaacgta aggactacct   33240
gaagaaagcc ctgaacccga ccatgctggg ctacgcagcg ttgactcgaa gttcccacac   33300
tggtgccccg ctgtccatcg tttcgatgat ggctggtgcc gctgggttcc aagacgccaa   33360
catgctgcgc tccaccatct tacctaagga ggaacaattc cagaagaaag atggagcgtc   33420
caaaggtcga gccgagtcga gcaaccttgc gggtaactta gggtctcagg tcccagctct   33480
gggttacgta gggaacgtca ttgctaccgc caagaacgcc tacggtgttg ctacagcacc   33540
caacaagccg actgagcgtg actacatgac tggcctgatg aactccacca aggagcttgt   33600
tccgaacgac ccactgaccc agcagctcat catgaaaatc tatgaagcca acggggtcac   33660
catcaagcag cagccgaagc ctaactaatt aggacacact atagggagac cgattggttt   33720
ccccccttct cattcaacta aaggaggtca caatggacca agacattaaa acagtcattc   33780
agtacccagt aggggccact gagttcgaca tcccgttcga ctacctgtcc cgtaagtttg   33840
tccgtgtgtc gctggcagct gacgacaacc gcagactgct gagtaacatc actgagtacc   33900
gctacgtgtc taagaccaga gtgaagctcc ttgtggaaac taccgggttc gaccgtgtgg   33960
aaatccgcag attcacctca gcgtctgagc gtattgttga cttcagcgac ggctccgtac   34020
tgcgggcaac agaccttaac gtttctcaga ttcagtctgc ccatatcgca gaggaagcac   34080
gtgattcagc actgttggct atgccgcagg atgatgctgg caaccttgat gcccgtaacc   34140
gcagaatcgt tcggctggct ccgggtgtcg aaggtacgga tgcaatcaac aagaaccagc   34200
tggacaccac cttaggtgaa gctggtggca tcctgtcgga aatcaaacag accgagaagg   34260
acattcagga ttacatcgag aactttgcag atgcacacca gtctctcaag gaatcaact   34320 gggtgtataa caatgggtcg gccaatggtg gcgagacctc catcctgatt acccgcgagg   34380
ggccagtgtt cgctgtgcct accatttaca tcaatgggga cagacagtct gttggttacc   34440
actactctta cgactccggt gataagacca ttcacctagt taagccgcta actgctggag   34500
actttgtgga atgtgttacc tctgagggcg tactgccgct gtctaatctt ctgtcgacac   34560
cagacggggc cagtcagatt ggcactaaaa gcggcctgac tgtgcaagac taccttaacg   34620
gcgtgaagtc cgctaccatc ctgcgcaaca ttgagccagt cattgatgga cagcgcatcg   34680
tcctctctga gattagcccc actttggggc ctaagtctgg aggtaccttg gtgtacgacc   34740
agtctgatac atcctctgtg gacgacgggt acactgtttt cgtgacagct ggcggtaaac   34800
ggtggaagcg agaagagtcc tacattgacg tagcgtggtt cggtcctaac tttggccttg   34860
ccttacagac cgctgttaac ctcgttgaca actacgtgag aactgtcggt ttctacagtc   34920
gcaagaccat ctacattgca gctggtacct atacgacaga ccgtcaggtg gacattccat   34980
cttatgtctc tgtggtggcc ataggtaacg ttagcatcaa tggttctggg cttccagtaa   35040
actcctacgt actccgcata acgaacaagg ttggtgcat tgtcacaacc caccactcag   35100
ggtggaacct cggggccgta ggtgggaccc ttcgtcttgt aggaaacggc aacaccgggc   35160
```

```
aagtggatgg gctttatgtg ggcggtgcga cttctatgag cgacgtacgg aacgttagcc   35220
tttacgctgt gtcaacttcg ggtgttcgct atgggctaac atttggtagc accaacactt   35280
acctcttcac ggcaaccaaa tgccactttg agacgtctct tgtaaacctg tacattccgg   35340
gcaccacaag ctctaactca ggggagaaga tggtattcaa tgatactgtg ttcggtggct   35400
catctaggaa ccatgtagag gtaagcaccc caggcatgga cctcacgttc ataactgct    35460 ctttcgactt cacaagcggt agcgtcctgt acgggacaga gacttgggc tatgcgaaag    35520 taggcatgaa taattgccac ttcgaggggt tcaatagttt gtggataaag gtggatgccc   35580
cgcaaggtgg attcattggg tcaaaccgag cgataaccgt atcaaacgcc acagtccttc   35640
ctaggcttcg ctccaacact gctggaacaa actcggcgag ccgtatgcac attgatgcca   35700
agtctacccc ggtgtatatc agtgggctgg acctacggca cgaggtcgta ccatacaccg   35760
aggaaatctt catggcttca gctgaaacta ccctgtctct gcaaggatat cttaaggacc   35820
cgcatttcca gattccaagt gctgcgcaca ttcagaaccg tgggtggaac atcgctgacg   35880
aaacaactgg aactgttgtg aacagccccg caaccttgga ttcccttacg cgatttacat   35940
gcaccgagag gaacgcgatg tctgcggctg tggtcgatgg tggaacttct ggtaagctct   36000
tagcaatgac tggagcgggt gggtatttca ctctggtcac taaaggattc attccggtga   36060
gtacgttcca acggattggc ggagcaatgt cgattcaggc agcagcaagt accggaaaca   36120
tccagtgcac gcttggtgtc cagtggttcg actacgatgg taacctaatc gggacagacc   36180 aagccttttgc gattaacatg cgtgaggtgt tcaacaactc ttctctacct aacttcgccg   36240
aaggcaacaa ccgcttcatc tctacatctg cgagaacatt ccgtgcgcca gcgggggccg   36300
ctaagtgtaa accattgtgg cgaatctctg gtcatactgg cgttgtgaac atctcgagat   36360
tagcatcatt tgttttataa ggagacaaca tgctgaatga tttaaaccaa ccacgaggct   36420
cgacgctggg cctctttact ccaaaccttc cgttgaagaa gcggttggac accttaccaa   36480 acatttaga ttttgattca gacagcctta acgatgatag cactcggttt caaaaggcta    36540
ttacagctgg tgtgaaatct ttatacgtcc cagaacctca gttctttggc aacaataagc   36600
ctcttaaaat tgctaacgtt gacattgtga ccaatatgca catctacggg aacggctcag   36660
cgggataccg tcaggttggc ggggccatca ccatcctaga tggagcggac tatgggttta   36720
aactggctgg tgtcgactct cagacgcgaa acattggagg ccgcattgac ggtctctcgt   36780
tccaaggtga gttcccaacg accgtggccg acgccatccg gtgccaatct gccagtagct   36840
tcgcgctggt caacctctcg ttcaggaacc tctccgggtc cgctctggac ctgcgtgact   36900
tcatggagag ccacattgag cactgctact ttaactcagt aggttccgac acaaagaacc   36960
caatcaacat cggggacttc gtcgggtcgg ctccttggaa cgtcaacaac ctgcacattg   37020
agaacaacac cttcgggtca tgtagtggga acattatcaa cattagtgac tcagctaacg   37080
ccgacctcat ttggattctc aacaataaat tcgaatggga ctcgacccca gtaagcccca   37140
acgtttccaa caaggcggtg gcatacatcg ggcgagccga gcgtgtaaat gtgtccggta   37200
acggcttcgt gtactactac ccggcccaca caagtacga tgcccttatc cgagtttccg    37260
ataagtcggc ctatgtaac ttgttctctg ataataccgc ttggggctgt acgcctcctt    37320
caggtagtga cctcactcca gcgttctatt gggacattgc tggtgggtcg tctgcggggt   37380
ctaacaacaa ggctaacaca aacctcccta cgcgctgcac cagtatccac tctcaggata   37440
tcgacgagcc gctggtaagg actactccgg gtaaccgacc aaacctccag agcatcgggg   37500
caatgtctcc cggatatctc tctgcgcact ccttaggtgg ggctaacgct tccaacttct   37560
```

```
ttgtgccaga cactggtgct accaagtacg gtacggtgct agaggctcaa actggtggtg   37620
aggttcgccg cttgttcatt cctaaggaca ttgttagcca gcgtgcttgc gttcgagttc   37680
aggccagagt gatgccgtcg ccgacagctg atgcccttgt ggggctgacc tgtgacggct   37740
ccattgtttc caccacaatc caaggcgcaa cccaagacta ccatacggtg gcggctggtg   37800
gcggctggca gattgtcgag tggctcatcc cggcgtctag ttacactgcg ggccagttaa   37860
tcttcacgaa ccgtagtgac accgtcaagt tcaaacttga tggcgtccgt gtgtcacgtg   37920
cagacttcgt agatgtgacg attgcatgga gtccgacccc aatctccgca gggtctgtgg   37980
taaacaccac tgcatcaatc actcgcgtaa gttcccacgt ggtcggcact agtggtctga   38040
agacagacgg tacgttaggt ggcgctgtta gtagctctta tttcaaccgt ggggccaata   38100
ccttagtggt acagctggca gcactcacag cagccactcc gtcaatcact caggttacgg   38160
ttaggctgtt ccttaactaa ggaggtaaca tgttgtccct agacttcaac aacgaagtta   38220
tcaaggcggc tcccattgcg ggggtcgctg gggccgatgg tgtagcgagg ctcttctggg   38280
gcctctcact caacgagtgg ttctacgtcg cggcaatcgc ctacacagtg gttcagattg   38340
gtgccaaggt agtcgacaaa atcattgact ggaagaaagc aaataaggag taacatatgg   38400
acctgattaa gttcctcgaa atgttagata ctgagatggc tcagcagatg ctcatggacc   38460
tgaagaatcc cgagaagcga acccctcagc tgtacaacgc cattggtaaa ctactggagc   38520
gccataagtt ccaaatctct aagctgaccc ctgacgttaa catcttgggc ggactggctg   38580
agggtctgga ggcttacaac tccaaggtgg gcgccgatgg tctgacagac gacgatacgt   38640
tcaccctaca gtgatatact caaggtacta ctatatgtag tgcctttatg gatgtcattg   38700
cactacgcta ggcgttccta cgtgaaatct gagaaacaac gggaggcatt atgctggagt   38760
tcacaaagag aatcgtcccg tatcttgtgg ctatcatggt gtttgccttc gggtggcact   38820
tggggtctca atctacggac gctaaatgga aggaggtagt acagcatgaa tacgttaaga   38880
agcaaacggc tagagctgaa actcagaaag cgattgacgc aatatcggct aagtaccaag   38940
cagaccttga ggggctggag ggcagcactg atagggttat tgctgatttg cgtagcgaca   39000
ataagcggct gcgcgtcaga gtcaaaccta ccagtgtcgc cgcaggacca gacggtcgat   39060
gcctcgttga tggttccgtc gaactacacg aagcaactgc tcgaagtctt atcgcaataa   39120
cccagaaggc cgacctcaaa gagaaggccc tacaggacac tattcgcaag ctacagcgga   39180
aaggaggtga acattgagta actctcagca agccaagaac gccttaatca ttgcgcaact   39240
gaagggtgac tttgtcgcct ttctcttcgt gctctggaag gccctgaacc tgccggaacc   39300
aaccaagtgt caaatcgaca tggccaagtg tctggcgaac ccaaagaaca agaagtttat   39360
ccttcaggct ttccgtggta tcgggaagtc attcatcacg tgtgcgttcg tagtgtggac   39420
cctgtggcgt gaccctcagt taaagatact gattgtctcg gcctcaaagg aacgtgcgga   39480
cgctaactcc atcttcatca agaacatcat cgacttgttg cctttcctga gtgagctaaa   39540
gccccgcccc ggtcagcgtg actccgtgat tagctttgat gtaggccctg ccaagccaga   39600
ccacagcccg tcagttaagt ctgtgggtat tactggtcag cttactggta gccgtgctga   39660
tatcatcatt gcggatgacg tggagattcc cggtaactct gcaacccaag cgctcgtga   39720 gaaactctgg acgctggttc aggagttcgc cgcactgttg aaacctctgc cgactagccg   39780
tgttatctat ctgggtacac ctcagaccga gatgacgctc tacaaggaac ttgaggacaa   39840
ccgtgggtac tccaccatta tctggcctgc acagtatcct cgctccaaag aggaggacct   39900
```

```
gtactatggc gaccgactgg ccccgatgct ccgtagtgag tacgatgagg acaaagaggg    39960
cctcagcagt cagcctactg acccggttcg attcgactcc atggaccttc aggaacgtga    40020
ggtggaatac ggcaaggctg gctatacgct tcagttcatg ctcaacccga acctcagtga    40080
cgccgagaag tacccgctac gcctccgtga cgctatcgtg tgcggtctac agatggacaa    40140
ggccccaatg cattaccagt ggttgccgaa ccgtcagaac cgcaatgagg agcttcctaa    40200
cgtgggcatg aagggtgacg agatttactc cttccataca gcctcaagta acactggcgc    40260
gtatcagggt aagattctgg tcattgaccc cagcggtcgc ggtaaggatg agactggctg    40320
gtgcgtactg tacaccctca acggttacat ctacttgatg gacgctggcg gtactcgtgg    40380
gtacgaagag aagtcccttg agttcctcgc taagaaagcc aaacagtggc aggttcagac    40440
tgtggtcttc gagagcaact tcggtgacgg tatgttcggt aacgtgttcc agcctgtgct    40500
cctgaagcat cacccagcgc aactcgaaga gattcgtgct cgtggtatga agaggtccg    40560 tatctgcgat acccttgagc ctgtactggc aagtcaccgc ttggtcatcc gtgatgaggt    40620
tatccgacag gactaccaga cggcacgtga tgcagacggt aagcacgctc tgaagtacag    40680
tctgttctac cagatgaccc gtatgagccg tgagaagggc gcggtggcac acgatgaccg    40740
acttgatgcg ttagcattgg gtgtcgagtt cctacgctct acgatgcagc aggacgctgt    40800
gaagatagag gctgaggtac ttcaggagtt cttggagcac cacatggaga agcccctgag    40860
taacatctcc cagttccggg ccaccagtag caacggtgtg gacatccgat gggaagacga    40920
tggggatgac actatgttca tcgcatggtg attatgcagg gattgtgcat aaggattcat    40980
taggccacgg aaggccactt tgaggaaact ccatgtataa cagacacttg gaattaggac    41040
ccactatagg gagagaccct tgaagactta ctataagaca acttaaagat tcattcatat    41100
agttattcac tttaagtctc cttaaaggca gagggtagtg atgataatat caccctctca    41160
ctataagaca ctaagagcca acataaggag gacctatgcg cttattgtta accttactgc    41220
gccatagggc tacttggcga tttctgctgg tacttgctgg tgcccttggg gcttcactgg    41280
ttactcagca gcaactcagt ggactggaga ctctcgtgtg ctctctactc acttgtagcg    41340
attagggtct tcctgacgcg ctagggattc cgtagtgatg cttatcagca tacaccactc    41400
catccctcta cagtcaatac ttaaagttaa ccttaggtga ttcactgggt ctacctacgg    41460
gtctatgcaa tgacctgagg agtacctgag gttaccttta agaattttac ataaagttct    41520
gagtgtacat ctcacagttt acactttggg ttatccccc ggtaccctcc agttcaccca    41580
aagtaaccta gggtacccct ctttaccttt ggtttaacct tggtggtac cttgggaatc    41640 ccttaggtga taccatatgt tggggtaatg gtgacctgag gacactatat gttgatgtct    41700
ctgtgtccct ttaattaa                                                  41718
```

<210> SEQ ID NO 2
<211> LENGTH: 40467
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
tctcacagtg tacggaccta aagttccccc ataggggta cctaaagccc agccaatcac    60
ctaaagtcaa ccttcggttg accttgaggg ttccctaagg gttggggatg acccttgggt    120
ttgtctttgg gtgttacctt gagtgtctct ctgtgtccct atctgttaca gtctcctaaa    180
```

```
gtatcctcct aaagtcacct cctaacgtcc atcctaaagc caacacctaa agcctacacc    240
taaagaccca tcaagtcaac gcctatctta aagtttaaac ataaagacca gacctaaaga    300
ccagacctaa agacactaca taaagaccag acctaaagac gccttgttgt tagccataaa    360
gtgataacct ttaatcattg tctttattaa tacaactcac tataaggaga acaacttaa    420 agagacttaa aagattaatt taaaatttat caaaaagagt attgacttaa agtctaacct    480
ataggatact tacagccatc gagagggaca cggcgaatag ccatcccaat cgacaccggg    540
gtcaaccgga taagtagaca gcctgataag tcgcacgaaa acaggtatt gacaacatga    600 agtaacatgc agtaagatac aaatcgctag gtaacactag cagcgtcaac cgggcgcaca    660
gtgccttcta ggtgacttaa gcgcaccacg gcacataagg tgaaacaaaa cggttgacaa    720
catgaagtaa acacggtacg atgtaccaca tgaaacgaca gtgagtcacc acactgaaag    780
gtgatgcggt ctaacgaaac ctgacctaag acgctcttta acaatctggt aaatagctct    840
tgagtgcatg actagcggat aactcaaggg tatcgcaagg tgcccttat gatattcact    900 aataactgca cgaggtaaca caagatggct atgtctaaca tgacttacaa caacgttttc    960
gaccacgctt acgaaatgct gaaagaaaac atccgttatg atgacatccg tgacactgat    1020
gacctgcacg atgctattca catggctgcc gataatgcag ttccgcacta ctacgctgac    1080
atctttagcg taatggcaag tgagggcatt gaccttgagt tcgaagactc tggtctgatg    1140
cctgacacca aggacgtaat ccgcatcctg caagcgcgta tctatgagca attaacgatt    1200
gacctctggg aagacgcaga agacttgctc aatgaatact tggaggaagt cgaggagtac    1260
gaggaggatg aagagtaatg tctactacca acgtgcaata cggtctgacc gctcaaactg    1320
tacttttcta tagcgacatg gtgcgctgtg gctttaactg gtcactcgca atggcacagc    1380
tcaaagaact gtacgaaaac aacaaggcaa tagcttaga atctgctgag tgatagactc    1440
aaggtcgctc ctagcgagtg gcctttatga ttatcacttt acttatgagg gagtaatgta    1500
tatgcttact atcggtctac tcaccgctct aggtctagct gtaggtgcat cctttgggaa    1560
ggctttaggt gtagctgtag gttcctactt taccgcttgc atcatcatag gaatcatcaa    1620 agggcacta cgcaaatgat gaagcactac gttatgccaa tccacacgtc caacggggca    1680
accgtatgta cacctgatgg gttcgcaatg aaacaacgaa tcgaacgcct taagcgtgaa    1740
ctccgcatta accgcaagat taacaagata ggttccggct atgacagaac gcactgatgg    1800
cttaaagaaa ggttatatgc ccaatggcac actatacgct gcaaatcggc gaatagtgag    1860
aacttggcga gagaacaacc tcgaacgccg caaggacaag agagggcggc gtggcataga    1920
cgaaaggaaa aggttaaagc caagaaactc gccgcacttg aacaggcact agccaacaca    1980
ctgaacgcta tctcataacg aacataaagg acacaatgca atgaacatta ccgacatcat    2040
gaacgctatc gacgcaatca aagcactgcc aatctgtgaa cttgacaagc gtcaaggtat    2100
gcttatcgac ttactggtcg agatggtcaa cagcgagacg tgtgatggcg agctaaccga    2160
actaaatcag gcacttgagc atcaagattg gtggactacc ttgaagtgtc tcacggctga    2220
cgcagggttc aagatgctcg gtaatggtca cttctcggct gcttatagtc acccgctgct    2280
acctaacaga gtgattaagg tgggctttaa gaaagaggat tcaggcgcag cctataccgc    2340
attctgccgc atgtatcagg gtcgtcctgg tatccctaac gtctacgatg tacagcgcca    2400
cgctggatgc tataccggtgg tacttgacgc acttaaggat tgcgagcgtt tcaacaatga    2460
tgcccattat aaatacgctg agattgcaag cgacatcatt gattgcaatt cggatgagca    2520
tgatgagtta actggatggg atggtgagtt tgttgaaact tgtaaactaa tccgcaagtt    2580
```

-continued

```
ctttgagggc atcgcctcat tcgacatgca tagcgggaac atcatgttct caaatggaga    2640
cgtaccatac atcaccgacc cggtatcatt ctcgcagaag aaagacggtg gcgcattcag    2700
catcgaccct gaggaactca tcaaggaagt cgaggaagtc gcacgacaga agaaattga    2760 ccgcgctaag gcccgtaaag aacgtcacga ggggcgctta gaggcacgca gattcaaacg    2820
tcgcaaccgc aaggcacgta aagcacacaa agctaagcgc gaaagaatgc ttgctgcgtg    2880
gcgatgggct gaacgtcaag aacggcgtaa ccatgaggta gctgtagatg tactaggaag    2940
aaccaataac gctatgctct gggtcaacat gttctctggg gactttaagg cgcttgagga    3000
acgaatcgcg ctgcactggc gtaatgctga ccggatggct atcgctaatg gtcttacgct    3060
caacattgat aagcaacttg acgcaatgtt aatgggctga tagtcttatc ttacaggtca    3120
tctgcgggtg gcctgaatag gtacgattta ctaactggaa gaggcactaa atgaacacga    3180
ttaacatcgc taagaacgac ttctctgaca tcgaactggc tgctatcccg ttcaacactc    3240
tggctgacca ttacggtgag cgtttagctc gcgaacagtt ggcccttgag catgagtctt    3300
acgagatggg tgaagcacgc ttccgcaaga tgtttgagcg tcaacttaaa gctggtgagg    3360
ttgcggataa cgctgccgcc aagcctctca tcactaccct actccctaag atgattgcac    3420
gcatcaacga ctggtttgag gaagtgaaag ctaagcgcgg caagcgcccg acagccttcc    3480
agttcctgca agaaatcaag ccggaagccg tagcgtacat caccattaag accactctgg    3540
cttgcctaac cagtgctgac aatacaaccg ttcaggctgt agcaagcgca atcggtcggg    3600
ccattgagga cgaggctcgc ttcggtcgta tccgtgacct tgaagctaag cacttcaaga    3660
aaaacgttga ggaacaactc aacaagcgcg tagggcacgt ctacaagaaa gcatttatgc    3720
aagttgtcga ggctgacatg ctctctaagg gtctactcgg tggcgaggcg tggtcttcgt    3780
ggcataagga agactctatt catgtaggag tacgctgcat cgagatgctc attgagtcaa    3840
ccggaatggt tagcttacac cgccaaaatg ctggcgtagt aggtcaagac tctgagacta    3900
tcgaactcgc acctgaatac gctgaggcta tcgcaacccg tgcaggtgcg ctggctggca    3960
tctctccgat gttccaacct tgcgtagttc ctcctaagcc gtggactggc attactggtg    4020
gtggctattg ggctaacggt cgtcgtcctc tggcgctggt gcgtactcac agtaagaaag    4080
cactgatgcg ctacgaagac gtttacatgc ctgaggtgta caaagcgatt aacattgcgc    4140
aaaacaccgc atggaaaatc aacaagaaag tcctagcggt cgccaacgta atcaccaagt    4200
ggaagcattg tccggtcgag gacatccctg cgattgagcg tgaagaactc ccgatgaaac    4260
cggaagacat cgacatgaat cctgaggctc tcaccgcgtg gaaacgtgct gccgctgctg    4320
tgtaccgcaa ggacaaggct cgcaagtctc gccgtatcag ccttgagttc atgcttgagc    4380
aagccaataa gtttgctaac cataaggcca tctggttccc ttacaacatg gactggcgcg    4440
gtcgtgttta cgctgtgtca atgttcaacc cgcaaggtaa cgatatgacc aaaggactgc    4500
ttacgctggc gaaaggtaaa ccaatcggta aggaaggtta ctactggctg aaaatccacg    4560
gtgcaaactg tgcgggtgtc gataaggttc cgttccctga gcgcatcaag ttcattgagg    4620
aaaaccacga gaacatcatg gcttgcgcta agtctccact ggagaacact tggtgggctg    4680
agcaagattc tccgttctgc ttccttgcgt tctgctttga gtacgctggg gtacagcacc    4740
acggcctgag ctataactgc tcccttccgc tggcgtttga cgggtcttgc tctggcatcc    4800
agcacttctc cgcgatgctc cgagatgagg taggtggtcg cgcggttaac ttgcttccta    4860
gtgaaaccgt tcaggacatc tacgggattg ttgctaagaa agtcaacgag attctacaag    4920
```

```
cagacgcaat caatgggacc gataacgaag tagttaccgt gaccgatgag aacactggtg    4980
aaatctctga gaaagtcaag ctgggcacta aggcactggc tggtcaatgg ctggcttacg    5040
gtgttactcg cagtgtgact aagcgttcag tcatgacgct ggcttacggg tccaaagagt    5100
tcggcttccg tcaacaagtg ctggaagata ccattcagcc agctattgat tccggcaagg    5160
gtctgatgtt cactcagccg aatcaggctg ctggatacat ggctaagctg atttgggaat    5220
ctgtgagcgt gacggtggta gctgcggttg aagcaatgaa ctggcttaag tctgctgcta    5280
agctgctggc tgctgaggtc aaagataaga agactggaga gattcttcgc aagcgttgcg    5340
ctgtgcattg ggtaactcct gatggtttcc ctgtgtggca ggaatacaag aagcctattc    5400
agacgcgctt gaacctgatg ttcctcggtc agttccgctt acagcctacc attaacacca    5460
acaaagatag cgagattgat gcacacaaac aggagtctgg tatcgctcct aactttgtac    5520
acagccaaga cggtagccac cttcgtaaga ctgtagtgtg ggcacacgag aagtacggaa    5580
tcgaatcttt tgcactgatt cacgactcct tcggtaccat tccggctgac gctgcgaacc    5640
tgttcaaagc agtgcgcgaa actatggttg acacatatga gtcttgtgat gtactggctg    5700
atttctacga ccagttcgct gaccagttgc acgagtctca attggacaaa atgccagcac    5760
ttccggctaa aggtaacttg aacctccgtg acatcttaga gtcggacttc gcgttcgcgt    5820
aacgccaaat caatacgact cactatagag ggacaaactc aaggtcattc gcaagagtgg    5880
cctttatgat tgaccttctt ccggttaata cgactcacta taggagaacc ttaaggttta    5940
actttaagac ccttaagtgt taattagaga tttaaattaa gaattacta agagaggact    6000 ttaagtatgc gtaacttcga aaagatgacc aaacgttcta accgtaatgc tcgtgacttc    6060
gaggcaacca aggtcgcaa gttgaataag actaagcgtg accgctctca aagcgtagc    6120 tgggagggtc agtaagatgg gacgtttata tagtggtaat ctggcagcat tcaaggcagc    6180
aacaaacaag ctgttccagt tagacttagc ggtcatttat gatgactggt atgatgccta    6240
tacaagaaaa gattgcatac ggttacgtat tgaggacagg agtggaaacc tgattgatac    6300
tagcaccttc taccaccacg acgaggacgt tctgttcaat atgtgtactg attggttgaa    6360
ccatatgtat gaccagttga aggactggaa gtaatacgac tcagtatagg acaatgctt    6420 aaggtcgctc tctaggagtg gccttagtca tttaaccaat aggagataaa cattatgatg    6480
aacattaaga ctaaccgtt taagccgtg tcttcgtag agtctgccat taagaaggct    6540
ctggataacg ctgggtatct tatcgctgaa atcaagtacg atggtgtacg cgggaacatc    6600
tgcgtagaca atactgctaa cagttactgg ctctctcgtg tatctaaaac gattccggca    6660
ctggagcact taaacgggtt tgatgttcgc tggaagcgtc tactgaacga tgaccgttgc    6720
ttctacaaag atggctttat gcttgatggg gaactcatgg tcaagggcgt agactttaac    6780
acagggtccg gcctactgcg taccaaatgg actgacacga agaaccaaga gttccatgaa    6840
gagttattcg ttgaaccaat ccgtaagaaa gataaagttc cctttaagct gcacactgga    6900
caccttcaca taaaactgta cgctatcctc ccgctgcaca tcgtggagtc tggagaagac    6960
tgtgatgtca tgacgttgct catgcaggaa cacgttaaga acatgctgcc tctgctacag    7020
gaatacttcc ctgaaatcga atggcaagcg gctgaatctt acgaggtcta cgatatggta    7080
gaactacagc aactgtacga gcagaagcga gcagaaggcc atgagggtct cattgtgaaa    7140
gacccgatgt gtatctataa gcgcggtaag aaatctggct ggtggaaaat gaaacctgag    7200
aacgaagctg acggtatcat tcagggtctg gtatggggta caaaggtct ggctaatgaa    7260 ggtaaagtga ttggttttga ggtgcttctt gagagtggtc gtttagttaa cgccacgaat    7320
```

```
atctctcgcg ccttaatgga tgagttcact gagacagtaa aagaggccac cctaagtcaa    7380
tggggattct ttagcccata cggtattggc gacaacgatg cttgtactat taacccttac    7440
gatggctggg cgtgtcaaat tagctacatg gaggaaacac ctgatggctc tttgcggcac    7500
ccatcgttcg taatgttccg tggcaccgag gacaaccctc aagagaaaat gtaatcacac    7560
tggctcacct tcgggtgggc ctttctgcgt ttataaggag acactttatg tttaagaagg    7620
ttggtaaatt ccttgcggct ttggcagcta tcctgacgct tgcgtatatt cttgcggtat    7680
accctcaagt agcactagta gtagttggcg cttgttactt agcggcagtg tgtgcttgcg    7740
tgtggagtat agttaactgg taatacgact cactaaagga ggtacacacc atgatgtact    7800
taatgccatt actcatcgtc attgtaggat gccttgcgct ccactgtagc gatgatgata    7860
tgccagatgg tcacgcttaa tacgactcac taaaggagac actatatgtt tcgacttcat    7920
tacaacaaaa gcgttaagaa tttcacggtt cgccgtgctg accgttcaat cgtatgtgcg    7980
agcgagcgcc gagctaagat acctcttatt ggtaacacag ttcctttggc accgagcgtc    8040
cacatcatta tcacccgtgg tgactttgag aaagcaatag acaagaaacg tccggttctt    8100
agtgtggcag tgacccgctt cccgttcgtc cgtctgttac tcaaacgaat caaggaggtg    8160
ttctgatggg actgttagat ggtgaagcct gggaaaaaga aaacccgcca gtacaagcaa    8220
ctgggtgtat agcttgctta gagaaagatg accgttatcc acacacctgt aacaaaggag    8280
ctaacgatat gaccgaacgt gaacaagaga tgatcattaa gttgatagac aataatgaag    8340
gtcgcccaga tgatttgaat ggctgcggta ttctctgctc caatgtccct tgccacctct    8400
gccccgcaaa taacgatcaa aagataacct taggtgaaat ccgagcgatg gacccacgta    8460
aaccacatct gaataaacct gaggtaactc ctacagatga ccagccttcc gctgagacaa    8520
tcgaaggtgt cactaagcct tcccactaca tgctgtttga cgacattgag gctatcgaag    8580
tgattgctcg ttcaatgacc gttgagcagt tcaagggata ctgcttcggt aacatcttaa    8640
agtacagact acgtgctggt aagaagtcag agttagcgta cttagagaaa gacctagcga    8700
aagcagactt ctataaagaa ctctttgaga aacataagga taaatgttat gcataacttc    8760
aagtcaaccc cacctgccga cagcctatct gatgacttca catcttgctc agagtggtgc    8820
cgaaagatgt gggaagagac attcgacgat gcgtacatca agctgtatga actttggaaa    8880
tcgagaggtc aatgactatg tcaaacgtaa atacaggttc acttagtgtg gacaataaga    8940
agttttgggc taccgtagag tcctcggagc attccttcga ggttccaatc tacgctgaga    9000
ccctagacga agctctggag ttagccgaat ggcaatacgt tccggctggc tttgaggtta    9060
ctcgtgtgcg tccttgtgta gcaccgaagt aatacgactc actattaggg aagactccct    9120
ctgagaaacc aaacgaaacc taaggagat taacattatg gctaagaaga ttttcacctc    9180
tgcgctgggt accgctgaac cttacgctta catcgccaag ccggactacg caacgaaga    9240 gcgtggcttt gggaaccctc gtggtgtcta taaagttgac ctgactattc caacaaaga    9300 cccgcgctgc cagcgtatgg tcgatgaaat cgtgaagtgt cacgaagagg cttatgctgc    9360
tgccgttgag gaatacgaag ctaatccacc tgctgtagct cgtggtaaga aaccgctgaa    9420
accgtatgag ggtgacatgc cgttcttcga taacggtgac ggtacgacta cctttaagtt    9480
caaatgctac gcgtctttcc aagacaagaa gaccaaagag accaagcaca tcaatctggt    9540
tgtggttgac tcaaaaggta agaagatgga agacgttccg attatcggtg gtggctctaa    9600
gctgaaagtt aaatattctc tggttccata caagtggaac actgctgtag gtgcgagcgt    9660
```

-continued

```
taagctgcaa ctggaatccg tgatgctggt cgaactggct acctttggtg gcggtgaaga    9720
cgattgggct gacgaagttg aagagaacgg ctatgttgcc tctggttctg ccaaagcgag    9780
caaaccacgc gacgaagaaa gctgggacga agacgacgaa gagtccgagg aagcagacga    9840
agacggagac ttctaagtgg aactgcggga gaaaatcctt gagcgaatca aggtgacttc    9900
ctctgggtgt tgggagtggc agggcgctac gaacaataaa gggtacgggc aggtgtggtg    9960
cagcaatacc ggaaaggttg tctactgtca tcgcgtaatg tctaatgctc cgaaaggttc   10020
taccgtcctg cactcctgtg ataatccatt atgttgtaac cctgaacacc tatccatagg   10080
aactccaaaa gagaactcca ctgacatggt aaataagggt cgctcacaca aggggtataa   10140
actttcagac gaagacgtaa tggcaatcat ggagtccagc gagtccaatg tatccttagc   10200
tcgcacctat ggtgtctccc aacagactat ttgtgatata cgcaaaggga ggcgacatgg   10260
caggttacgg cgctaaagga atccgaaagg ttggagcgtt tcgctctggc ctagaggaca   10320
aggtttcaaa gcagttggaa tcaaaaggta ttaaattcga gtatgaagag tggaaagtgc   10380
cttatgtaat tccggcgagc aatcacactt acactccaga cttcttactt ccaaacggta   10440
tattcgttga cacaagggt ctgtgggaaa gcgatgatag aaagaagcac ttattaatta   10500
gggagcagca ccccgagcta gacatccgta ttgtcttctc aagctcacgt actaagttat   10560
acaaaggttc tccaacgtct tatggagagt tctgcgaaaa gcatggtatt aagttcgctg   10620
ataaactgat acctgctgag tggataaagg aacccaagaa ggaggtcccc tttgatagat   10680 taaaaggaa aggaggaaag aaataatggc tcgtgtacag tttaaacaac gtgaatctac   10740
tgacgcaatc tttgttcact gctcggctac caagccaagt cagaatgttg gtgtccgtga   10800
gattcgccag tggcacaaag agcagggttg gctcgatgtg ggataccact ttatcatcaa   10860
gcgagacggt actgtggagg caggacgaga tgagatggct gtaggctctc acgctaaggg   10920
ttacaaccac aactctatcg gcgtctgcct tgttggtggt atcgacgata aggtaagtt   10980 cgacgctaac tttacgccag cccaaatgca atcccttcgc tcactgcttg tcacactgct   11040
ggctaagtac gaaggcgctg tgcttcgcgc ccatcatgag gtggcgccga aggcttgccc   11100
ttcgttcgac cttaagcgtt ggtgggagaa gaacgaactg gtcacttctg accgtggata   11160
attaattgaa ctcactaaag ggagaccaca gcggtttccc tttgttcgca ttggaggtca   11220
aataatgcgc aagtcttata acaattcta taaggctccg aggaggcata tccaagtgtg   11280
ggaggcagcc aatgggccta ccaaaaggt ttattatata gaccacattg acggcaatcc   11340
actcaacgac gccttagaca atctccgtct ggctctccca aaagaaaact catgaacat   11400 gaagactcca aagagcaata cctcaggact aaagggactg agttggagca aggaaaggga   11460
gatgtggaga ggcactgtaa cagctgaggg taaacagcat aactttcgta gtagagatct   11520
attggaagtc gttgcgtgga tttatagaac taggagggaa ttgcatggac aattcgcacg   11580
attccgatag tgtatttctt taccacattc cttgtgacaa ctgtgggagt agtgatggga   11640
actcgctgtt ctctgacgga cacacgttct gctacgtatg cgagaagtgg actgctggta   11700
atgaagacac taagagagg gcttcaaaac ggaaaccctc aggaggtaaa ccaatgactt   11760
acaacgtgtg gaacttcggg gaatccaatg gacgctactc cgcgttaact gcgagaggaa   11820
tctccaagga aacctgtcag aaggctggct actggattgc caaagtagac ggtgtgatgt   11880
accaagtggc tgactatcgg gaccagaacg gcaacattgt gagtcagaag gttcgagata   11940
aagataagaa ctttaagacc actggtagtc acaagagtga cgctctgttc gggaagcact   12000
tgtggaatgg tggtaagaag attgtcgtta cagaaggtga aatcgacatg cttaccgtga   12060
```

```
tggaacttca agactgtaag tatcctgtag tgtcgttggg tcacggtgcc tctgccgcta   12120
agaagacatg cgctgccaac tacgaatact ttgaccagtt cgaacagatt atcttaatgt   12180
tcgatatgga cgaagcaggg cgcaaagcag tcgaagaggc tgcacaggtt ctacctgctg   12240
gtaaggtacg agtggcagtt cttccgtgta aggatgcaaa cgagtgtcac ctaaatggtc   12300
acgaccgtga aatcatggag caagtgtgga atgctggtcc ttggattcct gatggtgtgg   12360
tatcggctct ttcgttacgt gaacgaatcc gtgagcacct atcgtccgag gaatcagtag   12420
gtttactttt cagtggctgc actggtatca acgataagac cttaggtgcc cgtggtggtg   12480
aagtcattat ggtcacttcc ggttccggta tgggtaagtc aacgttcgtc cgtcaacaag   12540
ctctacaatg gggcacagcg atgggcaaga aggtaggctt agcgatgctt gaggagtccg   12600
ttgaggagac cgctgaggac cttataggtc tacacaaccg tgtccgactg agacaatccg   12660
actcactaaa gagagagatt attgagaacg gtaagttcga ccaatggttc gatgaactgt   12720
tcggcaacga tacgttccat ctatatgact cattcgccga ggctgagacg gatagactgc   12780
tcgctaagct ggcctacatg cgctcaggct tgggctgtga cgtaatcatt ctagaccaca   12840
tctcaatcgt cgtatccgct tctggtgaat ccgatgagcg taagatgatt gacaacctga   12900
tgaccaagct caaagggttc gctaagtcaa ctggggtggt gctggtcgta atttgtcacc   12960
ttaagaaccc agacaaaggt aaagcacatg aggaaggtcg ccccgtttct attactgacc   13020
tacgtggttc tggcgcacta cgccaactat ctgatactat tattgccctt gagcgtaatc   13080
agcaaggcga tatgcctaac cttgtcctcg ttcgtattct caagtgccgc tttactggtg   13140
atactggtat cgctggctac atggaataca acaaggaaac cggatggctt gaaccatcaa   13200
gttactcagg ggaagaagag tcacactcag agtcaacaga ctggtccaac gacactgact   13260
tctgacagga ttcttgatga ctttccagac gactacgaga agtttcgctg gagagtccca   13320
ttctaatacg actcactaaa ggagacacac catgttcaaa ctgattaaga agttaggcca   13380
actgctggtt cgtatgtaca acgtggaagc caagcgactg aacagaggag atatacaatg   13440
gtcttcacac tcgaagattt cgttgggac tggcgacaga cagccggcta caacctggac   13500
caagtccttg aacagggagg tgtgtccagt ttgtttcaga atctcggggt gtccgtaact   13560
ccgatccaaa ggattgtcct gagcggtgaa atgggctga agatcgacat ccatgtcatc   13620
atcccgtatg aaggtctgag cggcgaccaa atgggccaga tcgaaaaaat ttttaaggtg   13680
gtgtaccctg tggatgatca tcactttaag gtgatcctgc actatggcac actggtaatc   13740
gacggggtta cgccgaacat gatcgactat ttcggacggc cgtatgaagg catcgccgtg   13800
ttcgacggca aaaagatcac tgtaacaggg accctgtgga acggcaacaa aattatcgac   13860
gagcgcctga tcaaccccga cggctccctg ctgttccgag taaccatcaa cggagtgacc   13920
ggctggcggc tgtgcgaacg cattctggcg taagatgagg ctcgtaaaga ggccacacag   13980
tcacgcgctc tggcgattcg ctccaacgaa ctggctgaca gtgcatccac taaagttacc   14040
gaggctgccc gtgtggcaaa ccaagctcaa cagctttcca aattctttga gtaatcaaac   14100
aggagaaacc attatgtcta acgtagctga aactatccgt ctatccgata cagctgacca   14160
gtggaaccgt cgagtccaca tcaacgttcg caacggtaag cgactatgg tttaccgctg   14220 gaaggactct aagtcctcta agaatcacac tcagcgtatg acgttgacag atgagcaagc   14280
actgcgtctg gtcaatgcgc ttaccaaagc tgccgtgaca gcaattcatg aagctggtcg   14340
cgtcaatgaa gctatggcta tcctcgacaa gattgataac taagagtggt atcctcaagg   14400
```

```
tcgccaaagt ggtggccttc atgaatacta ttcgactcac tataggagat attaccatgc   14460
gtgaccctaa agttatccaa gcagaaatcg ctaaactgga agctgaactg gaggacgtta   14520
agtaccatga agctaagact cgctccgctg ttcacatctt gaagaactta ggctggactt   14580
ggacaagaca gactggctgg aagaaaccag aagttaccaa gctgagtcat aaggtgttcg   14640
ataaggacac tatgacccac atcaaggctg gtgattgggt taaggttgac atgggagttg   14700
ttggtggata cggctacgtc cgctcagtta gtggcaaata tgcacaagtg tcatacatca   14760
caggtgttac tccacgcggt gcaatcgttg ccgataagac caacatgatt cacacaggtt   14820
tcttgacagt tgtttcatat gaagagattg ttaagtcacg ataatcaata ggagaaatca   14880
atatgatcgt ttctgacatc gaagctaacg ccctcttaga gagcgtcact aagttccact   14940
gcggggttat ctacgactac tccaccgctg agtacgtaag ctaccgtccg agtgacttcg   15000
gtgcgtatct ggatgcgctg gaagccgagg ttgcacgagg cggtcttatt gtgttccaca   15060
acggtcacaa gtatgacgtt cctgcattga ccaaactggc aaagttgcaa ttgaaccgag   15120
agttccacct tcctcgtgag aactgtattg acacccttgt gttgtcacgt ttgattcatt   15180
ccaacctcaa ggacaccgat atgggtcttc tgcgttccgg caagttgccc ggaaaacgct   15240
ttgggtctca cgctttggag gcgtggggtt atcgcttagg cgagatgaag ggtgaataca   15300
aagacgactt taagcgtatg cttgaagagc agggtgaaga atacgttgac ggaatggagt   15360
ggtggaactt caacgaagag atgatggact ataacgttca ggacgttgtg gtaactaaag   15420
ctctccttga gaagctactc tctgacaaac attacttccc tcctgagatt gactttacgg   15480
acgtaggata cactacgttc tggtcagaat cccttgaggc cgttgacatt gaacatcgtg   15540
ctgcatggct gctcgctaaa caagagcgca acgggttccc gtttgacaca aaagcaatcg   15600
aagagttgta cgtagagtta gctgctcgcc gctctgagtt gctccgtaaa ttgaccgaaa   15660
cgttcggctc gtggtatcag cctaaaggtg gcactgagat gttctgccat ccgcgaacag   15720
gtaagccact acctaaatac cctcgcatta agacacctaa agttggtggt atctttaaga   15780
agcctaagaa caaggcacag cgagaaggcc gtgagccttg cgaacttgat acccgcgagt   15840
acgttgctgg tgctccttac accccagttg aacatgttgt gtttaaccct tcgtctcgtg   15900
accacattca gaagaaactc aagaggctgg ggtgggtccc gaccaagtac accgataagg   15960
gtgctcctgt ggtggacgat gaggtactcg aaggagtacg tgtagatgac cctgagaagc   16020
aagccgctat cgacctcatt aaagagtact tgatgattca gaagcgaatc ggacagtctg   16080
ctgagggaga caaagcatgg cttcgttatg ttgctgagga tggtaagatt catggttctg   16140
ttaaccctaa tggagcagtt acgggtcgtg cgacccatgc gttcccaaac cttgcgcaaa   16200
ttccgggtgt acgttctcct tatggagagc agtgtcgcgc tgcttttggc gctgagcacc   16260
atttggatgg gataactggt aagccttggg ttcaggctgg catcgacgca tccggtcttg   16320
agctacgctg cttggctcac ttcatggctc gctttgataa cggcgagtac gctcacgaga   16380
ttcttaacgg cgacatccac actaagaacc agatagctgc tgaactacct acccgagata   16440
acgctaagac gttcatctat gggttcctct atggtgctgg tgatgagaag attggacaga   16500
ttgttggtgc tggtaaagag cgcggtaagg aactcaagaa gaaattcctt gagaacaccc   16560
ccgcgattgc agcactccgc gagtctatcc aacagacact tgtcgagtcc tctcaatggg   16620
tagctggtga gcaacaagtc aagtggaaac gccgctggat taaaggtctg gatggtcgta   16680
aggtacacgt tcgtagtcct cacgctgcct tgaataccct actgcaatct gctggtgctc   16740
tcatctgcaa actgtggatt atcaagaccg aagagatgct cgtagagaaa ggcttgaagc   16800
```

```
atggctggga tggggacttt gcgtacatgg catgggtaca tgatgaaatc caagtaggct    16860
gccgtaccga agagattgct caggtggtca ttgagaccgc acaagaagcg atgcgctggg    16920
ttggagacca ctggaacttc cggtgtcttc tggataccga aggtaagatg ggtcctaatt    16980
gggcgatttg ccactgatac aggaggctac tcatgaacga agacactta acaggtgctg    17040 cttctgaaat gctagtagcc tacaaattta ccaaagctgg gtacactgtc tattacccta    17100
tgctgactca gagtaaagag gacttggttg tatgtaagga tggtaaattt agtaaggttc    17160
aggttaaaac agccacaacg gttcaaacca acacaggaga tgccaagcag gttaggctag    17220
gtggatgcgg taggtccgaa tataaggatg agacttttga cattcttgcg gttgtggttg    17280
acgaagatgt gcttattttc acatgggacg aagtaaaagg taagacatcc atgtgtgtcg    17340
gcaagagaaa caaaggcata aaactatagg agaaattatt atggctatga caaagaaatt    17400
taaagtgtcc ttcgacgtta ccgcaaagat gtcgtctgac gttcaggcaa tcttagagaa    17460
agatatgctg catctatgta agcaggtcgg ctcaggtgcg attgtcccca atggtaaaca    17520
gaaggaaatg attgtccagt tcctgacaca cggtatggaa ggattgatga cattcgtagt    17580
acgtacatca tttcgtgagg ccattaagga catgcacgaa gagtatgcag ataaggactc    17640
tttcaaacaa tctcctgcaa cagtacggga ggtgttctga tgtctgacta cctgaaagtg    17700
ctgcaagcaa tcaaaagttg ccctaagact ttccagtcca actatgtacg gaacaatgcg    17760
agcctcgtag cggaggccgc ttcccgtggt cacatctcgt gcctgactac tagtggacgt    17820
aacggtggcg cttgggaaat cactgcttcc ggtactcgct ttctgaaacg aatgggagga    17880
tgtgtctaat gtctcgtgac cttgtgacta ttccacgcga tgtgtggaac gatatacagg    17940
gctacatcga ctctctggaa cgtgagaacg atagccttaa gaatcaacta atggaagctg    18000
acgaatacgt agcggaacta gaggagaaac ttaatggcac ttcttgacct aaacaattc    18060 tatgagttac gtgaaggctg cgacgacaag ggtatccttg tgatggacgg cgactggctg    18120
gtcttccaag ctatgagtgc tgctgagttt gatgcctctt ggaggaaga gatttggcac    18180 cgatgctgtg accacgctaa ggcccgtcag attcttgagg attccattaa gtcctacgag    18240
acccgtaaga aggcttgggc aggtgctcca attgtccttg cgttcaccga tagtgttaac    18300
tggcgtaaag aactggttga cccgaactat aaggctaacc gtaaggccgt gaagaaacct    18360
gtagggtact ttgagttcct tgatgctctc tttgagcgcg aagagttcta ttgcatccgt    18420
gagcctatgc ttgagggtga tgacgttatg ggagttattg cttccaatcc gtctgccttc    18480
ggtgctcgta aggctgtaat catctcttgc gataaggact ttaagaccat ccctaactgt    18540
gacttcctgt ggtgtaccac tggtaacatc ctgactcaga ccgaagagtc cgctgactgg    18600
tggcacctct tccagaccat caagggtgac atcactgatg ttactcagg gattgctgga    18660 tggggtgata ccgccgagga cttcttgaat aacccgttca taaccgagcc taaaacgtct    18720
gtgcttaagt ccggtaagaa caaaggccaa gaggttacta aatgggttaa acgcgaccct    18780
gagcctcatg agacgctttg ggactgcatt aagtccattg gcgcgaaggc tggtatgacc    18840
gaagaggata ttatcaagca gggccaaatg gctcgaatcc tacggttcaa cgagtacaac    18900
tttattgaca aggagattta cctgtggaga ccgtagcgta tattggtctg ggtctttgtg    18960
ttctcggagt gtgcctcatt tcgtggggcc tttgggactt agccagaata atcaagtcgt    19020
tacacgacac taagtgataa actcaaggtc cctaaattaa tacgactcac tataggagga    19080 tagggggcctt tacgattatt actttaagat ttaactctaa gaggaatctt tattatgtta    19140
```

```
acacctatta accaattact taagaaccct aacgatattc cagatgtacc tcgtgcaacc   19200
gctgagtatc tacaggttcg attcaactat gcgtacctcg aagcgtctgg tcatatagga   19260
cttatgcgtg ctaatggttg tagtgaggcc cacatcttgg gtttcattca gggcctacag   19320
tatgcctcta acgtcattga cgagattgag ttacgcaagg aacaactaag agatgatggg   19380
gaggattgac actatgtgtt tctcaccgaa aattaaaact ccgaagatgg ataccaatca   19440
gattcgagcc gttgagccag cgcctctgac ccaagaagtg tcaagcgtgg agttcggtgg   19500
gtcttctgat gagacggata ccgagggcac cgaagtgtct ggacgcaaag gcctcaaggt   19560
cgaacgtgat gattccgtag cgaagtctaa agccagcggc aatggctccg ctcgtatgaa   19620
atcttccatc cgtaagtccg catttggagg taagaagtga tgtctgagtt cacatgtgtg   19680
gaggctaaga gtcgcttccg tgcaatccgg tggactgtgg aacaccttgg gttgcctaaa   19740
ggattcgaag acactttgt gggctacagc ctctacgtag acgaagtgat ggacatgtct    19800
ggttgccgtg aagagtacat tctggactct accggaaaac atgtagcgta cttcgcgtgg   19860
tgcgtaagct gtgacattca ccacaaagga gacattctgg atgtaacgtc cgttgtcatt   19920
aatcctgagg cagactctaa gggcttacag cgattcctag cgaaacgctt aagtaccttc   19980
gcggaactcc acgattgcga ttgggtgtct cgttgtaagc atgaaggcga gacaatgcgt   20040
gtatacttta aggaggtata agttatgggt aagaaagtta agaaggccgt gaagaaagtc   20100
accaagtccg ttaagaaagt cgttaaggaa ggggctcgtc cggttaaaca ggttgctggc   20160
ggtctagctg gtctggctgg tggtactggt gaagcacaga tggtggaagt accacaagct   20220
gccgcacaga ttgttgacgt acctgagaaa gaggtttcca ctgaggacga agcacagaca   20280
gaaagcggac gcaagaaagc tcgtgctggc ggtaagaaat ccttgagtgt agcccgtagc   20340
tccggtggcg gtatcaacat ttaatcagga ggttatcgtg gaagactgca ttgaatggac   20400
cggaggtgtc aactctaagg gttatggtcg taagtgggtt aatggtaaac ttgtgactcc   20460
acataggcac atctatgagg agacatatgg tccagttcca acaggaattg tggtgatgca   20520
tatctgcgat aaccctaggt gctataacat aaagcacctt acgcttggaa ctccaaagga   20580
taattccgag gacatggtta ccaaaggtag acaggctaaa ggagaggaac taagcaagaa   20640
acttacagag tcagacgttc tcgctatacg ctcttcaacc ttaagccacc gctccttagg   20700
agaactgtat ggagtcagtc aatcaaccat aacgcgaata ctacagcgta agacatggag   20760
acacatttaa tggctgagaa acgaacagga cttgcggagg atggcgcaaa gtctgtctat   20820
gagcgtttaa agaacgaccg tgctccctat gagacacgcg ctcagaattg cgctcaatat   20880
accatcccat cattgttccc taaggactcc gataacgcct ctacagatta tcaaactccg   20940
tggcaagccg tgggcgctcg tggtctgaac aatctagcct ctaagctcat gctggctcta   21000
ttccctatgc agacttggat gcgacttact atatctgaat atgaagcaaa gcagttactg   21060
agcgaccccg atggactcgc taaggtcgat gagggcctct cgatggtaga gcgtatcatc   21120
atgaactaca ttgagtctaa cagttaccgc gtgactctct ttgaggctct caaacagtta   21180
gtcgtagctg gtaacgtcct gctgtaccta ccggaaccgg aagggtcaaa ctataatccc   21240
atgaagctgt accgattgtc ttcttatgtg gtccaacgag acgcattcgg caacgttctg   21300
caaatggtga ctcgtgacca gatagctttt ggtgctctcc ctgaggacat ccgtaaggct   21360
gtagaaggtc aaggtggtga gaagaaagct gatgagacaa tcgacgtgta cactcacatc   21420
tatctggatg aggactcagg tgaataccctc cgatacgaag aggtcgaggg tatggaagtc   21480
caaggctccg atgggactta tcctaaagag gcttgcccat acatcccgat tcggatggtc   21540
```

```
agactagatg gtgaatccta cggtcgttcg tacattgagg aatacttagg tgacttacgg   21600
tcccttgaaa atctccaaga ggctatcgtc aagatgtcca tgattagctc taaggttatc   21660
ggcttagtga atcctgctgg tatcacccag ccacgccgac tgaccaaagc tcagactggt   21720
gacttcgtta ctggtcgtcc agaagacatc tcgttcctcc aactggagaa gcaagcagac   21780
tttactgtag ctaaagccgt aagtgacgct atcgaggctc gcctttcgtt tgcctttatg   21840
ttgaactctg cggttcagcg tacaggtgaa cgtgtgaccg ccgaagagat tcggtatgta   21900
gcttctgaac ttgaagatac tttaggtggt gtctactcta tcctttctca agaattacaa   21960
ttgcctctgg tacgagtgct cttgaagcaa ctacaagcca cgcaacagat tcctgagtta   22020
cctaaggaag ccgtagagcc aaccattagt acaggtctgg aagcaattgg tcgaggacaa   22080
gaccttgata agctggagcg tgtgtcact gcgtgggctg cactggcacc tatgcgggac   22140
gaccctgata ttaaccttgc gatgattaag ttacgtattg ccaacgctat cggtattgac   22200
acttctggta ttctactcac cgaagaacag aagcaacaga atgatgggccca acagtctatg   22260 caaatgggta tggataatgg tgctgctgcg ctggctcaag gtatggctgc acaagctaca   22320
gcttcacctg aggctatggc tgctgccgct gattccgtag gtttacagcc gggaatttaa   22380
tacgactcac tatagggaga cctcatcttt gaaatgagcg atgacaagag gttggagtcc   22440
tcggtcttcc tgtagttcaa ctttaaggag acaataataa tggctgaatc taatgcagac   22500
gtatatgcat cttttggcgt gaactccgct gtgatgtctg gtggttccgt tgaggaacat   22560
gagcagaaca tgctggctct tgatgttgct gcccgtgatg gcgatgatgc aatcgagtta   22620
gcgtcagacg aagtggaaac agaacgtgac ctgtatgaca actctgaccc gttcggtcaa   22680
gaggatgacg aaggccgcat tcaggttcgt atcggtgatg ctctgagcc gaccgatgtg   22740 gacactggag aagaaggcgt tgagggcacc gaaggttccg aagagtttac cccactgggc   22800
gagactccag aagaactggt agctgcctct gagcaacttg gtgagcacga gagggcttc   22860 caagagatga ttaacattgc tgctgagcgt ggcatgagtg tcgagaccat tgaggctatc   22920
cagcgtgagt acgaggagaa cgaagagttg tccgccgagt cctacgctaa gctggctgaa   22980
attggctaca cgaaggcttt cattgactcg tatatccgtg tcaagaagc tctggtggag   23040 cagtacgtaa acagtgtcat tgagtacgct ggtggtcgtg aacgttttga tgcactgtat   23100
aaccaccttg agacgcacaa ccctgaggct gcacagtcgc tggataatgc gttgaccaat   23160
cgtgacttag cgaccgttaa ggctatcatc aacttggctg gtgagtctcg cgctaaggcg   23220
ttcggtcgta agccaactcg tagtgtgact aatcgtgcta ttccggctaa acctcaggct   23280
accaagcgtg aaggctttgc ggaccgtagc gagatgatta agctatgag tgaccctcgg   23340 tatcgcacag atgccaacta tcgtcgtcaa gtcgaacaga aagtaatcga ttcgaacttc   23400
tgatagactt cgaaattaat acgactcact ataggagac cacaacggtt ccctctaga   23460 aataattttg tttaacttta agaaggagat atacatatgg ctagcatgac tggtggacag   23520
caaatgggta ctaaccaagg taaaggtgta gttgctgctg gagataaact ggcgttgttc   23580
ttgaaggtat ttggcggtga agtcctgact gcgttcgctc gtacctccgt gaccacttct   23640
cgccacatgg tacgttccat ctccagcggt aaatccgctc agttccctgt tctgggtcgc   23700
actcaggcag cgtatctggc tccgggcgag aacctcgacg ataaacgtaa ggacatcaaa   23760
cacaccgaga aggtaatcac cattgacggt ctcctgacgg ctgacgttct gatttatgat   23820
attgaggacg cgatgaacca ctacgacgtt cgctctgagt atacctctca gttgggtgaa   23880
```

```
tctctggcga tggctgcgga tggtgcggtt ctggctgaga ttgccggtct gtgtaacgtg   23940
gaaagcaaat ataatgagaa catcgagggc ttaggtactg ctaccgtaat tgagaccact   24000
cagaacaagg ccgcacttac cgaccaagtt gcgctgggta aggagattat tgcggctctg   24060
actaaggctc gtgcggctct gaccaagaac tatgttccgg ctgctgaccg tgtgttctac   24120
tgtgacccag atagctactc tgcgattctg gcagcactga tgccgaacgc agcaaactac   24180
gctgctctga ttgaccctga aggggttct atccgcaacg ttatgggctt tgaggttgta    24240
gaagttccgc acctcaccgc tggtggtgct ggtaccgctc gtgagggcac tactggtcag   24300
aagcacgtct tccctgccaa taaaggtgag ggtaatgtca aggttgctaa ggacaacgtt   24360
atcggcctgt tcatgcaccg ctctgcggta ggtactgtta agctgcgtga cttggctctg   24420
gagcgcgctc gccgtgctaa cttccaagcg gaccagatta tcgctaagta cgcaatgggc   24480
cacggtggtc ttcgcccaga agctgctggt gcagtggttt tcaaagtgga gtaatgctgg   24540
gggtggcctc aacggtcgct gctagtcccg aagaggcgag tgttacttca acagaagaaa   24600
ccttaacgcc agcacaggag gccgcacgca cccgcgctgc taacaaagcc cgaaaggaag   24660
ctgagttggc tgctgccacc gctgagcaat aactagcata accccttggg gcctctaaac   24720
gggtcttgag gggttttttg ctgaaaggag gaactatatg cgctcatacg atatgaacgt   24780
tgagactgcc gctgagttat cagctgtgaa cgacattctg gcgtctatcg gtgaacctcc   24840
ggtatcaacg ctggaaggtg acgctaacgc agatgcagcg aacgctcggc gtattctcaa   24900
caagattaac cgacagattc aatctcgtgg atggacgttc aacattgagg aaggcataac   24960
gctactacct gatgtttact ccaacctgat tgtatacagt gacgactatt tatccctaat   25020
gtctacttcc ggtcaatcca tctacgttaa ccgaggtggc tatgtgtatg accgaacgag   25080
tcaatcagac cgctttgact ctggtattac tgtgaacatt attcgtctcc gcgactacga   25140
tgagatgcct gagtgcttcc gttactggat tgtcaccaag gcttcccgtc agttcaacaa   25200
ccgattcttt ggggcaccgg aagtagaggg tgtactccaa gaagaggaag atgaggctag   25260
acgtctctgc atggagtatg agatggacta cggtgggtac aatatgctgg atggagatgc   25320
gttcacttct ggtctactga ctcgctaaca ttaataaata aggaggctct aatggcactc   25380
attagccaat caatcaagaa cttgaagggt ggtatcagcc aacagcctga catccttcgt   25440
tatccagacc aagggtcacg ccaagttaac ggttggtctt cggagaccga gggcctccaa   25500
aagcgtccac ctcttgtttt cttaaataca cttggagaca acggtgcgtt aggtcaagct   25560
ccgtacatcc acctgattaa ccgagatgag cacgaacagt attacgctgt gttcactggt   25620
agcggaatcc gagtgttcga cctttctggt aacgagaagc aagttaggta tcctaacggt   25680
tccaactaca tcaagaccgc taatccacgt aacgacctgc gaatggttac tgtagcagac   25740
tatacgttca tcgttaaccg taacgttgtt gcacagaaga acacaaagtc tgtcaactta   25800
ccgaattaca accctaatca agacggattg attaacgttc gtggtggtca gtatggtagg   25860
gaactaattg tacacattaa cggtaaagac gttgcgaagt ataagatacc agatggtagt   25920
caacctgaac acgtaaacaa tacggatgcc caatggttag ctgaagagtt agccaagcag   25980
atgcgcacta acttgtctga ttggactgta aatgtagggc aagggttcat ccatgtgacc   26040
gcacctagtg gtcaacagat tgactccttc acgactaaag atggctacgc agaccagttg   26100
attaaccctg tgacccacta cgctcagtcg ttctctaagc tgccacctaa tgctcctaac   26160
ggctacatgg tgaaaatcgt aggggacgcc tctaagtctg ccgaccagta ttacgttcgg   26220
tatgacgctg agcggaaagt ttggactgag actttaggtt ggaacactga ggaccaagtt   26280
```

```
ctatgggaaa ccatgccaca cgctcttgtg cgagccgctg acggtaattt cgacttcaag    26340
tggcttgagt ggtctcctaa gtcttgtggt gacgttgaca ccaacccttg gccttctttt    26400
gttggttcaa gtattaacga tgtgttcttc ttccgtaacc gcttaggatt ccttagtggg    26460
gagaacatca tattgagtcg tacagccaaa tacttcaact tctaccctgc gtccattgcg    26520
aaccttagtg atgacgaccc tatagacgta gctgtgagta ccaaccgaat agcaatcctt    26580
aagtacgccg ttccgttctc agaagagtta ctcatctggt ccgatgaagc acaattcgtc    26640
ctgactgcct cgggtactct cacatctaag tcggttgagt tgaacctaac gacccagttt    26700
gacgtacagg accgagcgag acctttgggg attgggcgta atgtctactt tgctagtccg    26760
aggtccagct tcacgtccat ccacaggtac tacgctgtgc aggatgtcag ttccgttaag    26820
aatgctgagg acattacatc acacgttcct aactacatcc ctaatggtgt gttcagtatt    26880
tgcggaagtg gtacggaaaa cttctgttcg gtactatctc acggggaccc tagtaaaatc    26940
ttcatgtaca aattcctgta cctgaacgaa gagttaaggc aacagtcgtg gtctcattgg    27000
gactttgggg aaaacgtaca ggttctagct tgtcagagta tcagctcaga tatgtatgtg    27060
attcttcgca atgagttcaa tacgttccta gctagaatct ctttcactaa gaacgccatt    27120
gacttacagg gagaacccta tcgtgccttt atggacatga agattcgata cacgattcct    27180
agtggaacat acaacgatga cacattcact acctctattc atattccaac aatttatggt    27240
gcaaacttcg ggaggggcaa aatcactgta ttggagcctg atggtaagat aaccgtgttt    27300
gagcaaccta cggctgggtg gaatagcgac ccttggctga gactcagcgg taacttggag    27360
ggacgcatgg tgtacattgg gttcaacatt aacttcgtat atgagttctc taagttcctc    27420
atcaagcaga ctgccgacga cgggtctacc tccacggaag acattgggcg cttacagtta    27480
cgccgagcgt gggttaacta cgagaactct ggtacgtttg acatttatgt tgagaaccaa    27540
tcgtctaact ggaagtacac aatggctggt gcccgattag gctctaacac tctgagggct    27600
gggagactga acttagggac cggacaatat cgattccctg tggttggtaa cgccaagttc    27660
aacactgtat acatcttgtc agatgagact accccctctga acatcattgg gtgtggctgg    27720
gaaggtaact acttacggag aagttccggt atttaattaa atattctccc tgtggtggct    27780
cgaaattaat acgactcact atagggagaa caatacgact acgggagggt tttcttatga    27840
tgactataag acctactaaa agtacagact ttgaggtatt cactccggct caccatgaca    27900
ttcttgaagc taaggctgct ggtattgagc cgagtttccc tgatgcttcc gagtgtgtca    27960
cgttgagcct ctatgggttc cctctagcta tcggtggtaa ctgcggggac cagtgctggt    28020
tcgttacgag cgaccaagtg tggcgactta gtggaaaggc taagcgaaag ttccgtaagt    28080
taatcatgga gtatcgcgat aagatgcttg agaagtatga tactctttgg aattacgtat    28140
gggtaggcaa tacgtcccac attcgttttc tcaagactat cggtgcggta ttccatgaag    28200
agtacacacg agatggtcaa tttcagttat ttacaatcac gaaaggagga taaccatatg    28260
tgttgggcag ccgcaatacc tatcgctata tctggcgctc aggctatcag tggtcagaac    28320
gctcaggcca aaatgattgc cgctcagacc gctgctggtc gtcgtcaagc tatggaaatc    28380
atgaggcaga cgaacatcca gaatgctgac ctatcgttgc aagctcgaag taaacttgag    28440
gaagcgtccg ccgagttgac ctcacagaac atgcagaagg tccaagctat tgggtctatc    28500
cgagcggcta tcgagagag tatgcttgaa ggttcctcaa tggaccgcat taagcgagtc    28560
acagaaggac agttcattcg ggaagccaat atggtaactg agaactatcg ccgtgactac    28620
```

-continued

| | | | | | |
|---|---|---|---|---|---|
| caagcaatct | tcgcacagca | acttggtggt | actcaaagtg | ctgcaagtca | gattgacgaa 28680 |
| atctataaga | gcgaacagaa | acagaagagt | aagctacaga | tggttctgga | cccactggct 28740 |
| atcatggggt | cttccgctgc | gagtgcttac | gcatccggtg | cgttcgactc | taagtccaca 28800 |
| actaaggcac | ctattgttgc | cgctaaagga | accaagacgg | ggaggtaatg | agctatgagt 28860 |
| aaaattgaat | ctgcccttca | agcggcacaa | ccgggactct | ctcggttacg | tggtggtgct 28920 |
| ggaggtatgg | gctatcgtgc | agcaaccact | caggccgaac | agccaaggtc | aagcctattg 28980 |
| gacaccattg | gtcggttcgc | taaggctggt | gccgatatgt | ataccgctaa | ggaacaacga 29040 |
| gcacgagacc | tagctgatga | acgctctaac | gagattatcc | gtaagctgac | ccctgagcaa 29100 |
| cgtcgagaag | ctctcaacaa | cgggacccct | ctgtatcagg | atgacccata | cgctatggaa 29160 |
| gcactccgag | tcaagactgg | tcgtaacgct | gcgtatcttg | tggacgatga | cgttatgcag 29220 |
| aagataaaag | agggtgtctt | ccgtactcgc | gaagagatgg | aagagtatcg | ccatagtcgc 29280 |
| cttcaagagg | gcgctaaggt | atacgctgag | cagttcggca | tcgaccctga | ggacgttgat 29340 |
| tatcagcgtg | gtttcaacgg | ggacattacc | gagcgtaaca | tctcgctgta | tggtgcgcat 29400 |
| gataacttct | tgagccagca | agctcagaag | ggcgctatca | tgaacagccg | agtggaactc 29460 |
| aacggtgtcc | ttcaagaccc | tgatatgctg | cgtcgtccag | actctgctga | cttctttgag 29520 |
| aagtatatcg | acaacggtct | ggttactggc | gcaatcccat | ctgatgctca | agccacacag 29580 |
| cttataagcc | aagcgttcag | tgacgcttct | agccgtgctg | gtggtgctga | cttcctgatg 29640 |
| cgagtcggtg | acaagaaggt | aacacttaac | ggagccacta | cgacttaccg | agagttgatt 29700 |
| ggtgaggaac | agtggaacgc | tctcatggtc | acagcacaac | gttctcagtt | tgagactgac 29760 |
| gcgaagctga | acgagcagta | tcgcttgaag | attaactctg | cgctgaacca | agaggaccca 29820 |
| aggacagctt | gggagatgct | tcaaggtatc | aaggctgaac | tagataaggt | ccaacctgat 29880 |
| gagcagatga | caccacaacg | tgagtggcta | atctccgcac | aggaacaagt | tcagaatcag 29940 |
| atgaacgcat | ggacgaaagc | tcaggccaag | gctctggacg | attccatgaa | gtcaatgaac 30000 |
| aaacttgacg | taatcgacaa | gcaattccag | aagcgaatca | acggtgagtg | ggtctcaacg 30060 |
| gatttttaagg | atatgccagt | caacgagaac | actggtgagt | tcaagcatag | cgatatggtt 30120 |
| aactacgcca | ataagaagct | cgctgagatt | gacagtatgg | acattccaga | cggtgccaag 30180 |
| gatgctatga | agttgaagta | ccttcaagcg | gactctaagg | acggagcatt | ccgtacagcc 30240 |
| atcggaacca | tggtcactga | cgctggtcaa | gagtggtctg | ccgctgtgat | taacggtaag 30300 |
| ttaccagaac | gaaccccagc | tatggatgct | ctgcgcagaa | tccgcaatgc | tgaccctcag 30360 |
| ttgattgctg | cgctatacc | agaccaagct | gagctattcc | tgacgatgga | catgatggac 30420 |
| aagcagggta | ttgaccctca | ggttattctt | gatgccgacc | gactgactgt | taagcggtcc 30480 |
| aaagagcaac | gctttgagga | tgataaagca | ttcgagtctg | cactgaatgc | atctaaggct 30540 |
| cctgagattg | cccgtatgcc | agcgtcactg | cgcgaatctg | cacgtaagat | ttatgactcc 30600 |
| gttaagtatc | gctcggggaa | cgaaagcatg | gctatggagc | agatgaccaa | gttccttaag 30660 |
| gaatctacct | acacgttcac | tggtgatgat | gttgacggtg | ataccgttgg | tgtgattcct 30720 |
| aagaatatga | tgcaggttaa | ctctgacccg | aaatcatggg | agcaaggtcg | ggatattctg 30780 |
| gaggaagcac | gtaagggaat | cattgcgagc | aacccttgga | taaccaataa | gcaactgacc 30840 |
| atgtattctc | aaggtgactc | catttacctt | atggacacca | caggtcaagt | cagagtccga 30900 |
| tacgacaaag | agttactctc | gaaggtctgg | agtgagaacc | agaagaaact | cgaagagaaa 30960 |
| gctcgtgaga | aggctctggc | tgatgtgaac | aagcgagcac | ctatagttgc | cgctacgaag 31020 |

```
gcccgtgaag ctgctgctaa acgagtccga gagaaacgta aacagactcc taagttcatc    31080
tacggacgta aggagtaact aaaggctaca taaggaggcc ctaaatggat aagtacgata    31140
agaacgtacc aagtgattat gatggtctgt tccaaaaggc tgctgatgcc aacggggtct    31200
cttatgacct tttacgtaaa gtcgcttgga cagaatcacg atttgtgcct acagcaaaat    31260
ctaagactgg accattaggc atgatgcaat ttaccaaggc aaccgctaag gccctcggtc    31320
tgcgagttac cgatggtcca gacgacgacc gactgaaccc tgagttagct attaatgctg    31380
ccgctaagca acttgcaggt ctggtaggga agtttgatgg cgatgaactc aaagctgccc    31440
ttgcgtacaa ccaaggcgag ggacgcttgg gtaatccaca acttgaggcg tactctaagg    31500
gagacttcgc atcaatctct gaggagggac gtaactacat gcgtaacctt ctggatgttg    31560
ctaagtcacc tatggctgga cagttggaaa cttttggtgg cataacccca aagggtaaag    31620
gcattccggc tgaggtagga ttggctggaa ttggtcacaa gcagaaagta acacaggaac    31680
ttcctgagtc cacaagtttt gacgttaagg gtatcgaaca ggaggctacg gcgaaaccat    31740
tcgccaagga cttttgggag acccacggag aaacacttga cgagtacaac agtcgttcaa    31800
ccttcttcgg attcaaaaat gctgccgaag ctgaactctc caactcagtc gctgggatgg    31860 cttttccgtgc tggtcgtctc gataatggtt ttgatgtgtt taaagacacc attacgccga    31920
ctcgctggaa ctctcacatc tggactccag aggagttaga gaagattcga acagaggtta    31980
agaaccctgc gtacatcaac gttgtaactg gtggttcccc tgagaacctc gatgacctca    32040
ttaaattggc taacgagaac tttgagaatg actcccgcgc tgccgaggct ggcctaggtg    32100
ccaaactgag tgctggtatt attggtgctg gtgtggaccc gcttagctat gttcctatgg    32160
tcggtgtcac tggtaagggc tttaagttaa tcaataaggc tcttgtagtt ggtgccgaaa    32220
gtgctgctct gaacgttgca tccgaaggtc tccgtaccte cgtagctggt ggtgacgcag    32280
actatgcggg tgctgcctta ggtggctttg tgtttggcgc aggcatgtct gcaatcagtg    32340
acgctgtagc tgctggactg aaacgcagta aaccagaagc tgagttcgac aatgagttca    32400
tcggtcctat gatgcgattg gaagcccgtg agacagcacg aaacgccaac tctgcggacc    32460
tctctcggat gaacactgag aacatgaagt ttgaaggtga acataatggt gtcccttatg    32520
aggacttacc aacagagaga ggtgccgtgg tgttacatga tggctccgtt ctaagtgcaa    32580
gcaacccaat caacccctaag actctaaaag agttctccga ggttgaccct gagaaggctg    32640
cgcgaggaat caaactggct gggttcaccg agattggctt gaagaccttg gggtctgacg    32700
atgctgacat ccgtagagtg gctatcgacc tcgttcgctc tcctactggt atgcagtctg    32760
gtgcctcagg taagttcggt gcaacagctt ctgacatcca tgagagactt catggtactg    32820
accagcgtac ttataatgac ttgtacaaag caatgtctga cgctatgaaa gaccctgagt    32880
tctctactgg cggcgctaag atgtcccgtg aagaaactcg atacactatc taccgtagag    32940
cggcactagc tattgagcgt ccagaactac agaaggcact cactccgtct gagagaatcg    33000
ttatggacat cattaagcgt cactttgaca ccaagcgtga acttatggaa aacccagcaa    33060
tattcggtaa cacaaaggct gtgagtatct tccctgagag tcgccacaaa ggtacttacg    33120
ttcctcacgt atatgaccgt catgccaagg cgctgatgat tcaacgctac ggtgccgaag    33180
gtttgcagga agggattgcc cgctcatgga tgaacagcta cgtctccaga cctgaggtca    33240
aggccagagt cgatgagatg cttaaggaat tacacgggggt gaaggaagta acaccagaga    33300
tggtagagaa gtacgctatg gataaggctt atggtatctc ccactcagac cagttcacca    33360
```

```
acagttccat aatagaagag aacattgagg gcttagtagg tatcgagaat aactcattcc   33420
ttgaggcacg taacttgttt gattcggacc tatccatcac tatgccagac ggacagcaat   33480
tctcagtgaa tgacctaagg gacttcgata tgttccgcat catgccagcg tatgaccgcc   33540
gtgtcaatgg tgacatcgcc atcatgaggt ctactggtaa aaccactaag gaacttaagg   33600
atgagatttt ggctctcaaa gcgaaagctg agggagacgg taagaagact ggcgaggtac   33660
atgctttaat ggataccgtt aagattctta ctggtcgtgc tagacgcaat caggacactg   33720
tgtgggaaac ctcactgcgt gccatcaatg acctagggtt cttcgctaag aacgcctaca   33780
tgggtgctca gaacattacg gagattgctg ggatgattgt cactggtaac gttcgtgctc   33840
tagggcatgg tatcccaatt ctgcgtgata cactctacaa gtctaaacca gtttcagcta   33900
aggaactcaa ggaactccat gcgtctctgt tcgggaagga ggtggaccag ttgattcggc   33960
ctaaacgtgc tgacattgtg cagcgcctaa gggaagcaac tgataccgga cctgccgtgg   34020
cgaacatcgt agggaccttg aagtattcaa cacaggaact ggctgctcgc tctccgtgga   34080
ctaagctact gaacggaacc actaactacc ttctggatgc tgcgcgtcaa ggtatgcttg   34140
gggatgttat tagtgccacc ctaacaggta agactacccg ctgggagaaa gaaggcttcc   34200
ttcgtggtgc ctccgtaact cctgagcaga tggctgcat caagtctctc atcaaggaac   34260
atatggtacg cggtgaggac gggaagttta ccgttaagga caagcaagcg ttctctatgg   34320
acccacgggc tatggactta tggagactgg ctgacaaggt agctgatgag gcaatgctgc   34380
gtccacataa ggtgtcctta caggattccc atgcgttcgg agcactaggt aagatggtta   34440
tgcagtttaa gtctttcact atcaagtccc ttaactctaa gttcctgcga accttctatg   34500
atggatacaa gaacaaccga gcgattgacg ctgcgctgag catcatcacc tctatgggtc   34560
tcgctggtgg tttctatgct atggctgcac acgtcaaagc atacgctctg cctaaggaga   34620
aacgtaagga gtacttggag cgtgcactgg acccaaccat gattgcccac gctgcgttat   34680
ctcgtagttc tcaattgggt gctccttttg ctatggttga cctagttggt ggtgttttag   34740
ggttcgagtc ctccaagatg gctcgctcta cgattctacc taaggacacc gtgaaggaac   34800
gtgacccaaa caaaccgtac acctctagag aggtaatggg cgctatgggt tcaaaccttc   34860
tggaacagat gccttcggct ggctttgtgg ctaacgtagg ggctaccttg atgaatgctg   34920
ctggcgtggt caactcacct aataaagcaa ccgagcagga cttcatgact ggtcttatga   34980
actccacaaa agagttagta ccgaacgacc cattgactca acagcttgtg ttgaagattt   35040
atgaggcgaa cggtgttaac ttgagggagc gtaggaaata atacgactca ctataggag   35100 aggcgaaata atcttctccc tgtagtctct tagatttact ttaaggaggt caaatggcta   35160
acgtaattaa aaccgttttg acttaccagt tagatggctc caatcgtgat tttaatatcc   35220
cgtttgagta tctagcccgt aagttcgtag tggtaactct tattggtgta gaccgaaagg   35280
tccttacgat taatacagac tatcgctttg ctacacgtac tactatctct ctgacaaagg   35340
cttggggtcc agccgatggc tacacgacca tcgagttacg tcgagtaacc tccactaccg   35400
accgattggt tgactttacg gatggttcaa tcctccgcgc gtatgacctt aacgtcgctc   35460
agattcaaac gatgcacgta gcggaagagg cccgtgacct cactacggat actatcggtg   35520
tcaataacga tggtcacttg gatgctcgtg gtcgtcgaat tgtgaaccta gcgaacgccg   35580
tggatgaccg cgatgctgtt ccgtttggtc aactaaagac catgaaccag aactcatggc   35640
aagcacgtaa tgaagcctta cagttccgta atgaggctga gactttcaga aaccaagcgg   35700
agggctttaa gaacgagtcc agtaccaacg ctacgaacac aaaagcagtg gcgcgatgaga   35760
```

| | | | | |
|---|---|---|---|---|
| ccaagggttt | ccgagacgaa | gccaagcggt | tcaagaatac | ggctggtcaa tacgctacat | 35820 |
| ctgctgggaa | ctctgcttcc | gctgcgcatc | aatctgaggt | aaacgctgag aactctgcca | 35880 |
| cagcatccgc | taactctgct | catttggcag | aacagcaagc | agaccgtgcg aacgtgagg | 35940 |
| cagacaagct | ggaaaattac | aatggattgg | ctggtgcaat | tgataaggta gatggaacca | 36000 |
| atgtgtactg | gaaaggaaat | attcacgcta | acgggcgcct | ttacatgacc acaaacggtt | 36060 |
| ttgactgtgg | ccagtatcaa | cagttctttg | gtggtgtcac | taatcgttac tctgtcatgg | 36120 |
| agtggggaga | tgagaacgga | tggctgatgt | atgttcaacg | tagagagtgg acaacagcga | 36180 |
| taggcggtaa | catccagtta | gtagtaaacg | gacagatcat | cacccaaggt ggagccatga | 36240 |
| ccggtcagct | aaaattgcag | aatgggcatg | ttcttcaatt | agagtccgca tccgacaagg | 36300 |
| cgcactatat | tctatctaaa | gatggtaaca | ggaataactg | gtacattggt agagggtcag | 36360 |
| ataacaacaa | tgactgtacc | ttccactcct | atgtacatgg | tacgaccta acactcaagc | 36420 |
| aggactatgc | agtagttaac | aaacacttcc | acgtaggtca | ggccgttgtg gccactgatg | 36480 |
| gtaatattca | aggtactaag | tggggaggta | aatggctgga | tgcttaccta cgtgacagct | 36540 |
| tcgttgcgaa | gtccaaggcg | tggactcagg | tgtggtctgg | tagtgctggc ggtgggtaa | 36600 |
| gtgtgactgt | ttcacaggat | ctccgcttcc | gcaatatctg | gattaagtgt gccaacaact | 36660 |
| cttggaactt | cttccgtact | ggccccgatg | gaatctactt | catagcctct gatggtggat | 36720 |
| ggttacgatt | ccaaatacac | tccaacggtc | tcggattcaa | gaatattgca gacagtcgtt | 36780 |
| cagtacctaa | tgcaatcatg | gtggagaacg | agtaattggt | aaatcacaag gaaagacgtg | 36840 |
| tagtccacgg | atggactctc | aaggaggtac | aaggtgctat | cattagactt taacaacgaa | 36900 |
| ttgattaagg | ctgctccaat | tgttgggacg | ggtgtagcag | atgttagtgc tcgactgttc | 36960 |
| tttgggttaa | gccttaacga | atggttctac | gttgctgcta | tcgcctacac agtggttcag | 37020 |
| attggtgcca | aggtagtcga | taagatgatt | gactggaaga | aagccaataa ggagtgatat | 37080 |
| gtatggaaaa | ggataagagc | cttattacat | tcttagagat | gttggacact gcgatggctc | 37140 |
| agcgtatgct | tgcggacctt | tcggaccatg | agcgtcgctc | tccgcaactc tataatgcta | 37200 |
| ttaacaaact | gttagaccgc | cacaagttcc | agattggtaa | gttgcagccg gatgttcaca | 37260 |
| tcttaggtgg | ccttgctggt | gctcttgaag | agtacaaaga | gaaagtcggt gataacggtc | 37320 |
| ttacggatga | tgatatttac | acattacagt | gatatactca | aggccactac agatagtggt | 37380 |
| ctttatggat | gtcattgtct | atacgagatg | ctcctacgtg | aaatctgaaa gttaacggga | 37440 |
| ggcattatgc | tagaatttt | acgtaagcta | atcccttggg | ttctcgctgg gatgctattc | 37500 |
| gggttaggat | ggcatctagg | gtcagactca | atggacgcta | aatggaaaca ggaggtacac | 37560 |
| aatgagtacg | ttaagagagt | tgaggctgcg | aagagcactc | aaagagcaat cgatgcgta | 37620 |
| tctgctaagt | atcaagaaga | ccttgccgcg | ctggaaggga | gcactgatag gattatttct | 37680 |
| gatttgcgta | gcgacaataa | gcggttgcgc | gtcagagtca | aaactaccgg aacctccgat | 37740 |
| ggtcagtgtg | gattcgagcc | tgatggtcga | gccgaacttg | acgaccgaga tgctaaacgt | 37800 |
| attctcgcag | tgacccagaa | gggtgacgca | tggattcgtg | cgttacagga tactattcgt | 37860 |
| gaactgcaac | gtaagtagga | aatcaagtaa | ggaggcaatg | tgtctactca atccaatcgt | 37920 |
| aatgcgctcg | tagtggcgca | actgaaagga | gacttcgtgg | cgttcctatt cgtcttatgg | 37980 |
| aaggcgctaa | acctaccggt | gcccactaag | tgtcagattg | acatggctaa ggtgctggcg | 38040 |
| aatggagaca | acaagaagtt | catcttacag | gctttccgtg | gtatcggtaa gtcgttcatc | 38100 |

```
acatgtgcgt tcgttgtgtg gtccttatgg agagaccctc agttgaagat acttatcgta    38160
tcagcctcta aggagcgtgc agacgctaac tccatcttta ttaagaacat cattgacctg    38220
ctgccattcc tatctgagtt aaagccaaga cccggacagc gtgactcggt aatcagcttt    38280
gatgtaggcc cagccaatcc tgaccactct cctagtgtga aatcagtagg tatcactggt    38340
cagttaactg gtagccgtgc tgacattatc attgcggatg acgttgagat tccgtctaac    38400
agcgcaacta tgggtgcccg tgagaagcta tggactctgg ttcaggagtt cgctgcgtta    38460
cttaaaccgc tgccttcctc tcgcgttatc taccttggta cacctcagac agagatgact    38520
ctctataagg aacttgagga taaccgtggg tacacaacca ttatctggcc tgctctgtac    38580
ccaaggacac gtgaagagaa cctctattac tcacagcgtc ttgctcctat gttacgcgct    38640
gagtacgatg agaaccctga ggcacttgct gggactccaa cagacccagt gcgctttgac    38700
cgtgatgacc tgcgcgagcg tgagttggaa tacggtaagg ctggctttac gctacagttc    38760
atgcttaacc ctaaccttag tgatgccgag aagtacccgc tgaggcttcg tgacgctatc    38820
gtagcggcct tagacttaga gaaggcccca atgcattacc agtggcttcc gaaccgtcag    38880
aacatcattg aggaccttcc taacgttggc cttaagggtg atgacctgca tacgtaccac    38940
gattgttcca acaactcagg tcagtaccaa cagaagattc tggtcattga ccctagtggt    39000
cgcggtaagg acgaaacagg ttacgctgtg ctgtacacac tgaacggtta catctacctt    39060
atggaagctg gaggtttccg tgatggctac tccgataaga cccttgagtt actcgctaag    39120
aaggcaaagc aatggggagt ccagacggtt gtctacgaga gtaacttcgg tgacggtatg    39180
ttcggtaagg tattcagtcc tatccttctt aaacaccaca actgtgcgat ggaagagatt    39240
cgtgcccgtg gtatgaaaga gatgcgtatt tgcgataccc ttgagccagt catgcagact    39300
caccgccttg taattcgtga tgaggtcatt agggccgact accagtccgc tcgtgacgta    39360
gacggtaagc atgacgttaa gtactcgttg ttctaccaga tgacccgtat cactcgtgag    39420
aaaggcgctc tggctcatga tgaccgattg gatgcccttg cgttaggcat tgagtatctc    39480
cgtgagtcca tgcagttgga ttccgttaag gtcgagggtg aagtacttgc tgacttcctt    39540
gaggaacaca tgatgcgtcc tacggttgct gctacgcata tcattgagat gtctgtggga    39600
ggagttgatg tgtactctga ggacgatgag ggttacggta cgtctttcat tgagtggtga    39660
tttatgcatt aggactgcat agggatgcac tatagaccac ggatggtcag ttctttaagt    39720
tactgaaaag acacgataaa ttaatacgac tcactatagg gagaggaggg acgaaaggtt    39780
actatataga tactgaatga atacttatag agtgcataaa gtatgcataa tggtgtacct    39840
agagtgacct ctaagaatgg tgattatatt gtattagtat cacccttaact taaggaccaa    39900
cataaaggga ggagactcat gttccgctta ttgttgaacc tactgcggca tagagtcacc    39960
taccgatttc ttgtggtact ttgtgctgcc cttgggtacg catctcttac tggagacctc    40020
agttcactgg agtctgtcgt ttgctctata ctcacttgta gcgattaggg tcttcctgac    40080
cgactgatgg ctcaccgagg gattcagcgg tatgattgca tcacaccact tcatccctat    40140
agagtcaagt cctaaggtat acccataaag agcctctaat ggtctatcct aaggtctata    40200
cctaaagata ggccatccta tcagtgtcac ctaaagaggg tcttagagag gcctatgga    40260
gttcctatag ggtcctttaa aatataccat aaaaatctga gtgactatct cacagtgtac    40320
ggacctaaag ttccccata gggggtacct aaagcccagc caatcaccta aagtcaacct    40380
tcggttgacc ttgagggttc cctaagggtt ggggatgacc cttgggtttg tctttgggtg    40440
ttaccttgag tgtctctctg tgtccct                                       40467
```

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gttgatgtct ctgtgtccct ttaattaatc tcacagttta cacttttggt                50

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
taatgtcctc tcaatatgtt gtgtgt                                          26

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aactcaaggt cattactata tgtagt                                          26

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
attgtatacc tcctattaac gaccgatgag accctg                               36

<210> SEQ ID NO 7
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ctcatcggtc gttaatagga ggtatacaat ggtcttcaca c                         41

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tccttaagtt tctgattacg ccagaatgcg ttcgc                                35

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cgcattctgg cgtaatcaga aacttaagga ggacca                              36

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gtgacctcct ttagttgaat gaga                                           24

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aggacacact atagggagac                                                20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
agggacacag agacatcaac a                                              21

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gagatgcctg agtgtttccg                                                20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gaccaaccgt tgacctgaag                                                20

-continued

```
<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tctcacagtg tacggacct                                                   19

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gtatatctcc tctgttcagt cgcttggctt cca                                   33

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
caagcgactg aacagaggag atatacaatg gtcttcaca                             39

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tacgagcctc atcttaccat tcgccattca ggct                                  34

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tggcgaatgg taagatgagg ctcgtaaaga ggcc                                  34

<210> SEQ ID NO 20
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tgaatgtgtc atcgttgtat gttccactag gaatcgtg                              38

<210> SEQ ID NO 21
```

```
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tggaacatac aacgatgaca cattcactac ctct                          34

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
agggacacag agagacactc a                                        21

<210> SEQ ID NO 23
<211> LENGTH: 781
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
ctctcggttc ttcggagcgg aggacgtaga gaactctctg gcacaggaag agatggaagc    60
gcgtatggca tgcaacgagt acgagatgga cttcggtcag tacaacatgc ttgacggcga   120
cgcatacgtg cagggtctca tcggtcgtta ataggaggta tacaatggtc ttcacactcg   180
aagatttcgt tggggactgg cgacagacag ccggctacaa cctggaccaa gtccttgaac   240
agggaggtgt gtccagtttg tttcagaatc tcggggtgtc cgtaactccg atccaaagga   300
ttgtcctgag cggtgaaaat gggctgaaga tcgacatcca tgtcatcatc ccgtatgaag   360
gtctgagcgg cgaccaaatg ggccagatcg aaaaaatttt taaggtggtg taccctgtgg   420
atgatcatca ctttaaggtg atcctgcact atggcacact ggtaatcgac ggggttacgc   480
cgaacatgat cgactatttc ggacggccgt atgaaggcat cgccgtgttc gacggcaaaa   540
agatcactgt aacagggacc ctgtggaacg gcaacaaaat tatcgacgag cgcctgatca   600
accccgacgg ctccctgctg ttccgagtaa ccatcaacgg agtgaccggc tggcggctgt   660
gcgaacgcat tctggcgtaa tcagaaactt aaggaggacc aaatggctct cgtatcacaa   720
tcaatcaaga acctcaaggg aggcattagc cagcagcctg aaatcctacg gtacccagag   780
c                                                                  781

<210> SEQ ID NO 24
<211> LENGTH: 119
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
taatacgact cactataggg aggtcattac tatatgtagg ttttagagct agaaatagca    60
agttaaaata aggctagtcc gttatcaact tgaaaaagtg caccgagtc ggtgctttt    119
```

```
<210> SEQ ID NO 25
<211> LENGTH: 729
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
gcgtgaggca atcctgagca aagaggttgg cgaaacgtcc gtgcgtctgg ccgaagcgtc      60
agaagttaag tgataaactc aaggtcatta ctatatgtag aaggagattc aacatggtct    120
tcacactcga agatttcgtt ggggactggc gacagacagc cggctacaac ctggaccaag    180
tccttgaaca gggaggtgtg tccagtttgt ttcagaatct cggggtgtcc gtaactccga    240
tccaaaggat tgtcctgagc ggtgaaaatg ggctgaagat cgacatccat gtcatcatcc    300
cgtatgaagg tctgagcggc gaccaaatgg gccagatcga aaaaattttt aaggtggtgt    360
accctgtgga tgatcatcac tttaaggtga tcctgcacta tggcacactg gtaatcgacg    420
gggttacgcc gaacatgatc gactatttcg gacggccgta tgaaggcatc gccgtgttcg    480
acggcaaaaa gatcactgta acagggaccc tgtggaacgg caacaaaatt atcgacgagc    540
gcctgatcaa ccccgacggc tccctgctgt tccgagtaac catcaacgga gtgaccggct    600
ggcggctgtg cgaacgcatt ctggcgtaat ggcctttatg attatacaca caacatattg    660
agaggacatt accatgcgta aacctgaaga gattcgtaaa gagattgaag cgctgaacaa    720
agagctggc                                                            729
```